US012573473B2

(12) United States Patent　　　　　　　(10) Patent No.: US 12,573,473 B2
Landau et al.　　　　　　　　　　　　　　(45) Date of Patent: Mar. 10, 2026

(54) ULTRA-SENSITIVE DETECTION OF CIRCULATING TUMOR DNA THROUGH GENOME-WIDE INTEGRATION

(71) Applicants:CORNELL UNIVERSITY, Ithaca, NY (US); NEW YORK GENOME CENTER, New York, NY (US)

(72) Inventors: Dan Avi Landau, Brooklyn, NY (US); Asaf Zviran, Cresskill, NJ (US); Steven Thomas Kothen-Hill, Ithaca, NY (US)

(73) Assignees: CORNELL UNIVERSITY, Ithaca, NY (US); NEW YORK GENOME CENTER, New York, NY (US)

( * ) Notice: Subject to any disclaimer, the term of this patent is extended or adjusted under 35 U.S.C. 154(b) by 697 days.

(21) Appl. No.: 16/976,056

(22) PCT Filed: Feb. 27, 2019

(86) PCT No.: PCT/US2019/019905
§ 371 (c)(1),
(2) Date: Aug. 26, 2020

(87) PCT Pub. No.: WO2019/169042
PCT Pub. Date: Sep. 6, 2019

(65) Prior Publication Data
US 2021/0043275 A1　　Feb. 11, 2021

Related U.S. Application Data

(60) Provisional application No. 62/636,135, filed on Feb. 27, 2018.

(51) Int. Cl.
*G16B 25/10* (2019.01)
*G16B 20/00* (2019.01)
(Continued)

(52) U.S. Cl.
CPC ............. *G16B 25/10* (2019.02); *G16B 20/00* (2019.02); *G16B 20/20* (2019.02); *G16B 40/20* (2019.02)

(58) Field of Classification Search
None
See application file for complete search history.

(56) References Cited

U.S. PATENT DOCUMENTS 7,115,400 B1　10/2006　Adessi et al.
7,572,584 B2　8/2009　Shanks et al.
(Continued)

FOREIGN PATENT DOCUMENTS

CN　　105950750　　9/2016
CN　　107447258　　12/2017
(Continued)

OTHER PUBLICATIONS

Phallen, Jillian, et al. "Direct detection of early-stage cancers using circulating tumor DNA." Science translational medicine 9.403 (2017): eaan2415. (Year: 2017).*
(Continued)

*Primary Examiner* — Karlheinz R. Skowronek
*Assistant Examiner* — Mary C Leverett
(74) *Attorney, Agent, or Firm* — NORTON ROSE FULBRIGHT US LLP

(57) ABSTRACT
The disclosure relates to systems, software and methods for diagnosing tumor diseases in a patient.

30 Claims, 41 Drawing Sheets

110 — Receiving a subject-specific genome-wide compendium of reads associated with a plurality of genetic markers 120 — Removing artefactual reads by statistically classifying each read as Signal or Noise on the basis of probability of detection of noise ($P_N$) as a function of (1) base-quality (BQ); (2) mapping-quality (MQ); (3) estimated fragment size and/or (4) estimated allele fraction (VAF)

130 — Adaptively and/or systemically filtering sequencing noise associated with each read in the compendium by utilizing machine learning (ML) approach to discriminate between cancer-related mutation features and PCR or sequencing error related features 140 — Compiling a subject-specific signature comprising a plurality of true reads in the compendium based on the noise removal step 120 and Filtering step 130

150 — Statistically quantitating a confidence estimate that the subject's biological sample comprises circulating tumor DNA (ctDNA) based on a match between the subject-specific signature and a cancer signature 160 — Screening the subject for cancer based on the confidence estimate that the subject's biological sample contains cancer related mutational signature

(51) Int. Cl.
    *G16B 20/20*     (2019.01)
    *G16B 40/20*     (2019.01)

(56)           References Cited

U.S. PATENT DOCUMENTS

| | | | |
|---|---|---|---|
| 7,718,403 B2 | 5/2010 | Kamberov et al. | |
| 7,741,463 B2 | 6/2010 | Gormley et al. | |
| 8,932,812 B2 | 1/2015 | Hogers et al. | |
| 9,218,450 B2 | 12/2015 | Chen et al. | |
| 2015/0178445 A1 | 6/2015 | Cibulskis et al. | |
| 2016/0032396 A1 | 2/2016 | Diehn et al. | |
| 2017/0220735 A1* | 8/2017 | Duenwald | G16B 20/20 |
| 2017/0329894 A1* | 11/2017 | Kennedy | G16H 40/63 |
| 2018/0251848 A1 | 9/2018 | Diehn et al. | |
| 2021/0002728 A1 | 1/2021 | Landau et al. | |
| 2023/0295738 A1 | 9/2023 | Landau et al. | |

FOREIGN PATENT DOCUMENTS

| | | | |
|---|---|---|---|
| WO | 2016/109452 A1 | 7/2016 | |
| WO | WO 2016/109452 | 7/2016 | |
| WO | WO 2016/134136 | 8/2016 | |
| WO | WO 2017/123864 | 7/2017 | |
| WO | 2017/161175 A1 | 9/2017 | |
| WO | 2017/191073 A1 | 11/2017 | |
| WO | WO 2017/201497 | 11/2017 | |
| WO | WO-2017201497 A1 * | 11/2017 | A61K 31/513 |
| WO | WO 2018/009723 | 1/2018 | |

OTHER PUBLICATIONS

Baine, Michael J., et al. "Differential gene expression analysis of peripheral blood mononuclear cells reveals novel test for early detection of pancreatic cancer." Cancer biomarkers 11.1 (2012): 1-14. (Year: 2012).*

Zhao, Eric Y., et al. "Homologous recombination deficiency and platinum-based therapy outcomes in advanced breast cancer." Clinical Cancer Research 23.24 (2017): 7521-7530. (Year: 2017).*

De Souza, Jorge ES, et al. "S-score: a scoring system for the identification and prioritization of predicted cancer genes." PLoS One 9.4 (2014): e94147. (Year: 2014).*

Underhill, Hunter R., et al. "Fragment length of circulating tumor DNA." PLoS genetics 12.7 (2016): e1006162. (Year: 2016).*

Singapore Search Report and Written Opinion issued in corresponding Singapore application No. 11202007899Q, mailed Mar. 28, 2022.

European Extended Search Report and Written Opinion issued in corresponding European application No. 19761020.7, mailed May 4, 2022.

Angermueller, C. et al., Deep learning for computational biology. Molecular systems biology, Jul. 29, 2016, vol. 12, No. 7, pp. 878.

Cibulskis, K. et al., Sensitive detection of somatic point mutations in impure and heterogeneous cancer samples. Computational Biology, Feb. 10, 2013, vol. 31, No. 3, pp. 213-219.

Huang, X, et al., Detecting presence of mutational signatures in cancer with confidence. Bioinformatics, Sep. 22, 2017, vol. 34, No. 2, pp. 330-337.

Mouliere, F et al., "Selecting short DNA fragments in plasma improves detection of circulating tumour DNA," BioRXiv; May 5, 2017.

Miller, CA et al., "ReadDepth: A Parallel R Package for Detecting Copy Number Alterations from Short Sequencing Reads," PloS One; Jan. 31, 2011, vol. 6, No. 1.

Desvillechabrol, D et al., "Detection and characterization of low and high genome coverage regions using anefficient running median and a double threshold approach," BioRXiv.; Dec. 8, 2016.

International Search Report and Written Opinion from International Application No. PCT/US2019/019905, dated Apr. 16, 2019, 12 pages.

Kothen-Hill et al., "Deep Learning Mutation Prediction Enables Early Stage Lung Cancer Detection in Liquid Biopsy," Workshop Track—ICLR 2018; Publication (online). Feb. 15, 2018 [retrieved Aug. 21, 2020]. Retrieved from the Internet: <URL: https://openreview.net/forum?id=H1DkN7ZC&noteId=H1DkN7ZCZ>; pp. 1-24.

Adalsteinsson, V. et al., "Scalable whole-exome sequencing of cell-free DNA reveals high concordance with metastatic tumors", Nature Communications, 8(1), 2017.

European Office Action issued in corresponding European Application No. 19761020.7, dated Jun. 2, 2023.

Carmichael, H. et al., "Breast cancer screening of pregnant and breastfeeding women with BRCA mutations", Breast Cancer Res Treat, 162: 225-230, 2017.

Office Action issued in corresponding Chinese Application No. 201980028168.4, dated Jul. 21, 2023. (English Translation Provided).

Pan, Y. et al., "Double-stranded DNA microarray: Principles, techniques and applications", Heredity, 35(3): 287-306, 2013. (English Machine Translation Provided).

Abbosh et al., "Phylogenetic ctDNA analysis depicts early stage lung cancer evolution", Nature, 545(7655):446-451, 2017.

Alexandrov et al., "Mutational signatures: the patterns of somatic mutations hidden in cancer genomes", Curr Opin Genet Dev., 24:52-60, 2014.

Alexandrov et al., "Signatures of mutational processes in human cancer", Nature, 500(7463):415-421, 2013.

Barnes, W., "PCR amplification of up to 35-kb DNA with high fidelity and high yield from λ bacteriophage templates", PNAS USA, 91:2216, 1994.

Bettegowda et al., "Detection of circulating tumor DNA in early- and late-stage human malignancies", Sci Transl Med., 6(224):224ra24, 2014.

Burger et al., "Clonal evolution in patients with chronic lymphocytic leukaemia developing resistance to BTK inhibition," Nature communications, 2016, 7, 11589.

Chen et al., "Circulating Tumor DNA Detection in Early-Stage Non-Small Cell Lung Cancer Patients by Targeted Sequencing," Scientific Reports, 2016, 6, 31985.

Chen et al., "DNA damage is a pervasive cause of sequencing errors, directly confounding variant identification", Science, 355(6326):752-756, 2017.

Coate et al., "Molecular predictive and prognostic markers in non-small-cell lung cancer", Lancet Oncol, 10(10):1001-1010, 2009.

Collisson et al., "Comprehensive molecular profiling of lung adenocarcinoma", Nature, 511(7511):543-550, 2014.

Diehl et al., "Circulating mutant DNA to assess tumor dynamics", Nature medicine, 14(9):985-990, 2008.

Dietz et al., "Low Input Whole-Exome Sequencing to Determine the Representation of the Tumor Exome in Circulating DNA of Non-Small Cell Lung Cancer Patients," PloS one, 2016, 11, e0161012.

Duric et al., "Patients' preferences for adjuvant chemotherapy in early breast cancer: a review of what makes it worthwhile?", Lancet Oncol., 2(11):P691-697, 2001.

Ewing et al., "Base-Calling of Automated Sequencer Traces UsingPhred. I. Accuracy Assessment", Genome Res. 8(3):175-185, 1998.

Fong et al., "Inhibition of Poly(ADP-Ribose) Polymerase in Tumors from BRCA Mutation Carriers", N Engl J Med., 361(2):123-34, 2009.

Greenman et al., "Patterns of somatic mutation in human cancer genomes", Nature, 446(7132): 153-158, 2007.

Harewood et al., "Economic analysis of combined endoscopic and endobronchial ultrasound in the evaluation of patients with suspected non-small cell lung cancer," Lung Cancer, 2010, 67, pp. 366-371.

He et al. "Deep Residual Learning for Image Recognition", In Proceedings of the IEEE conference on computer vision and pattern recognition, pp. 770-778, 2016.

Herbst et al., "Lung Cancer", N Engl J Med., 359(13):1367-1380, 2008.

Hill et al., "A Deep Recurrent Neural Network Discovers Complex Biological Rules to Decipher RNA Protein-Coding Potential", bioRxiv, pp. 200758, 2017.

(56) References Cited

OTHER PUBLICATIONS

Hiramatsu et al., "Pulmonary ground-glass opacity (GGO) lesions-large size and a history of lung cancer are risk factors for growth," Journal of thoracic oncology : official publication of the International Association for the Study of Lung Cancer, 2008, 3, pp. 1245-1250.

Izumchenko et al., "Targeted sequencing reveals clonal genetic changes in the progression of early lung neoplasms and paired circulating DNA," Nature Communications, 2015, 6, 8258.

Jamal-Hanjani et al., "Detection of ubiquitous and heterogeneous mutations in cell-free DNA from patients with early-stage non-small-cell lung cancer," Annals of Oncology Official Journal of the European Society for Medical Oncology / ESMO, 2016, 27, 862-867.

Jiang et al., "Lengthening and shortening of plasma DNA in hepatocellular carcinoma patients", PNAS USA, 112(11):E1317-E1325, 2015.

Karlsson et al., "Amplification-free sequencing of cell-free DNA for prenatal non-invasive diagnosis of chromosomal aberrations", Genomics, 105(3):150-8, 2015.

Kim et al., "Ultraviolet radiation-induced non-melanoma skin cancer: Regulation of DNA damage repair and inflammation", Genes & Disease, 1(2):188-198, 2014.

Kobayashi et al., "EGFR mutation and resistance of non-small-cell lung cancer to gefitinib," The New England Journal of Medicine, 2005, 352, 786-792.

Kratz et al., "ternational trial of adjuvant therapy in high risk stage I nonsquamous cell carcinoma identified by a 14-gene prognostic signature", Transl Lung Cancer Res., 2(3):222-225, 2013.

Kurzawski et al., "Importance of microsatellite instability (MSI) in colorectal cancer: MSI as a diagnostic tool", Annals of Oncology, 15 (Supp. 4):283-284, 2004.

Landau et al, "Locally disordered methylation forms the basis of intratumor methylome variation in chronic lymphocytic leukemia," Cancer Cell, vol. 26, Issue 6, pp. 813-825, Dec. 8, 2014.

Landau et al., "Quantitative Clonal Dynamics Define Mechanisms of CLL Evolution in Response to Combination Chemotherapy," Blood (2015) 126 (23): 362.

Lawrence et al., "Discovery and saturation analysis of cancer genes across 21 tumour types", Nature, 505(7484):495-501, 2014.

Li et al., "Mapping short DNA sequencing reads and calling variants using mapping quality scores", Genome Research, 18:1851-1858, 2008.

Li et al., "The Sequence Alignment/Map format and SAMtools", Bioinformatics, 25(16):2078-2079, 2009.

Malapelle et al., "Next generation sequencing techniques in liquid biopsy: focus on non-small cell lung cancer patients," Translational Lung Cancer Research, 2016, 5, pp. 505-510.

Mao et al., "Capture-Based Targeted Ultradeep Sequencing in Paired Tissue and Plasma Samples Demonstrates Differential Subclonal ctDNA-Releasing Capability in Advanced Lung Cancer," Journal of Thoracic Oncology: Official Publication of the International Association for the Study of Lung Cancer, 2017, 12, 663-672.

Marshall et al., "Screening for lung cancer with low-dose computed tomography: a review of current status," Journal of Thoracic Disease, 2013, 5 Suppl 5, pp. S524-539.

Martincorena et al., "Universal Patterns of Selection in Cancer and Somatic Tissues", Cell, 171(5):1029-1041.e21, 2017.

Morales et al., "Review of Poly (ADP-ribose) Polymerase (PARP) Mechanisms of Action and Rationale for Targeting in Cancer and Other Diseases", Crit Rev Eukaryot Gene Expr., 24(1):15-28, 2014.

Need et al., "A Genome-Wide Investigation of SNPs and CNVs in Schizophrenia", PLoS Genet., 5(2):e1000373, 2009.

Newman et al., "An ultrasensitive method for quantitating circulating tumor DNA with broad patient coverage," Nature Medicine, 2014, 20, pp. 548-554.

Newman et al., "Integrated digital error suppression for improved detection of circulating tumor DNA," Nature Biotechnology, May 2016, vol. 34, No. 5, 547-560.

Ngeow et al., "Precision medicine in heritable cancer: when somatic tumour testing and germline mutations meet", npj Genomic Medicine, 1(15006):1-3, 2016.

O'Fallon et al., "A support vector machine for identification of single-nucleotide polymorphisms from next-generation sequencing data," Bioinformatics, vol. 29, No. 11, 2013, pp. 1361-1366.

Pirooznia et al., "Whole-genome CNV analysis: advances in computational approaches", Front Genet., 6(138), 9 pages, 2015.

Poplin et al., "Creating a universal SNP and small indel variant caller with deep neural networks", bioRxiv, pp. 092890, 2016.

Ravdin et al., "Survey of breast cancer patients concerning their knowledge and expectations of adjuvant therapy", J Clin Oncol., 16(2):515-521, 1998.

Roberts et al., "An APOBEC Cytidine Deaminase Mutagenesis Pattern is Widespread in Human Cancers", Nat Genet., 45(9):970-976, 2013.

Rosell et al., "The biology of non-small-cell lung cancer: identifying new targets for rational therapy", Lung Cancer, 46(2):135-148, 2004.

Rosenfeld et al., "Estimates of penetrance for recurrent pathogenic copy-number variations", Genet Med., 15(6):478-481, 2013.

Sasco et al., "Tobacco smoking and cancer: a brief review of recent epidemiological evidence", Lung Cancer, 45(Suppl 2):S3-9, 2004.

Saunders et al., "Strelka: accurate somatic small-variant calling from sequenced tumor-normal sample pairs", Bioinformatics, 28(14):1811-1817, 2012.

Sebat et al., "Large-Scale Copy Number Polymorphism in the Human Genome", Science, 305(5683):525-528, 2004.

Simes et al., "Patient Preferences for Adjuvant Chemotherapy of Early Breast Cancer: How Much Benefit Is Needed?", J Natl Cancer Inst Monogr., 30:146-152, 2001.

Simonyan et al., "Very Deep Convolutional Networks for Large-Scale Image Recognition", arXiv:1409.1556, revised Apr. 10, 2015.

Snyder et al., "Cell-free DNA Comprises an In Vivo Nucleosome Footprint that Informs Its Tissues-of-Origin," Cell, 2016, 164, pp. 57-68.

Soo et al., "Comparison of Circulating Tumor DNA Recovery from Plasma and Serum," Blood 130 (Suppl. 1): 2756, Dec. 7, 2017, 4 pages.

Sozzi et al., "Quantification of Free Circulating DNA as a Diagnostic Marker in Lung Cancer", Journal of Clinical Oncology, 21(21):3902-3908, 2003.

Spinella et al., "SNooPer: a machine learning-based method for somatic variant identification from low-pass next-generation sequencing", BMC Genomics, 17(912), 11 pages, 2016.

Thompson et al., "Detection of Therapeutically Targetable Driver and Resistance Mutations in Lung Cancer Patients by Next-Generation Sequencing of Cell-Free Circulating Tumor DNA," Clinical Cancer Research: An Official Journal of the American Association for Cancer Research, 22, pp. 5772-5782.

Tie et al., "Circulating tumor DNA analysis detects minimal residual disease and predicts recurrence in patients with stage II colon cancer", Science translational medicine, 8(346):346ra92, 21 pages, 2016.

Torracinta et al., "Training Genotype Callers with Neural Networks", bioRxiv, pp. 097469, 2016.

Vilar et al., "Microsatellite instability in colorectal cancer-the stable evidence", Nat Rev Clin Oncol., 7(3):153-62, 2010.

Wang et al., "PennCNV: An integrated hidden Markov model designed for high-resolution copy number variation detection in whole-genome SNP genotyping data", Genome Res., 17(11):1665-1674, 2007.

Wang et al., "Potential Clinical Significance of a Plasma-Based KRAS Mutation Analysis in Patients with Advanced Non-Small Cell Lung Cancer", Clinical Cancer Research, 16(4):1324-1330, 2010.

Welch et al., "The Origin and Evolution of Mutations in Acute Myeloid Leukemia", Cell, 150(2):264-278, 2012.

Wilm et al., "LoFreq: a sequence-quality aware, ultra-sensitive variant caller for uncovering cell-population heterogeneity from high-throughput sequencing datasets", Nucleic acids research, 40(22):11189-11201, 2012.

(56)  References Cited

OTHER PUBLICATIONS

Wouters et al., "Trade-off preferences regarding adjuvant endocrine therapy among women with estrogen receptor-positive breast cancer", Ann Oncol., 24(9):2324-9, 2013.

Wu et al., "Estimating error models for whole genome sequencing using mixtures of Dirichlet-multinomial distributions", Bioinformatics, 33(15):2322-2329, 2017.

Yatabe et al., "Do all lung adenocarcinomas follow a stepwise progression?" Lung Cancer, 2011, 74, pp. 7-11.

Penault-Llorca et al., "Biomarkers of residual disease after neoadjuvant therapy for breast cancer," Nature Reviews Clinical Oncology, 2016, 13, pp. 487-503.

Stumm et al., Diagnostic accuracy of random massively parallel sequencing for non-invasive prenatal detection of common autosomal aneuploidies: a collaborative study in Europe, 2014, Prenatal Diagnosis, 34, p. 185-191.

Talevich et al., "CNVkit: Genome-Wide-Copy Number Detection and Visualization from Targeted DNA Sequencing," PLOS Computation Biology, 2016, pp. 1-18.

* cited by examiner

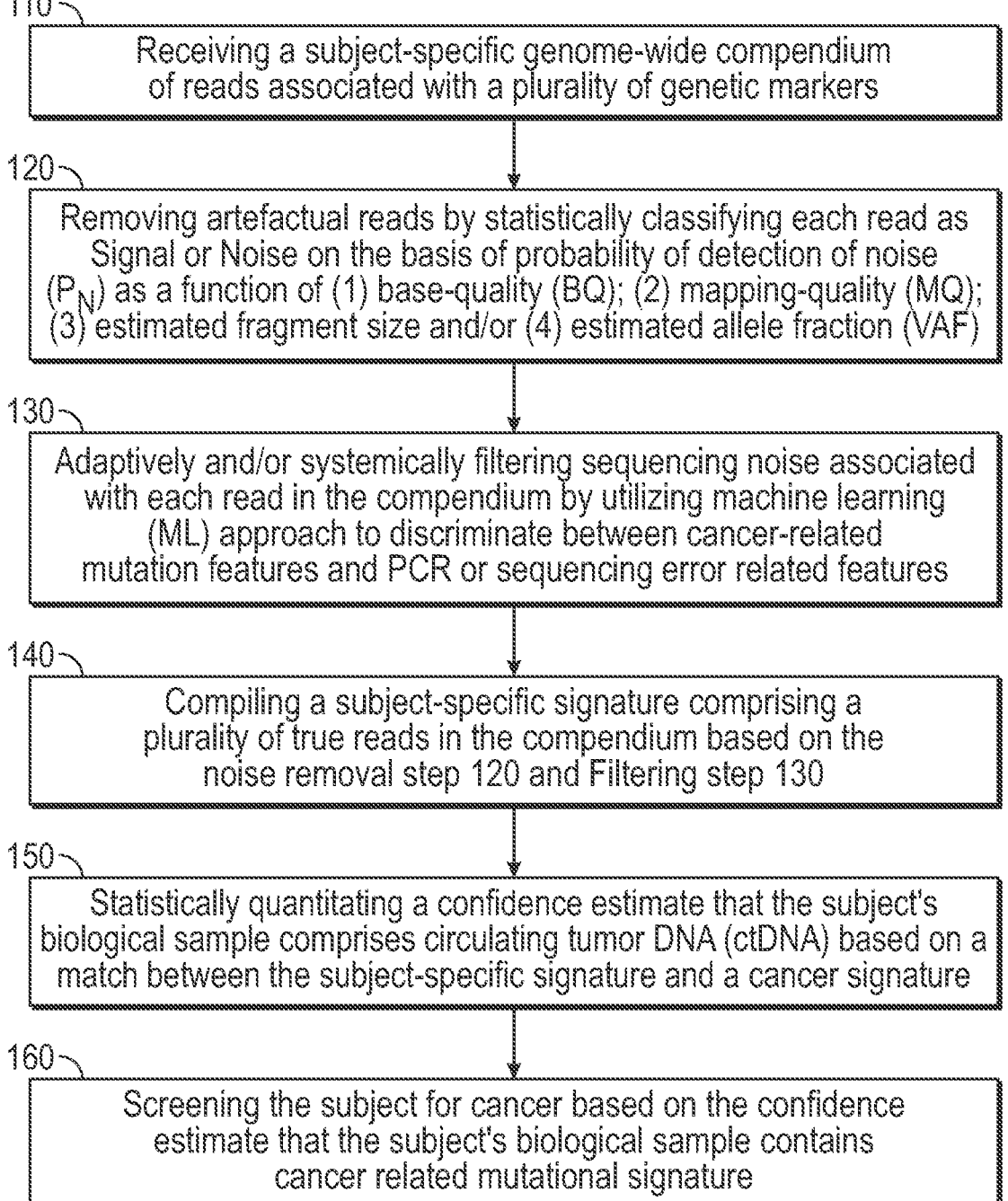

110 — Receiving a subject-specific genome-wide compendium of reads associated with a plurality of genetic markers 120 — Removing artefactual reads by statistically classifying each read as Signal or Noise on the basis of probability of detection of noise ($P_N$) as a function of (1) base-quality (BQ); (2) mapping-quality (MQ); (3) estimated fragment size and/or (4) estimated allele fraction (VAF)

130 — Adaptively and/or systemically filtering sequencing noise associated with each read in the compendium by utilizing machine learning (ML) approach to discriminate between cancer-related mutation features and PCR or sequencing error related features 140 — Compiling a subject-specific signature comprising a plurality of true reads in the compendium based on the noise removal step 120 and Filtering step 130

150 — Statistically quantitating a confidence estimate that the subject's biological sample comprises circulating tumor DNA (ctDNA) based on a match between the subject-specific signature and a cancer signature 160 — Screening the subject for cancer based on the confidence estimate that the subject's biological sample contains cancer related mutational signature

FIG. 1A

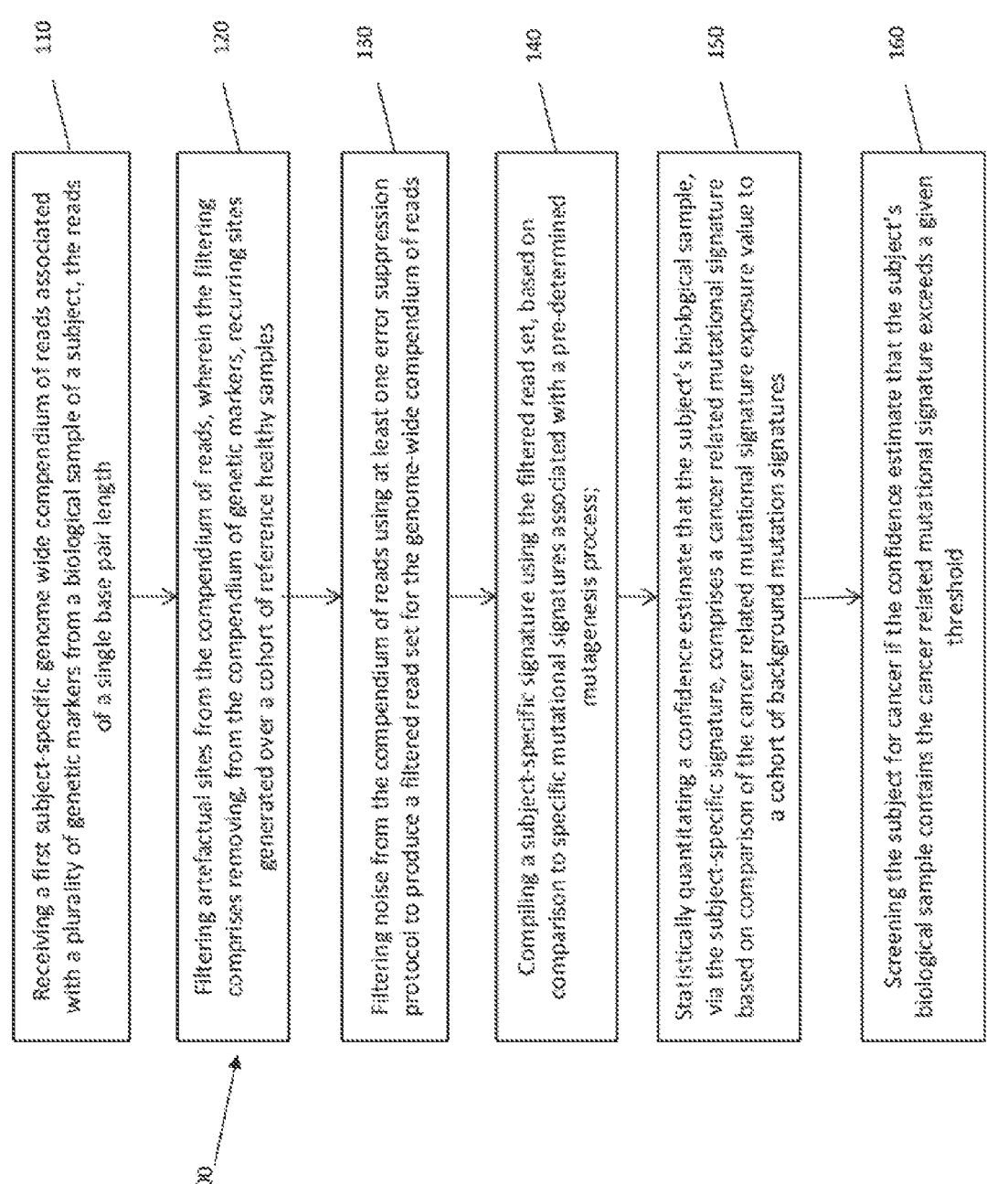

110 — Receiving a first subject-specific genome wide compendium of reads associated with a plurality of genetic markers from a biological sample of a subject, the reads of a single base pair length 120 — Filtering artefactual sites from the compendium of reads, wherein the filtering comprises removing, from the compendium of genetic markers, recurring sites generated over a cohort of reference healthy samples 130 — Filtering noise from the compendium of reads using at least one error suppression protocol to produce a filtered read set for the genome-wide compendium of reads 140 — Compiling a subject-specific signature using the filtered read set, based on comparison to specific mutational signatures associated with a pre-determined mutagenesis process;

150 — Statistically quantitating a confidence estimate that the subject's biological sample, via the subject-specific signature, comprises a cancer related mutational signature based on comparison of the cancer related mutational signature exposure value to a cohort of background mutation signatures 160 — Screening the subject for cancer if the confidence estimate that the subject's biological sample contains the cancer related mutational signature exceeds a given threshold

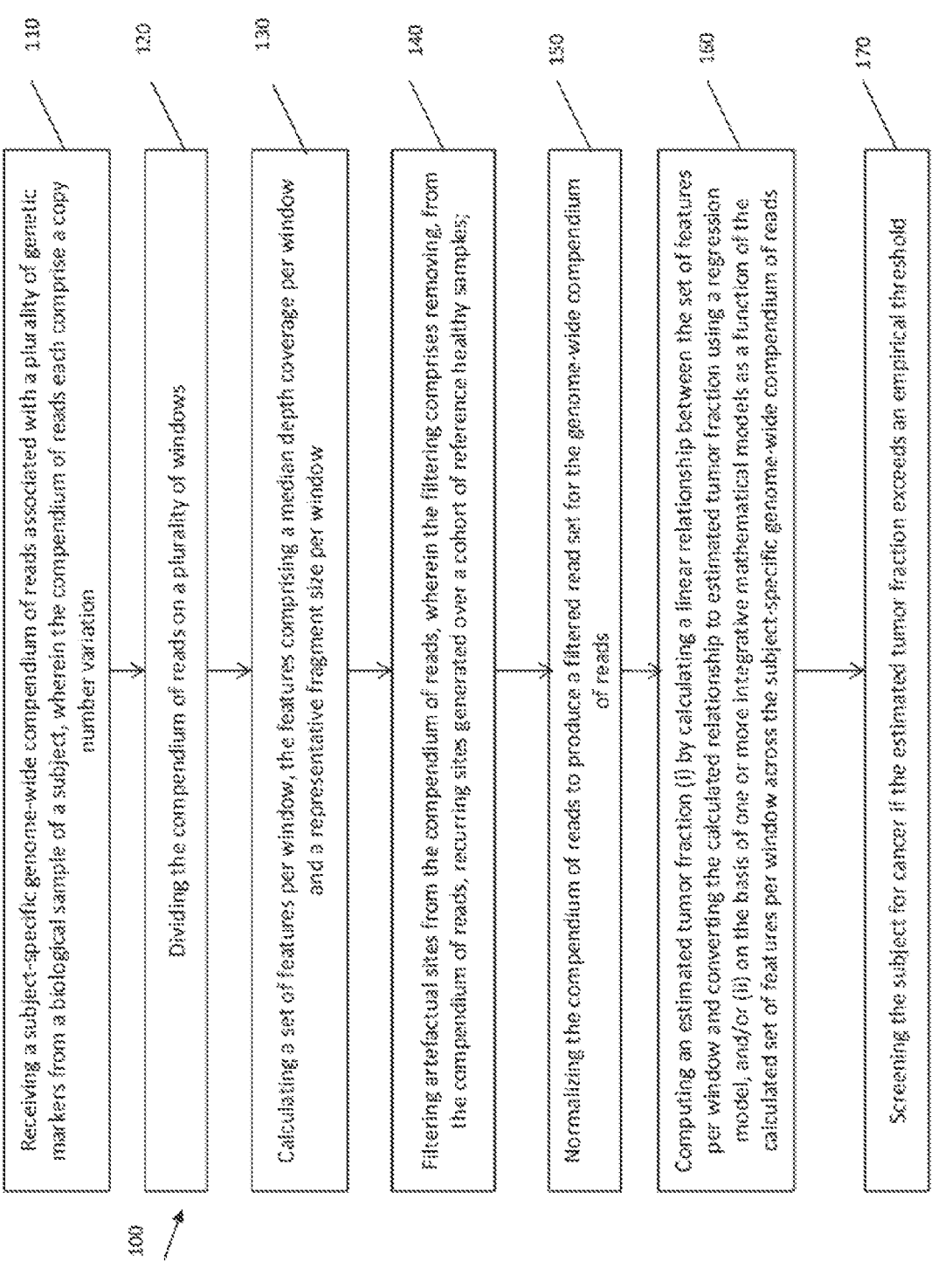

110

Receiving a subject-specific genome-wide compendium of reads associated with a plurality of genetic markers from a biological sample of a subject, wherein the compendium of reads each comprise a copy number variation

120

Dividing the compendium of reads on a plurality of windows

130

Calculating a set of features per window, the features comprising a median depth coverage per window and a representative fragment size per window

140

Filtering artefactual sites from the compendium of reads, wherein the filtering comprises removing, from the compendium of reads, recurring sites generated over a cohort of reference healthy samples;

150

Normalizing the compendium of reads to produce a filtered read set for the genome-wide compendium of reads

160

Computing an estimated tumor fraction (j) by calculating a linear relationship between the set of features per window and converting the calculated relationship to estimated tumor fraction using a regression model, and/or (ii) on the basis of one or more integrative mathematical models as a function of the calculated set of features per window across the subject-specific genome-wide compendium of reads

170

Screening the subject for cancer if the estimated tumor fraction exceeds an empirical threshold

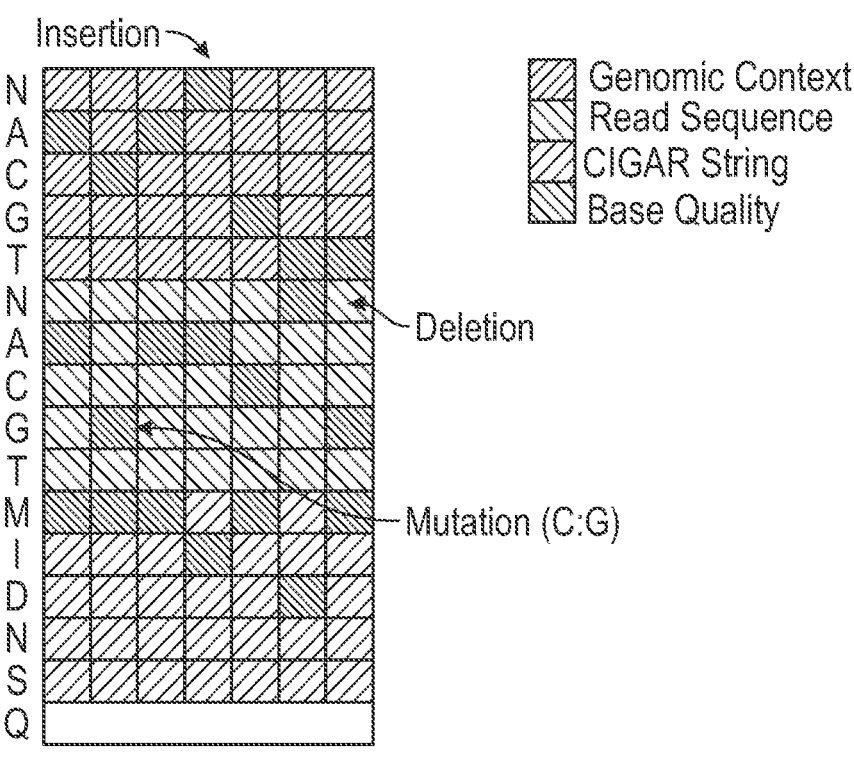
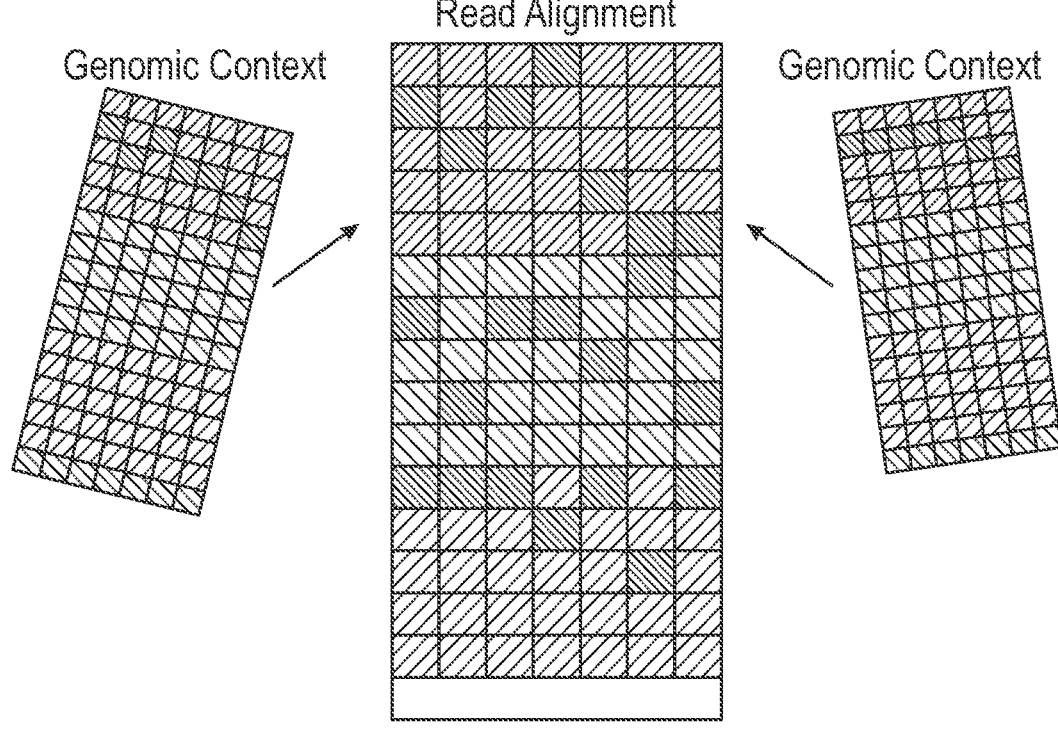
FIG. 6

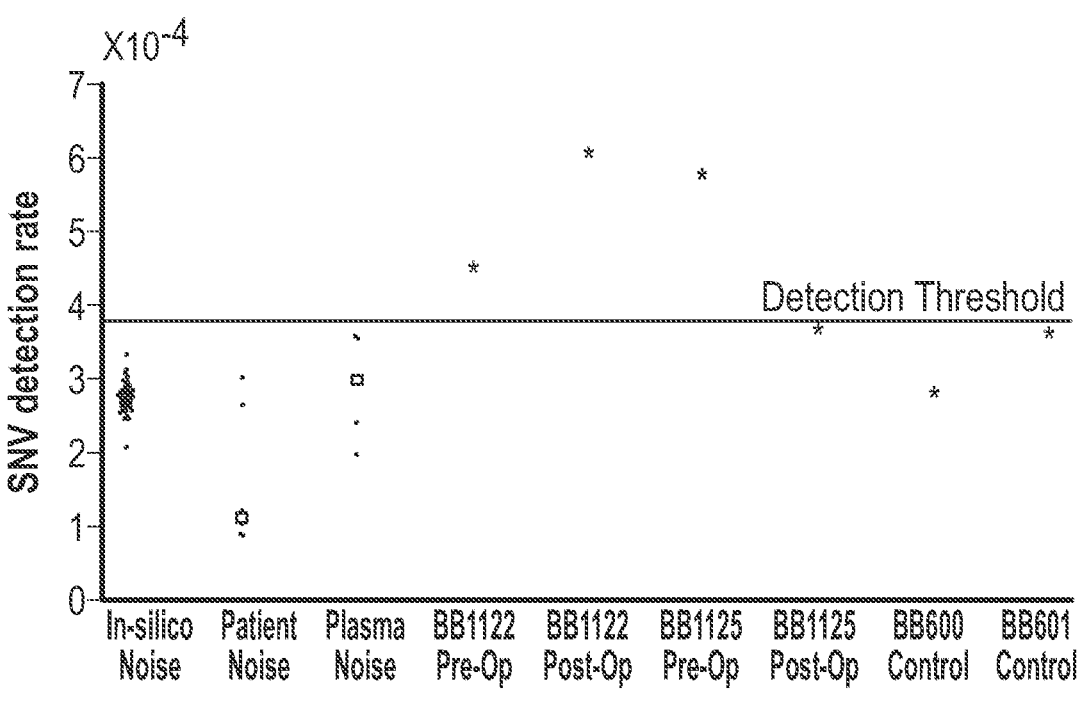

FIG. 10

| Histology | Age | Sex | Ethnicity | Smoker | Cigarette Pack Years | Cancer Stage | Tumor Size (cm) | Comments | Days between blood samples |
|---|---|---|---|---|---|---|---|---|---|
| Adenocarcinoma | 72 | F | Unknown | Former | 14 | IA | 2.6 | | 11 |
| Adenocarcinoma | 69 | M | White | Former | 38 | IIA | 2.1 | | 22 |
| Adenocarcinoma | 87 | F | Unknown | Former | 15 | IIIA | 4.4 | | 10 |
| Adenocarcinoma | 79 | M | White | Former | 30 | IIA | 2.3 | | 16 |
| Adenocarcinoma | 73 | F | | Never | 0 | IA | 3 | | 90 |
| Benign process | 75 | M | Unknown | Current | 50 | NA | NA | COPD | |
| Benign process | 70 | F | Unknown | Former | 20 | NA | NA | Bronchiectasis | |
| Benign process | 64 | M | Unknown | Former | 30 | NA | NA | ILD. | |

FIG. 11

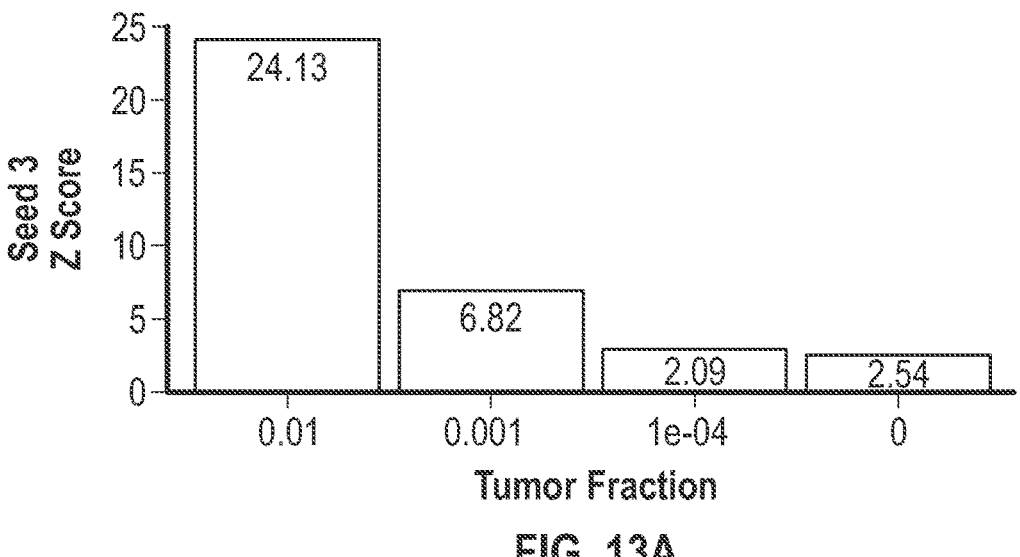
FIG. 13A
FIG. 13B
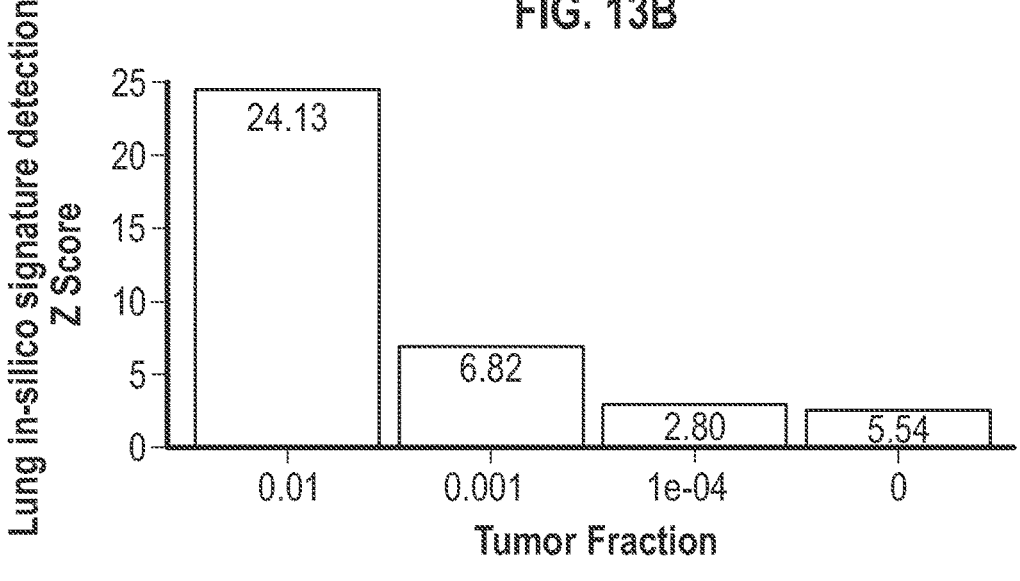
FIG. 13C

ULTRA-SENSITIVE DETECTION OF CIRCULATING TUMOR DNA THROUGH GENOME-WIDE INTEGRATION

CROSS-REFERENCE TO RELATED APPLICATION

The present application is a U.S. National Stage patent application of International Patent Application No. PCT/US2019/019905, filed on Feb. 27, 2019, which claims the benefit of U.S. Prov. No. 62/636,135, filed on Feb. 27, 2018, the benefit of which is claimed and the disclosures of which are incorporated herein by reference in their entireties.

TECHNICAL FIELD

Embodiments of the disclosure generally relate to the field of medical diagnostics. In particular, embodiments of the disclosure relate to compositions, methods, and systems for tumor detection and diagnosis.

BACKGROUND

The tremendous burden imposed by cancers such as solid tumors of lung, breast, prostate, liver, and brain, on human health is well-documented in medical literature. Most subjects are diagnosed with advanced tumor disease, which are associated with dismal outcome. Recently, computed tomography (CT) was found to improve early detection and was adopted for screening high-risk populations by the US Task Force. Nevertheless, this approach is limited by high false positive rate, leading to costly and potentially risky follow-up evaluation.

One approach used in cancer diagnosis is the analysis of tumor samples for genetic cues or markers. The cancer genome acquires somatic mutations which drive its proliferative capacity (Lawrence et al., *Nature*, 505(7484):495-501, 2014). Mutations in the cancer genome also provide critical information regarding the evolutionary history and mutational processes active in each cancer (Martincorena et al., *Cell*, 171(5):1029-1041.e21, 2017; Alexandrov et al., *Nature*, 500(7463):415-421, 2013). Cancer mutation calling in patient biopsies has become a pivotal step in evaluating patient outcome and therapeutic nomination. Identifying cancer driver mutations in liquid biopsy samples, such as cell-free circulating DNA (cfDNA), has been suggested as a transformative platform for early-stage cancer screening.

Statistical methods for analyzing genomic markers such as somatic mutations in DNA, e.g., single-nucleotide variants (SNVs), require multiple independent observations (supporting reads) of the somatic variant at any genomic location to distinguish true mutations from sequencing errors. One technique used in differentiating true mutations from sequencing errors is increasing depth of sequencing, which is useful as long as the tumor sample contains a high proportion of tumor cells. When the tumor cell content in the sample drops, for example due to the presence of normal cells such as immune cells in the sample, each somatic variant is no longer supported by multiple reads, precluding the use of these mutation callers. MUTECT for example is the current state-of-the-art low-allele frequency somatic mutation caller. At its core, MUTECT subjects a SNV to two Bayesian classifiers, one assumes that the SNV results from random noise and the other that the site contains a true variant. It then filters a SNV based on a log-likelihood ratio from the two models. This is fundamentally different than the cfDNA setting. In a benchmarking setting when the mutation allele frequency drops to 0.05 and the tumor sample sequencing depth goes down to 10×, MUTECT's sensitivity decreases to below 0.1 (Cibulskis et al., *Nature Biotechnology*, 31(3), 213, 2013). While MUTECT is currently the state-of-the art somatic mutation caller in low-frequency settings, it is still unable to identify somatic mutations in tumor fractions like those observed in cfDNA.

A fundamental limitation of MUTECT and other mutation callers is the below-acceptable level of clinical sensitivity when input material is limited (such as in the early cancer disease setting). Such low amount of cfDNA translates into only hundreds to few thousands of genomic equivalents. Thus, ultra-deep sequencing (e.g., 100,000×) may be rendered ineffective by the limited number of physical fragments that cover each site that are present in the sample (e.g., 1000 genomic equivalents in 6 ng of cfDNA). Even with ultra-deep sequencing and advanced molecular error suppression, the limited input material imposes a detection limit on tumor fraction (TF) frequencies lower than 0.1-1%.

This limitation was exemplified by Abbosh et al. (Nature, 545(7655):446-451, 2017), which applied advanced sequencing methods, including technically-challenging lung adenocarcinoma patient-specific targeted deep sequencing, to identify about 18 mutations at a median sequencing depth of 42,000×. However, cfDNA scarcity likely led to cancer detection in cfDNA of only 19% of early subjects, even with the inclusion of more advanced stage III tumors in the study group. Moreover, all of these positively-identified patients had lesions detectable by CT scanning. These data demonstrate that in early disease context, even ultra-deep sequencing currently underperforms imaging technology with regard to inclusivity and/or precision.

There is a need for improved methods and systems for identifying low abundance disease markers such as somatic mutations in cfDNA (including distinct subject-specific signatures), which are indicative of tumor disease. Additionally, there is a need for systems and methods that utilize such high quality markers that may be used in the early diagnosis of tumors, thereby arming clinicians with better options for disease management and/or therapeutic intervention and also greatly improving outcome of disease (e.g., improved survival and/or quality of life).

SUMMARY

Provided herein are programs, systems, and methods for screening subjects for cancer and using the information obtained from the screening for early detection and disease stratification. In some embodiments, the programs, systems and methods of the disclosure allows a user, e.g., a clinician, to diagnose cancer early.

In some aspects, the present disclosure provides for a classifier that is trained to discriminate between systemic errors and somatic mutations caused by cancer, e.g., tobacco induced lung cancer. Taking advantage of the fact that both cancer mutations and sequencing errors are systemic and governed by distinct signatures that can be learned and used for efficient signal to noise discrimination, the classifier integrates such knowledge to improve accuracy of diagnosis and/or detection of cancer. For instance, in the genomic context, the cancer signature may comprise base substitutions giving rise to cancer associated mutagenesis. Such genomic signatures are especially unique in cancers caused by exposure to tobacco and UV light, including, cancers that are associated with deregulated DNA checkpoint and/or repair enzyme activity, e.g., BRCA (BRCA1 or BRCA2), p53, APOBEC1, etc.

The disclosure also relates to a plurality of indicators that are capable of suggesting that a variant detected via sequencing is not a true somatic mutation but rather an artifact of sequencing or mapping technology. In this context, previous studies have demonstrated that sequencing errors are not random and are likely related to both DNA sequence context and technical factors consequential of the sequencing technologies. The fidelity of sequencing is also limited by the length of each sequencing-read, with an increase in error rate as the read length increases. Errors may be imposed when reads are mapped to a reference genome. The mapping process is computationally intensive and complicated by the fact that the genome has variable regions, motifs, and repeatable elements. Short nucleotide reads may map to more than one location or not map at all. These limitations with the existing methodologies for sequencing/mapping genomic data may be rectified using the systems and methods of the disclosure. The indicators of the disclosure are capable of calling true mutations from errors by analyzing a plurality of factors such as (i) low base quality; (ii) low mapping quality; (iii) estimated fragment size of the read (RP); (iv) estimated allele fraction of the read (VAF); (v) sequence context; (vi) abundance; (vii) sequencing depth; and/or (viii) sequencing error.

The present systems and methods are especially adapted to detection of low abundance markers which are predictive of cancer. The inventors of the present disclosure have recognized that sequencing breadth, which is not limited by the abundance of input material, can supplant methods that rely on depth sequencing. As breadth sequencing is less dependent on the abundance of input material, it can be used to improve both accuracy and sensitivity of detection. From a statistical perspective, the inventors first demonstrated that sequencing breadth (e.g., 10× sequencing of 10,000 mutations) is equivalent to depth (100,000× sequencing of a single mutation), and can be performed on as little as 1 ng of cfDNA. Thus, the analytic approach of the present disclosure integrates genome-wide mutational information for sensitive analysis of samples containing cfDNA for detection and/or precise diagnosis of tumors (e.g., tobacco induced cancer) easily and non-invasively.

In this context, simulated testing of plasma somatic mutation calling using synthetic mixtures of tumor and normal whole genome-sequencing data from lung patients with variable fraction of tumor reads ranging from 1% to 0.001% (1/10,000) reveals the strength and accuracy of the present methods over existing techniques. The performance of the instant technique was further benchmarked by first characterizing the patient-specific somatic cancer SNVs using standard mutation calling on the patient's pure tumor and normal samples; and then detecting cancer mutations in the plasma samples using several methods, including convolutional networks of the present disclosure. The sensitivity and precision of each method using pure tumor mutation calling as a reference demonstrates high signal and/or low noise for the analytical methods of the instant disclosure. Finally, validation studies performed with actual cfDNA samples from patients with early stage lung cancer demonstrates significantly superior sensitivity and precision when compared to current state-of-the art methods.

The disclosure relates to the following non-limiting embodiments:

In accordance with various embodiments, a method for genetic screening a subject for cancer is provided. The method comprises receiving a subject-specific genome-wide compendium of reads associated with a plurality of genetic markers from a biological sample of a subject. The biological sample can comprise a tumor sample. The compendium of reads can each comprise reads of a single base pair length. The method can further comprise filtering artefactual sites from the compendium of reads. The filtering can comprise removing, from the compendium of reads, recurring sites generated over a cohort of reference healthy samples. Alternatively, or in combination, the filtering can comprise identifying germ line mutations in the biological sample and/or identifying shared mutations between the tumor sample and peripheral blood mononuclear cells of the normal cell sample as germ line mutations, and removing said germ line mutations from the compendium of reads. The method can further comprise filtering noise from genome-wide compendium of reads using at least one error suppression protocol to produce a filtered read set for the genome-wide compendium of reads. The at least one error suppression protocol can comprise calculating the probability that any single nucleotide variation in the compendium is an artefactual mutation, and removing said mutation. The probability can be calculated as a function of features selected from the group comprising mapping-quality (MQ), variant base-quality (MBQ), position-in-read (PIR), mean read base quality (MRBQ), and combinations thereof.

Alternatively, or in combination, the at least one error suppression protocol can comprise removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family. The method can comprise compiling a subject-specific signature using the filtered read set, based on comparison to specific mutational signatures associated with a pre-determined mutagenesis process. The method can further comprise statistically quantitating a confidence estimate that the subject's biological sample, via the subject-specific signature, comprises a cancer related mutational signature based on comparison of the cancer related mutational signature exposure value to a cohort of background mutation signatures. The method can comprise screening the subject for cancer if the confidence estimate that the subject's biological sample contains the cancer related mutational signature exceeds a given threshold.

In accordance with various embodiments, a method for genetic screening a subject for cancer is provided. The method comprises receiving a subject-specific genome-wide compendium of reads associated with a plurality of genetic markers from a biological sample of a subject. The biological sample can comprise a tumor sample. The compendium of reads can each comprise a copy number variation (CNV). The method can comprise dividing the compendium of reads into a plurality of windows. The method can comprise calculating a set of features per window. The features can comprise a median depth coverage per window and a representative fragment size per window. The method can comprise filtering artefactual sites from the compendium of reads. The filtering can comprise removing, from the compendium of reads, recurring sites generated over a cohort of reference healthy samples. The method can comprise normalizing the compendium of reads to produce a filtered read set for the genome-wide compendium of reads. The method can comprise computing an estimated tumor fraction using the filtered read set by calculating a linear relationship between the set of features per window and converting the calculated relationship to estimated tumor fraction using a regression model. Alternatively, or in combination, the method can comprise computing an estimated tumor fraction on the basis of one or more integrative mathematical models as a function of the calculated set of features per window across the subject-specific genome-wide compendium of reads. The method can comprise screening the subject for cancer if the estimated tumor fraction exceeds an empirical threshold.

In accordance with various embodiments, a system for genetic screening a subject for cancer is provided. The system comprises an analyzing unit, the analyzing unit comprising a pre-filter engine configured and arranged to receive a subject-specific genome-wide compendium of reads associated with a plurality of genetic markers from a biological sample of a subject, the biological sample comprising a tumor sample, wherein the compendium of reads each comprise reads of a single base pair length. The pre-filter engine can be configured and arranged to filter artefactual sites from the compendium of reads, wherein the filtering comprises removing, from the compendium of reads, recurring sites generated over a cohort of reference healthy samples. The pre-filter engine can be configured and arranged to also, or in combination, identify germ line mutations in the biological sample and/or identifying shared mutations between the tumor sample and peripheral blood mononuclear cells of the normal cell sample as germ line mutations, and remove said germ line mutations from the compendium of reads. The analyzing unit can comprise a correction engine configured and arranged to filter noise from the compendium of reads using at least one error suppression protocol to produce a filtered read set for the genome-wide compendium of reads. The at least one error suppression protocol can comprise calculating the probability that any single nucleotide variation in the compendium is an artefactual mutation, and removing said mutation, wherein the probability is calculated as a function of features selected from the group comprising mapping-quality (MQ), variant base-quality (MBQ), position-in-read (PIR), mean read base quality (MRBQ), and combinations thereof. The at least one error suppression protocol can also, or in combination, comprise removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family. The system can comprise a computing unit configured and arranged to compile a subject-specific signature using the filtered read set, based on comparison to specific mutational signatures associated with a pre-determined mutagenesis process. The computing unit can be configured and arranged to statistically quantitate a confidence estimate that the subject's biological sample, via the subject-specific signature, comprises a cancer related mutational signature based on comparison of the cancer related mutational signature exposure value to a cohort of background mutation signatures. The computing unit can be configured and arranged to screen the subject for cancer if the confidence estimate that the subject's biological sample contains the cancer related mutational signature exceeds a given threshold.

In accordance with various embodiments, a system for genetic screening a subject for cancer is provided. The system comprises an analyzing unit, the analyzing unit comprising a binning engine configured and arranged to receive a subject-specific genome-wide compendium of reads associated with a plurality of genetic markers from a biological sample of a subject, the biological sample comprising a tumor sample, wherein the compendium of reads each comprise a copy number variation (CNV). The binning engine can be configured and arranged to divide the compendium of reads into a plurality of windows. The binning engine can be configured and arranged to calculate a set of features per window, the features comprising a median depth coverage per window and a representative fragment size per window. The system can comprise a pre-filter engine configured and arranged to filter artefactual sites from the compendium of reads, wherein the filtering comprises removing, from the compendium of reads, recurring sites generated over a cohort of reference healthy samples. The system can comprise a normalization engine configured and arranged to normalize the compendium of reads to produce a filtered read set for the genome-wide compendium of reads. The system can comprise a computing unit configured and arranged to compute an estimated tumor fraction (eTF) using the filtered read set. The computing unit can compute the eTF by calculating a linear relationship between the set of features per window and converting the calculated relationship to estimated tumor fraction using a regression model. Alternatively, or in combination, the computing unit can compute the eTF by on the basis of one or more integrative mathematical models as a function of the calculated set of features per window across the subject-specific genome-wide compendium of reads. The computing unit can be configured and arranged to screen the subject for cancer if the estimated tumor fraction exceeds an empirical threshold.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature.

In some embodiments of the present methods, the subject's biological sample comprises plasma, cerebral spinal fluid, pleural fluid, ocular fluid, stool, urine, or a combination thereof.

In some embodiments of the present methods, the cancer signature comprises COSMIC tobacco signature, UV signature, Breast Cancer (BRCA) signature, microsatellite instability (MSI) signature, apolipoprotein B mRNA editing enzyme, poly (ADP-ribose) polymerase (PARP) hyperactivity signature, catalytic polypeptide-like (APOBEC) signature. Particularly, in some embodiments, the cancer signature comprises pattern associated with tissue specific epigenetic pattern, such as tissue specific chromatin accessibility pattern.

In some embodiments of the present methods, the sequencing noise associated with each read in the compendium is filtered by utilizing a machine learning (ML) approach to discriminate between cancer related mutation features (true-positive) and PCR or sequencing error related features (false-positive). In some embodiments, the machine learning method comprises deep convolutional neural network (CNN), recurrent neural network (RNN), random forest (RF), support vector machine (SVM), discriminant analysis, nearest neighbor analysis (KNN), ensemble classifier, or a combination thereof. In some embodiments, the ML has been trained to distinguish between cancer altered sequencing reads and reads altered by sequencing or PCR errors. In some embodiments, the ML has been trained on a large whole-genome sequenced (WGS) cancer dataset comprising billions of reads across tumor mutations and normal sequencing errors. In some embodiments, the ML is capable of (a) identifying, with high precision, sequencing or PCR artifacts and (b) integrating sequence context and read specific features.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach comprising implementing an optimal receiver operating characteristic (ROC) curve which comprises a probabilistic classification of the genetic markers in the compendium based on a joint base-quality (BQ), mapping-quality (MQ) score and fragment size; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature.

In some embodiments of the present methods, the tumor is a tumor includes heterogeneous or homogenous brain cancer, lung cancer, skin cancer, nose cancer, throat cancer, liver cancer, bone cancer, lymphomas, pancreatic cancer, skin cancer, bowel cancer, rectal cancer, thyroid cancer, bladder cancer, kidney cancer, mouth cancer, stomach cancer, solid state tumor, non-small-cell lung carcinoma (NSCLC), tobacco-induced cancer (TIC), UV light-induced cancer, a cancer mediated by apolipoprotein B mRNA editing enzyme catalytic protein (APOBEC) activity, a cancer comprising breast cancer protein (BRCA) mutation, a cancer comprising poly (ADP-ribose) polymerase (PARP) activity, and a tumor comprising micro-satellite instability (MSI). In some embodiments of the present methods, the screening method permits diagnosis of early cancer disease in an undiagnosed and or asymptomatic patient. Particularly, the subject is a patient with early stage cancer which is in stage I to III.

In some embodiments, the disclosure relates to a method for genetic screening a subject for cancer and nominating a therapy, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; (f) screening the subject for cancer based on the confidence estimate that the subject's biological sample contains cancer related mutational signature; and (g) nominating a signature-based therapy based on the patient specific signature employed in the diagnosis. In some embodiments, the treatment nomination comprises PARP-inhibitor for BRCA signature, immunotherapy for MSI signature. In some embodiments, the PARP inhibitor is PARP inhibitor is niraparib, olaparib, veliparib, rucaparib and/or talazoparib. In some embodiments, immunotherapy for MSI signature comprises anti-PD-1 antibody (e.g., nivolumab or pembrolizumab) or anti-CTLA4 antibody (e.g., nivolumab or pembrolizumab). In some embodiments, the tumor includes heterogeneous or homogenous brain cancer, lung cancer, skin cancer, nose cancer, throat cancer, liver cancer, bone cancer, lymphomas, pancreatic cancer, skin cancer, bowel cancer, rectal cancer, thyroid cancer, bladder cancer, kidney cancer, mouth cancer, stomach cancer, solid state tumor, lung adenocarcinoma, ductal adenocarcinoma (breast tumor), non-small-cell lung carcinoma lung adenocarcinoma (NSCLC LUAD), cutaneous melanoma, urothelial carcinoma (bladder tumor), colorectal cancer (Lynch), or osteosarcoma.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1)

base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature, wherein step (f) comprises solving the linear optimization problem—$\min\|Ax-b\|$, $x \geq 0$, where A is the mutational signature sequence context matrix, x is the contribution of each cosmic mutational signature (the variable) and b is the patient specific sequence context compendium. In some embodiments, the optimization problem is solved by Non-Negative Least square method (NNLS), Cross-Entropy global optimization method, Golden-section search method, or a combination thereof. In some embodiments, the method further comprises validating for confidence using a comparison of a cancer mutation signature to a plurality of random background signatures, e.g., using a comparison of a cancer mutation signature to a plurality of random background signatures. In some embodiments, the comparison step comprises assessment of a zscore, wherein a zscore above a threshold value indicates that the subject-specific signature is specific to the cancer signature and not associated with random signature.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature, wherein step (b) comprises (1) removing low mapping quality reads (e.g., <29, ROC optimized); building duplication families (representing multiple PCR/sequencing copies of the same DNA fragment) and producing corrected read based on a consensus test; (3) removing low base quality reads (e.g., <21, ROC optimized); and/or (4) removing high fragment size reads (e.g., >160, ROC optimized) and step (f) comprises calculating sequence context similarity between the patient sequence-context compendium to a specific cosmic sequence-context compendium.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature, wherein step (f) comprises estimating the similarity between the subject-specific signature and a cancer signature based on cosine-similarity, correlation, mutual-information, or a combination thereof. In some embodiments, the method further comprises validating for confidence using a comparison of a cancer mutation signature to a plurality of random background signatures, e.g., using a comparison of a cancer mutation signature to a plurality of random background signatures. In some embodiments, the comparison step comprises assessment of a zscore, wherein a zscore above a threshold value indicates that the subject-specific signature is specific to the cancer signature and not associated with random background signature.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature, wherein step (f) comprises comparing the cancer specific signature confidence (zscore) to an empirical threshold calculated by background noise model. In some embodiments, the empirical noise model is defined by measuring the cancer specific signature confidence (zscore) in normal healthy samples and translated to basal noisy zscore estimation, where zscore estimation noise threshold is between 1 to 5.

In some embodiments of the foregoing cancer screening/diagnostic methods, the subject-specific signature is matched with a cancer-specific mutation signature comprising markers that are differentially expressed in tumors but not in normal samples. In some embodiments, the tumor sample comprises lung tumor, breast tumor, melanoma, bladder tumor, colorectal tumor, or bone tumor.

In some embodiments of the foregoing cancer screening/diagnostic methods, the method permits early detection in at least 50% of the subjects.

In some embodiments of the foregoing cancer screening/diagnostic methods, the method comprises further implementing computer tomography (CT) screening, wherein the CT screening step is carried out prior to, concurrently with, or subsequently after the genetic screening. In some embodiments, the cancer is a solid tumor and the CT screening comprises detection of suspicious nodules, e.g., in a patient with a benign lesion. In some embodiments, the benign lesion is identified via advanced CT screening, histopathology, and/or biopsy.

In some embodiments of the foregoing cancer screening/diagnostic methods, the method comprises discriminating between malignant and benign nodules which increases the positive predictive value (PPV) of CT screening, e.g., by at least 30%, at least 40%, at least 50, at least 60%, at least 80%, or at least 90%.

In some embodiments of the foregoing cancer screening/diagnostic methods, the method comprises early detection (ED) of a malignant tumor.

In some embodiments, the disclosure relates to a method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a match between the subject-specific signature and a cancer signature; and (f) screening the subject for cancer based on the confidence estimate that the subject's biological sample contains cancer related mutational signature, wherein step (a) comprises aggregating genome-wide mutation data by whole genome sequencing and step (c) comprises detecting mutational signature using a mathematical optimizing step. In some embodiments, the mathematical optimizing step comprises employing non-negative least square.

In some embodiments, the disclosure relates to methods for detecting a pre-malignant tumor signature in a subject comprising (a) generating a subject-specific genome-wide compendium of reads associated with a plurality of genetic markers from a biological sample of a subject, wherein the compendium of genetic markers is selected from the group consisting of single nucleotide variation (SNV), short insertions and deletions (Indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; and/or (3) estimated fragment size of the read (4) allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and optional filtering step (b); (e) statistically quantitating a confidence estimate that the subject's biological sample comprises circulating tumor DNA (ctDNA) based on a match between the subject-specific signature and a cancer signature; and (f) detecting a pre-malignant tumor signature based on the confidence estimate that the subject's biological sample contains cancer related mutational signature. In some embodiments, the pre-malignant tumor includes heterogeneous or homogenous brain cancer, lung cancer, skin cancer, nose cancer, throat cancer, liver cancer, bone cancer, lymphomas, pancreatic cancer, skin cancer, bowel cancer, rectal cancer, thyroid cancer, bladder cancer, kidney cancer, mouth cancer, stomach cancer, solid state tumor, lung adenocarcinoma, ductal adenocarcinoma (breast tumor), non-small-cell lung carcinoma lung adenocarcinoma (NSCLC LUAD), cutaneous melanoma, urothelial carcinoma (bladder tumor), colorectal cancer (Lynch), or osteosarcoma, particularly, Lynch syndrome or BRCA genetic deficiency.

In some embodiments of the foregoing methods, the machine learning (ML) comprises a deep convolutional neural network (CNN) that adaptively and/or systemically filters sequencing noise. In some embodiments, the CNN comprises employing a deep learning algorithm over a pan-tumor cohort to identify signatures that discriminate between true tumor mutations and artefactual errors; assigning a confidence estimate to each individual mutation detected in a sample from tumor patients; integrating the confidence estimates across the entire genome; and employing a non-negative least square of specific cosmic mutational signatures in the sample.

In some embodiments, the disclosure relates to a computer readable medium comprising computer-executable instructions, which, when executed by a processor, cause the processor to carry out a method or a set of steps for early detection of tumor or detection of premalignant tumor lesion, the method or steps comprising, (a) generating a subject-specific genome-wide compendium of reads associated with a plurality of genetic markers from a biological sample of a subject, wherein the compendium of genetic markers is selected from the group consisting of single nucleotide variation (SNV), short insertions and deletions (Indels), copy number variation, structural variants (SV) and combinations thereof; (b) removing artefactual reads from the compendium by statistically classifying each read in the compendium as signal or noise on the basis of probability of detection of noise $(P_N)$ as a function of (1) base-quality (BQ) of the read, (2) mapping-quality (MQ) of the read; and/or (3) estimated fragment size of the read (4) allele fraction of the read (VAF); (c) adaptively and/or systemically filtering sequencing noise associated with each read in the compendium by utilizing machine learning (ML) approach to discriminate between cancer related mutation features and PCR or sequencing error related features; (d) compiling a subject-specific signature comprising a plurality of true reads in the compendium based on the noise removal step (c) and optional filtering step (b); (e) statistically quantitating a confidence estimate that the subject's biological sample comprises circulating tumor DNA (ctDNA) based on a match between the subject-specific signature and a cancer signature; and (f) detecting a pre-malignant tumor signature based on the confidence estimate that the subject's biological sample contains cancer related mutational signature. In some embodiments, the ML comprises a layered convolutional neural network (CNN) with a single fully connected layer at one end, wherein the CNN maintains spatial invariance when convolving over trinucleotide windows; and maintains quality map by collapsing the read fragment into a plurality of segments, each representing approximately an eight-nucleotide region.

In some embodiments of the foregoing computer-readable media or methods, the CNN comprises 8 layers comprising a single fully connected layer at one end and two successive convolutional layers, the output of which is down-sampled by maxpooling with a receptive field of two and a stride of two; wherein the 8-layered CNN maintains quality map by collapsing the read fragment into about 25 individual segments and convolves over columns at a position in the genomic read using a perceptive field of size three; and wherein the output of the last convolutional layer is applied directly to a sigmoid fully connected layer, from which a final classification of the marker is made. In some embodiments, the CNN comprises a read representation that jointly captures the genomic context of alignment, the complete read sequence, and the integration of the quality score per base. In some embodiments of the foregoing computer-readable media or methods, the CNN provides enrichment of tumor specific markers comprising somatic mutations in a genomic read by about 1.12-fold to about 30-fold compared to MUTECT.

In some embodiments, the disclosure relates to computer readable media comprising computer-executable instructions, which, when executed by a processor, cause the processor to carry out a method or a set of steps for diagnosing a cancer in a subject in need of the diagnosis, the medium comprising a convolutional neural network (CNN) developed by the method of: (A) receiving in a compendium of genetic markers received from a subject's sample, wherein the genetic markers comprise somatic single nucleotide variations (sSNVs); somatic copy number variations (sCNVs); insertions/deletions (indel); or structural variations (SV) in a genomic read; (B) processing the compendium of genetic markers for each subject over a pan-tumor cohort to identify signatures that discriminate between true cancer markers and artefactual errors; (C) assigning a confidence estimate to each signature in the compendium based on the processing step (B); (D) integrating the confidence estimates for each signature of step (C) across the genomic read to build tumor signature; and (E) mathematically optimizing the tumor signature. In some embodiments, the assignment of confidence estimate comprises (1) calculating a confidence metric for the contribution of a cosmic mutational signature using a linear mixture optimization; or (2) calculating the similarity of the patient sequence-context compendium to a specific cosmic signature. In some embodiments, the linear mixture optimization comprises solving an algebraic function $\min\|Ax{-}b\|$, $x{\geq}0$, wherein A is the mutational signature sequence context matrix, x is the contribution of each cosmic mutational signature and b is the patient specific sequence context compendium. In some embodiments, A in the algebraic function $\min\|Ax{-}b\|$, $x{\geq}0$ comprises the at least 5, at least 10, at least 15, at least 20, at least 25 or at least 30 COSMIC signatures along with 100 random mutational signatures. In some embodiments, the linear mixture optimization comprises calculating a distribution of the contribution of random signatures comprising extraction E_random (average contribution score) and std_random (std contribution score); and checking the confidence of contribution detection for each COSMIC signature by zscore, comprising computing a metric (cosmic_sig_contribution-E_random)/std_random, wherein the metric represents the significance of a particular signature in comparison to a random set. In some embodiments, the mathematical optimizing step comprises employing a non-negative least square (NNLS).

In some embodiments, the disclosure relates to systems for diagnosing a tumor in a subject in need thereof, comprising: a data acquisition unit configured to receive a plurality of reads comprising genetic markers amplified and sequenced from a biological sample comprising a plasma sample and a normal cell sample of the subject; a marker identification unit configured to identify a plurality of subject-specific markers in the subject-specific compendium of genetic markers, the marker identification unit communicatively connected to the data acquisition unit, comprising: a noise removing unit that removes artefactual noise on the basis of base quality of the read, mapping quality of the read, fragment size of the read, and/or variable allele frequency of the read (VAF); and a classification engine configured to statistically classify each noise-removed read in the compendium on the basis of a confidence interval score which indicates a statistical level of a statistical association between the read and the tumor, wherein the classification engine utilizes machine learning (ML) to adaptively and systematically filter noise introduced during the amplification step or the sequencing step and further match the noise-removed ML-filtered reads in the compendium with one or more known cancer signatures; and; a diagnosing unit configured to diagnose a tumor based on the match.

In some embodiments of the systems of the disclosure, the classification engine is further configured to match the noise-removed ML-filtered reads in the compendium with one or more known cancer signatures by computing a confidence metric using a linear mixture optimization problem.

In some embodiments of the systems of the disclosure, the linear mixture optimization comprises computing a zscore confidence estimation for the association between tumor incidence and a tumor mediator selected from tobacco exposure, UV light exposure, deregulated DNA repair, faulty DNA editing, microsatellite instability, or a combination thereof.

In some embodiments of the systems of the disclosure, the artefactual noise-removing engine is configured to implement an optimal receiver operating characteristic (ROC) curve which comprises a probabilistic classification of the reads in the compendium based on base-quality (BQ) score of the read; mapping-quality (MQ) score of the read; fragment size of the read; or variable allele frequency (VAF) of the read. In some embodiments of the systems of the disclosure, the artefactual noise-removing engine is further configured to filter noise on the basis of (iii) position in the read (RP); (iv) sequence context (SC) of the read; (v) abundance of the read; (vi) sequencing depth and/or (vii) sequencing error.

In some embodiments of the systems of the disclosure, the confidence metric computation comprises zscore confidence estimation via solving an algebraic function comprising $min\|Ax-b\|$, $x \geq 0$, wherein A is the mutational signature sequence context matrix, x is the contribution of each cosmic mutational signature; and b is the patient specific sequence context compendium. In some embodiments, the zscore confidence estimation comprises solving an algebraic function comprising $min\|Ax-b\|$, $x \geq 0$, wherein A comprises 30 cosmic signatures and 100 random mutational signatures; and calculating a distribution of the contribution of cosmic signatures (CSC) random signatures (E_random) comprising an average contribution score (ACS) and a standard contribution score (std_random); and checking the confidence of contribution for each cosmic signature by computing a zscore metric with the function (CSC-E_random)/std_random, wherein the zscore represents the significance of a particular signature contribution in comparison to the random set. In some embodiments, the zscore confidence estimation comprises calculating the similarity of the patient sequence-context compendium to a specific cosmic signature. In some embodiments, the zscore confidence estimation comprises normalizing a patient sequence-context compendium to obtain a density function; calculating a cosine-similarity between the patient sequence-context density function and the cosmic signature density function; and normalize the cosine similarity by dividing by the cosine similarity between the patient sequence-context density function and non-informative uniform density function. In some embodiments, the zscore confidence estimation comprises checking whether the zscore exceeds a detection threshold, wherein the threshold comprises empirically estimated basal noise in healthy samples. In some embodiments, the cancer signature comprises tobacco signature, and a positive confidence interval comprises a zscore that is greater than 2, 3, 4, preferably greater than 5 standard deviations.

In some embodiments of the methods and systems of the disclosure, the genetic markers comprise SNVs, CNVs, indels and/or SVs in the DNA and the receiving unit receives whole genome sequenced (WGS) genetic data, e.g., genetic data from a biological sample comprising a plasma sample comprises cell-free DNA (cfDNA); a normal cell sample comprises peripheral mononuclear blood cells (PMBC) and wherein the genetic data comprises a plurality of markers comprises somatic single nucleotide variation (sSNV) or somatic copy number variation (sCNV) or a combination thereof. In some embodiments, the amount of cfDNA in the sample is between about 0.1 ng/ml to about 20.0 ng/ml. In some embodiments, the sample has a low tumor fraction (TF), as measured by ratio of an amount of tumor DNA molecules in relation to normal DNA molecules, e.g., between about 0.0001% (1 to a million molecules) to about 20%

BRIEF DESCRIPTION OF THE DRAWINGS

The details of one or more embodiments of the disclosure are set forth in the accompanying drawings/tables and the description below. Other features, objects, and advantages of the disclosure will be apparent from the drawings/tables and detailed description, and from the claims.

FIG. 1A shows a representative flow-chart of the diagnostic methods of the disclosure. In the first step 110, a subject-specific genome-wide compendium of reads associated with a plurality of genetic markers (e.g., somatic SNVs) is received from a subject's sample, e.g., generated via whole genome sequencing. Artefactual reads are removed in step 120 by statistically classifying each read as Signal (S) or Noise (N) on the basis of probability of detection of noise ($P_N$) as a function of (1) base-quality (BQ); (2) mapping-quality (MQ); (3) estimated fragment size and/or (4) estimated allele fraction (VAF). Other secondary parameters such as (v) position size of the read (vi) sequence context (SC); (vii) abundance; (viii) sequencing depth and/or (ix) sequencing error, may also be used. The noise-reduced reads may be fed into a convolutional neural network that has been trained using an in silico dataset and/or dataset from pan-cancer cohort. The neural network adaptively and systematically filters sequencing noise in step 130. Next, a subject-specific signature comprising a plurality of true reads in the compendium based on the noise removal step 120 and the filtering step 130 is compiled in step 140. Next, in step 150, a confidence estimate that the subject's biological sample comprises circulating tumor DNA (ctDNA) is made by matching the subject-specific signature and a cancer signature. The subject is screened for cancer in step 160 based on the confidence estimate. FIG. 1B shows a representative workflow for cancer screening in a subject, in accordance with various embodiments. FIG. 1C shows a representative workflow for cancer screening in a subject, in accordance with various embodiments.

FIGS. 3A-3C chart probability of detection of a parameter as a function of various parameters. In FIG. 3A, the chart shows that the probability of detection diminishes rapidly with samples containing low tumor fraction (TF). FIG. 3B charts predicted average number of detected sites, as well as the probability for at least one detection, as a function of the number of unique DNA fragments (genomic equivalent or coverage), mutation load (N) and tumor fraction (TF). FIG. 3C shows that integrating over 20,000 sSNVs (about 10 mutations/mega base pairs found in 17% of human cancer) can provide a high detection probability (up to 0.98) even at TF of 1:100,000, at a modest sequencing effort (20× coverage), which can be readily achieved with standard whole genome sequencing (WGS).

FIG. 4A shows a linear relationship between the number of artefactual SNV detections (error) and the total number of unique reads checked. This represents an error rate which correspond to 1 error for every 1,000 reads, which indicates that this error is predominantly due to sequencing error rate ($\frac{1}{1000}$). Each dot is a control sample (TF=0), these points were generated from 6 different patients' PBMC data with 3 different cancer types (lung, melanoma and breast) multiple coverages ranging (2× to 25×) and multiple independent replicates. All apparently fall on the same regression line, so this is invariant to cancer type. FIG. 4B shows the receiver operating characteristic (ROC) curve for base-quality filtration (BQ). FIG. 4C shows a line graph of number of reads checked (x axis) versus number of errors detected (y axis) in a filtered multi-cancer error model, demonstrating a linear relationship between the number of artefactual SNV detections (error) and the total number of unique reads checked. The SNV detection (error) is performed after applying an optimized BQ and MQ filter. FIG. 4D shows the effect of applying a joint BQ and MQ optimized filter allows about a seven fold-change suppression in sequencing error. Evaluation of error rate distribution across multiple replicates using control samples. Pre-filter noise shows a rate of ~$2\times10^{-3}$ for both lung and melanoma cancer types, post filter noise rate decrease to ~$2\times10^{-4}$ for both cancer types. FIG. 4E shows a heat map of error rate (red indicating more errors and blue indicating fewer errors) as a function of plasma coverage (x axis) and tumor load (y axis). Estimated error rates (e.g., number of detected SNV divided by the total number of unique reads checked) at various coverage and tumor mutation loads (tumor mutation load was modified by subsampling the original patient-specific tumor mutation list) are shown. Each entry to the matrix is the mean of multiple independent replicates. This shows somewhat invariant error rate (around $2\text{-}3*10^{-4}$) to the coverage and mutation load, for every mutation load that is above 2000. This indicates that the aforementioned results are robust for any tumor with more than 1 mutation per mega base pair (>1/Mbp).

FIG. 6 shows a typical pad comprising a matrix for genomic reads (e.g., 16×200 base pairs for 150 base pair reads). The top panel shows representation of a read and its alignment as seen by Engine. The bottom panel shows genomic context is appended to the ends of the read. Zeroes are padded for non-context features.

FIG. 8 shows properties of datasets and results of Engine signature analysis.

FIG. 9 shows line charts of various performance-associated properties of ENGINE of the disclosure in comparison to art-known mutation callers.

FIG. 10 shows SNV detection rates in ctDNA samples obtained in silico or from control subjects (BB600; BB601) or cancer patients (BB1122 or BB1125) using the methods and systems of the disclosure.

FIG. 11 is a table showing clinical characteristics of subjects that were diagnosed as having adenocarcinoma or having benign nodules.

FIGS. 12A-12D show tumor-specific signatures that are differentially-expressed in various tumors. FIG. 12A shows application of tumor specific signatures (UV, tobacco) provides high specificity in lung carcinoma and melanoma samples. FIG. 12B shows differential expression of gene signatures in normal (PBMC) versus tumor samples in lung patient (left panel) and/or melanoma patient (right panel). FIG. 12C shows expression of various COSMIC signatures (and their associated zscores) in patients with breast cancer, melanoma, or lung adenocarcinoma.

FIGS. 13A-13C show that a cancer signature can be detected in synthetic plasma down to a tumor fraction (TF) of about $\frac{1}{1000}$. FIG. 13A and FIG. 13B, which represent data from two seeds, seed 3 and seed 4, show that a tobacco signature can be detected in synthetic plasma down to a tumor fraction (TF) of about $\frac{1}{1000}$. FIG. 13C, which represent data from a single seed, shows that a lung signature can be detected in synthetic plasma down to a tumor fraction (TF) of about $\frac{1}{1000}$.

FIG. 14A shows mutation signature detection of Tobacco-associated signature, in zscore versus background random signatures, for lung cancer patients (blue) and patients with benign nodules (red, detected by CT). This show the ability to discriminate between benign and malignant nodules based on non-invasive blood test. Tobacco signature (signature 4/8) is detected in early stage cancer plasma from patients with tobacco exposure, but not in patients with benign nodules or no smoking history. N.D. denotes not detected samples. PY denotes the number of pack years each patient smoked. ED denotes early detection. FIG. 14B shows zscore spread of mutation signature detection in a cohort of samples obtained from subjects that are at various stages of lung cancer (e.g., stage IA, stage IB, stage IIA, stage IIb, and stage IIIa) in comparison to benign controls. In most cancer samples, a baseline sensitivity of at least 67% was attained, which elevated to about 100% for all high stage cases (e.g., stage IIIa and higher).

FIG. 17A shows fragment size distribution shown in healthy normal cfDNA sample. FIG. 17B shows a fragment size shift in breast tumor cfDNA (red and purple) show compared to normal cfDNA sample. FIG. 17C shows that in mouse xenograft (PDX) models, circulating DNA from the tumor origin is significantly shorter than circulating DNA that is from normal origin. FIG. 17D shows a line graph of the fragment DNA size (x-axis; number of bases) plotted against frequency of observing a fragment of said length across tumor and normal samples. FIG. 17E shows patient-specific mutation detections using orthogonal features such as correspondence of DNA fragments with tumor origin based on their fragment size distribution (x-axis) and the GMM joint log odds ratio (y-axis).

FIG. 18A shows a line graph of genomic region (bp) versus cumulative plasma depth coverage skew (bottom panel), plasma-vs-normal depth coverage skew (middle panel) and coverage (top panel). FIG. 18B shows relationship between the log 2 of the depth coverage (log 2>0.5=amplification, log 2<−0.5=deletion) and the local fragment size center-of-mass (COM) in that segment. FIG. 18C shows a dot plot of depth coverage Log 2 vs. fragment size center-of-mass (COM). Using the estimated Log 2 and COM values of all the windows across the genome the median sample center-of-mass (COM), the slope and R^2 of the Log 2/COM linear model is calculated at various time points (e.g., baseline 0 days, 21 days, and 42 days). FIG. 18D shows a correlation between Log 2/FS estimation and the fraction of tumor DNA. FIG. 18E shows a relationship between depth coverage based CNV detection and fragment size center-of-mass (COM) based CNV detection in patient samples. FIG. 18F shows lack of a relationship between depth coverage based CNV detection and fragment size center-of-mass (COM) based CNV detection in normal (healthy) plasma samples.

DETAILED DESCRIPTION

Figure 1D:
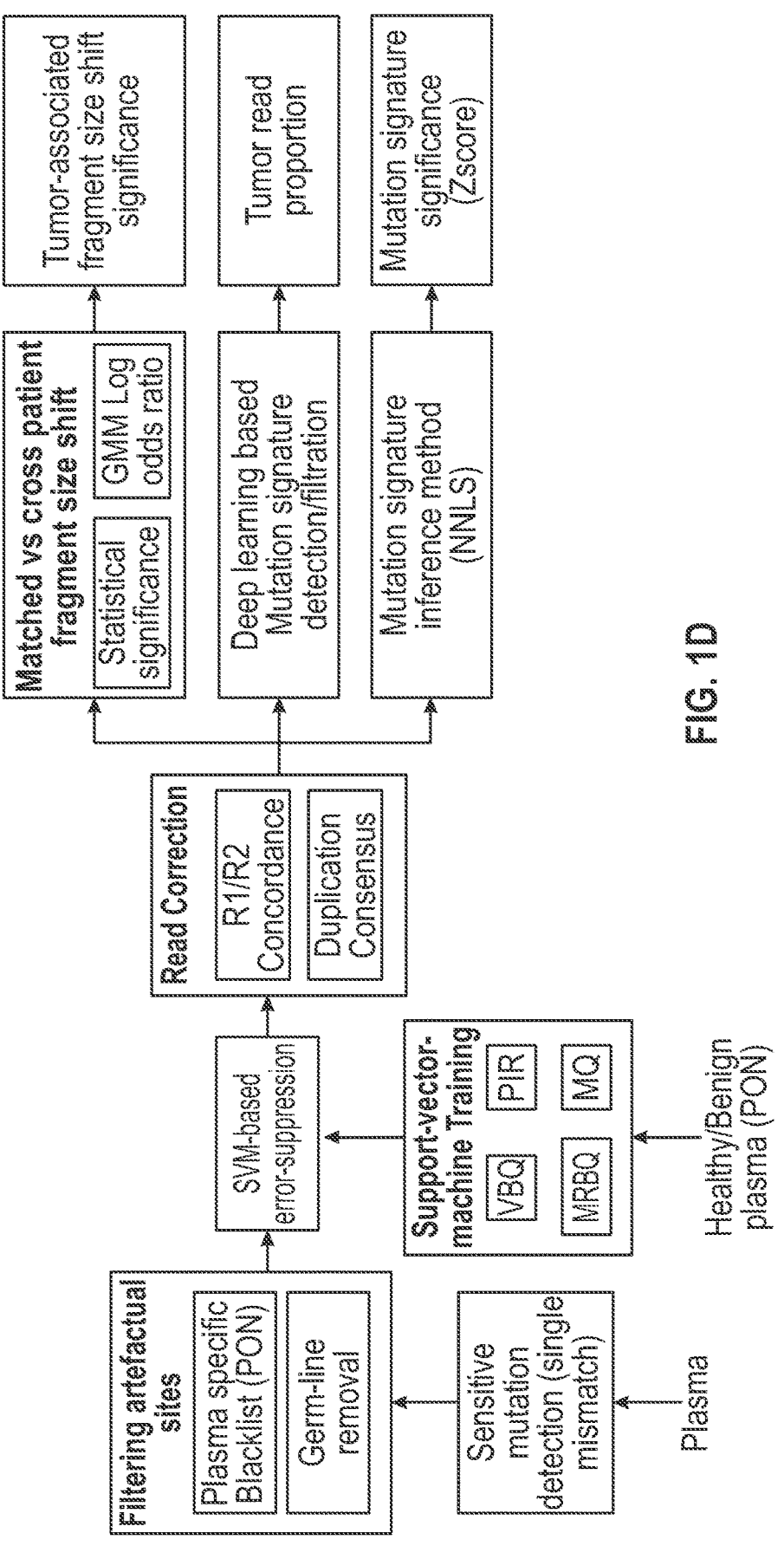
FIG. 1D shows a representative workflow for cancer screening in a subject based on measurement of single nucleotide polymorphisms (SNV) or indels.

The present disclosure will now be described in more detail with reference to the accompanying drawings, in which preferred embodiments of the disclosure are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

Unless otherwise defined, scientific and technical terms used in connection with the present teachings described herein shall have the meanings that are commonly understood by those of ordinary skill in the art. The terminology used in the description of the disclosure herein is for the purpose of describing particular embodiments only and is not intended to be limiting of the disclosure. Further, unless otherwise required by context, singular terms shall include pluralities and plural terms shall include the singular. Generally, nomenclatures utilized in connection with, and techniques of molecular biology, and protein and oligo- or polynucleotide chemistry and hybridization described herein are those well-known and commonly-used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., Molecular Cloning: A Laboratory Manual (Third ed., Cold Spring Harbor Laboratory Press, Cold Spring Harbor, N.Y. 2000). The nomenclatures utilized in connection with, and the laboratory procedures and techniques described herein are those well-known and commonly-used in the art.

The various embodiments of the present disclosure are further described in detail in the paragraphs below.

Definitions

As used in the description of the disclosure and the appended claims, the singular forms "a," "an," and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

The word "about" means a range of plus or minus 10% of that value, e.g., "about 5" means 4.5 to 5.5, "about 100" means 90 to 100, etc., unless the context of the disclosure indicates otherwise, or is inconsistent with such an interpretation. For example in a list of numerical values such as "about 49, about 50, about 55", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

Where a range of values is provided in this disclosure, it is intended that each intervening value between the upper and lower limit of that range and any other stated or intervening value in that stated range is encompassed within the disclosure. For example, if a range of 1 μM to 8 μM is stated, it is intended that 2 μM, 3 μM, 4 μM, 5 μM, 6 μM, and 7 μM are also explicitly disclosed.

As used herein, the term "plurality" can be 2, 3, 4, 5, 6, 7, 8, 9, 10, or more.

As used herein, the terms "screen" or "screening" has a broad meaning. It includes processes intended for the diagnosis or for determining the susceptibility, propensity, risk, or risk assessment of an asymptomatic subject for developing a disorder later in life. Screening also includes the prognosis of a subject, i.e., when a subject has been diagnosed with a disorder, determining in advance the progress of the disorder as well as the assessment of efficacy of therapy options to treat a disorder.

As used herein, the term "detecting," refers to the process of determining a value or set of values associated with a sample by measurement of one or more parameters in a sample, and may further comprise comparing a test sample against reference sample. In accordance with the present disclosure, the detection of tumors includes identification, assaying, measuring and/or quantifying one or more markers.

As used herein, the term "diagnosis" refers to methods by which a determination can be made as to whether a subject is likely to be suffering from a given disease or condition, including but not limited diseases or conditions characterized by genetic variations. The skilled artisan often makes a diagnosis on the basis of one or more diagnostic indicators, e.g., a marker, the presence, absence, amount, or change in amount of which is indicative of the presence, severity, or absence of the disease or condition. Other diagnostic indicators can include patient history; physical symptoms, e.g., unexplained weight loss, fever, fatigue, pains, or skin anomalies; phenotype; genotype; or environmental or heredity factors. A skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods of the disclosure can be used independently, or in combination with other diagnosing methods, to determine whether a course or outcome is more likely to occur in a patient exhibiting a given characteristic.

As used herein, the term "early detection" of a disease, e.g., cancer, refers to discovering the likelihood of disease manifestation, e.g., prior to metastasis in the context of cancer. Preferably, early detection refers to identification of the disease prior to observation of a morphological change in a tissue or cell. Furthermore, the term "early detection" of cell transformation refers to the high probability of a cell to undergo transformation in its early stages before the cell is morphologically designated as being transformed.

As used herein, the term "cell transformation" refers to the change in characteristics of a cell from one form to another form such as from normal to abnormal, non-tumorous to tumorous, undifferentiated to differentiated, homogeneous to heterogeneous. Furthermore, the transformation may be recognized by the morphology, phenotype, biochemical characteristics, e.g., growth property, apoptotic property, detachment, invasive property, etc., of the cell.

As used herein, the term "tumor" includes any cell or tissue that may have undergone transformation at the genetic, cellular, or physiological level compared to a normal or wild-type cell. The term usually denotes neoplastic growth which may be benign (e.g., a tumor which does not form metastases and destroy adjacent normal tissue) or malignant/cancer (e.g., a tumor that invades surrounding tissues, and is usually capable of producing metastases, may recur after attempted removal, and is likely to cause death of the host unless adequately treated). See Steadman's Medical Dictionary, 28' Ed Williams & Wilkins, Baltimore, MD (2005).

The term "cancer" (used interchangeably with "tumor") refers to human cancers and carcinomas, sarcomas, adenocarcinomas, lymphomas, leukemia, solid and lymphoid cancers, etc. Examples of different types of cancer include, but are not limited to, lung cancer, pancreatic cancer, breast cancer, gastric cancer, bladder cancer, oral cancer, ovarian cancer, thyroid cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer, renal cancer (e.g., RCC), pleural cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, etc. In some embodiments, "liquid" cancers, e.g., blood cancers such as lymphoma and/or leukemia are excluded.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, Merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

As used herein, "a high rate of somatic mutations" means a tumor having about 1, about 2, about 3, about 5, about 7, about 10, about 12, about 15, about 20, about 25, about 30, about 40, about 50, about 60, about 75, about 80, about 100, about 125, about 150, or more mutations per mega base pair (mutation/MBP) of the genome. See Collisson et al., Nature, 511(7511):543-50, 2014.

As used herein, the term "non-small cell lung carcinoma" or NSCLC as used herein refers to all lung cancers that are not small cell lung cancer and includes several sub-types including but not limited to large cell carcinoma, squamous cell carcinoma and adenocarcinoma. All stages and metastasis are included. Accounting for 25% of lung cancers, squamous cell carcinoma usually starts near a central bronchus. A hollow cavity and associated necrosis are commonly found at the center of the tumor. Well-differentiated squamous cell cancers often grow more slowly than other cancer types. Adenocarcinoma accounts for 40% of non-small cell lung cancers. It usually originates in peripheral lung tissue. Most cases of adenocarcinoma are associated with smoking; however, among people who have never smoked, adenocarcinoma is the most common form of lung cancer. See, Rosell et al., *Lung Cancer*, 46(2), 135-48, 2004; Coate et al., *Lancet Oncol*, 10, 1001-10, 2009.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

As used herein, the term "subject" means a mammalian animal, including a human, a veterinary or farm animal, a domestic animal or pet, and animals normally used for clinical research. Particularly, the subject is a human subject, e.g., a human patient diagnosed with a tumor or suspected of having a tumor.

As used herein, the term "subject-specific dataset" refers to a variety of information which is unique to each individual, such as, for example, genomic information, phenotypic information, biochemical information, metabolic information, micro biome sequence information, electronic medical record data, electronic health record data, drug prescriptions, biometric data, nutritional information, exercise information, family medical history information (e.g., as may be obtained via a family health history survey), in-application written chat logs, the subject's personal health care provider records and notes, the subject's insurance provider, patients advocate network information, social network information, and the like. In some embodiments, one or more of the subject specific datasets are routinely updated and/or supplemented. In some embodiments, one or more datasets are added to the plurality of subject-specific datasets.

The term "subject-specific genomic information" refers to the genetic makeup of an individual, including mutations (SNPs, Del/Dups, VUS, etc.) and mutation frequencies, familial genome sequence information, structural genomic information (including mutations (sequence, deletion, insertions)), single nucleotide polymorphism, personal immunomics information (i.e., the study of immune system regulation and response to pathogens using genome-wide approaches), functional genomic information (functional genomics focuses on the dynamic aspects such as gene transcription, translation, and protein-protein interactions), computational genomic information (the use of computational and statistical analysis to decipher, discover or predict biology from genome sequences and related data), epigenomics (reversible modifications of DNA or histones that affect gene expression without altering the DNA sequence (e.g. DNA methylation and histone modification)), pathogenomics information including personal genome-microbe interactions involved in disease states, regenomic information, behavior genomic information, metagenomics (i.e., personal genetic material recovered directly from environmental samples).

The term "subject-specific phenotypic information" refers to gender, race, height, weight, hair color, eye color, heart rate, taste preference, blood pressure, self-described medical symptoms, medically diagnosed symptoms, test results and/or diagnosis provided by medical professional, proteomic profile, and the like. The term "subject-specific biochemical information" refers to the results of clinical tests (e.g., sodium, magnesium, potassium, iron, blood urea nitrogen (BUN), uric acid, and the like), drug/medication levels in tissues, blood, etc.

The terms "subject-specific electronic medical record data" (EMR), "Electronic Health Records" (EHR), and "Personal Health Records" (PHRs) refer to medical and clinical data from individual health care providers, clinics, hospitals, care facilities, subject health history, subject predisposition to disease, subject medical history, diagnoses, medication/prescriptions, treatment plans, immunization dates, allergies, radiology images, laboratory and test results, advance directives, biopsies, data from home and mobile monitoring devices such as FITBIT, iWatch, Withings scale, wireless blood pressure cuff, etc., and the like.

As used herein, the term "sample" refers to a composition that is obtained or derived from a subject of interest that contains a cellular and/or other molecular entity that is to be characterized and/or identified, for example based on physical, biochemical, chemical and/or physiological characteristics. The source of the tissue sample may be blood or any blood constituents; bodily fluids; solid tissue as from a fresh, frozen and/or preserved organ or tissue sample or biopsy or aspirate; and cells from any time in gestation or development of the subject or plasma. Samples include, but not limited to, primary or cultured cells or cell lines, cell supernatants, cell lysates, platelets, serum, plasma, vitreous fluid, ocular fluid, lymph fluid, synovial fluid, follicular fluid, seminal fluid, amniotic fluid, milk, whole blood, urine, cerebrospinal fluid (CSF), saliva, sputum, tears, perspiration, mucus, tumor lysates, and tissue culture medium, as well as tissue extracts such as homogenized tissue, tumor tissue, and cellular extracts. Samples further include biological samples that have been manipulated in any way after their procurement, such as by treatment with reagents, solubilized, or enriched for certain components, such as proteins or nucleic acids, or embedded in a semi-solid or solid matrix for sectioning purposes, e.g., a thin slice of tissue or cells in a histological sample. Preferably, the sample is obtained from blood or blood components, including, e.g., whole blood, plasma, serum, lymph, and the like.

As used herein, the term "marker" refers to a characteristic that can be objectively measured as an indicator of normal biological processes, pathogenic processes or a pharmacological response to a therapeutic intervention, e.g., treatment with an anti-cancer agent. Representative types of markers include, for example, molecular changes in the structure (e.g., sequence) or number of the marker, comprising, e.g., gene mutations, gene duplications, or a plurality of differences, such as somatic alterations in cfDNA, copy number variations, tandem repeats, or a combination thereof.

As used herein the term "genetic marker" refers to a sequence of DNA that has a specific location on a chromosome that can be measured in a laboratory. The term "genetic marker" can also be used to refer to, e.g., a cDNA and/or an mRNA encoded by a genomic sequence, as well as to that genomic sequence itself. Genetic markers may include two or more alleles or variants. Genetic markers may be direct (e.g., located within the gene or locus of interest (e.g., candidate gene)), indirect (e.g., closely linked with the gene or locus of interest, e.g., due to proximity to but not within the gene or locus of interest). Moreover, genetic markers may also be unrelated to the genes or loci, e.g., SNVs, CNVs, or tandem repeats, which are present in non-coding segments of the genome. Genetic markers include nucleic acid sequences which either do or do not code for a gene product (e.g., a protein). Particularly, the genetic markers include single nucleotide polymorphisms/variations (SNPs/SNVs) or copy number variations (CNVs) or a combination thereof. Preferably, the genetic marker includes somatic variations in the DNA, e.g., sSNV or sCNV, or a combination thereof compared to a reference sample.

As used herein, the term "cell free DNA" or "cfDNA" refers to strands of deoxyribose nucleic acids (DNA) found free of cells, for example, as extracted or isolated from plasma/serum of circulating blood, extracted from lymph, cerebrospinal fluid (CSF), urine or other bodily fluids. The term "cfDNA" is contrasted with "circulating tumor DNA" or "ctDNA." Cell-free DNA (cfDNA) is a broader term which describes DNA that is freely circulating in the bloodstream, but is not necessarily of tumor origin.

As used herein, the term "single nucleotide polymorphism" or "single nucleotide variation" ("SNP" or "SNV") in reference to a mutation refers to a difference of at least one nucleotide in a sequence in comparison to another sequence. The term "copy number variation" or "CNV" refers to a comparative numerical change in the presence or absence/gain or loss, of gene fragments having the same nucleotide sequence.

The term "indel" as used herein, and generally in the art, refers to a location on a genome where one or more bases are present in one allele, with no bases present in another allele. Insertions or deletions are distinct from an evolutionary point of view, but during analysis such as described herein, they are often not distinguished as an insertion in one allele is equivalent to a deletion in the other allele. Thus the term indel is to refer to the location of the insertion/deletion between two alleles.

"Structural variants" involve changes in some parts of the chromosomes instead of changes in the number of chromosomes or sets of chromosomes in the genome. There are four common types of mutations which result in structural variants: deletions and insertions, for example duplications (involving a change in the amount of DNA in a chromosome, loss and gain of genetic material, respectively), inversions (involving a change in the arrangement of a chromosomal segment) and translocations (involving a change in the location of a chromosomal segment which can give rise to gene fusions). In the present invention, the term "structural variant" includes loss of genetic material, a gain of genetic material, a translocation, a gene fusion and combinations thereof.

As used herein, the term "germline DNA" or "gDNA" refers to DNA isolated or extracted from a patient's peripheral mononuclear blood cells, including lymphocytes that are in turn obtained from circulating blood.

As used herein, the term "variation" refers to a change or deviation. In reference to nucleic acid, a variation refers to a difference(s) or a change(s) between DNA nucleotide sequences, including differences in copy number (CNVs). This actual difference in nucleotides between DNA sequences may be an SNP, and/or a change in a DNA sequence, e.g., fusion, deletion, addition, repeats, etc., observed when a sequence is compared to a reference, such as, e.g., germline DNA (gDNA) or a reference human genome HG38 sequence. Preferably, the variation refers to difference between cfDNA sequence and a control DNA sequence that is not from a tumor cell, such as when cfDNA is compared to reference HG38 sequence; when cfDNA is compared to gDNA. Differences identified in both gDNA and cfDNA are considered "constitutional" and may be ignored.

A "locus" (plural "loci") corresponds to an identified location in a genome, and can span a single base or a sequential series of multiple bases. A locus is typically identified by using an identifier value or a range of identifier values with respect to a reference genome and/or a chromosome thereof; for example, the range of identifier values of "5100001" to "5800000" may refers to a particular location on chromosome 1 in the reference human genome. A "heterozygous locus" (also referred to as a "het") is a locus in a genome, where the two copies of a chromosome do not have the same sequence. These different sequences at a locus are called "alleles". A het can be a single-nucleotide polymorphism (SNP) if the reference genome location has two alleles that differ by a single base. A "het" can also be a reference genome location where there is an insertion or a deletion (collectively referred to as an "indel") of one or more nucleotides or one or more tandem repeats. A "homozygous locus" is a locus in a reference or a baseline genome, where the two copies of a chromosome have the same allele. "Haplotype" of a chromosome refers to whether the chromosome is present once or twice in a genome; for a genome of cancer or other tumor cells, a chromosome haplotype may be a value that is non-integer and/or is greater than two. A "region" in a genome may include one or more loci.

A "fragment" refers to a nucleic acid molecule (e.g., DNA) that is included in, or derived from (e.g., via amplification), a biological sample that is extracted from a target organism such as, for example, a human being. A fragment may include the entire arm of a chromosome, a whole chromosome, or a portion thereof.

"Fragment size" refers to the length of the fragment and can be expressed in any acceptable units, e.g., base pairs or daltons or the like. Representative fragments may be shorter than 200 bps; 200-500 bps; 500-1 Kb wherein 1 Kb=1000 bps; 1 Kb-10 Kb, 10 Kb-50 Kb, 50 Kb-100 Kb, and longer than 100 Kb, e.g., 1 mega base pair). Sequencing is used to determine information identifying one or more sequences (reads) of nucleotides in the fragment. Partial as well as full sequence information of the fragment may be generated. The sequence information may be determined with varying degrees of statistical reliability or confidence.

As used herein, the term "variant allele frequency" (VAF) or "variant allele fraction" refers to the fraction of one allele over the total amount of alleles in the DNA sample following genotyping. Conventionally, for biallelic polymorphic variants (PV), VAF refers to B-allele frequency (BAF) that is the fraction of B-alleles in the PV-typing data, which may be obtained from a DNA-sample by high throughput genotyping methods, e.g., SNP-arrays or NGS. In some embodiments, a VAF is a B-allele frequency. Alternately, A-allele frequencies (AAF) could be used as well. B-allele frequencies comprise A-allele frequency information and vice versa.

In general, a VAF value is expressed using a value from 0 to 1, as they refer to the frequency or fraction. In principle, VAF values may be expressed using a multiplicity of said value, e.g., using a value from 0 to 100. For example, a VAF value of 0.5 that indicates that half of total amount of alleles has the polymorphic variant allele, may be expressed as e.g., 50. In that instance, a VAF value of 1 (i.e., all alleles have the particular genotype) will be expressed as 100. Typically, $VAF_{max}$ indicates the maximal VAF value (i.e., all alleles have the particular genotype) and $VAF_{min}$ indicates the minimal VAF value (i.e., none of the alleles have the particular genotype). Throughout the present application, VAF (in particular BAF) values are indicated using a value from 0 to 1, thus $VAF_{min}$ being 0 and $VAF_{max}$ being 1. Nonetheless, embodiments of the invention are not restricted to VAF values expressed using this particular range. Detailed guidance on VAFs, including "flipped" VAFs, is provided in US 2016/0210402.

As used herein, a "read" refers to a set of one or more data values that represent one or more nucleotide bases. A read may be generated by a sequencing machine and/or associated logic that has performed a sequence determination of all or part of a nucleic acid fragment. A "mate pair" (also called "mated read" or "paired-end reads") refers to at least two reads (also called "arm reads") that have been determined from opposite ends of the same fragment. Two arm reads can be collectively called a mate pair, where a gap exists between the two arm reads with respect to the fragment from which that mate pair was sequenced. The two arm reads can be referred to individually as a "left" arm read and a "right" arm read; however, it is understood that any "left" (or "right") designation is not limited to being strictly on the left (or on the right) because the location of an arm read from a fragment can be reported with respect to various reference points such as an observer's orientation, a directionality (e.g., 5'-end to 3'-end, or vice versa) of a DNA strand, or the genome coordinate system that is chosen for a reference genome. A read may be stored with various information, e.g., a unique read identifier, an identifier of the fragment, or a mate-pair identifier for reads that are part of mate pairs.

An "artefact" as used herein refers to an observation in a scientific investigation or experiment that is not naturally present but occurs as a result of the preparative or investigative procedure. Artefacts in sequencing include, e.g., artefact peak (shadow band) and template related artefacts (false stop). Artefact peaks relate to peaks that can be seen in a separation that does not correspond to a correctly sized fragment terminated by the respective dideoxynucleotides triphosphates (ddNTP), which are used in Sanger dideoxy method to produce different lengths of DNA strands for DNA sequencing. Artefact peaks can be subdivided into primer induced artefact peaks and template induced artefact peaks. Primer related artefacts occur when the primer used has an affinity for binding to other regions of the template that it is not intended to bind to leading to the formation of DNA fragments unrelated to the intended sequence. Termination artefacts, by contrast, are generated as a result of the DNA polymerase falling off the template before a ddNTP has been included. It is thought that the secondary structure of the template DNA is responsible for this false termination. DNA polymerases also have a finite periodicity in terms of their association to the template, this is called processivity and short processivity frequencies are thought to increase the number of artefacts. For instance, Taq DNA polymerase has a processivity of approximately 40 base pairs and is thought not to contain primer associated artifact peak. False stops may arise during Sanger chain termination, when DNA polymerase is prevented from extending the growing chain as it encounters a ddNTP and the DNA chain extension is halted without including a ddNTP.

The term "allele" refers to one of two or more different nucleotide sequences that occur at a specific locus.

"Allele fraction" refers to the percentage(s) of one or more alleles, for a given locus in a genome, that are sequenced from the nucleic acid fragments included in a biological sample. With some exceptions (e.g., such as the Y chromosome in human males), diploid organisms such as humans typically have two copies of each chromosome. Thus, normally a locus in a genome can be either homozygous (e.g., having the same allele on both chromosome copies) or a heterozygous (e.g., having differing alleles on the two chromosome copies). Hence, an "equal allele fraction" value refers to a data value of 1.0 (e.g., 100% allele fraction for the alleles at a homozygous locus) or 0.5 (e.g., 50% allele fraction for the alleles at a heterozygous locus).

"Variable allele fraction" or "VAF" refers to a data value that is greater than zero but is different than 0.5 and 1.0. Variable allele fraction values can be used to address circumstances in which the alleles for a given locus may be represented in the nucleic acid fragments of a biological sample at fractions that are different than 0%, 50%, and 100%. Such circumstances may include, but are not limited to heterogeneity, contamination, and aneuploidy. For example, a tumor sample (e.g., a cancer sample) may be heterogeneous because of normal/stromal tissue contamination within the sample or because of multiple different tumor populations within the same tumor sample. In another example, a tumor sample may be aneuploid such that a chromosome (or a region thereof) has a copy number different than two, thereby causing an allele fraction to deviate from 50% for a het to 33% or 66% when three copies are present. Examples of variable allele fraction values include, but are not limited to values in the following ranges and/or combination of ranges: 0.005 to 0.10; 0.10 to 0.20; 0.20 to 0.30; 0.30 to 0.40; 0.40 to 0.49; 0.51 to 0.60; 0.60 to 0.70; 0.70 to 0.80; 0.80 to 0.90; 0.90 to 0.99; and more generally any values in the ranges 0.005 to 0.49 and 0.51 to 0.99.

The term "control," as used herein, refers to a reference for a test sample, such as control DNA isolated from peripheral mononuclear blood cells and lymphocytes, where these cells are not cancer cells, and the like. A "reference sample," as used herein, refers to a sample of tissue or cells that may or may not have cancer that are used for comparisons. Thus a "reference" sample thereby provides a basis to which another sample, for example plasma sample containing cfDNA can be compared. In contrast, a "test sample" refers to a sample compared to a reference sample or control sample. The reference sample need not be cancer free, such as when a reference sample and a test sample are obtained from the same patient separated by time.

In some embodiments, the reference sample or control may comprise a reference assembly. The term "reference assembly" refers to a digital nucleic acid sequence database, such as the human genome (HG38) database containing HG38 assembly sequences (assembled: December 2013). The gateway can be accessed through the Human (*Homo sapiens*) University of California Santa Cruz (UCSC) Genome Browser Gateway at the world-wide-web URL GENOME(dot)UCSC(dot)EDU. Alternately, the reference assembly may refer to the Genome Reference Consortium's Human Genomic Assembly (Build #38; Assembled: June, 2017), which is accessible on the internet via the U.S. National Center for Biotechnology Information's (NCBI) website.

As used herein, the term "sequencing" or "sequence" as a verb refers to a process whereby the nucleotide sequence of DNA, or order of nucleotides, is determined, such as a nucleotide order AGTCC, etc. The term "sequence" as a noun refers to the actual nucleotide sequence obtained from sequencing; for example, DNA having the sequence AGTCC. Wherein the "sequence" is provided and/or received in digital form, e.g., in a disk or remotely via a server, "sequencing" may refer to a collection of DNA that is propagated, manipulated and/or analyzed using the methods and/or systems of the disclosure.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "substantially purified" refers to cfDNA molecules that are removed from their natural environment, isolated or separated or extracted, and are at least 60% free, preferably 75% free, more preferably 90% free, and most preferably 99% free from other components with which they are naturally associated.

The term "whole genome sequencing" refers to a laboratory process that determines the DNA sequence of each DNA strand in a sample. The resulting sequences may be referred to as "raw sequencing data" or "read." As used herein, a read is a "mappable" read when the sequence has similarity to a region of a reference chromosomal DNA sequence. The term "mappable" may refer to areas that show similarity to and thus "mapped" to a reference sequence, for example, a segment of cfDNA showing similarity to reference sequence in a database, for example, cfDNA having a high percentage of similarity to human chromosomal region 8q48q24.3 in the human genome (HG38) database, is a "mappable read."

In addition to "WGS," the genomic compendiums may be obtained using targeted sequencing. In contrast to WGS, the term "targeted sequencing," as used herein, refers to a laboratory process that determines the DNA sequence of chosen DNA loci or genes in a sample, for example sequencing a chosen group of cancer-related genes or markers (e.g., a target). In this context, the term "target sequence" herein refers to a selected target polynucleotide, e.g., a sequence present in a cfDNA molecule, whose presence, amount, and/or nucleotide sequence, or changes therein, are desired to be determined. Target sequences are interrogated for the presence or absence of a somatic mutation. The target polynucleotide can be a region of gene associated with a disease, e.g., cancer. In some embodiments, the region is an exon.

As used herein, the term "low abundance" in reference to cfDNA refers to an amount of cfDNA in a sample that is less than about 20 ng/mL, e.g., about 15 ng/mL, about 10 ng/mL, or less, e.g., about 9 ng/mL, 8 ng/mL, 7 ng/mL, 6 ng/mL, 5 ng/mL, 4 ng/mL, 3 ng/mL, 2 ng/mL, 1 ng/mL, 0.7 ng/mL, 0.5 ng/mL, 0.3 ng/mL, or less, e.g., 0.1 ng/mL or even 0.05 ng/mL. In some embodiments, the term "low abundance" may be understood in the context of the uniqueness of the marker, e.g., length or base composition. For instance, although a subject's sample may comprise abundant amounts of cfDNA (e.g., >20 ng/mL), the actual number of unique genetic markers (e.g., sSNV) contained in the cfDNA may be very low. Typically, this parameter is expressed as genomic equivalence (GE) or coverage, as described below. In some embodiments, the term "low abundance" may be understood in the context of tumor-specificity of the marker. For example, although a subject's sample may comprise abundant amounts of cfDNA (e.g., >20 ng/mL), a vast majority of the genetic markers (e.g., sSNV) contained in the cfDNA may be redundant and/or associated with the reference (e.g., PBMC gDNA) as well. Typically, this parameter is expressed as tumor fraction (TF), as described below.

As used herein, the terms "tumor-specific" or "tumor-related" in reference to fDNA refers to differences in DNA sequences of cfDNA in a subject whose cancer formed a tumor, such as a lung cancer patient, when compared to reference DNA, such as when cfDNA is compared to control DNA (gDNA) from a cell that is not a tumor, as described herein. Alternatively, "tumor-specific" may relate to pre-treatment cfDNA when compared to cfDNA collected during or after treatment.

The term "genomic equivalence" or "GE" as used herein refers to the number of unique DNA fragments. In some embodiments, the sample comprises between 5 to about 10000 GE, preferably between 100 to about 5000 GE, particularly between about 200 to about 2000 GE, e.g., about 25, 50, 100, 200, 300, 400, 500, 600, 700, 800, 900, 1000, 1200, 1400, 1600, 2000 or 5000 GE. As is appreciated in the art, a typical sample comprising about 6 ng of cfDNA contains about 1000 or less GE. Preferably, the GE is more than 1 (e.g., more than 2, 5, 10, 15, 20, 25, 50, 100, 200, 500, or 1000). It is contemplated that 10-20 ml of blood contains about 10,000 GE. Thus, in some embodiments, a suitable sample may contain about 20 ml, 15 ml, 10 ml, 5 ml, 4 ml, 3 ml, 2 ml, 1 ml, 0.5 ml, 0.1 ml, 0.01 ml, or 0.001 ml of plasma.

The term "coverage" or "read depth" relates to the sequencing effort. For instance, coverage of 20× signifies a modest sequencing effort, while a coverage of 35× or more signifies a high sequencing effort and coverage of 5× signifies a low sequencing effort. In embodiments of the present disclosure, the coverage is typically between about 5× to about 100×, particularly between 15× to about 40×, e.g., 20×, 30×, 35×, 40×, 50×, 70×, or more.

As used herein, the term "mutation load" or "N" refers to a level, e.g., number, of an alteration (e.g., one or more genetic alterations, esp., one or more somatic alterations) per a preselected unit (e.g., per mega base pair) in a predetermined genomic window. Mutation load can be measured, e.g., on a whole genome or exome basis, or on the basis of a subset of genome or exome. In certain embodiments, the mutation load measured on the basis of a subset of genome or exome can be extrapolated to determine a whole genome or exome mutation load. In certain embodiments, the mutation load is measured in a sample, e.g., a tumor sample (e.g., a lung tumor sample or a sample acquired or derived from a lung tumor), from a subject, e.g., a subject described herein. Preferably, the mutational load is a measure of the number of mutations per mega base-pairs (1,000,000 bp or MBP) of cfDNA. As is known in the art, the mutation load may vary depending on the type of tumor, genetic lineage, and other subject-specific characteristics such as age, sex, tobacco consumption, etc. In the context of tumor diagnosis, the mutation load may be between about 1000 to about 10000 mutations per MBP, e.g., about 1000, 2000, 4000, 6000, 8000, 10000, 12000, 15000, 20000, 25000, 30000, 40000, 50000, 60000, 70000, 80000, 90000, 10000, or more e.g., about 200000, per MBP. Typically, the mutation load is about 8,000 per MBP in a non-smoker to over 40,000 per MBP in a subject having melanoma.

The term "genomic window," as used herein, refers to a region of DNA within chosen nucleotide sequence boundaries. Windows may be separate from one another or overlap with one another.

As used herein, the term "tumor fraction" or "TF" relates to a level, e.g., amount, of tumor DNA molecules in relation to normal DNA molecules. In some embodiments, "tumor fraction" refers to the proportion of circulating cell free tumor DNA (ctDNA) relative to the total amount of cell free DNA (cfDNA). Tumor fraction is believed to be indicative of the size of the tumor. Typically, the tumor fraction (TF) is between about 0.001% to about 1%, e.g., about 0.001%, 0.05%, 0.1%, 0.2%, 03%, 0.4%, 0.5%, 0.6%, 0.7%, 0.8%, 0.9%, 1%, or more, e.g., 2%.

The term "abundance" can refer to binary (e.g., absent/present), qualitative (e.g., absent/low/medium/high), or quantitative information (e.g., a value proportional to number, frequency, or concentration) indicating the presence of a particular molecular species. In this context, mutations that are present in higher relative concentrations are associated with a greater number of malignant cells, e.g., with cells that have transformed earlier during the tumorigenic process relative to other malignant cells in the body (Welch et al., Cell, 150: 264-278, 2012). Such mutations, due to their higher relative abundance, are expected to exhibit a higher diagnostic sensitivity for detecting cancer DNA than those with lower relative abundance.

As used herein, "sequencing error rate" relates to the proportion of sequenced nucleotide being incorrect. For example, in the context of whole genome sequencing, sequencing error rates of about 1 per 1000 bases have been reported in literature (range: error rates are on the order of 0.1-1% per base-call; Wu et al., *Bioinformatics,* 33(15): 2322-2329, 2017).

As used herein, the term "sequencing depth" relates to the number of times the sequenced region is covered by the sequence reads. For example, an average sequencing depth of 10-fold means that each nucleotide within the sequenced region is covered on average by 10 sequence-reads. The chance of detecting a cancer-associated mutation would be expected to increase when the sequencing depth is increased. However, in reality, the odds of detection do not increase linearly with the sequencing depth, as evidenced by the fact that even at a median depth of 42,000×, the fundamental limitation of cfDNA abundance resulted in positive detection of only about 19% of early lung adenocarcinomas (Abbosh et al., *Nature,* 545(7655):446-451, 2017).

As used herein, the term "base quality" score of a given base in a sequencing read is the probability that the base is called incorrectly by a sequencer. Each base in a read is assigned a quality score by a Phred-like algorithm (representative methods described in Ewing et al., *Genome Res.* 8(3):175-185, 1998; Ewing et al., *Genome Res.* 8(3):186-194, 1998), similar to that originally developed for Sanger sequencing experiments. In some embodiments, the base quality (BQ) includes variable base quality (VBQ) or mean read base quality (MRBQ), both of which are variants of the base quality metric.

As used herein, the term "PCR error" indicates error introduced via the polymerase chain reaction (PCR) amplification step in sequencing. A typical PCR error rate is about 1 error in 105 base pairs (Barnes et al., *PNAS USA,* 91:2216, 1994).

As used herein, the term "mapping quality" scores indicate the confidence that a particular sequence read is accurately placed with respect to a reference sequence. A method for determining mapping quality scores are provided by Li et al. *Genome Research,* 18:1851-1858, 2008. Mapping quality scores may be provided by mapping algorithms after mapping a sequence read to a reference sequence.

The terms "read position" or "position in read (PIR)" relate to location on a read (e.g., marker) in a nucleotide sequence. As is understood in genomics, many sequencing protocols are prone to various types of amplification induced biases and errors, which may be reduced with the implementation of filters such as "read direction" and "read position" filters. Read direction filter removes variants that are almost exclusively present in either forward or reverse reads. For many sequencing protocols such variants are most likely to be the result of amplification induced errors. Read position filters are implemented to remove systematic errors in a similar fashion as the "read direction filter", but that is also suitable for hybridization-based data. It removes variants that are located differently in the reads carrying it, than would be expected given the general location of the reads covering the variant site. This is done by categorizing each sequenced nucleotide (or gap) according to the mapping direction of the read and also where in the read the nucleotide is found; each read is divided in parts (e.g., 5 parts) along its length and the part number of the nucleotide is recorded. This gives a total of ten categories for each sequenced nucleotide and a given site will have a distribution between these ten categories for the reads covering the site. If a variant is present in the site, one would expect the variant nucleotides to follow the same distribution. The read position filter carries out a test for measuring significance of the read position, e.g., measuring whether the read position distribution of the variant carrying reads is different from that of the total set of reads covering the site.

As used herein, the term "bin" refers to a group of DNA sequences grouped together, such as in a "genomic bin." In a particular case, the bin may comprise a group of DNA sequences that are binned based on a "genomic bin window," which includes grouping DNA sequences using genomic windows.

By way of illustration only, and as summary to the following detailed description below, various embodiments herein relate to algorithms and software involved in running the diagnostic engine of the disclosure (Engine). Engine utilizes read representation that jointly captures the genomic context of alignment, the complete read sequence, and the integration of the quality score per base. In contrast, representations that are used in art-known sequence analytical software consider piles of reads as single features, losing valuable information about the sequence alignment itself and the per-base quality associated with a read (Poplin et al., *bioRxiv*, pp. 092890, 2016; Torracinta & Campagne, *bioRxiv*, pp. 097469, 2016).

Methods

The systems and methods of the disclosure are useful in the diagnosis, prognosis and monitoring of various human diseases. For instance, numerous cancers may be detected using the methods and systems described herein. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as mutations. This phenomenon may be used to detect the presence or absence of cancers individuals using the methods and systems described herein.

In accordance with the present disclosure, blood from subjects at risk for cancer may be drawn and prepared as described herein to generate a population of cell free polynucleotides. In one example, the population may include cell free DNA. The systems and methods of the disclosure may be employed to detect markers (e.g., SNVs, CNVs, indels, and/or SVs) that are present in certain cancers. The method may help detect the presence of cancerous cells in the body, despite the absence of symptoms or other hallmarks of disease. The methods of the disclosure can be applied to diagnose or prognosticate any type of cancer or tumor. Accordingly, the types of cancers that may be detected include, but are not limited to blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors. Both heterogeneous tumors and homogenous tumors may be diagnosed or prognosticated in accordance with the disclosure.

The system and methods may be used to detect any number of genetic aberrations that may cause or result from cancers. These may include but are not limited to mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer. Additionally, the systems and methods described herein may also be used to help characterize certain cancers. Genetic data produced from the system and methods of this disclosure may allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer. The systems and methods provided herein may be used to monitor already known cancers, or other diseases in a particular subject. This may allow either a subject or practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive or dormant. The system and methods of this disclosure may be useful in determining disease progression.

Further, the systems and methods described herein may be useful in determining the efficacy of a particular treatment option. In one example, successful treatment options may actually increase the amount of copy number variation or mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the systems and methods described herein may be useful in monitoring residual disease or recurrence of disease.

The methods and systems described herein may not be limited to detection of mutations and copy number variations associated with only cancers. Preferably, the methods and systems of the disclosure are useful in the early diagnosis or early detection of cancers.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The methods of this disclosure may be used to generate or profile, fingerprint or set of data that is a summation of genetic information derived from different cells in a heterogeneous disease. This set of data may comprise copy number variation and mutation analyses alone or in combination. Additionally, the systems and methods of the disclosure may be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

The aforementioned diagnostic methods may be used in combination with other common diagnostic procedures, e.g., review of health history, physical examination, laboratory tests (blood, urine, etc.), biopsy imaging tests (e.g., X-ray, PET/CT, MRI, ultrasound, etc.) Nuclear medicine scans (e.g., bone scans), endoscopy, familial history, or the like.

Preferably, the diagnostic methods of the disclosure improve predicted prognostic value (PPV) of common diagnostic procedures (e.g., CT scan) by at least 20%, at least 30%, at least 40%, or more, e.g., at least 50%.

Figure 1E:
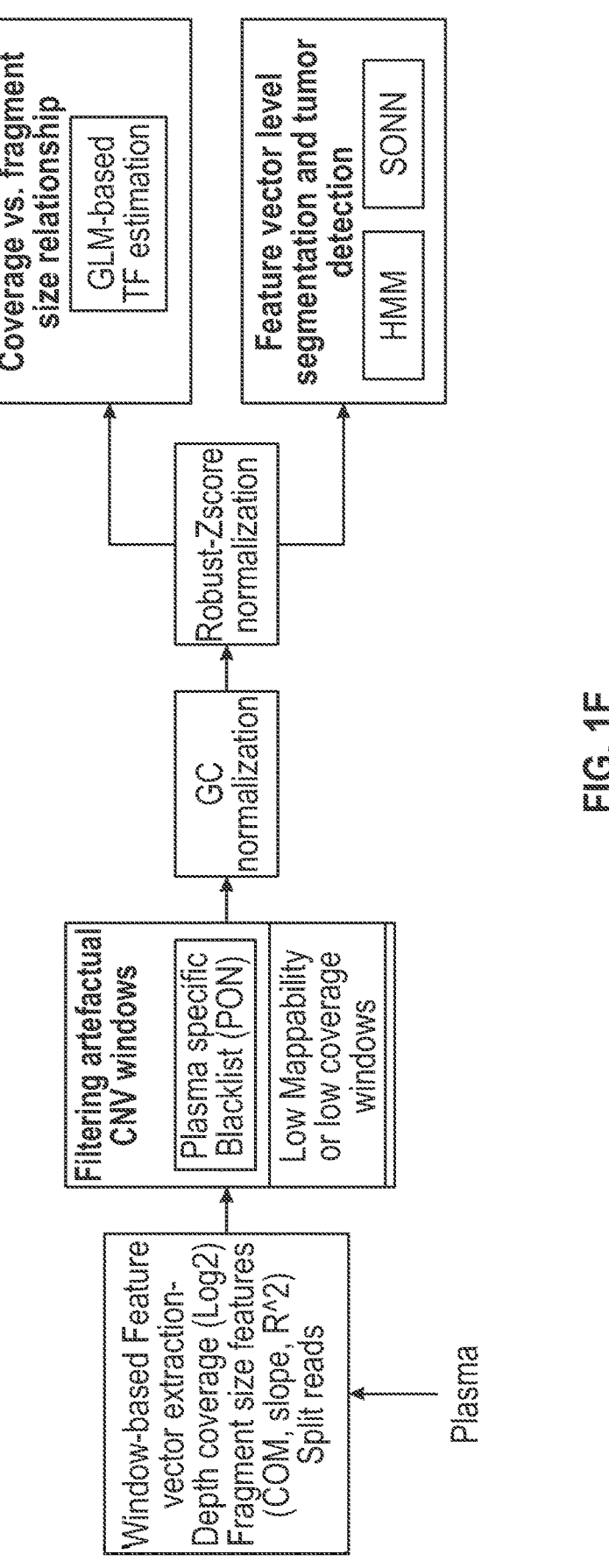
FIG. 1E shows a representative workflow for cancer screening in a subject based on measurement of copy number variations (CNV) or structural variations (SV).
Figure 1F:
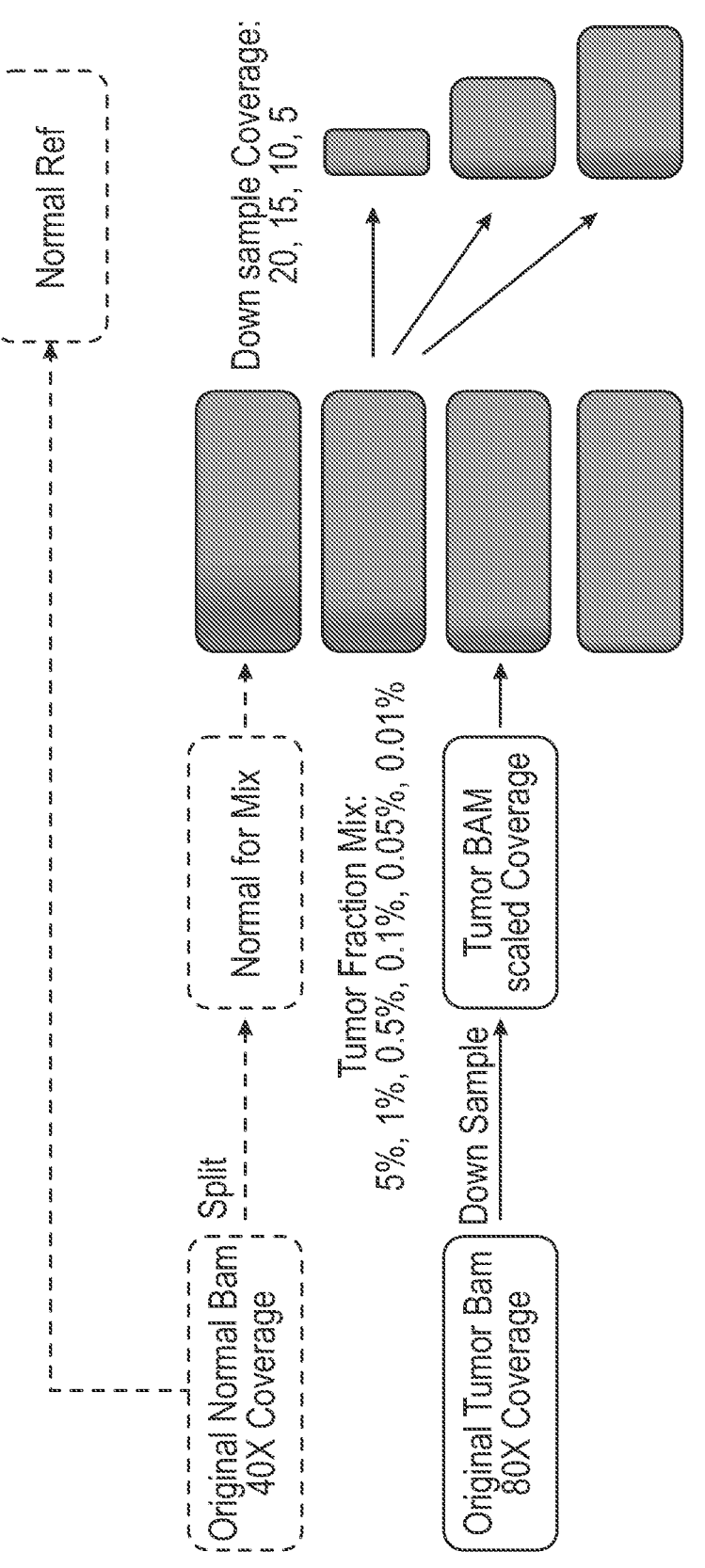
FIG. 1F shows representative a scheme for the generation of an silico database for synthetic plasma, as generated over 7 cancer patients-2 melanoma, 3 lung adenocarcinoma, and 2 breast (SCHEME A).
Figure 2:
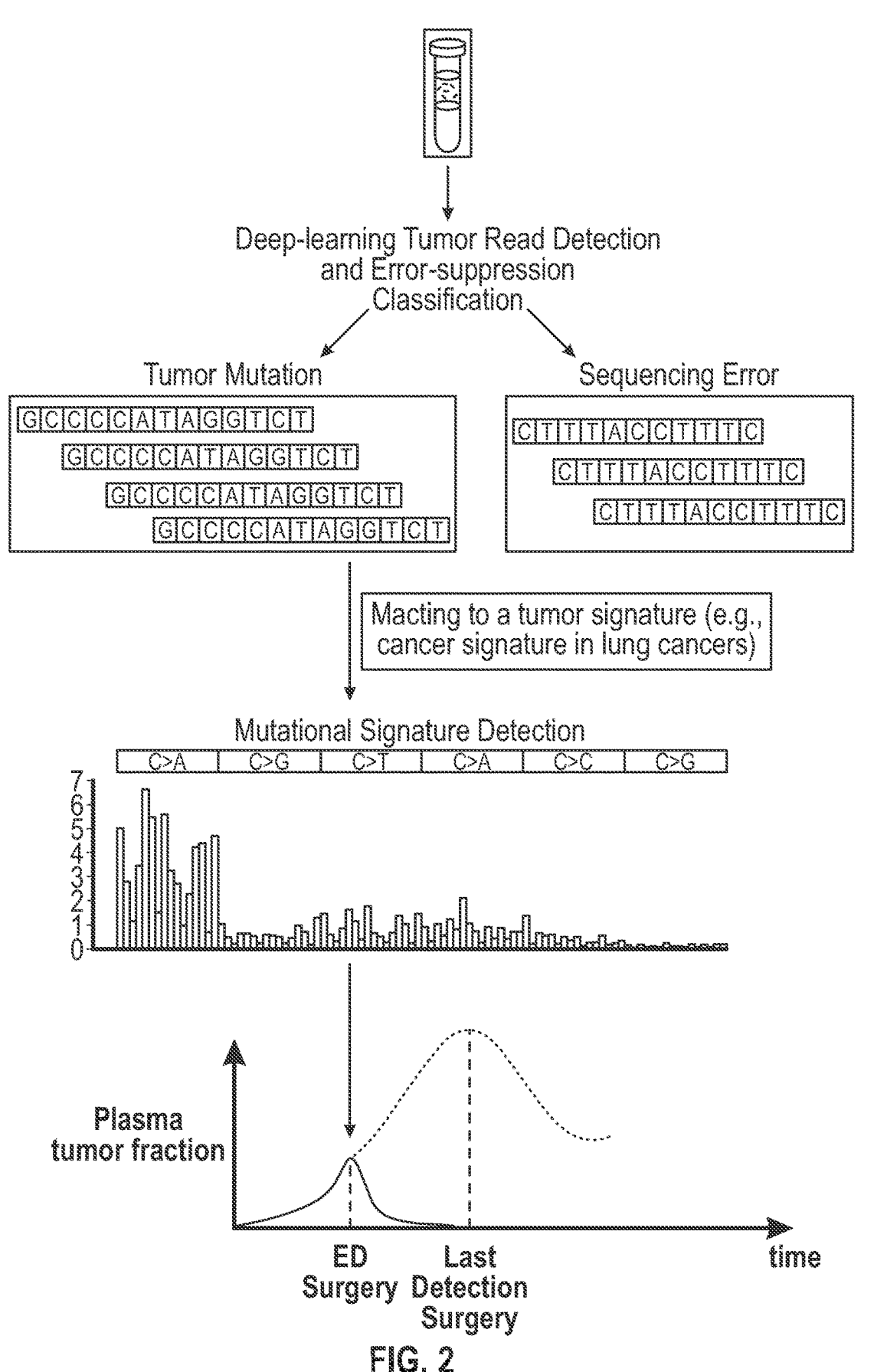
FIG. 2 provides a representative flowchart outlining the use of the systems and methods of the disclosure to aid in the early detection of cancer, which reduces, if not eliminates, the need for surgical and/or therapeutic intervention. Numerous economic and health benefits that can be derived from early cancer detection, including, avoiding risks of surgery (e.g., pneumonia, bleeding, infection, blood clotting (hematoma), and reactions to the anesthesia), side effects of chemo-therapy or immunotherapy (e.g., fatigue, hair loss, easy bruising and bleeding, infection, anemia, nausea and vomiting, appetite changes, constipation, diarrhea, mouth, tongue, and throat problems, nerve and muscle problems such as numbness, tingling, and pain; skin and nail changes such as dry skin and color change; urine and bladder changes and kidney problems; weight fluctuations).
Figure 7:
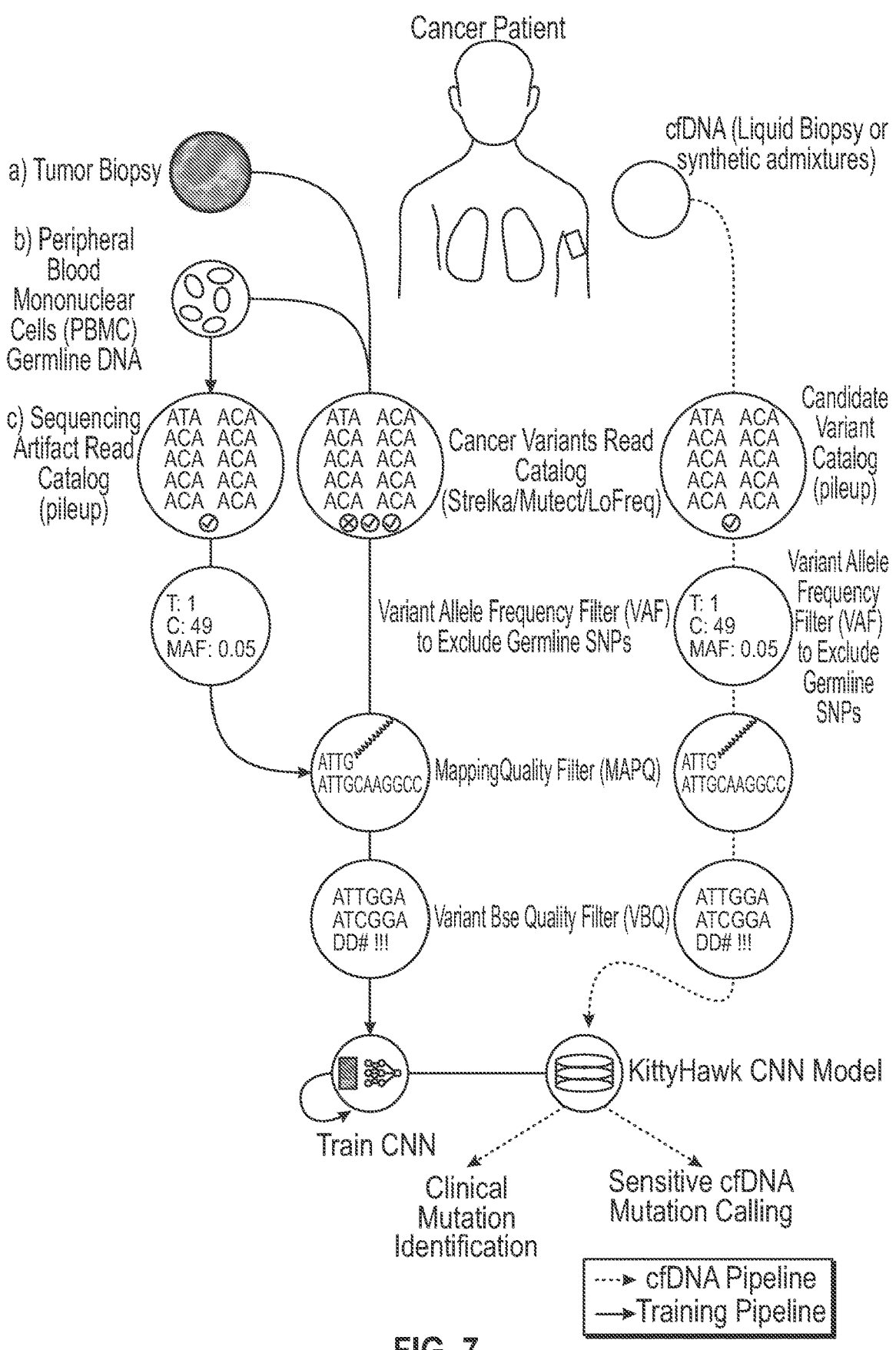
FIG. 7 shows a schematic diagram of an exemplary method of the disclosure, as applied in the clinical setting. As shown, a biopsy sample obtained from a subject (e.g., cancer patient or a subject suspected of having a tumor) containing cell free DNA (cfDNA), e.g., plasma sample, is processed (e.g., sequenced) to obtain genetic data of the patient (e.g., a VCF file), which are cataloged using PILEUP (or a similar program). VAF filters are applied to exclude germline markers (e.g., SNVs, CNVs, indels, or SVs). Mapping quality (MQ), positional filters (PIR) and/or base quality (BQ) filters are further applied to filter artefactual noise. In the next step, deep learning is applied to the filtered genetic data. The deep learning method involves training a machine with genetic data containing a compendium of markers from admixed tumor biopsy sample and peripheral blood mononuclear cells (PMBC; controls), which have been subjected to the aforementioned filters (e.g., artefactual read catalog via PILEUP, VAF filter to exclude germline variations, BQ filter to eliminate markers of low base quality and MQ to eliminate markers that are poorly mapped). The machine may also be trained with datasets. A product of the systems and the methods described above is identification of a plurality of markers in cfDNA that are clinically relevant in the context of cancer diagnosis, which assist in the early diagnosis and prognosis of cancers.

Representative, non-limiting, schematic outlines of the diagnostic methods are provided in FIG. 1, FIG. 2 and FIG. 7 of the Drawings.

Workflow

FIG. 1A is a flow chart illustrating a method 100 for diagnosing a tumor disease, e.g., early tumor disease, in accordance with the various embodiments of the present disclosure. Method 100 is illustrative only and embodiments can use variations of method 100. Method 100 can include steps for receiving a compendium of markers; filtering noise associated with the markers based on a number of features; apply a convolutional neural network that has been trained with an in silico dataset and/or patient dataset to adaptively and systematically filter noise; eliminating artefactual noise markers from the compendium to generate subject-specific markers, which are statistically matched to a dataset to generate a confidence interval; and diagnose the disease based on the confidence interval.

In step 110 of method 100 of FIG. 1A, a compendium of genetic markers is received from a subject. In some embodiments, the compendium of genetic markers is received in a variant call format (VCF) file. As is understood in the art, VCF files are used in bioinformatics for storing gene sequence variations. The VCF format has been developed with the advent of large-scale genotyping and DNA sequencing projects, such as the 1000 Genomes Project. Alternately, the compendium may be provided in a general feature format (GFF) containing all of the genetic data. Generally, GFF provides features that are redundant because they are shared across the genomes. In contrast, with VCF, only the variations need to be stored along with a reference genome. In some embodiments, the subject's sample is sequenced, e.g., using whole genome sequencing (WGS), and the sequence file is processed, e.g., using a tool such as, for example, genome VCF (gVCF).

Figure 3A:
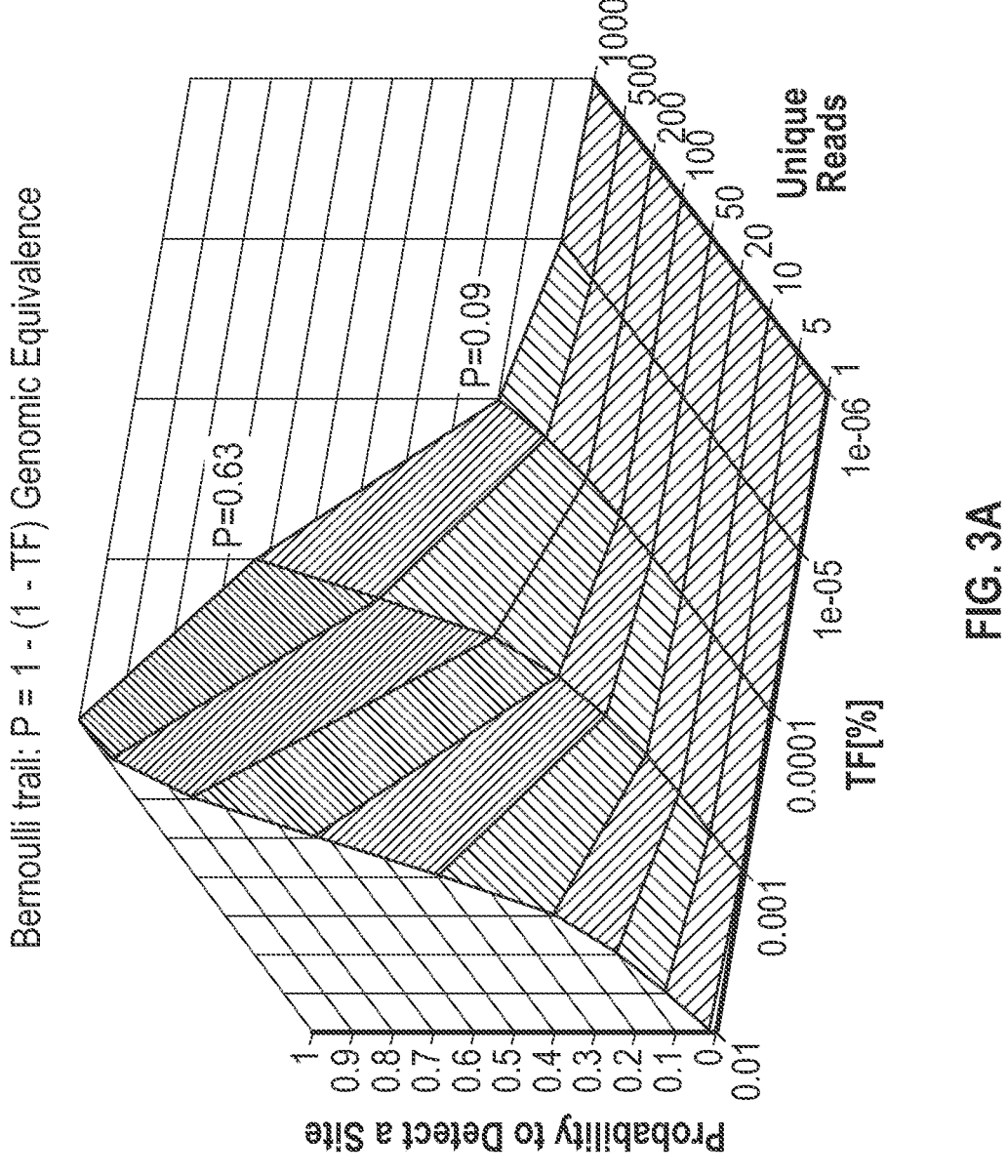

In step 120 of method 100 of FIG. 1A, the artefactual reads are filtered by statistically classifying each read as Signal or Noise on the basis of probability of detection of noise ($P_N$) as a function of (1) base-quality (BQ); (2) mapping-quality (MQ); (3) estimated fragment size and/or (4) estimated allele fraction (VAF). Other parameters such as (5) position in the read (RP); (6) sequence context (SC); (7) abundance; (8) sequencing depth and/or (9) sequencing error may also be used. The noise removal step 120 can comprise implementing an optimal receiver operating characteristic (ROC) curve which comprises a probabilistic classification of the genetic markers in the compendium based on a joint base-quality (BQ) and mapping-quality (MQ) score. Typically, the joint BQMQ score is provided as a matrix (x, y), wherein x is the BQ score and y is the MQ score. In exemplary embodiments, a joint BQMQ score between 10 and 50 (for each parameter) is typically employed, e.g., a BQMQ score of (10, 40), (15, 30), (20, 20), (20, 30), (30, 40). In some embodiments, classification of a marker comprises measurement of area under an ROC curve (AUC), which typically represents the probability that a candidate marker, randomly selected among potential markers, shows a value higher than a randomly-extracted control marker. For completely non-informative markers, the ROC curve will approach the rising diagonal (called "chance diagonal" or "chance line") and AUC will tend to 0.5, i.e., the expected probability for a classification due to chance alone. On the contrary, in the case of a perfect classification the ROC curve will reach the point of the highest theoretical accuracy (sensitivity and specificity both 100%) and AUC will tend to one, i.e., the highest probability value. A representative ROC is provided in FIG. 3B. Pre-filtration error model and post-filtration error model are shown in FIG. 3A and FIG. 3C, respectively.

Optionally, the genetic markers are weighed. In some embodiments wherein the marker is an SNV or a CNV, the weighing step is implemented so as to distinguish between true markers (e.g., mutations that are likely to be associated with the disorder) and common variations (e.g., random somatic SNPs that are not associated with the disorder). In some embodiments, the weighing step weighs the markers based on a probability score ($P_D$). Preferably, the weighting step 120 comprises measuring the probability of detection ($P_D$) based on the Bernoulli equation $P_D = 1 - [\![ 1 - TF ]\!]^{GE}$, wherein $P_D$ is the probability of detection, TF is tumor fraction and GE is the number of genomic equivalents present in the patient DNA. Implementation of weighing step is advantageous as it helps overcome depth of sequencing by increasing the number of detected sites (SNVs) through increased breadth, which results from repeating the Bernoulli trial for each SNV (a binomial distribution over the Bernoulli trial probability). In some embodiments the weighing step may additionally include binning the markers based on, e.g., increasing weights or weight ranges. For example, the genetic markers may be binned based on the $P_D$, wherein, markers with high $P_D$ are binned separately from markers with low $P_D$. For example, the genetic markers may binned based on a $P_D$ threshold value of at least about 0.60, e.g., at least about 0.65, 0.70, 0.75, 0.80, 0.90, 0.95, or more, e.g., at least about 0.98. Accordingly, if the $P_D$ of a marker is less than the threshold value, then it may be classified as a false positive and not included in the analysis.

In step 130 of method 100 of FIG. 1A, sequencing noise in each read in the compendium is filtered by utilizing machine learning (ML) approach to discriminate between cancer-related mutation features and PCR or sequencing error related features. In some embodiments, the diagnostic methods of the disclosure may utilize neural networks to systemically eliminate or reduce noise. The neural network may be applied at any step of the method, although it may be advantageous to implement the neural network after the artefactual markers have been removed, in accordance with aforementioned steps 120. In this regard, in the purely illustrative method 100 of FIG. 1A, a deep convolutional neural network (CNN) is optionally applied at step 130 to adaptively and/or systematically filter sequencing noise that are present in the filtered dataset. Preferably, the CNN comprises employing a deep learning algorithm over a pan-tumor cohort to identify signatures that discriminate between true tumor mutations and artefactual errors; assigning a confidence estimate to each individual mutation detected in a sample from tumor patients; integrating the confidence estimates across the entire genome; and employing a rigid analysis of specific cosmic mutational signatures, for example using non-negative least square (NNLS) for each marker, in the sample.

In some embodiments, the CNN is trained with an in silico dataset. For example, the in silico dataset may include synthetic plasma samples obtained from actual cancer patients, e.g., a cohort of breast or lung tumor cancer patients. The accuracy, sensitivity and/or precision of the CNN may be evaluated according to the methods described below. For instance, sensitivity may be determined as a ratio [TP/(TP+FN)], wherein TP is true positive and FN is false negative; precision may be determined as a ratio [TP/(TP+FP)], wherein TP is true positive and FP is false positive; and specificity may be determined as a ratio [TN/(TN+FN)] wherein TN is true negative and FN is false negative. Under a representative validation method, the accuracy of the CNN may be evaluated based on an average F1-score. For example, the F1 score may be computed as $2 \times [(\text{Precision} \times \text{Recall})/(\text{Precision} + \text{Recall})]$. In some embodiments, the CNN may achieve an F1-score of at least about 0.5, about 0.6, about 0.7, about 0.8, or even about 0.9 or more, e.g., 0.95 on the tumor control.

In some embodiments, the CNN may be trained with in silico patient-specific datasets comprising tumor and normal WGS reads that are admixed in varying proportions at different tumor fractions (0.00001, 0.00005, 0.0001, 0.0005 0.001, 0.005, 0.01) and coverages (5, 10, 15, 20, 35). Replicates and/or randomization seeds may be further employed to increase variability in the training datasets.

The architecture of the CNN will be discussed in greater detail below.

In step 140 of method 100 of FIG. 1A, a subject-specific signature comprising a plurality of true reads in the compendium is compiled by removing artefactual noise (see step 120) and/or sequencing noise (see step 130). Although not bound by any specific theory, in some embodiments, the elimination step filters "noise" markers having low base quality and/or mapping quality from the compendium of markers that are initially identified to be strongly associated with the disease. In some embodiments, the elimination step may comprise taking each marker that meets the threshold probability of detection ($P_N$) based on step 120, classifying said marker as signal or noise based on an ROC curve; and eliminating the marker from the compendium if it is classified as noise. Alternately, a scoring system comprising, for example, a ratio of probability of detection ($P_D$) to probability of noise ($P_N$) may be used to eliminate markers that do not meet a preset threshold score.

In step 150 of method 100 of FIG. 1A, a match between the subject-specific signature and a cancer signature is performed and a confidence estimate that the subject's biological sample comprises circulating tumor DNA (ctDNA) is quantitated. This may be accomplished using, e.g., probability density function (PDF) estimation and/or zscore estimation, both of which are explained in detail below.

In the estimation of confidence intervals, a weighting step may be optionally employed. For example, all markers that have been classified as true positives based on the noise removal step 120 and the noise filtration step 130 may be weighed identically. A modified weighing system, for example, based on scores assigned to the marker in pan-tumor networks, may be used. Diagnosis may further include use of threshold scores, e.g., a score obtained based on performing identical noise removal step 120 and the noise filtration step 130 in test markers, e.g., markers that are known to be associated with tumors. For example, such test markers may comprise unique SNVs and/or CNVs in cancer patient samples, which are absent in control (non-tumor) subjects.

As further provided by example workflow 100 illustrated in FIG. 1B, a method is provided for genetic screening a subject for cancer, in accordance with various embodiments. As provided in step 110, the method can comprise receiving a subject-specific genome-wide compendium of reads associated with a plurality of genetic markers from a biological sample of a subject. The biological sample can comprise a tumor sample. The compendium of reads can each comprise reads of a single base pair length.

As provided in step 120 of method 100 of FIG. 1B, the method can comprise filtering artefactual sites from the compendium of reads. The filtering can comprise removing, from the compendium of reads, recurring sites generated over a cohort of reference healthy samples. Alternatively, or in combination, the filtering can comprise identifying germ line mutations in the biological sample and/or identifying shared mutations between the tumor sample and peripheral blood mononuclear cells of the normal cell sample as germ line mutations, and removing said germ line mutations from the compendium of reads.

As provided in step 130 of method 100 of FIG. 1B, the method can comprise filtering noise from genome-wide compendium of reads using at least one error suppression protocol to produce a filtered read set for the genome-wide compendium of reads. The at least one error suppression protocol can comprise calculating the probability that any single nucleotide variation in the compendium is an arte-factual mutation, and removing said mutation. The probability can be calculated as a function of features selected from the group comprising mapping-quality (MQ), variant base-quality (MBQ), position-in-read (PIR), mean read base quality (MRBQ), and combinations thereof. Alternatively, or in combination, the at least one error suppression protocol can comprise removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family.

As provided in step 140 of method 100 of FIG. 1B, the method can comprise compiling a subject-specific signature using the filtered read set, based on comparison to specific mutational signatures associated with a pre-determined mutagenesis process.

As provided in step 150 of method 100 of FIG. 1B, the method can comprise statistically quantitating a confidence estimate that the subject's biological sample, via the subject-specific signature, comprises a cancer related mutational signature based on comparison of the cancer related mutational signature exposure value to a cohort of background mutation signatures.

As provided in step 160 of method 100 of FIG. 1B, the method can comprise screening the subject for cancer if the confidence estimate that the subject's biological sample contains the cancer related mutational signature exceeds a given threshold.

As further provided by example workflow 100 illustrated in FIG. 1C, a method is provided genetic screening a subject for cancer. As provided in step 110, the method can comprise receiving a subject-specific genome-wide compendium of reads associated with a plurality of genetic markers from a biological sample of a subject. The biological sample can comprise a tumor sample. The compendium of reads can each comprise a copy number variation (CNV).

As provided in step 120 of method 100 of FIG. 1C, the method can comprise dividing the compendium of reads into a plurality of windows.

As provided in step 130 of method 100 of FIG. 1C, the method can comprise calculating a set of features per window. The features can comprise a median depth coverage per window and a representative fragment size per window.

As provided in step 140 of method 100 of FIG. 1C, the method can comprise filtering artefactual sites from the compendium of reads. The filtering can comprise removing, from the compendium of reads, recurring sites generated over a cohort of reference healthy samples.

As provided in step 150 of method 100 of FIG. 1C, the method can comprise normalizing the compendium of reads to produce a filtered read set for the genome-wide compendium of reads.

As provided in step 160 of method 100 of FIG. 1C, the method can comprise computing an estimated tumor fraction using the filtered read set by calculating a linear relationship between the set of features per window and converting the calculated relationship to estimated tumor fraction using a regression model. Alternatively, or in combination, the method can comprise computing an estimated tumor fraction on the basis of one or more integrative mathematical models as a function of the calculated set of features per window across the subject-specific genome-wide compendium of reads.

As provided in step 170 of method 100 of FIG. 1C, the method can comprise screening the subject for cancer if the estimated tumor fraction exceeds an empirical threshold.

Exemplary Workflows for Implementing the Screening Methods Based on Marker Type

FIG. 1D and FIG. 1E show schematic workflows for practicing the methods of the disclosure. FIG. 1D outlines a workflow that is typically used in cases where the markers of interest comprise SNV/indels; FIG. 1E outlines a workflow that is typically used in cases where the markers of interest comprise CNV/CV. It should be noted that although separate workflows are provided for the purpose of illustration, it is not necessary that they are carried out separately to implement the methods of the disclosure. For example, certain features/elements of the workflows may be utilized in combination to generate an output (e.g., combined estimated tumor fraction based on SNV/indel and CNV/SV) which output is associated with the outcome of interest (e.g., whether the subject has or is likely to develop cancer).

SNV-Based Cancer Screening

The disclosure provides systems, methods and algorithms for cancer screening based on detection of SNV/indel markers in a subject's biological sample. As shown in FIG. 1B, cancer diagnosis based on SNV/indel markers typically utilizes steps for receiving the genetic data; detecting mutations (e.g., single mismatch); removing/filtering artefactual sites; suppressing errors using algorithms, including, machine learning; correcting reads; detecting cancer based on one or more mathematical models; and optionally, orthogonally integrating analysis of secondary features in the genomic data (e.g., fragment size shifts), so as to improve sensitivity, specificity and/or reliability of detection.

In the first step of FIG. 1D, genetic data from a biological sample (typically a plasma sample) is received. Next, sensitive mutation calling is performed on the plasma sample using PILEUP (or other single-supporting read caller). Germline SNPs are detected using GATK germline caller on the plasma sample or by using mutation calling on matched peripheral blood mononuclear cells (PBMC). A buccal swab may also be used instead of PBMCs. Successively or in parallel, recurrent artifactual sites are generated over a cohort of healthy plasma samples (panel of normal (PON) blacklist or mask), which are removed from the detected mutations in order to remove common sequencing or alignment artifacts.

Next, a highly sensitive method that is capable of detecting a single mutated fragment is employed. This step includes one or more error suppression steps. In a first error suppression step, a filtration scheme is used to analyze on a single read basis and quantify the probability for the read to be representing an artifactual mutation. In some implementations, a multidimensional classification framework using support vector machine (SVM) classification with a linear kernel may be implemented on this step. The classification framework is trained on germline SNP compared to low variant-allele-fraction (VAF) sequencing artifacts in normal PBMC samples. Here, the classification decision boundary was defined over a multidimensional space including-variant base-quality (VBQ), mapping-quality (MQ), position-in-read (PIR), and/or mean read base quality (MRBQ). To evaluate the classification scheme, validation metrics of the SVM classification scheme was compared after 10-fold cross validation to Random Forest under the same protocol. SVM classification showed high classification performance, moderately outperforming the random-forest model. The SVM achieved a mean 90.7% sensitivity and 83.9% specificity across all patients (N=10 samples, F1=87.7%, PPV=84.9%).

In a second error suppression step, artifactual mutations generated by PCR or sequencing were corrected using the comparison of independent replicates of the same original DNA fragment. In cfDNA samples, typically paired-end 150 bp sequencing were applied, resulting in overlapping paired reads (overlapping R1 and R2 sequence) given the short size of the typical cfDNA fragment (~165 bp). Therefore, any discordance between R1 and R2 pairs are regarded as potential sequencing artifacts, which are corrected back to the corresponding reference genome. In addition, recognizing the potential for the creation of independent duplications with any DNA molecule copied multiple times during sequencing and PCR, the duplication families were recognized by 5' and 3' similarity as well as alignment position. Each duplication family is then used to check the consensus of a specific mutation across independent replicates, correcting artifactual mutations that do not show concordance in a majority of the duplication family.

The resulting set of confident de-novo plasma mutations is used to identify tumor signatures using one or more of the identification steps. A first method involves identification of tumor signature in the resulting set using a mutation signature inference method, e.g., non-negative least squares (NNLS) method. This method outputs a confidence score (e.g., zscore) which can be used in determining whether the subject has cancer. In this regard, a threshold confidence score (e.g., zscore of about 2) may be used to make a reliable determination that the subject has cancer. A second method, which utilizes a deep learning method for detection of mutation signatures, may be employed. This method outputs a tumor proportion score (e.g., eTF) which can be used in determining whether the subject has cancer. These methods are described in greater detail below:

Cancer-Specific Mutagenesis Signatures

Cancer mutagenesis is dominated by sequence context specific signatures that relates to different mutagenesis processes, such as tobacco smoking, UV light and more. These mutation signatures are unique to the cancer tissue and do not appear in the normal PBMC samples. Herein, gene signatures are differentially expressed in lung cancer patients (exposed to tobacco) and melanoma patients (exposed to UV) compared to normal samples (PBMC). Recognizing this feature, a novel analytical method for sensitive detection was developed. The method is based on a model which utilizes non-negative least square (NNLS) of specific mutational signatures in a single plasma sample. Signature detection was further validated for confidence using a comparison of the cancer-specific mutation signature exposure values to the exposure values inferred for 100 random background signatures, setting a confidence threshold for z-score>2std.

Deep Learning Mutation Signature Detection

To further suppress artefactual sequencing errors and increase ctDNA sensitivity, a machine learning method was developed for distinguishing between cancer altered sequencing reads and reads altered by sequencing errors, allowing adaptive and specific filter for systemic sequencing noise. A deep convolutional neuronal network (CNN) based on artificial intelligence technology was applied. The CNN allows learning and integration of a high number of features in a supervised fashion for classification problems. This instant approach is grounded in a rethinking of the mutation calling challenge, as it aims to distinguish between a read that contains a true variant versus reads that contain a sequencing artifact. This allows to train the CNN on millions of true mutated reads and error using a large collection of tumor and normal WGS data, achieving very high sensitivity and specificity over various patients and tumor types.

Implementation of the above features in deep CNN training results in independent capture of sequence context signatures that are known to occur in lung cancer and melanoma. First, to apply the CNN in the early detection (ED) framework, the CNN algorithm was trained over a pan-lung cancer cohort (5 patients with deep tumor and PBMC WGS) utilizing the supervised learning for identifying signatures that discriminate between true tumor mutations and artifactual errors. The resulting model was utilized to infer and to assign a confidence estimate to each individual mutation detected in our ED plasma samples from lung adenocarcinoma early stage patients that could be integrated to an estimation of the tumor read proportion in a given sample. The model was able to identify specific tobacco and/or UV signatures, which, when utilized on patient samples, was able to detect, with high accuracy, patients that were early stage for the respective cancers.

Additionally, the ability of the instant methods in improving the low positive predictive value (PPV) of current lung cancer CT screening in at-risk tobacco exposed populations was evaluated by applying the method to plasma samples from 21 early stage lung patients and 12 CT-detected patients with benign nodules. The results show 14 positive detections for the early-stage lung cancer samples and 3 positive detections for the benign nodules, thus showing an improved PPV of 80%, in contrast to the 40%-50% PPV in the current CT-based screening scheme. These data show a significant improvement over existing methods for early detection of lung cancer and melanoma patients.

Integration of Orthogonal Features

Optionally, the base workflow described above may orthogonally integrate secondary features contained in the genetic data in the final analytical model. For instance, to improve robustness, accuracy, and/or sensitivity/specificity of the detection methods, read-based features, e.g., shifts in fragment sizes of DNA, may be orthogonally integrated into the mathematical model. The significance of the orthogonal feature integration (in cancer detection) may be calculated using probabilistic mixture model (e.g., Gaussian mixture model). See the Examples section and the corresponding data in FIG. 17 and FIG. 18.

CNV-Based Cancer Screening

Alternately or additionally, the disclosure provides systems, methods and algorithms for cancer screening based on detection of CNV/SV markers in a subject's biological sample. As shown in FIG. 1E, cancer detection based on CNV/SV markers typically utilizes steps for receiving the genetic data; extraction of window-based feature vectors in the genetic data; filtering artefactual CNV windows; normalization of filtered genetic data using one or more normalization steps; detection of tumors following feature vector segmentation; and optionally, orthogonally integrating analysis of secondary features in the genomic data (e.g., analysis of fragment size shifts), so as to improve sensitivity, specificity and/or reliability of detection.

In the first step of FIG. 1E, genetic data from a biological sample (typically a plasma sample) is received. Next, window-based feature vectors are extracted from the genetic data. For e.g., depth coverage features (represented by Log 2) and/or fragment size features (represented by COM) are extracted. Using the estimated Log 2 and COM values of all the windows across the genome the median sample center-of-mass (median COM over neutral regions), the slope and R^2 of the Log 2/COM linear model is calculated. Further, split reads may also be extracted. Split reads typically arise when one portion of an NGS read maps to one location of the genome and other portion of the same read maps to a different location of a genome, thereby resulting in discordance.

Next, windows with low mappability and/or coverage are filtered. Successively or in parallel, recurrent artifactual sites are generated over a cohort of healthy plasma samples (panel of normal (PON) blacklist or mask), which are removed from windows in order to filter artifactual windows. The filtered high confidence reference CNV/SV segments are normalized. Typically, the normalization step comprises guanine-cytosine (GC) normalization and/or zscore normalization.

Next, the feature vectors are segmented using one or more mathematical models. In some implementations, a hidden Markov model (HMM) is used. In some implementations, self-organizing neural networks (SONN) which are based on mathematical models, e.g., adaptive resonance theory (ART) or self-organizing map (SOM), are used. Copy number variation (CNV) detection and cancer diagnosis is carried out by analyzing the segmented data using one or more of these mathematical models.

Herein too, it is possible to orthogonally integrate secondary features of the genetic data in the final analytical model. For instance, to improve robustness, accuracy, and/or sensitivity/specificity of the detection methods. Aggregating Log 2/COM correlation (R^2), Log 2/COM slope and sample median fragment-size center-of-mass (COM) allow to define a classification model to classify between tumor and healthy samples and to calculate estimated TF, e.g., using a generalized linear model (GLM).

The significance of the orthogonal feature integration (in cancer detection) may be calculated using probabilistic mixture model (e.g., Gaussian mixture model).

It should be appreciated that, with some modifications, the workflows disclosed herein, can also be broadly used for detection of residual disease during or after chemotherapy, immunotherapy, targeted therapy, or a combination thereof; and/or in the course of monitoring the effectiveness of such therapy.

Use of Aforementioned Methods for Early Tumor Diagnosis

The methods of the disclosure are particularly useful in the early diagnosis of tumors. Preferably, the diagnostic methods of the disclosure are performed non-invasively. The diagnostic methods may be performed prior to surgery or therapy of the tumor.

The methods of the disclosure may be carried out even with low tumor fractions (TF). Generally, in samples with lower TF, art-existing methods are unable to accurately and reliably diagnose tumor diseases as the probability of detection is low. In contrast, the methods of the disclosure permit detection of markers and accurate diagnosis of tumor diseases at low tumor fractions, e.g., at $\frac{1}{1000}$, or $\frac{1}{10,000}$ or even $\frac{1}{20,000}$. The sensitivity of the methods and systems of the instant disclosure is particularly evidenced by the fact that even at very low tumor fractions (e.g., $\frac{1}{10,000}$ or less), the methods of the disclosure detects about 10 to 15 sSNVs contained in a single supporting read. This detection enables distinctions to be drawn between normal samples and tumor samples with a high level of fidelity and accuracy, which the art-existing tools fail to provide. It should be understood that diagnosis is not limited to sSNV detection. For instance, the diagnosis may be made based on the detection of about 10, 20, 30, 40, 50, 60, 70, 80, 90, 100 or more, e.g., 150, 200, or 250 copy altered segments (genome-wide) that are frequently observed in human cancers.

The disclosure especially relates to methods for early diagnosis of tumors characterized by a high rate of somatic mutations. Preferred types of tumors that may be diagnosed or detected in accordance with the present disclosure include, e.g., non-small-cell lung carcinoma (NSCLC), tobacco-induced cancer (TIC), UV light-induced cancer, a cancer mediated by apolipoprotein B mRNA editing enzyme catalytic protein (APOBEC) activity, a cancer comprising breast cancer protein (BRCA) mutation and/or a cancer comprising poly (ADP-ribose) polymerase (PARP) hyperactivity, a tumor comprising micro-satellite instability (MSI). The methods may be adapted to diagnose liquid tumors, solid tumors, or a mixture thereof, e.g., heterogeneous tumors comprising, for e.g., lymphomas that have metastasized to extra lymphatic organs, such as the liver, lungs, or brain, or the like.

The following tumors may be especially early diagnosed in accordance with the present disclosure: lung adenocarcinoma, ductal adenocarcinoma (breast tumor), cutaneous melanoma, urothelial carcinoma (bladder tumor) or osteosarcoma. Particularly, the tumor comprises non-small-cell lung carcinoma lung adenocarcinoma (NSCLC LUAD).

The disclosure especially relates to early diagnosis or detection of non-small cell lung carcinoma, preferably tobacco-induced cancers of the lung, which are characterized by a high rate of somatic mutations. Tobacco use (e.g., smoking or chewing) is a well-established risk factor or causative agent of epithelial cancers of the oral cavity, pharynx, larynx, esophagus, lung, stomach, cervix, and colon/rectum. See, Sasco et al., *Lung Cancer* 45, Suppl 2, S3-9, 2004.

The disclosure also relates to diagnosis or detection of UV-induced cancers, e.g., cancers of the skin. Exposure to ultraviolet (UV) radiation is associated with approximately 65% of melanoma cases, and 90% of non-melanoma skin cancers (NMSC), including basal cell carcinoma (BCC) and squamous cell carcinoma (SCC). See, Kim et al., *Genes & Disease,* 1(2):188-198, 2014. Preferably, the UV-induced cancer is selected from melanoma and SCC, both of which are characterized by a high rate of somatic mutations. See, Alexandrov et al., *Curr Opin Genet Dev.* 24, 52-60, 2014.

The disclosure also relates to early diagnosis of cancers having a high rate of somatic mutations due to perturbations in enzymes associated with gene editing/DNA checkpoint. In some embodiments, the disclosure relates to diagnosis of a cancer mediated by a gene editing enzyme, such as, e.g., apolipoprotein B mRNA editing enzyme catalytic protein (APOBEC). APOBEC-mediated mutational patterns are commonly found in bladder, cervical, breast, head and neck, and lung cancers. See, Roberts et al., *Nat Genet.,* 45(9):970-6, 2013.

In some embodiments, the disclosure relates to early diagnosis of a cancer mediated by breast cancer protein (BRCA) mutation, e.g., a cancer mediated by BRCA1 mutation or BRCA2 mutation or a combination thereof. Reports estimate that more than 50% of women with BRCA1 mutations will develop breast cancer by age 70 and more than $\frac{1}{3}$rd of them will develop ovarian cancer by that age. In addition to breast and ovarian cancer, BRCA2 mutation relates to risks of male breast and pancreatic cancers, and also melanoma. Both BRCA$\frac{1}{2}$ mutations associate with prostate cancer risk in males. See, Ngeow et al., *npj Genomic Medicine* 1, 15006, 2016.

In some embodiments, the disclosure relates to early diagnosis of cancers induced by microsatellite instability (MSI). MSI-induced cancers generally arise out of mutations in DNA mismatch repair genes (e.g., MLH1, MSH2 or MSH6) and are characterized by errors in repetitive sequences. MSI can occur in tumors of many organs, but it is mainly the hallmark of colorectal cancer. Kurzawski et al., *Annals of Oncology,* 15 (Supp. 4), 283-284, 2004. MSI is also observed in endometrial cancer, ovarian cancer, gastric cancer, sebaceous carcinoma, glioblastoma, lymphoma/leukemia, and a tumor of Lynch syndrome (hereditary nonpolyposis CRC (HNPCC)). Vilar et al., *Nat Rev Clin Oncol.,* 7(3): 153-62, 2010.

In some embodiments, the disclosure relates to early diagnosis of cancers induced by PPAR activity, e.g., mediated via compensatory homologous recombination activity of PARP. For example, certain tumors defective in homologous recombination mechanisms, may rely on PARP-mediated DNA repair for survival, and are sensitive to its inhibition PARP. Thus PARP inhibition is a potential synthetic lethal therapeutic strategy for the treatment of cancers with specific DNA-repair defects, e.g., those arising in carriers of a BRCA1 or BRCA2 mutation (Morales et al., *Crit Rev Eukaryot Gene Expr.,* 24(1): 15-28, 2014; Fong et al., *N Engl J Med.,* 361(2):123-34, 2009).

The diagnostic methods of the disclosure involve first receiving a subject's sample comprising a plurality of genetic markers. In some embodiments, the subject's sample containing DNA/RNA are sequenced and the genetic markers therein are received for analysis. In other embodiments, the genetic markers may be received from a dataset, e.g., genomic sequencing information that has been compiled and/or stored in a computer or remotely (e.g., in a server). The genetic markers may be received by sequencing a variety of samples. Preferably, the samples comprise biological samples, e.g., cells, tissues, organs, including, biological fluids, e.g., blood, plasma, lymph or the like. Alternately, the sample comprises a primary or metastatic tumor.

A variety of methods may be used to obtain the samples. Tissue biopsy is often used to obtain a representative piece of tumor tissue. Tumor cells can also be obtained indirectly in the form of tissues or fluids that are known or thought to contain the tumor cells of interest. For instance, biological samples of lung cancer lesions may be obtained by resection, bronchoscopy, fine needle aspiration, bronchial brushings, or from sputum, pleural fluid or blood. Tumor that has metastasized may be sampled from nearby tissues or lymph nodes (primary metastasis) or from parts of the body that are farther away (distant metastasis).

Preferably, the sample comprises plasma sample comprising circulating DNA and peripheral blood mononuclear cells (PMBC). In this context, the sample may be obtained from a subject using routine techniques, e.g., blood-draw (phlebotomy), biopsy (including liquid biopsy), surgical resection, tracheal swabbing, expectoration, etc. The samples thus obtained may be optionally processed, e.g., to purify and/or isolate markers that are useful in the diagnosis. The presence of cfDNA in a sample may be examined using routine methods, e.g., PCR using universal primers, followed by electrophoresis. The cfDNA in the subject's sample may be purified using routine techniques, e.g., DNA isolation kits described in the Examples section of the present disclosure.

In some embodiments, the sample comprises a biological fluid selected from blood, cerebral spinal fluid, pleural fluid, ocular fluid, urine, or a combination thereof.

In some embodiments, the samples containing somatic mutations in cfDNA are obtained using liquid biopsy technology (LBT), a transformative, non-invasive technique that allows for detection of tumor DNA in a patient's plasma cfDNA sample and permits characterization of the somatic malignant genome.

In a specific embodiment, the biological sample is a plasma sample comprising cell-free DNA (cfDNA). Typically, the amount of cfDNA in the sample is between about 0.1 ng/ml to about 20.0 ng/ml; preferably, between about 1 ng/ml to about 10 ng/ml. A normal cell sample comprising peripheral mononuclear blood cells (PMBC) may be used as a control. In both samples, genetic markers comprising single nucleotide variation (SNV) (preferably somatic SNV), copy number variation (CNV)(preferably somatic CNV), short insertions and deletions (indels), structural variants (SV) or a combination thereof may be analyzed.

In some embodiments, the genetic marker comprises a combination of SNVs and CNVs. Such combinations are typically employed in samples which contain a low SNV mutation load but high CNV load. In exemplary embodiments, samples containing an SNV mutation load of fewer than 8000 mutations per mega base pair (MBP) may be analyzed by additionally detecting CNVs. Typically, in such cases, a CNV load of at least 50 per mega base pair (MBP), e.g., at least 60, at least 70, at least 80, at least 90, at least 100 or more, e.g., 200, CNVs/MBP of DNA is desirable as it is likely to be of diagnostic significance.

As is known in the field of genetics, the significance of variations, e.g., SNV or CNV, is profoundly influenced by the distinction between germline and soma. Mutations in somatic (body) cells are not transferred to offspring. Mutations that occur in a somatic cell, for example in the lung, may damage the cell, make the cell cancerous or even kill the cell. However, mutated DNA can only be passed to the next generation if it is present in the germline of gametes. Therefore, comparing germline sequences (e.g., using it as a control) allows one to identify changes in somatic cells or cancer cells specific to that subject that are not present in noncancerous cells of that same subject. While comparisons between germline sequences and gamete sequences indicate variations, a comparison between cancerous cells and non-cancerous cells is also useful. For example, peripheral white blood cells or lymphocytes of the subject can be used as a control, as representing non-cancerous somatic cell sequences. In this manner, mutations found in both cancerous and non-cancerous cells can be ignored.

Preferably, the genetic markers of the disclosure, e.g., sSNV, sCNV, indels or SVs in cfDNA, may be detected by comparing the cfDNA sequence to a reference sequence, e.g., a germline DNA sequence.

In some embodiments, the methods of the disclosure may involve detection of variations between the genetic marker and a reference (e.g., a control) sequence. In some embodiments, variations may be uniform, semi-uniform or dynamic across samples. Variations that are temporally dynamic include, e.g., differences between cfDNA collected during treatment or after treatment compared to pretreatment samples.

Variations in the cfDNA may also be detected by generating a genome-wide compendium of genetic markers and subtracting therefrom, genetic markers present in the control (e.g., germline) sample. In this context, the term "genome-wide" refers to and includes the genetic material of an organism, both germline and somatic. The compendium of markers may include, e.g., a plurality of sSNV, sCNV, indels, SVs, including other variations such as fusions, etc. in the DNA.

Typically, the samples are characterized by low tumor fractions (TF). In some embodiments, the TF is between about 0.0001% to about 1%, preferably between about 0.001% to about 0.1% and especially less than 0.1%, e.g., 0.005%, 0.02%, 0.03%, 0.04%, 0.05%, 0.06%, 0.07%, 0.08%, 0.09%.

Additionally, the samples comprising cfDNA are characterized by a genomic equivalence (e.g., number of unique DNA fragments, as determined via random sampling of the entire pool of cfDNA fragments in the subject's sample) that is between about 100 to about 20,000; preferably between about 1000 to about 10000.

In some embodiments, the cfDNA samples are characterized by a mutation load (N) that is about 3,000 to about 100,000; preferably about 5000 to about 40000.

A representative method for generating genome-wide compendium may include sequencing. Typically, sequencing is performed using a purified nucleic acid sample. Especially, the genome-wide compendiums used in the diagnostic methods and/or systems of the disclosure are attained using whole genome sequencing. For example, WGS may be carried out using routine techniques and may include amplification (e.g., PCR amplification). Amplification-free sequencing may also be used using methods and reagents that are known in the art. See, Karlsson et al., *Genomics,* 105(3):150-8, 2015. Purely as an exemplary method, in some embodiments, the genetic markers in cfDNA may be detected by whole genome sequencing (WGS) the subject's tumor, whole genome sequencing (WGS) the subject's normal cells, admixing tumor and normal WGS reads in varying proportions to generate a dataset of subject-specific samples of different tumor fractions and coverage, and down sampling the dataset to generate a complementary dataset of down sampled normal reads without admixture of reads from tumor. The complementary dataset may be filtered by eliminating noise-associated markers, as described below.

Genome-wide compendiums of genetic markers may also be generated by targeted sequencing (TS) or a combination of WGS and TS.

The following publications, which relate to whole genome sequencing and/or targeted sequencing, are incorporated by reference herein in their entirety: U.S. Pat. Nos. 7,115,400; 7,718,403; 7,741,463; 8,932,812; 7,572,584; and 9,218,450.

Once the DNA samples are received, the diagnostic methods may be implemented. The genetic markers that are contained in the sample are preferably analyzed for mutations, e.g., somatic mutations. The most common type of somatic mutations in DNA is single-nucleotide variants (SNVs), which occur at a frequency of 1-100/Mbp (mega base pair). These variants are typically identified in shot gun sequencing data through a careful comparison of the DNA sequencing reads which map to a particular locus in the cancer sample and the germline normal DNA sample (control). This complex process has been developed using techniques/tools of ever-increasing sophistication that refine the statistical comparison between the number of supporting reads with the variant in the cancer and germline samples. See, Cibulskis et al., *Nature Biotechnology,* 31(3):213-219, 2013; Saunders et al., *Bioinformatics,* 28(14):1811-1817, 2012; Wilm et al., *Nucleic acids research,* 40 (22):11189-11201, 2012.

The analysis of variants may be carried out using a variety of techniques, including, but not limited to, array-based methods (e.g., DNA microarrays, etc.), real-time/digital/quantitative PCR instrument methods; and whole or targeted nucleic acid sequencing systems (e.g., whole genome sequencing (WGS) services offered by Illumina, Helicos Biosciences, Pacific Biosciences, Complete Genomics, Sequenom, ION Torrent Systems, Halcyon Molecular).

Preferably, the genetic markers are analyzed for somatic mutations and/or copy number variations using whole genome sequencing (WGS). Whole genome sequencing methods are able to resolve genetic reads at single base resolution. In the context of DNA (deoxyribonucleic acid), the methods resolve reads at the level of DNA's basic constituents, e.g., A (adenine), T (thymine), C (cytosine), and G (guanine). In the context of RNA (ribonucleic acid), the methods resolve reads at the level of DNA's basic constituents, e.g., A, U (uracil), G, and C.

The products of the aforementioned sequencers/sequencing methods comprise "sequencing data" "sequencing information" or "sequencing reads" which include information about the order of one or more of the aforementioned bases in a polynucleotide molecule (e.g., whole genome, whole transcriptome, exome, oligonucleotide, polynucleotide, fragment, etc.). By comparing the order of the read of DNA in a sample (e.g., cfDNA contained in a patient's plasma sample) to a control (e.g., whole genome sequence of PMBC), genetic markers (e.g., somatic SNV or somatic CNV) of interest can be identified. It should be understood that the presently disclosed identification methods are applicable with all types of sequencing techniques, platforms or technologies, including, but not limited to, capillary electrophoresis, microarrays, ligation-based systems, polymerase-based systems, hybridization-based systems, direct or indirect nucleotide identification systems, pyrosequencing, ion-based or pH-based detection systems, electronic signature-based systems, etc.

The next step in the early diagnostic method of the disclosure comprises identifying low abundance, tumor-specific markers.

The instant disclosure relates to determination of error probability in a read based on a plurality of factors selected from (1) base-quality (BQ) of the read, (2) mapping-quality (MQ) of the read; and/or (3) estimated fragment size of the read (4) estimated allele fraction of the read (VAF), which either solely or together affect the quality of signal. Other secondary parameters such as (5) position in the read (PIR); (6) sequence context (SC); (7) abundance; (8) sequencing depth and/or (9) sequencing error, may also be employed.

Generally, base quality (BQ) relates to a confidence of the sequencing quality at each base and the mapping-quality (MQ) score relates to a confidence estimate regarding the accuracy of the mapping of the marker with the genome. In the context of sSNV markers, the base quality (BQ) score is a measure of the quality of the identification of the nucleobases generated by automated DNA sequencing. It may be determined using routine methods, e.g., Phred quality scores, which are assigned to each nucleotide base call in automated sequencer traces. Phred quality scores (Q) are defined as a property which is logarithmically related to the base-calling error probabilities (P). For example, if Phred assigns a quality score of 30 to a base, the chances that this base is called incorrectly are 1 in 1000. Typically, the BQ of a sequencing read is between 10 and 50, e.g., a BQ score of 10, 15, 20, 25, 30 35 or 40.

Also in the context of sSNV markers, the mapping quality (MQ) score is a measure of the confidence that a read actually comes from the position it is aligned to by the mapping algorithm. It may be determined using routine methods, e.g., mapping quality scores (see, Li et al., *Genome Research* 18:1851-8, 2008). Typically, the MQ of a read is between 10 and 50, e.g., a MQ score of about 10, 15, 20, 25, 30, 35, or 40.

In some embodiments, the noise removal step comprises implementing an optimal receiver operating characteristic (ROC) curve which comprises a probabilistic classification of the genetic markers in the compendium based on a joint base-quality (BQ) and mapping-quality (MQ) score. Typically, the joint BQMQ score is provided as a matrix (x, y), wherein x is the BQ score and y is the MQ score. In exemplary embodiments, a joint BQMQ score between 10 and 50 (for each parameter) is typically employed, e.g., a BQMQ score of (10, 40), (15, 30), (20, 20), (20, 30), (30, 40).

Noise removal step may include implementation of additional filters. For example, an extra source of information contained in the read-pair that comes from the DNA fragment can be used to determine both the strand of origin (Watson or Crick) and to estimate the DNA fragment size. It has been observed that ctDNA have a distinct fragment size distribution compared to regular circulating healthy DNA (Underhill et al., *PLoS genetics,* 12(7):e1006162, 2016). More specifically, fragment lengths from cell-free DNA between a tumor patient and healthy controls found that the mutant alleles occurred more commonly at a shorter fragment length than the fragment length of the wild-type allele. Similarly, size-selecting for shorter cell-free DNA fragment lengths substantially increased the mutant allele frequency in human lung cancer (Jiang et al., *PNAS USA,* 112.11, E1317-E1325, 2015; Mouliere et al., *bioRxiv,* 134437, 2017; Underhill, supra). Accordingly, specific subsets of fragment lengths from cell-free DNA detection may be used to improve ctDNA detection. In some embodiments, the fragment sizes of the reads are preferably less than 160 bp, e.g., 160 bp, 140 bp, 120 bp, 100 bp, 75 bp, 50 bp, or less, e.g., 20 bp.

Additionally, artefactual noise may be eliminated based on variable allele frequency (VAF). In some embodiments, low allele-fraction mutation sites are removed from the sample, e.g., a VAF of about 1% or less. In some embodiments, only markers (e.g., SNVs) having a threshold VAF are retained for downstream analysis. For instance, mutation sites with a VAF of at least 1%, at last 2%, at least 3%, at least 4%, at least 5% (as determined via amplicon sequencing on a PGM instrument) may be retained. As it is known in the art, VAF values of a particular allele (e.g., BRAF V600R) are not static and may change in time (due to cancer development and/or progression) and also due to therapy, e.g., immunotherapy, chemotherapy or targeted therapy. However, a threshold VAF of less than 1%, e.g., a VAF of 0.05, 0.1, 0.2, 0.3, 0.4, 0.5, 0.6, 0.7, 0.8, can be reliably used to estimate that the particular allele is not associated with a tumor.

In one specific embodiment, artefactual noise is removed by performing one or more, preferably all of the following steps: (a) removing low mapping quality reads (e.g., <29, ROC optimized); (b) building duplication families (e.g., representing multiple PCR/sequencing copies of the same DNA fragment) and producing corrected read based on a consensus test; (c) removing low base quality reads (e.g. <21, ROC optimized); and/or (d) removing high fragment size reads (e.g. >160, ROC optimized).

In addition to using the aforementioned BQ/MQ, VAF, and fragment size filters, other factors such as read position (RP or PIR) may be used to filter artefactual noise since RP affects the quality of the signal. In the context of sSNV markers, RP may be mapped, for example, by mapping the position of the initial base of the sequencing read. Other factors that influence marker quality include, e.g., specific sequence contexts that are associated with higher probability of sequencing errors (Chen et al., *Science,* 355(6326):752-756, 2017). In this regard, true mutations are frequently mappable to their own specific sequence contexts, while errors are not. For example, tobacco related mutations tend to occur at CC contexts, and mutations related to the activity of APOBEC enzyme prefer the TpC context for inserting somatic mutations (see, Greenman et al., *Nature,* 446(7132): 153-158, 2007). Thus, sequence context may be used to help identify changes that are more likely to result from sequencing artifacts as well as changes more likely to result from prevalent mutational processes.

In some embodiments, the markers may be further weighed by measuring the probability of detection based on the Bernoulli equation $P_D=1-[(1-TF)]^{GE}$, wherein $P_D$ is the probability of detection, TF is tumor fraction and GE is the number of genomic equivalents present in the patient DNA. The genetic markers are then weighted based on the $P_D$, wherein, markers with high $P_D$ are binned. For example, the genetic markers may binned based on a $P_D$ threshold value of at least about 0.60, e.g., at least about 0.65, 0.70, 0.75, 0.80, 0.90, 0.95, or more, e.g., at least about 0.98. Accordingly, if the $P_D$ of a marker is less than the threshold value, then it may be classified as a false positive and not included in the analysis.

Once the artefactual noisy reads are removed from the compendium of reads, the remnant markers are fed into a deep learning inference model trained to separate between tumor related signatures and PCR/sequencing error signatures. This step involves classifying, in a read-based manner, cancer-mutation supporting reads and artefactual-mutation (error) reads. In one embodiment, the sequence-context distribution of the cancer-mutation supporting reads is calculated and the contribution of known mutational signatures is classified using machine learning (ML).

The reads that have been noise filtered for artefacts and/or classified as being supported by cancer mutations, are matched to cancer signatures. In some embodiments, a dataset comprising such cancer signatures (e.g., Catalog of Somatic Mutations in Cancer; COSMIC) may be used. As of February 2018, 30 distinct cancer signatures have been accessioned in the database, the details of which are summarized below:

Signature 1 (found in all cancer types) is the result of an endogenous mutational process initiated by spontaneous deamination of 5-methylcytosine;

Signature 2 (found in 22 cancer types) has been attributed to activity of the AID/APOBEC family. On the basis of similarities in the sequence context of cytosine mutations caused by APOBEC enzymes in experimental systems, a role for APOBEC1, APOBEC3A and/or APOBEC3B in human cancer appears more likely than for other members of the family;

Signature 3 (breast, ovarian, and pancreatic cancer) is associated with failure of DNA double-strand break-repair by homologous recombination;

Signature 4 (head and neck cancer, liver cancer, lung adenocarcinoma, lung squamous carcinoma, small cell lung carcinoma, and oesophageal cancer) is associated with smoking and its profile is similar to the mutational pattern observed in experimental systems exposed to tobacco carcinogens (e.g., benzo[a]pyrene). Signature 4 is likely due to tobacco mutagens;

Signature 5 (etiology unknown) has been found in all cancers and most cancer samples;

Signature 6 (found in 17 cancer types and is most common in colorectal and uterine cancers) is associated with defective DNA mismatch repair and is found in microsatellite unstable tumors;

Signature 7 (skin cancers and in cancers of the lip; head and neck or oral squamous cancers) is associated with ultraviolet light exposure;

Signature 8 (found in breast cancer and medulloblastoma) has unknown etiology;

Signature 9 (found in CLL and malignant B-cell lymphomas) is attributed to polymerase q, which is implicated with AID activity during somatic hypermutation;

Signature 10 (found in six cancer types, notably colorectal and uterine cancer) is due to altered activity of the error-prone polymerase POLE. Recurrent POLE somatic mutations, Pro286Arg and Val411Leu, are mostly associated with Signature 10 mutations;

Signature 11 (found in melanoma and glioblastoma) exhibits a mutational pattern resembling that of alkylating agents;

Signature 12 (found in liver cancer) has unknown etiology;

Signature 13 (found in 22 cancer types and seems to be commonest in cervical and bladder cancers) has been attributed to activity of the AID/APOBEC family of cytidine deaminases converting cytosine to uracil;

Signature 14 (etiology unknown) has been found in four uterine cancers and a single adult low-grade glioma sample;

Signature 15 (found in several stomach cancers and a single small cell lung carcinoma) is associated with defective DNA mismatch repair;

Signature 16 (found in liver cancer) has unknown etiology;

Signature 17 (found in oesophagus cancer, breast cancer, liver cancer, lung adenocarcinoma, B-cell lymphoma, stomach cancer and melanoma) has unknown etiology;

Signature 18 (found in neuroblastoma and also observed in breast and stomach carcinomas) has unknown etiology;

Signature 19 (found in pilocytic astrocytoma) has unknown etiology;

Signature 20 (found in stomach and breast cancers) is associated with defective DNA mismatch repair;

Signature 21 (found in stomach cancer) has unknown etiology;

Signature 22 (found in urothelial (renal pelvis) carcinoma and liver cancers) is associated with exposures to aristolochic acid;

Signature 23 (found in liver cancer) has unknown etiology;

Signature 24 (found in subset of liver cancer) is associated with exposures to aflatoxin;

Signature 25 (found in Hodgkin's lymphoma) has unknown etiology;

Signature 26 (found in breast cancer, cervical cancer, stomach cancer and uterine carcinoma) is associated with DNA mismatch repair;

Signature 27 (found in subset of kidney clear cell carcinomas) has unknown etiology;

Signature 28 (found in stomach cancer) has unknown etiology;

Signature 29 (found in in gingivo-buccal oral squamous cell carcinoma) is associated with people who chew tobacco;

Signature 30 (found in a small subset of breast cancers) has unknown etiology.

In some embodiments, the matching step involves linear mixture optimization (e.g., the zscore confidence estimation of a contribution by tobacco exposure or BRCA mutation or APBEC1 activity) is used to calculate the confidence metric for the contribution of a COSMIC mutational signature. Purely as a representative, non-limiting example, linear optimization problem may be solved using an algebraic function, min∥Ax−b∥, x≥0, where A is the mutational signature sequence context matrix, x is the contribution of each cosmic mutational signature (the variable) and b is the patient specific sequence context compendium.

In some embodiments, in the linear optimization method used above, A may include any number of cosmic signatures, including, random mutational signatures. For instance, A may include about 20, 30, 40, 50, or more, e.g., 70 cosmic signatures and about 50, 60, 80, 100, or more, e.g., 150 random mutational signatures. The distribution of the contribution of random signatures is calculated using extraction methods, e.g., E_random, which computes average contribution score; and std_random, which computes standard contribution score. The confidence associated with the contribution of each cosmic signature may be computed statistically, e.g., using zscore. For example, the Z score may be computed as (cosmic_sig_contribution−E_random)/std_random. Accordingly, as in a permutation score, the Z score represents the significance of a signature contribution in comparison to the random set.

In some embodiments, a similarity of the patient sequence-context compendium to a specific cosmic signature is calculated using statistical methods, e.g., probability density function (PDF). Purely as a representative example, to compute PDF, patient sequence-context compendium is normalized to generate a density function. The cosine-similarity between the patient sequence-context density function and the cosmic signature density function is calculated. The cosine-similarity is then normalized by dividing by the cosine similarity between the patient sequence-context density function and non-informative uniform density function.

In step 160 of method 100 of FIG. 1A, the confidence estimate calculated in step 150 is used to screen the subject for cancer, e.g., early detection of tumor. As is known in the art, confidence intervals consist of a range of values (interval) that act as good estimates of the unknown population parameter (e.g., likelihood that a non-symptomatic subject has cancer). The desired level of confidence is set by the researcher (not determined by data). Most commonly, the 95% confidence level is used; however, other confidence levels can be used, for example, any value between 80% and 99%, e.g., 80%, 90%, 98% or even 99%.

In some embodiments, the confidence interval may be unitary (e.g., based on a single read) or composite (e.g., based on multiple reads). Confidence bands or confidence regions may also be used. Confidence regions generalize the confidence interval concept to deal with multiple quantities and may be useful to reveal extent of likely sampling errors and/or unreliability of a quantity used in statistical analysis. Confidence bands may be used to represent the uncertainty in an estimate of a curve or function based on limited or noisy data; prediction bands may be used to represent the uncertainty about the value of a new data point on the curve (subject to noise).

Optionally, the computed confidence metric for the contribution of a COSMIC mutational signature may be checked against a detection threshold. In some embodiments the threshold is defined by empirically measured basal noise detection estimations from healthy samples, e.g., a zscore of at least 2 standard deviations (STD) above threshold, particularly at least 3 STD above threshold, preferably at least 4 STD above threshold, and especially at least 5 STD above threshold, is indicative that the confidence metric is significant.

Purely by the way of illustration, in an exemplary embodiment, the methods of the disclosure relate to diagnosing a tumor in a subject by first receiving a plurality of genetic markers sequenced from a biological sample of the subject (e.g., a sample comprising a plasma sample and a normal cell sample) to generate a subject-specific genome-wide compendium of genetic reads containing markers (e.g., sSNVs, CNVs, indels, and/or SVs); and filtering artefactual noise from the compendium of reads using one or more of the parameters selected from BQ, MQ, position in read (PIR), fragment size and/or VAF; inputting the noise-removed reads into a neural network that can discriminate true markers from noise generated by PCR and/or sequencing errors; generating a filtered, noise-removed subject-specific signature which is matched to a cancer signature (e.g., COSMIC signature), wherein the matching comprises computation of zscores for all markers or a subset thereof OR assessment of probability density function between the subject's signature and reference cancer signature; outputting a confidence interval, which is indicative that the subject's signature comprises a tumor signature, thereby diagnosing the tumor in the subject. A representative method is illustrated in the flowchart of FIG. 1A. The details of this method are provided in the examples below.

In some embodiments, the cancer signature may include patterns associated with tissue specific epigenetic pattern, such as tissue specific chromatin accessibility pattern (e.g., methylation status).

In some embodiments, the diagnostic methods may further employ karyotyping. For instance, datasets comprising tumor-specific, low abundance markers may be further karyotyped, e.g., by eliminating markers that are proximal to the centrosome. This step may be carried out using the mapping technique described above. Additionally, the dataset comprising low-abundance markers may be orthogonally integrated with aneuploidy markers, e.g., markers which are indicative of gene amplifications or gene deletions.

Systems and Devices for Implementing the Diagnostic/Screening Methods

The methods described herein such as, for example, method 100, can be can be implemented using computer system 400 as a standalone device or on a distributed network of shared computer processing resources such as a cloud computing network. As such, a non-transitory computer-readable medium can be provided in which a first program is stored for causing a computer to perform the disclosed methods for removing artefactual noise (e.g., associated with low BQ/MQ markers, markers that are larger than a threshold fragment size of about 160 bp; and markers that have VAF less than a threshold value of about 4%). The non-transitory computer-readable medium can be provided in which a second program is stored for adaptively and systematically filtering noise (e.g., associated with PCR/sequencing errors). The non-transitory computer-readable medium can be provided in which a second program is stored for matching the noise-filtered, CNN-processed subject-specific signature with a cancer signature, e.g., by determining zscores or by analyzing probability density function, and outputting a confidence interval (CI) for the match, wherein a CI that is $\geq$a threshold value (e.g., 80%, 90%, 95%, or 99%) is indicative that the subject is afflicted with the tumor. In some embodiments, each of the first, second, third, programs may be provided or used separately (e.g., in standalone form); in some embodiments, each of the first, second, third, programs may be provided or used together (e.g., as a package).

It should also be understood that the preceding embodiments can be provided, whole or in part, as a system of components integrated to perform the methods described. For example, the workflow of FIG. 1A can be provided as a system of components or stations for identifying high-quality low-abundance, tumor-specific markers present in cfDNA of cancer patients and further enabling early diagnosis in a sensitive, precise and accurate manner.

As detailed above, one of the salient features of the systems and methods of the disclosure is use of an Engine that can adaptively and systematically filter noise. A representative Engine is described in detail below. The Engine may be implemented in the diagnostic method of the disclosure (as discussed in detail below) according to, for example, the flow chart of FIG. 1A (Note: the positioning of Engine in the flowchart is only exemplary so as to fit the representative methodology). The Engine may comprise a convolutional neural network (CNN) that is able to capture the invariance in the markers (e.g., somatic mutations comprising sSNV). The CNN, and its corresponding architecture, will be discussed in detail below with reference to the section entitled "Convolutional Neural Network (CNN)."

The ability of Engine to eliminate low quality markers may be evaluated across synthetic plasma samples as well as real plasma DNA samples. The synthetic plasma samples may be generated from test sample (e.g., lung sample) by randomly sampling from the patient's healthy DNA and from the patient's tumor DNA. For real plasma DNA analysis, plasma samples obtained from a tobacco smoking lung cancer patients may be used. For controls, the patient's PMBC may be used. Alternately, plasma samples obtained from non-cancer or healthy subjects may be used as controls.

Figure 5:
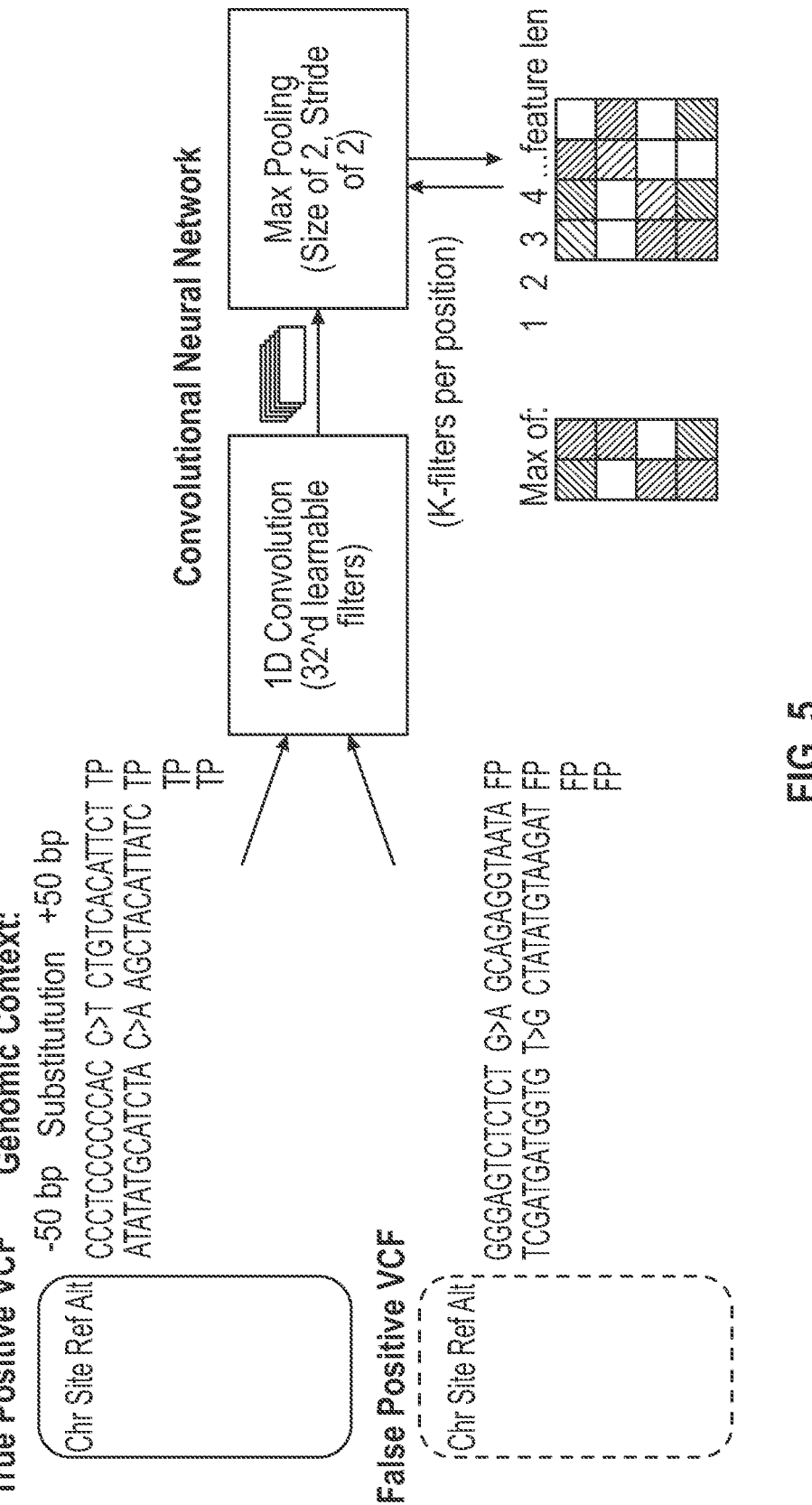
FIG. 5 provides a chart of deep learning based de-novo mutation detection and noise suppression.

An exemplary outline of how machine learning (ML) may be used to suppress noise de novo (e.g., errors during amplification (PCR), errors during sequencing, errors in mapping, and other false positive markers such as mutations seen in control samples) and detect mutations in subject's samples is provided in FIG. 5. As shown, genetic data is received from subjects in an appropriate format (e.g., variant called VCF format), which may be true positive or false positive. These data are inputted into a machine learning tool, e.g., n dimensional convolutional neural network (CNN). The CNN may have K-filters per position and a total of $32^D$ learnable filters, wherein D is the number of dimensions in the CNN. The genetic data are max pooled, e.g., using a size of 2 and a stride of 2. The sequencing reads are captured using any method for representation in discrete features. For example, a spatially-oriented representation comprising a maximum of 1, 2, 3, 4 . . . n feature lengths may be used.

An exemplary feature is provided in FIG. 8. As shown, the first five rows represent the reference context (e.g., the sequence in the human genome), the next five rows represent the read sequence (base pairs in the read), rows 11-15 represent the alignment string (CIGAR), and the final row represents the quality score at each position in the read. Each column of the feature represents an indicator vector referring to the presence or absence of a specific base. The read, genomic context, and CIGAR rows are mutually exclusive, such as in a one-hot encoding. The details on the construction and implementation of the feature are provided in the representative Examples below.

Engine may be used as a stand-alone tool or together with other art-known mutation callers such as PILEUP (Li et al., *Bioinformatics,* 25(16):2078-2079, 2009), STRELKA (Saunders et al., *Bioinformatics,* 28(14):1811-1817, 2012), LOFREQ (Wilm et al., *Nucleic acids research,* 40 (22): 11189-11201, 2012), etc. An exemplary outline of the position and input/output of Engine is shown in FIG. 7. Note: although Engine is positioned at the distal end of the pipeline in this figure, in actuality, Engine may be placed at any level or stage in the process. To train ENGINE, genetic data containing a compendium of markers from admixed tumor biopsy sample and peripheral blood mononuclear cells (PMBC; controls) is optionally subjected to the aforementioned filters (e.g., artefactual read cataloging via PILEUP; excluding germline variations using VAF; elimination of markers of low base quality using appropriate BQ filters; and elimination of markers poorly mapped using appropriate MQ filters). The machine may also be trained with datasets.

Figure 8A:
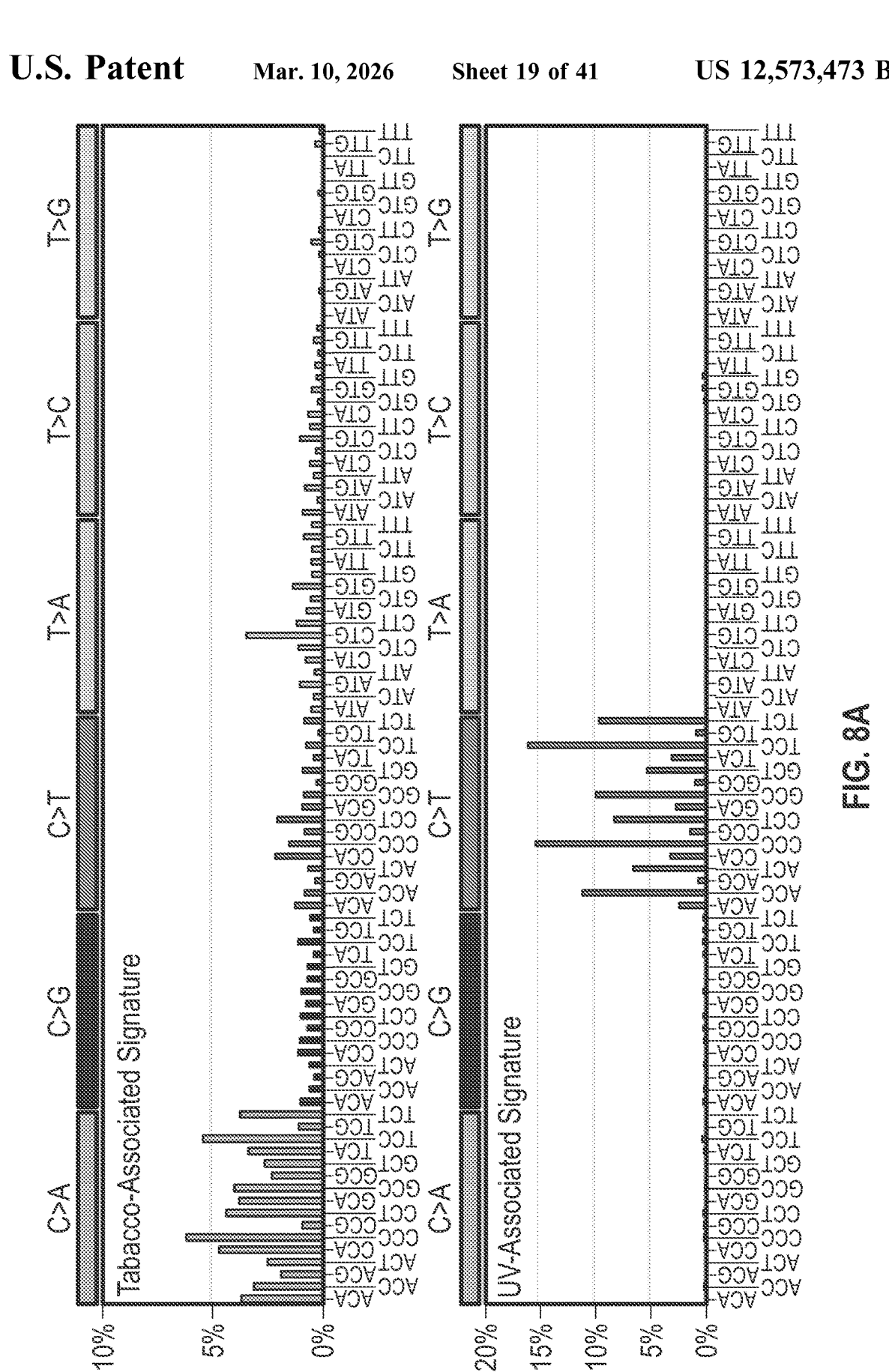
FIG. 8A shows COSMIC signatures associated with tobacco (top) and melanoma (bottom) from Alexandrov et al. (supra, 2013).

When Engine was implemented using independent samples from lung cancer patients, it was found to discriminate between true somatic mutations and noise with high degree of sensitivity and precision. Results are shown in FIG. 8 and FIG. 9. Experiments conducted with synthetic plasma reveals that Engine is especially precise and sensitive at low tumor fractions (TF) and is superior to state-of-the art callers such as MUTECT (Cibulskis et al., *Nature biotechnology,* 31(3):213-219, 2013) and/or PILEUP. In particular, Engine showed strong performance in both in silico analysis as well as in the clinical setting. Engine performed particularly well compared to programs such as MUTECT in the balanced tumor fraction setting. For example, on sensitivity metrics, it was superior to MUTECT, SNOOPER (Spinella et al., *BMC Genomics,* 17(1):912, 2016) and STRELKA. See, FIG. 9A. In precision metrics, it was superior to PILEUP at all tumor fractions and roughly by about 25-fold in low TF (TF=0.0001). It further maintained a large portion of its performance even in the simulated plasmas. Engine also achieved an enrichment of about 30-fold in TF of 0.0001 (over PILEUP), suggesting the ability to capture relevant somatic mutations even when they are 10 times rarer than sequencing noise itself. See, FIG. 9C. In contrast, MUTECT provided a modest improvement of about 2-fold (compared to PILEUP) in all tumor fractions. Further, Engine allows the user to minimize false negatives, and for applications for which specificity is a priority, Engine can be set to minimize false positives. The Engine variant identification system can simultaneously minimize false positives and false negatives, detecting variants with unmatched precision and accuracy (see summary in Table 4).

Particularly, Engine can be applied, optionally together with noise cancellation filters such as mutational frequency (MF) filters and/or base quality mapping quality (BQMQ) filters, to significantly improve the precision of the art-known mutational callers. A representative pipeline employing the mutational caller PILEUP, together with downstream noise-cancellation filters and Engine, is described in the examples section below. In the context of real plasma samples, the aforementioned pipeline comprising PILEUP, noise cancellation filters (based on mutational frequency (MF) and quality (BQMQ)) and Engine significantly suppresses false positives while significantly enriching the sample for tumor DNA analysis. Taken together, these results demonstrate that Engine can be used to greatly improve the performance of mutational callers while suffering little, if any, loss in sensitivity.

The performance of Engine shows that integrating features across a read and its alignment has set the stage for a new set of somatic mutation callers using the full mutational profile of a sample, rather than just those which are covered with high depth. Capturing mutations at such a sensitive level with a simple measurement tool allows for new and improved diagnostic platforms which can be used in the therapy and/or management of cancer patients.

The present disclosure relates to at least three potential applications of Engine, namely improved somatic SNV mutation detection, especially in cancer diagnosis, prognosis and care, and other clinical contexts; improved structural variant detection for genetic disease diagnosis and disease risk estimation; and/or improved germline genomic SNV detection in biomedical research, disease diagnosis, and/or therapy. See, FIG. 10.

Based on the state of the prior art, Engine is the first somatic mutation caller designed to function in the low allele frequency setting, such as liquid biopsy for early stage cancer detection. To achieve the early-detection goal, a novel representation of a read-along was implemented with a custom architecture so as to best capture the expected features associated with a read and its alignment. Accordingly, the disclosure provides a new family of somatic mutation callers to aid detection in liquid biopsy, paving the way for pivotal, non-invasive methods for cancer diagnostics, especially in the context of early tumor detection and also detection of residual tumors.

Computer Systems

Figure 15:
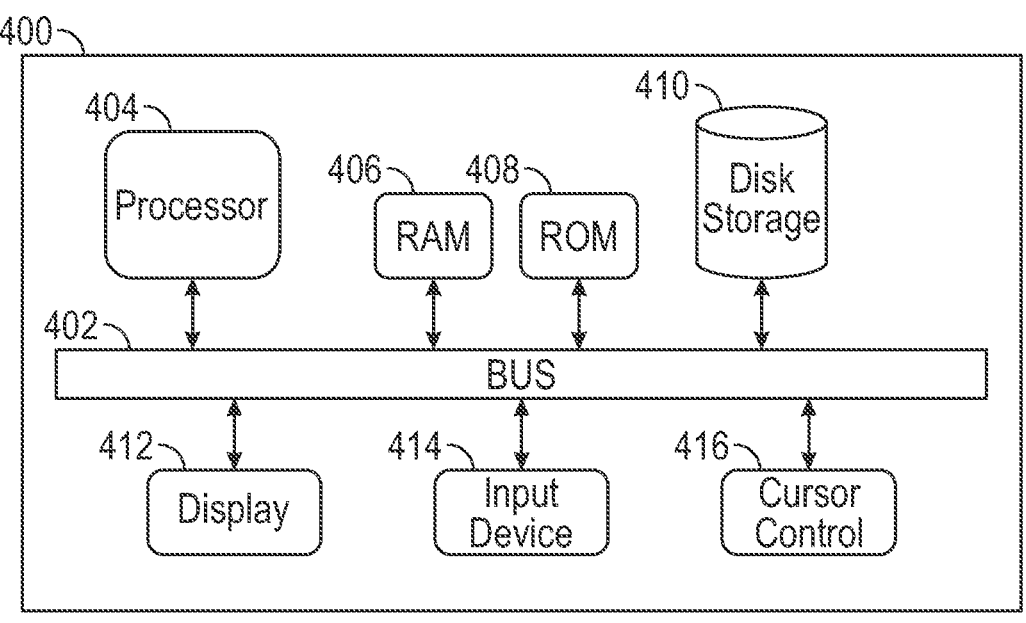
FIG. 15 provides a schematic representation of the computer systems of the instant disclosure.

In some embodiments, the diagnostic methods of the disclosure are implemented on a computer system. Purely as a representative example, the schematic representation of such computer systems is provided in FIG. 15. FIG. 15 is a block diagram that illustrates a computer system 400, upon which, embodiments or portions of the embodiments, of the present disclosure may be implemented. In various embodiments of the present disclosure, computer system 400 can include a bus 402 or other communication mechanism for communicating information, and a processor 404 coupled with bus 402 for processing information. In various embodiments, computer system 400 can also include a memory, which can be a random access memory (RAM) 406 or other dynamic storage device, coupled to bus 402 for determining instructions to be executed by processor 404. Memory also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions. In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a trackball or cursor direction keys for communicating direction information and command selections to processor 404 and for controlling cursor movement on display 412. This input device 414 typically has two degrees of freedom in two axes, a first axis (e.g., x) and a second axis (e.g., y), that allows the device to specify positions in a plane. However, it should be understood that input devices 414 allowing for 3 dimensional (x, y and z) cursor movement are also contemplated herein.

Consistent with certain implementations of the present disclosure, results can be provided by computer system 400 in response to processor 404 executing one or more sequences of one or more instructions contained in memory 406. Such instructions can be read into memory 406 from another computer-readable medium or computer-readable storage medium, such as storage device 410. Execution of the sequences of instructions contained in memory 406 can cause processor 404 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 404 for execution. Such a medium can take many forms, including but not limited to, non-volatile media, volatile media, and transmission media. Examples of non-volatile media can include, but are not limited to, optical, solid state, magnetic disks, such as storage device 410. Examples of volatile media can include, but are not limited to, dynamic memory, such as memory 406. Examples of transmission media can include, but are not limited to, coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, data can be provided as signals on transmission media included in a communications apparatus or system to provide sequences of one or more instructions to processor 404 of computer system 400 for execution. For example, a communication apparatus may include a transceiver having signals indicative of instructions and data. The instructions and data are configured to cause one or more processors to implement the functions outlined in the disclosure herein. Representative examples of data communications transmission connections can include, e.g., telephone modem connections, wide area networks (WAN), local area networks (LAN), infrared data connections, NFC connections, etc.

It should be appreciated that the methodologies described herein, including flow charts, diagrams and accompanying disclosure can be implemented using computer system 400 as a standalone device or on a distributed network of shared computer processing resources such as a cloud computing network.

Systems

Figure 16A:
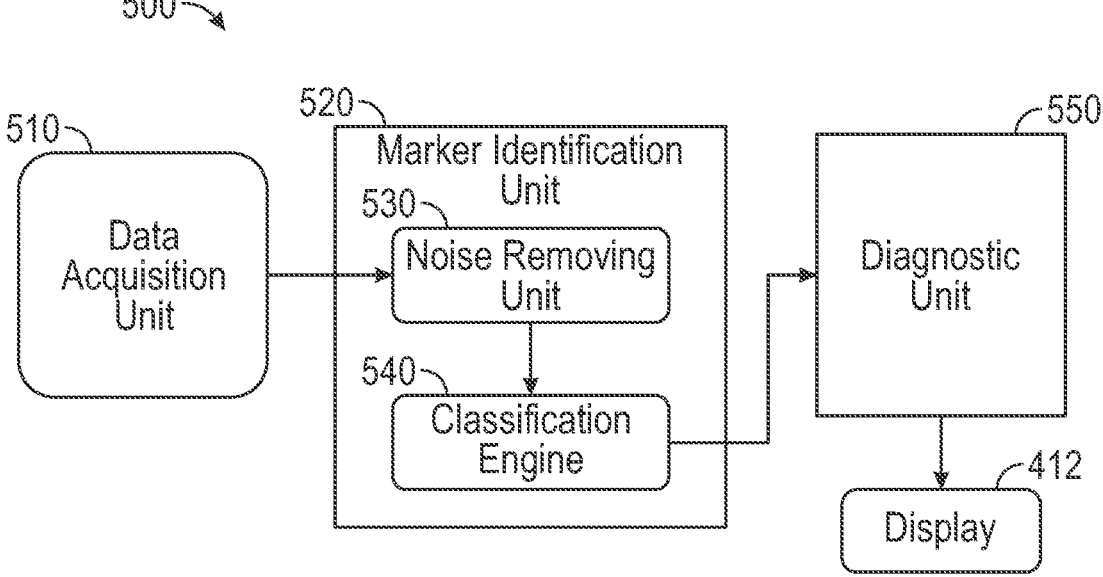
FIG. 16A-16C provide schematic representations of the various systems of the instant disclosure. Shown are the various units contained in the representative systems.

The disclosure further relates to systems for carrying out the methods of the disclosure. Representative systems are provided in the schematic diagrams of FIG. 16A-16C. FIG. 16A illustrates an exemplary system for implementing the diagnostic method of the disclosure. As depicted herein, a system 500 is provided that can include a data acquisition unit 510, a marker identification unit 520, a diagnosing unit 550, and a display 412 for outputting data and receiving user input via an associated input device (not pictured). Marker identification unit 520 can include a noise removing unit 530 and a classification engine 540. It should be noted that FIG. 16A illustrates one configuration of a system. The orientation and configuration of these components can vary as needed. Moreover, additional components can be added to this system (e.g., a convolutional neural network). These various components, their various operations, their various orientations, and various associations between each other will be discussed in detail below.

Data acquisition 510 unit of FIG. 16A can be configured and arranged to receive a genetic compendium from a subject, for example, a plurality of genetic markers sequenced from a biological sample comprising a plasma sample and a normal cell sample of the subject to generate a subject-specific genome-wide compendium of genetic markers. In some embodiments, the compendium of genetic markers is received in a variant call format (VCF) file in a physical disk (e.g., compact disk, DVD) or via the internet (e.g., as provided by a server or cloud). In some embodiments, the subject's sample is sequenced, e.g., using whole genome sequencing (WGS), and the sequence file is directly transmitted to data acquisition unit 510. In some embodiments, data acquisition unit 510 can reformat, organize, categorize or otherwise reconfigure the received data for further analysis within system 500. In some embodiments, unit 510 can receive data, for example, via display 412, a data or user input associated therewith, a memory associated therewith, or another memory component associated with computer system 400.

Data acquired by data acquisition unit can be transferred to the marker identification unit 520. Marker identification unit 520 can include one or more engines for analyzing the markers in the subject-specific compendium of genetic markers. Noise removing unit 530, as one of those components of unit 520, can include one or more programs for filtering artefactual noise by weighing markers on the basis of BQ, MQ, fragment size and/or VAF, including, one or more of the secondary features detailed above, e.g., position in the read (RP); sequence context (SC); abundance; sequencing depth and/or sequencing error. Preferably, the noise removing unit includes programs for computing optimal receiver operating characteristic (ROC) curve which includes probabilistic classification of the genetic markers in the compendium based on a score, e.g., joint base-quality (BQ) and mapping-quality (MQ) score, which are integrated with fragment size score and/or VAF score. The noise removing unit may include programs for measuring area under an ROC curve (AUC), which typically represents the probability that a candidate marker, randomly selected among potential markers, shows a value higher than a randomly-extracted control marker. The classifier may include programs for evaluating whether a particular binned marker is a "chance" marker or a "true" marker based on the ROC curve.

In some embodiments, the noise removing unit may weigh markers based on a probability score ($P_D$). Preferably, the program measures the probability of detection ($P_D$) based on the Bernoulli equation $P_D = 1 - [(1-TF)]^{GE}$, wherein $P_D$ is the probability of detection, TF is tumor fraction and GE is the number of genomic equivalents present in the patient DNA. Each genetic marker may be weighted based on the $P_D$, wherein, markers with highest $P_D$ are binned. For example, the genetic markers may be binned based on a $P_D$ threshold value of at least about 0.60, e.g., at least about 0.65, 0.70, 0.75, 0.80, 0.90, 0.95, or more, e.g., at least about 0.98. Accordingly, if the $P_D$ of a marker is below the threshold value, then it may be classified as a false positive and not included in the analysis.

Marker identification unit 520 may include a classification engine 540, which can examine, for example, the likelihood that a marker is associated with noise. The classifier may include a classification scheme comprising an algorithm or neural network that can adaptively recognize erroneous markers (e.g., errors due to PCR or sequencing). In one specific embodiment, classification unit 540 comprises a deep convolutional neural network (CNN) to adaptively and/or systemically filter sequencing noise that can affect accurate detection of tumor-specific low abundance markers. The CNN can be provided as a separate engine within marker identification unit 520, or can be provided as separate unit, for example, between marker identification unit 520 and diagnosing unit 550. The features of the CNN (not illustrated in FIG. 16A) are described in detail below.

Finally, a subject-specific signature comprising markers that are noise-filtered and processed by CNN can be provided as a file to diagnosing unit 550, which is configured and arranged to diagnose a disease (e.g., tumor disease) based on a statistical score that is indicative a match between the subject-specific signature and a cancer signature. The diagnosing unit may contain a repository containing cancer signatures, e.g., Catalogue of Somatic Mutations in Cancer (COSMIC) database or Latin-American Consortium for the Investigation of Lung Cancer (CLICaP) database. The diagnosing unit 550 may contain one or more software or algorithm for comparing between known cancer mutation signatures (e.g., any one of Signatures 1 to 30 of COSMIC) and the subject-specific mutation signature. Representative examples of such comparison software include, e.g., measurement of confidence estimation at the level of the individual marker as well as a pool comprising, 2, 5, 10, 20, 50, 100, 200, 500, 1000 or more, e.g., 5000 unique markers. Representative methods include, estimation of the Z score confidence level using linear optimization (described above) or ascertaining similarities in normalized probability density functions (PDF) using cosine-similarity functions (described above.

The output of the diagnostic engine can be outputted, for example, to display 412 for user review. In some embodiments, the output may include a raw confidence interval (CI) score or an ordinal score (e.g., score in a scale of 1 to 10, 10 being highly likely and 1 being unlikely that the subject has a tumor disease).

As it relates to orientation, marker identification unit 520 of system 500 of FIG. 16A can be communicatively connected to the data acquisition unit 510. Moreover, each component (e.g., engine, module, etc.) depicted as part of marker identification unit 520 (and described herein) can be implemented as hardware, firmware, software, or any combination thereof. In various embodiments, the marker identification unit 520 can be implemented as an integrated instrument system assembly with data acquisition unit 510. That is, unit 520 and unit 510 can be housed in the same housing assembly and communicate via conventional device/component connection means (e.g. serial bus, optical cabling, electrical cabling, etc.). In various embodiments, marker identification unit 520 can be implemented as a standalone computing device (as shown in FIG. 16) that is communicatively connected to the data acquisition unit 510 via an optical, serial port, network or modem connection, e.g., via a LAN or WAN connection that allows for the transmission of imaging data acquired by the data acquisition unit 510 to marker identification unit 520 of analysis. In various embodiments, the functions of marker identification unit 520 can be implemented on a distributed network of shared computer processing resources (such as a cloud computing network) that is communicatively connected to data acquisition unit 510 via a WAN (or equivalent) connection. For example, the functionalities of marker identification unit 520 can be divided up to be implemented in one or more computing nodes on a cloud processing service such as AMAZON WEB SERVICES™.

Figure 16B:
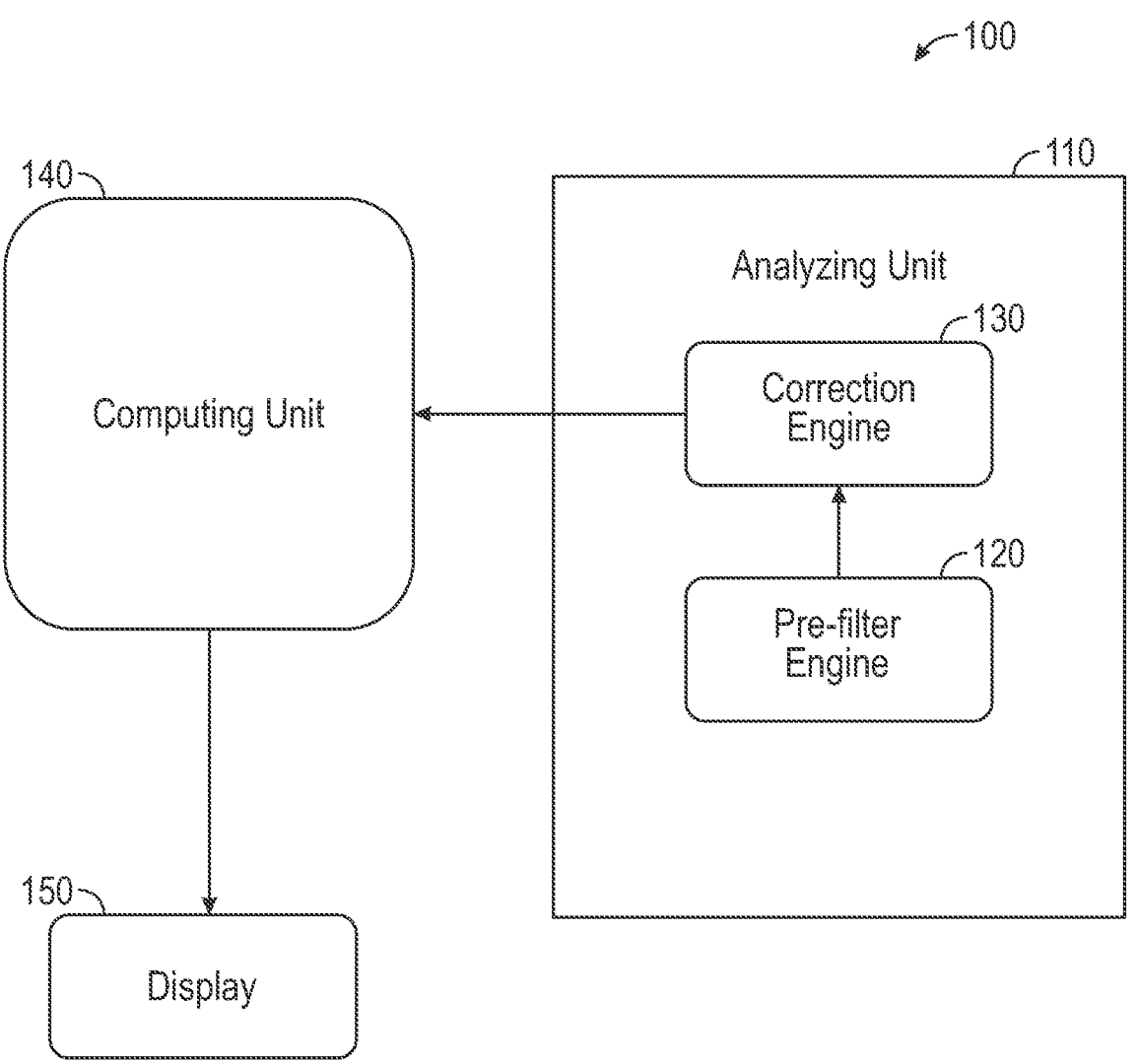

FIG. 16B illustrates a second exemplary system for implementing the diagnostic method of the disclosure. As illustrated in FIG. 16B, an example system 100 is provided that is configured and arranged for genetic screening of a subject for cancer in need thereof. Referring to FIG. 16B, system 100 can comprise an analyzing unit 110 and a computing unit 140. Analyzing unit 110 can comprise a pre-filter engine 120 and a correction engine 130. These system components and associate engines will be discussed in more detail below.

Referring again to FIG. 16B, pre-filter engine 120, of analyzing unit 110, can be configured and arranged to receive a subject-specific genome wide compendium of reads associated with a plurality of genetic markers from a biological sample of a subject. As discussed with regards to workflows herein, and in accordance with various embodiments, the biological sample can comprise a tumor sample; the compendium of reads can each comprise reads of a single base pair length.

Pre-filter engine 120 can also be configured and arranged to filter artefactual sites from the compendium of reads. As discussed with regards to workflows herein, and in accordance with various embodiments, the filtering can comprise removing, from the compendium of reads, recurring sites generated over a cohort of reference healthy samples, and/or identifying germ line mutations in the biological sample and/or identifying shared mutations between the tumor sample and peripheral blood mononuclear cells of the normal cell sample as germ line mutations, and removing said germ line mutations from the compendium of reads.

Correction engine 130, of analyzing unit 110, can be configured and arranged to receive output from engine 120. Correction engine 130 can be configured and arranged to filter noise from genome-wide compendium of reads using at least one error suppression protocol to produce a filtered read set for the genome-wide compendium of reads.

As discussed with regards to workflows herein, and in accordance with various embodiments, the at least one error suppression protocol can comprise calculating the probability that any single nucleotide variation in the compendium is an artefactual mutation, and removing said mutation.

As discussed with regards to workflows herein, and in accordance with various embodiments, the probability can be calculated as a function of features selected from the group consisting of mapping-quality (MQ), variant base-quality (MBQ), position-in-read (PIR), mean read base quality (MRBQ), and combinations thereof.

As discussed with regards to workflows herein, and in accordance with various embodiments, the at least one error suppression protocol can include removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family.

Computing unit 140, of system 100, can be configured and arranged to receive output from correction engine 130, and compile a subject-specific signature using the filtered read set, based on comparison to specific mutational signatures associated with a pre-determined mutagenesis process.

Computing unit 140 can also be configured and arranged to statistically quantitate a confidence estimate that the subject's biological sample, via the subject-specific signature, comprises a cancer related mutational signature based on comparison of the cancer related mutational signature exposure value to a cohort of background mutation signatures. Computing unit 150 can be further configured and arranged to screen the subject for cancer if the confidence estimate that the subject's biological sample contains the cancer related mutational signature exceeds a given threshold.

System 100 can also include display 150, as illustrated in FIG. 16B. The display can be configured and arranged to receive output from computing unit 140. Output can include data related to screening for cancer in the subject/user. Alternatively, system 100 may exclude a display and can instead send data output from computing unit 140 to any form of storage or display device or location external to system 100. As also discussed herein, the components of system 100 can be integrated into one single unit or can be split up into more separate physical units than that which is illustrated in FIG. 16B. Moreover, system 100 can be part of a distributed network of systems each performing substantially similar tasks and transmit data from each system to a hub.

Figure 16C:
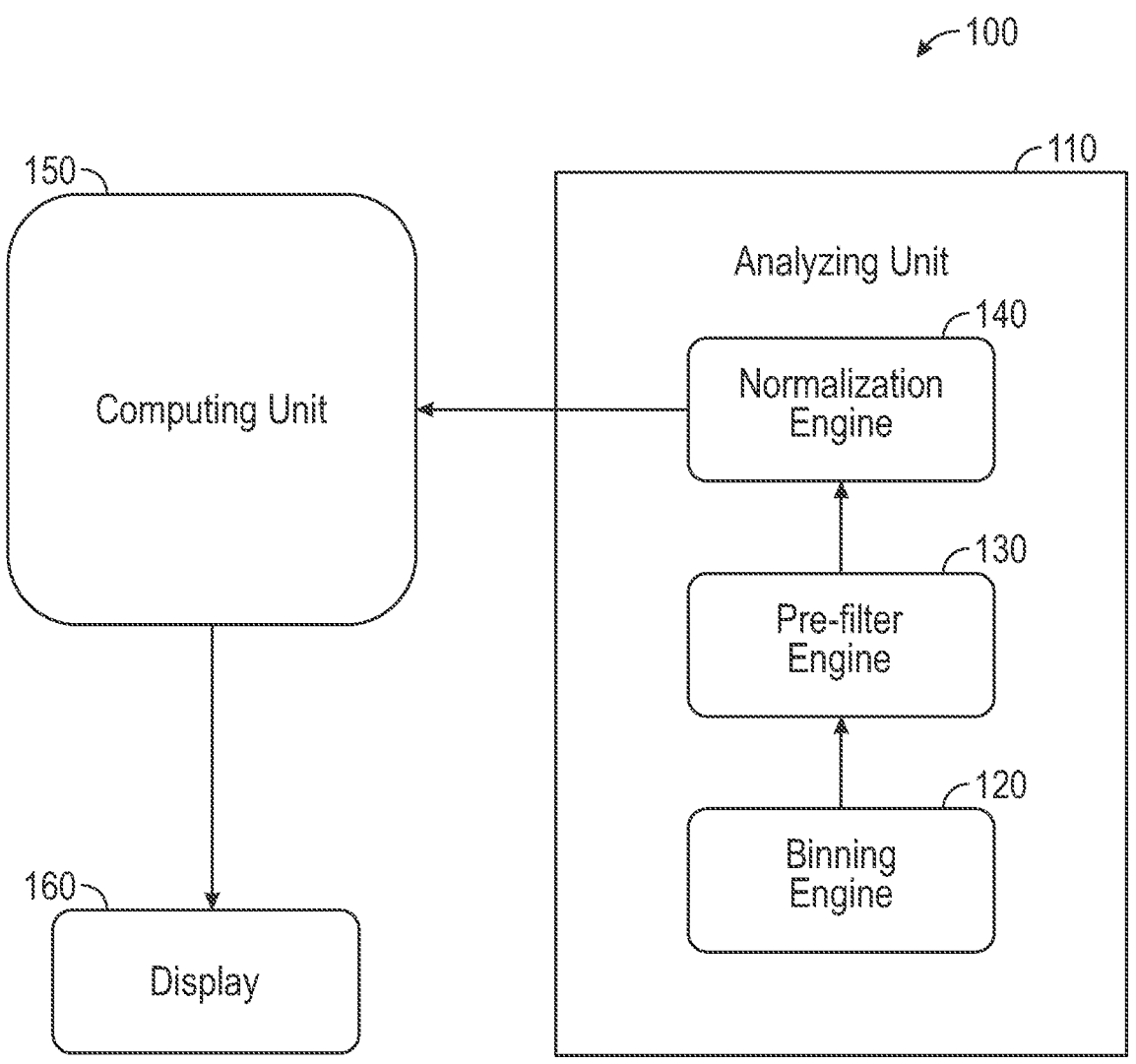

FIG. 16C illustrates a third exemplary system for implementing the diagnostic method of the disclosure. As illustrated in FIG. 16C, an example system 100 is provided that is configured and arranged to perform genetic screening for cancer in a subject in need thereof. System 100 can comprise an analyzing unit 110 and a computing unit 150. Analyzing unit 110 can comprise a binning engine 120, a pre-filter engine 130 and a normalization engine 140. These system components and associate engines will be discussed in more detail below.

Referring again to FIG. 16C, binning engine 120 can be configured and arranged to receive a subject-specific genome-wide compendium of reads associated with a plurality of genetic markers from a biological sample of a subject. As discussed with regards to workflows herein, and in accordance with various embodiments, the first biological sample can comprise a tumor sample; the first compendium of reads can comprise a copy number variation (CNV).

Binning engine 120 can be configured and arranged to divide the compendium of reads into a plurality of windows, and calculate a set of features per window. The features can comprise a median depth coverage per window and a representative fragment size per window.

Pre-filter engine 130 can be configured and arranged to filter artefactual sites from the compendium of reads. The filtering can comprise removing, from the compendium of reads, recurring sites generated over a cohort of reference healthy samples.

Normalization engine 140, of analyzing unit 110, can be configured and arranged to receive output from engine 130. Normalization engine 140 can be configured and arranged to normalize the compendium of reads to produce a filtered read set for the genome-wide compendium of reads. Normalization methods are discussed in detail herein and can be used in any contemplated combination to normalize reads as discussed.

Computing unit 150, of system 100, can be configured and arranged to receive output from normalization engine 140, and compute an estimated tumor fraction (eTF) using the filtered read set by calculating a linear relationship between the set of features per window and converting the calculated relationship to estimated tumor fraction using a regression model. Computing unit 150 can also, or in addition, be configured and arranged to compute an estimated tumor fraction on the basis of one or more integrative mathematical models as a function of the calculated set of features per window across the subject-specific genome-wide compendium of reads. Computing unit 150 can be further configured and arranged to screen the subject for cancer if the estimated tumor fraction exceeds an empirical threshold. The regression model, integrative mathematical models, and empirical threshold are discussed in detail herein.

System 100 can also include display 160, as illustrated in FIG. 16C. The display can be configured and arranged to receive output from computing unit 150. Output can include data related to detection of residual disease in the subject/user. Alternatively, system 100 may exclude a display and can instead send data output from computing unit 150 to any form of storage or display device or location external to system 100. As also discussed herein, the components of system 100 can be integrated into one single unit or can be split up into more separate physical units than that which is illustrated in FIG. 16C. Moreover, system 100 can be part of a distributed network of systems each performing substantially similar tasks and transmit data from each system to a hub.

Convolutional Neural Network (CNN)

The disclosure further relates to systems and programs that utilize convolutional neural networks (CNN), e.g., Engine, to adaptively and/or systemically filter sequencing noise.

The disclosure further relates to computer-readable storage medium containing a program for detecting tumor markers comprising somatic mutations in a genomic read, the program comprising a layered convolutional neural network (CNN).

As is known in the art, a convolutional neural network (CNN) generally accomplishes an advanced form of processing and classification/detection by first looking for low level features such as, for example, repeat sequences in a read, and then advancing to more abstract (e.g., unique to the type of reads being classified) concepts through a series of convolutional layers. A CNN can do this by passing data through a series of convolutional, nonlinear, pooling (or downsampling, discussed below), and fully connected layers, and get an output. Again, the output can be a single class or a probability of classes that best describes the data or detects objects on the data.

Regarding layers in a CNN, the first layer is generally a convolutional layer (conv). This first layer will process the read's representative array using a series of parameters. Rather than processing the data as a whole, a CNN will analyze a collection of data sub-sets using a filter (or neuron or kernel). The sub-sets will include a focal point in the array as well as surrounding points. For example, a filter can examine a series of 5×5 areas (or regions) in a 32×32 representation. These regions can be referred to as receptive fields. Since the filter generally will possess the same depth as the input, a representation with dimensions of 32×32×3 would have a filter of the same depth (e.g., 5×5×3). The actual step of convolving, using the exemplary dimensions above, would involve sliding the filter along the input data, multiplying filter values with the original representation values of the data to compute element wise multiplications, and summing these values to arrive at a single number for that examined region of the representation.

After completion of this convolving step, using a 5×5×3 filter, an activation map (or filter map) having dimensions of 28×28×1 will result. For each additional layer used, spatial dimensions are better preserved such that using two filters will result in an activation map of 28×28×2. Each filter will generally have a unique feature it represents that, together, represent the feature identifiers required for the final data output. These filters, when used in combination, allow the CNN to process data input to detect those features present at each representation. Therefore, if a filter serves as a curve detector, the convolving of the filter along the data input will produce an array of numbers in the activation map that correspond to high likelihood of a curve (high summed element wise multiplications), low likelihood of a curve (low summed element wise multiplications) or a zero value where the input volume at certain points provided nothing that would activate the curve detector filter. As such, the greater number of filters (also referred to as channels) in the Cony, the more depth (or data) that is provided on the activation map, and therefore more information about the input that will lead to a more accurate output.

Balanced with accuracy of the CNN is the processing time and power needed to produce a result. In other words, the more filters (or channels) used, the more time and processing power needed to execute the Conv. Therefore, the choice and number of filters (or channels) to meet the needs of the CNN method should be specifically chosen to produce as accurate an output as possible while considering the time and power available.

To further enable a CNN to detect more complex features, additional Convs can be added to analyze what outputs from the previous Conv (e.g., activation maps). For example, if a first Conv looks for a basic feature such as a curve or an edge, a second Conv can look for a more complex feature such as shapes, which can be a combination of individual features detected in an earlier Conv layer. By providing a series of Convs, the CNN can detect increasingly higher level features to eventually arrive at a probability of detecting the specific desired object. Moreover, as the Convs stack on top of each other, analyzing the previous activation map output, each Cony in the stack is naturally going to analyze a larger and larger receptive field by virtue of the scaling down that occurs at each Conv level, thereby allowing the CNN to respond to a growing region of representation space in detecting the object of interest.

A CNN architecture generally consists of a group of processing blocks, including at least one processing block for convoluting an input volume (data) and at least one for deconvolution (or transpose convolution). Additionally, the processing blocks can include at least one pooling block and unpooling block. Pooling blocks can be used to scale down data in resolution to produce an output available for Conv. This can provide computational efficiency (efficient time and power), which can in turn improve actual performance of the CNN. Those these pooling, or subsampling, blocks keep filters small and computational requirements reasonable, these blocks can coarsen the output (can result in lost spatial information within a receptive field), reducing it from the size of the input by a specific factor.

Unpooling blocks can be used to reconstruct these coarse outputs to produce an output volume with the same dimensions as the input volume. An unpooling block can be considered a reverse operation of a convoluting block to return an activation output to the original input volume dimension. However, the unpooling process generally just simply enlarges the coarse outputs into a sparse activation map. To avoid this result, the deconvolution block densifies this sparse activation map to produce both and enlarged and dense activation map that eventually, after any further necessary processing, a final output volume with size and density much closer to the input volume. As a reverse operation of the convolution block, rather than reducing multiple array points in the receptive field to a single number, the deconvolution block associate a single activation output point with a multiple outputs to enlarge and densify the resulting activation output.

It should be noted that while pooling blocks can be used to scale down data and unpooling blocks can be used to enlarge these scaled down activation maps, convolution and deconvolution blocks can be structured to both convolve/deconvolve and scale down/enlarge without the need for separate pooling and unpooling blocks.

The pooling and unpooling process can have drawbacks depending on the objects of interest being detected in data input. Since pooling generally scales down data by looking at sub-data windows without overlap of windows, there is a clear loss of spatial info as scale down occurs.

A processing block can include other layers that are packaged with a convolutional or deconvolutional layer. These can include, for example, a rectified linear unit layer (ReLU) or exponential linear unit layer (ELU), which are activation functions that examine the output from a Cony in its processing block. The ReLU or ELU layer acts as a gating function to advance only those values corresponding to positive detection of the feature of interest unique to the Conv.

Given a basic architecture, the CNN is then prepared for a training process to hone its accuracy in data classification/detection (of objects of interest). This involves a process called backpropagation (backprop), which uses training data sets, or sample data used to train the CNN so that it updates its parameters in reaching an optimal, or threshold, accuracy. Backpropagation involves a series of repeated steps (training iterations) that, depending on the parameters of the backprop, will either slowly or quickly train the CNN. Backprop steps generally include a forward pass, loss function, backward pass, and parameter (weight) update according to a given learning rate. The forward pass involves passing a training data through the CNN. The loss function is a measure of error in the output. The backward pass determines the contributing factors to the loss function. The weight update involves updating the parameters of the filters to move the CNN towards optimal. The learning rate determines the extent of weight update per iteration to arrive at optimal. If the learning rate is too low, the training may take too long and involve too much processing capacity. If the learning rate is too fast, each weight update may be too large to allow for precise achievement of a given optimum or threshold.

The backprop process can cause complications in training, thus leading to the need for lower learning rates and more specific and carefully determined initial parameters upon start of training. One such complication is that, as weight updates occur at the conclusion of each iteration, the changes to the parameters of the Convs amplify the deeper the network goes. For example, if a CNN has a plurality of Convs that, as discussed above, allows for higher level feature analysis, the parameter update to the first Cony is multiplied at each subsequent Conv. The net effect is that the smallest changes to parameters can have large impact depending on the depth of a given CNN. This phenomenon is referred to as internal covariate shift.

In general, the CNN of the disclosure can adaptively and/or systemically filter sequencing noise. In some embodiments, the CNN architecture was designed based on the inventors' recognition that tri-nucleotide contexts contain distinct signatures involved in mutagenesis. Accordingly, the CNN convolves over all features (columns) at a position using a perceptive field of size three. After two successive convolutional layers, down sampling is applied by maxpooling with a receptive field of two and a stride of two, forcing the model in the Engine to retain only the most important features in small spatial areas. The resulting architecture maintains spatial invariance when convolving over trinucleotide windows and captures a "quality map" by collapsing the read fragment into 25 segments, each representing approximately an eight-nucleotide region. The final classification is made by applying the output of the last convolutional layer directly to a sigmoid fully-connected layer. The CNN employs a simple logistic regression layer instead of a multi-layer perceptron or global average pooling in order to retain the features associated with position in the genomic read.

To train Engine, a variety of lung cancer patients and their matching systemic error profiles are first sampled. The goal of the training exercise is to use a training scheme that allows detection of true somatic mutations with high sensitivity and also reject candidate mutations caused by systemic errors. To this end, four individual samples, each comprising a complete tumor sample and a healthy tissue sample from the same patient, were selected from a variety of tobacco-smoking lung cancer patients for training (see, e.g., Table 3). For instance, a consensus of three art-known callers (STRELKA, LOFREQ, and MUTECT) may be taken to make a final call of somatic mutations. The reads supporting these mutations are then used as tumor reads for training Engine.

To ensure that the model Engine learns to discriminate against sequencing artifacts, reads from the healthy samples containing mutations that occur exactly once were collected. Since these variants are not supported by more than one read, they can be regarded, with high certainty, to be products of systemic errors. Variants which are of low quality were then filtered. For instance, reads with a base quality score at the mutation less than twenty or with a mapping quality less than forty (e.g., BQ20, MQ40) can be filtered. These thresholds, which are purely exemplary, may be identified by inspection of reads. Optionally, if desired, lower quality samples may be included in training Engine. Subsets of the training set may be used as a validation dataset, which may be used to both monitor training progress and to verify the performance of the model on independent reads.

In accordance with various embodiments herein, a computer readable medium is provided, the computer readable medium comprising computer-executable instructions, which, when executed by a processor, cause the processor to carry out a method or a set of steps for identifying low-abundance, tumor-specific markers in a compendium of genetic markers received from a subject's sample, wherein the genetic markers comprise SNVs (preferably sSNVs), CNVs (preferably sCNVs), indels, and/or SV (preferably translocations, gene fusions or combinations thereof) in a genomic read. Preferably, the medium comprises a layered convolutional neural network (CNN) with a single fully connected layer at one end, wherein the CNN maintains spatial invariance when convolving over trinucleotide windows; and maintains quality map by collapsing the read fragment into a plurality of segments, each representing approximately an eight-nucleotide region, wherein the CNN weighs each genetic marker in the compendium. For example, the CNN of the disclosure can comprise 8 layers comprising a single fully connected layer at one end and two successive convolutional layers, the output of which is down-sampled by maxpooling with a receptive field of two and a stride of two; wherein the 8-layered CNN maintains quality map by collapsing the read fragment into about 25 individual segments and convolves over columns at a position in the genomic read using a perceptive field of size three; and wherein the output of the last convolutional layer is applied directly to a sigmoid fully connected layer, from which a final classification of the marker is made.

The CNN can comprise a read representation that jointly captures the genomic context of alignment, the complete read sequence, and the integration of the quality score per base. Partly because of this arrangement and architecture, the CNN of the disclosure provides enrichment of tumor specific markers comprising somatic mutations in a genomic read by about 1.12-fold to about 12-fold compared to state-of-the-art mutational caller MUTECT.

The disclosure also relates to computer readable medium comprising computer-executable instructions, which, when executed by a processor, cause the processor to carry out a method or a set of steps for diagnosing a cancer in a subject in need of the diagnosis, the medium comprising a convolutional neural network (CNN). In some embodiments, the CNN is developed using a training dataset comprising tumor related signatures and PCR/sequencing error signatures to train the CNN to distinguish between cancer-mutation supporting reads and artefactual-mutation (error) reads; and optionally validating using actual samples from cancer patients or synthetic plasma obtained from datasets. receiving in a compendium of genetic markers received from a subject's sample, wherein the genetic markers comprise SNVs (preferably sSNVs), CNVs (preferably sCNVs), indels, and/or SV (preferably translocations, gene fusions or combinations thereof) in a genomic read.

In some embodiments, the mathematical optimizing step used in the development of the CNN comprises employing a non-negative least square (NNLS). Other representative methods include cross-entropy global optimization method, golden-section search method or a combination thereof.

Preferably, the CNN of the disclosure comprises a single fully connected layer at one end, wherein the program maintains spatial invariance when convolving over trinucleotide windows; and maintains quality map by collapsing the read fragment into a plurality of segments, each representing approximately an eight-nucleotide region.

In some embodiments, the systems of the disclosure comprises an 8-layered CNN which maintains quality map by collapsing the read fragment into about 25 individual segments and, which further convolves over all features (columns) at a position in the genomic read using a perceptive field of size three. In the context of analyzing genetic markers (e.g., sSNV) in cfDNA, the CNN may comprise two successive convolutional layers, the output of which is down sampled by maxpooling with a receptive field of two and a stride of two and the output of the last convolutional layer is applied directly to a sigmoid fully connected layer, from which a final classification of the marker is made.

The CNN configured in the aforementioned manner takes into account spatial invariance in true somatic mutations and errors due to mapping and simultaneously maintains base quality across the read and provides a read representation that jointly captures the genomic context of alignment, the complete read sequence, and the integration of the quality score per base.

The embodiments disclosed herein have several advantages versus known CNNs. These advantages include, for example, providing a CNN that greatly enhances precision and sensitivity. Particularly, the systems and networks of the disclosure provide enrichment (which measures a ratio of output precision versus input precision) of tumor specific markers comprising somatic mutations in a genomic read by about 1.12-fold to about 12-fold, e.g., about 2-fold, about 3-fold, about 4-fold, about 5-fold, about 6-fold, about 7-fold, about 8-fold, about 9-fold, about 10-fold, or more, compared to art-known programs such as MUTECT.

In some embodiments, CNN comprises employing a deep learning algorithm over a pan-cancer cohort to identify signatures that discriminate between true tumor mutations and artefactual errors. The algorithm performs this function by assigning a confidence estimate to each individual mutation detected in a sample from tumor patients; integrating the confidence estimates across the entire genome; and employing an algorithm to analyze mutational signatures in the sample. For example, in the context of diagnosing lung cancer, the algorithm may analyze for a lung tumor signature in samples. Likewise, in the context of diagnosing UV-induced melanoma, the algorithm may analyze for a UV signature in samples. Similarly, in the context of diagnosing breast cancer, the algorithm may analyze for a breast tumor (BRCA) signature in patient samples.

In some embodiments, the CNN of the disclosure includes algorithm that is capable of performing a NNLS analysis using art-recognized/accessioned mutational signatures, e.g., mutational signatures deposited in the catalogue of somatic mutations in cancer (COSMIC) database, across the sample. The disclosure further relates to CNN of the disclosure that are integrated with specific genomic atlases, e.g., TCGA Pan-Cancer dataset.

In accordance with various embodiments, the CNN of the disclosure may be trained with a deep learning algorithm developed over a pan-lung cancer cohort. In this case, the cohort may comprise WGS data on patients with deep tumor and PBMC (control). By utilizing the supervised learning, the CNN may be trained to identify signatures that discriminate between true tumor mutations and artefactual errors. The model thus obtained may be utilized to infer and to assign a confidence estimate to each individual mutation detected in plasma samples from cancer patients (e.g., early stage patients with lung adenocarcinoma). Next, a signal for tumor detection may be derived by integrating these confidence estimates across the entire genome, followed by a novel analytical method for sensitive detection, using non-negative least square (NNLS) of specific cosmic mutational signatures in a single plasma sample. The detection signal may be further validated for confidence using a comparison of cosmic mutation exposure values to the exposure values inferred for 100 random background signatures.

In some embodiments, the machine learning (ML) method used in the systems and/or methods of the disclosure comprises deep convolutional neural network (CNN), recurrent neural network (RNN), random forest (RF), support vector machine (SVM), discriminant analysis, nearest neighbor analysis (KNN), ensemble classifier, or a combination thereof.

The systems and/or methods of the disclosure permit early detection in at least 50%, at least 60%, at least 70%, at least 80%, or a greater %, e.g., 90% or even 95% of the subjects.

Other Applications

Patient reports which are compiled in accordance with the foregoing methods may be transmitted and accessed electronically via the internet. For instance, analysis of sequence data may occur at a site other than the location of the subject. A report is generated, optionally annotated, and transmitted to the subject's location, e.g., via an internet enabled computer. The annotated information can be used by a health care provider to select other drug treatment options and/or provide information about drug treatment options to an insurance company. The method can include annotating the drug treatment options for a condition in, for example, the NCCN Clinical Practice Guidelines in Oncology™ or the American Society of Clinical Oncology (ASCO) clinical practice guidelines. The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anti-cancer drugs that are included in standard medical compendia. The drugs used for annotating lists can be found in CMS approved compendia, including the National Comprehensive Cancer Network (NCCN) Drugs and Biologies Compendium™, Thomson Micromedex DrugDex®, Elsevier Gold Standard's Clinical Pharmacology compendium, and American Hospital Formulary Service-Drug Information Compendium®.

In some embodiments, the drug treatment options can be annotated by listing an experimental drug that may be useful in treating a cancer with one or more molecular markers of a particular status. The experimental drug can be a drug for which in vitro data, in vivo data, animal model data, preclinical trial data, or clinical-trial data are available. The data can be published in peer-reviewed medical literature found in journals listed in the CMS Medicare Benefit Policy Manual, including, for example, American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer, Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network (NCCN), Journal of Urology, Lancet, Lancet Oncology, Leukemia, The New England Journal of Medicine, or Radiation Oncology.

The drug treatment options can be annotated by providing a link on an electronic based report connecting a listed drug to scientific information regarding the drug. For example, a link can be provided to information regarding a clinical trial for a drug (clinicaltrials(dot)gov). If the report is provided via a computer or computer website, the link may be a footnote, a hyperlink to a website, a pop-up box, or a fly-over box with information, etc. The report and the annotated information can be provided on a printed form, and the annotations can be, for example, a footnote to a reference. The information for annotating one or more drug treatment options in a report can be provided by a commercial entity that stores scientific information. A health care provider can treat a subject, such as a cancer patient, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company.

The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs, one or more links to citations for scientific information regarding drugs, etc. The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

The system can also include reports on the effects of drugs on sample (e.g. tumor cells) isolated from a subject (e.g. cancer patient). An in vitro culture using a tumor from a cancer patient can be established using techniques known to those skilled in the art. The system can also include high-throughput screening of FDA approved off-label drugs or experimental drugs using said in vitro culture and/or xenograft model. The system can also include monitoring tumor antigen for recurrence detection.

In preferred embodiments, the annotated information may include treatment recommendation, including, annotation of the effects of PARP-inhibitor for BRCA signature, immunotherapy for MSI signature.

The aforementioned embodiments of the disclosure are further described in view of the following non-limiting examples.

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Background

Breadth of Sequencing can Supplant for Depth of Sequencing to Overcome Limitation on cfDNA Abundance in Sensitive Cancer Detection.

The above data demonstrates that detection of a single sSNV in a patient's plasma sample results from two consecutive statistical sampling processes. The first process provides the probability that the mutated fragment is sampled in the limited number of genomic equivalents present in a typical blood sample. The second process assesses the probability of detecting the mutated fragment in the sample given its abundance, sequencing depth and sequencing error (signal-to-noise). While the latter process has been at the focus of intensive investigation and technology development by the scientific community (e.g., ultra-deep error free sequencing protocols, the former stochastic process is infrequently addressed. Nevertheless, in low burden disease ctDNA detection, both processes play a critical role as shown above. If no physical fragments are present that represent the targeted sSNV, even ideal ultra-deep targeted sequencing will fail to discover the cancer signal, which is regarded to be one of the major factors responsible for the limited sensitivity of these approaches (~40%, Rosenfeld et al.). In practice this problem is further compounded by the fact that a single observation (mutated read) is rarely sufficient for confident detection.

To formulate the probability of sampling mutant fragments in a given cfDNA sample, cfDNA sampling was modeled as a Bernoulli trial, with an admixture of cfDNA fragments originating from two populations, cfDNA fragments originating from normal cells and cfDNA fragments originating from malignant origin with proportions defined by the tumor fraction (TF). Thus, the genomic equivalents present in a plasma sample constitute a random sampling of the entire pool of cfDNA fragments in the patient circulation. Therefore, the probability of sampling at least one mutant fragment in a plasma sample supporting a particular substitution can be defined as: $P=1-(1-TF)^{GE}$, where P is the probability; TF is the tumor fraction; and GE correspond to the number of genomic equivalents present in the patient cfDNA. The instant model predicts that the detection probability in TFs relevant to the early stage cancer regime (TF<1%), will exhibit a rapid decrease for low TF, and even at a frequency of 0.1% ($\frac{1}{1000}$), detection probability is predicted to be lower than 0.65 (FIG. 3A). It was noted that these limitations are observed even under idealize conditions of exhaustive sequencing that efficiently utilizes of 1000 genomic equivalents (~6 ng of cfDNA), and detection based on a single supporting DNA fragment with ideal signal-to-noise. These results show that the plasma sampling probability imposes a hard ceiling on mutation detection at low TF regimes, such as MRD and early cancer stage detection.

Figure 3B:
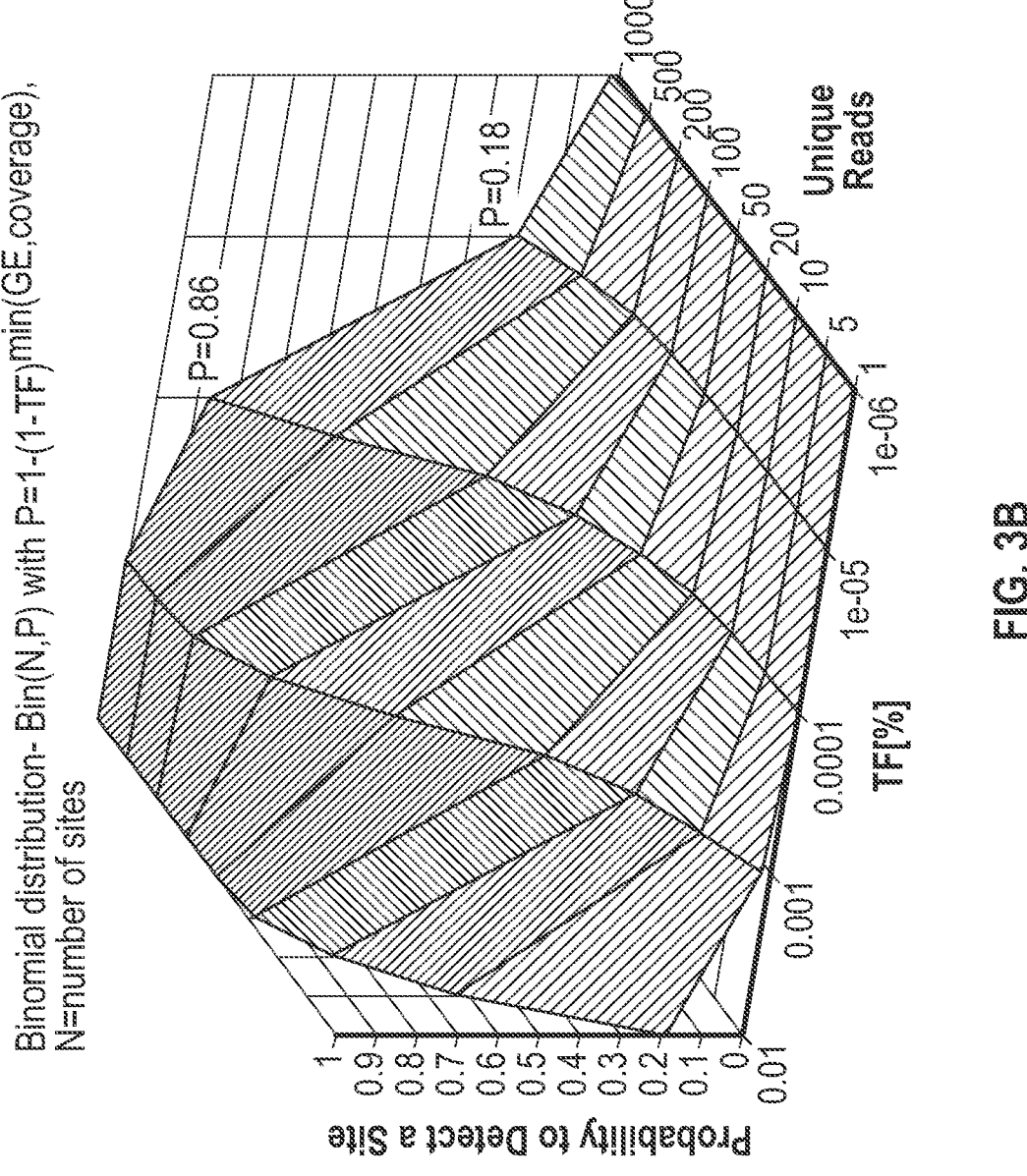
Figure 3C:
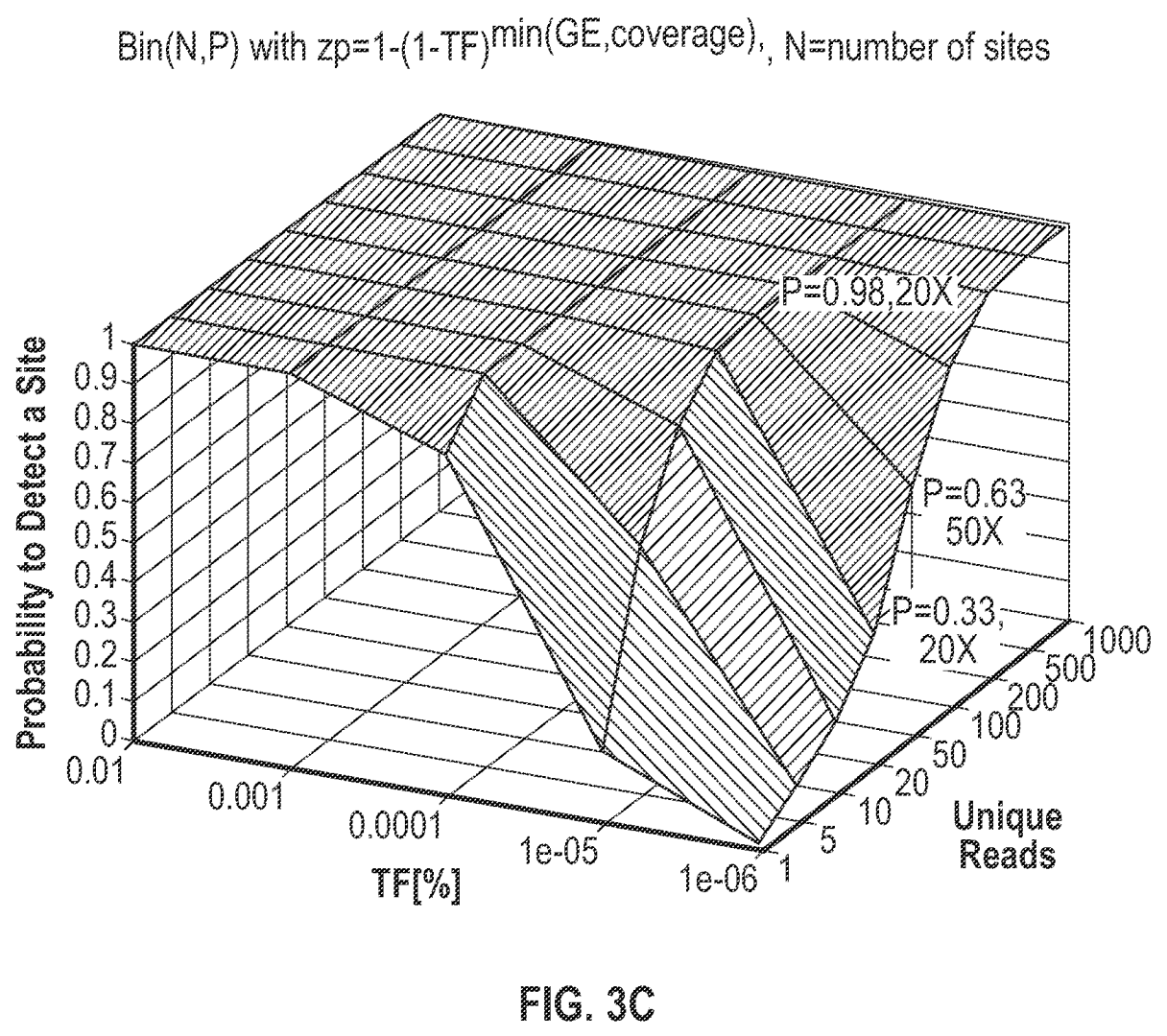
Figure 4A:
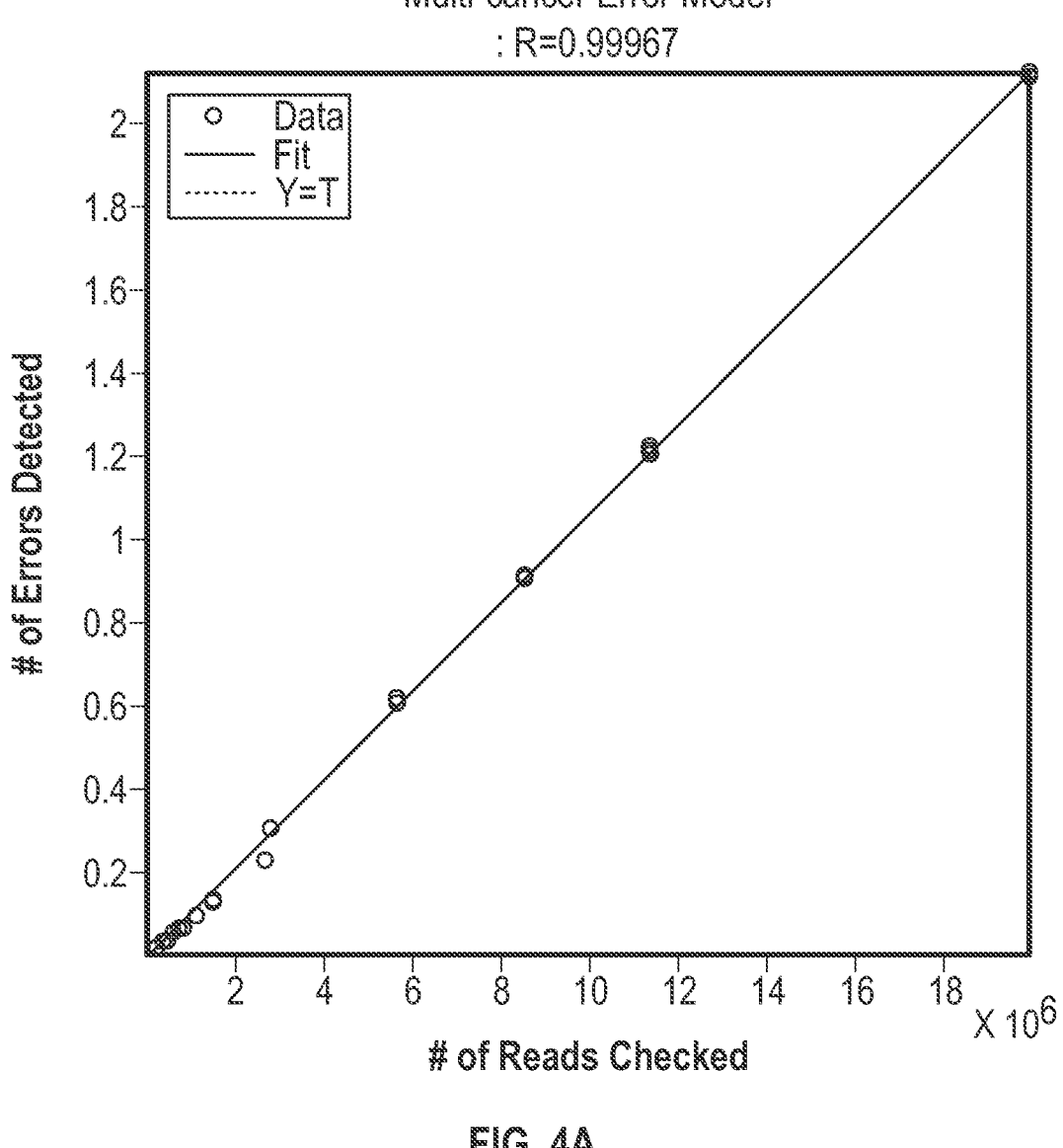
FIGS. 4A-4E show optimization of SNV markers.
Figure 4B:
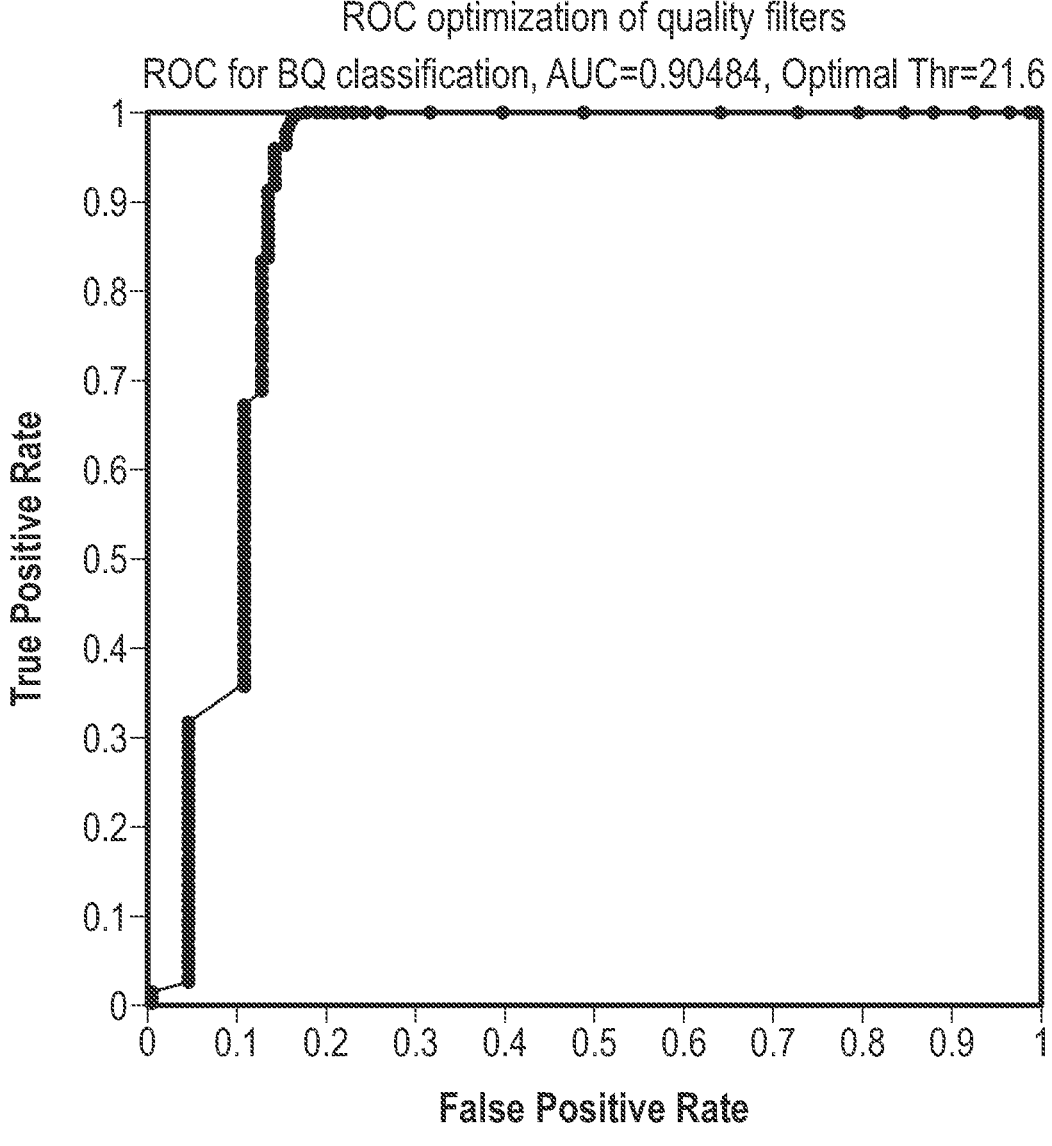
Figure 4C:
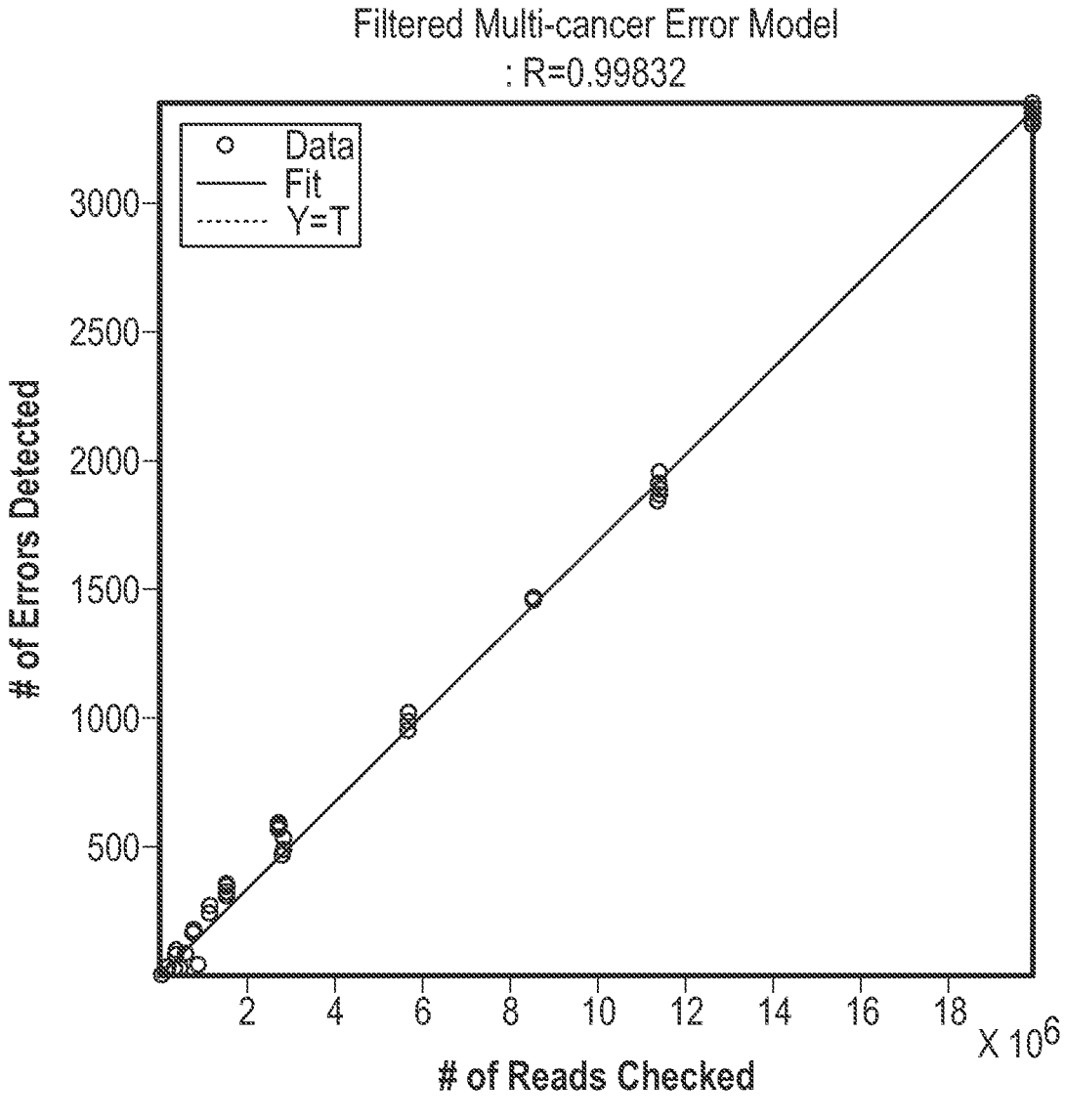
Figure 4D:
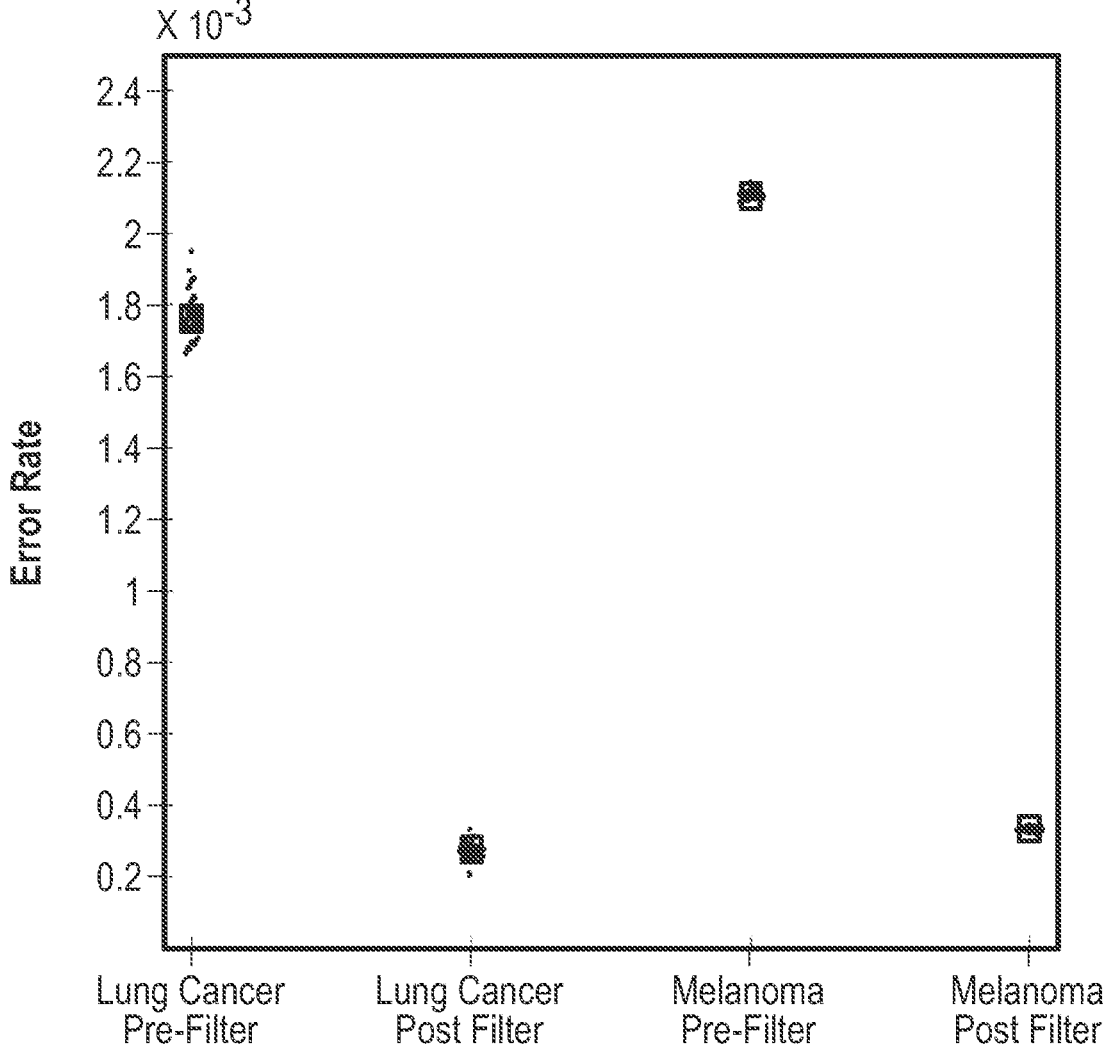
Figure 4E:
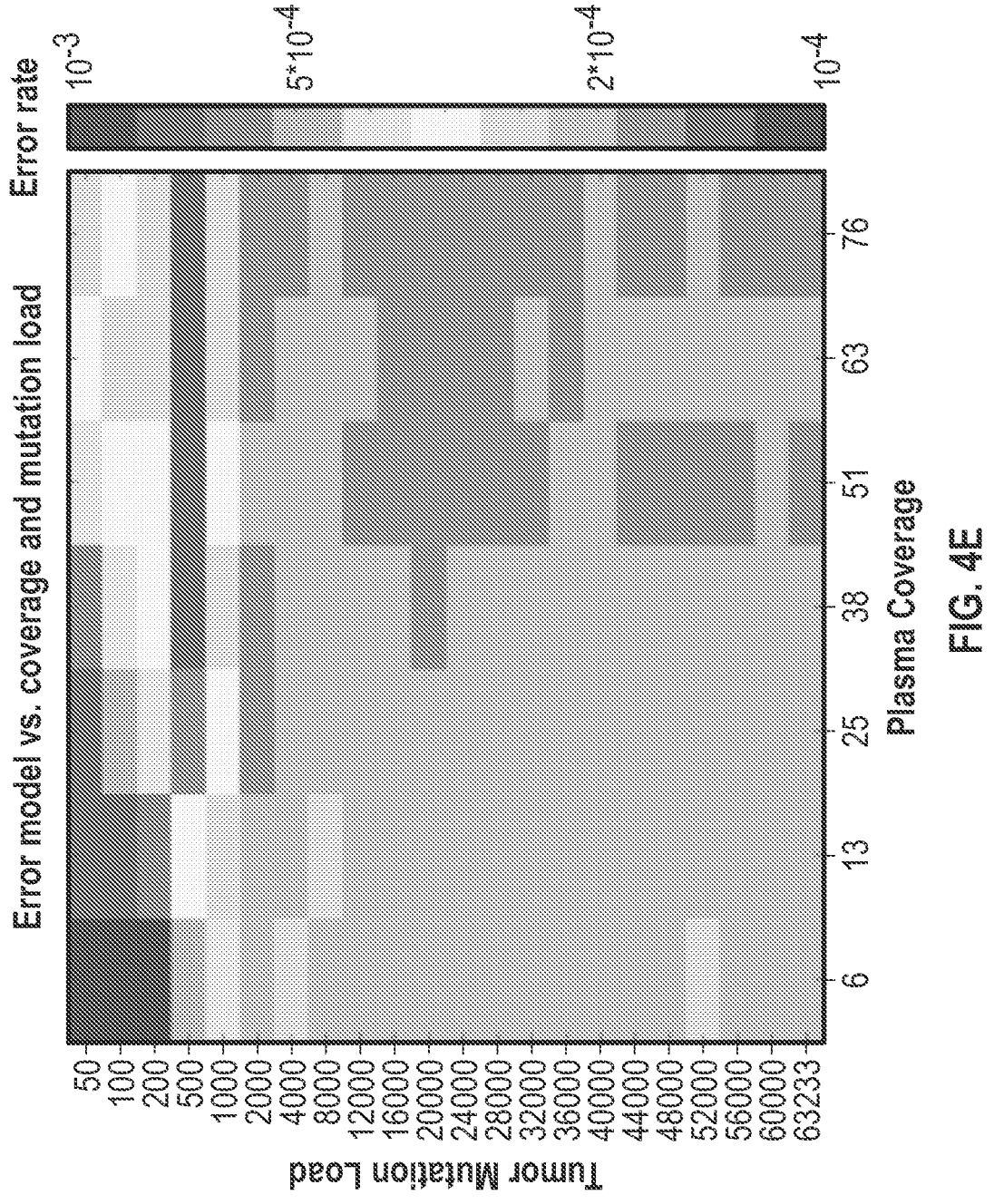

Conversely, the instant model also shows that this limitation on the depth of sequencing can be effectively overcome by increasing the number of detected sites (SNVs) through increased breadth, which results from repeating the Bernoulli trial for each SNV (a binomial distribution over the Bernoulli trial probability). This model can be represented by Bin(N,P), binomial distribution, where N represent the number of sites (mutations) tested and $P=1-(1-TF)$ GE is the detection probability for a single site. Importantly, the mathematical model predicts the average number of detected sites, as well as the probability for at least one detection, as a function of the number of unique DNA fragments (genomic equivalent or coverage), mutation load (N, can be used also as panel size) and TF (FIG. 3B). Utilizing this model, it was found that integrating over 20,000 sSNVs (about 10 mutations/mb found in 17% of human cancer) can provide a high detection probability (up to 0.98) even at TF of 1:100,000, at a modest sequencing effort (20× coverage), such that can be readily achieved with standard whole genome sequencing (WGS) (FIG. 3C).

Related Applications

Noninvasive Prenatal Testing (NIPT) of Chromosomal Aberration

The disclosure further relates to noninvasive prenatal testing (NIPT) of chromosomal aberration using the aforementioned systems, methods and algorithms. Preferably, NIPT may be carried out using the CNV/SV-based workflows outlined in FIG. 1C and FIG. 1E. Herein, de-novo amplifications and deletions can be called and used to diagnose the subject's sample (e.g., amniotic fluid or blood from a pregnant female carrying a fetus suspected of having chromosomal aberration). The method takes advantage of the unique log 2/fragment-size (same phenomena appear in fetal vs. normal DNA) relationship to increase sensitivity and specificity, e.g., FIG. 18E and FIG. 18F. Thus, the workflows of FIG. 1C and FIG. 1E allows the researcher or clinician to combine two sources of information that are correlated only in the CNV that is generated by fetal DNA and are not correlated to noise that correspond with sequencing, alignment, GC artifacts. Thus, the methods and systems of the disclosure allow the clinician to attain higher sensitivity and specificity for NIPT using de-novo CNV detections even if prior information about the CNV segments is not readily available.

Example 1: Design of a Somatic Mutation Classifier

When designing a model for somatic mutation classification, it is important to recognize the sources of error that may lead to false positive somatic mutations. A true mutation is likely to have a high base quality regardless of position in the read. Similarly, the read base, reference base, and alignment string (CIGAR) at the position of a true mutation are likely to be independent of the reads alignment. More specifically, one can expect a true somatic mutation to be spatially invariant. It is well known that systemic errors in sequencing experiments are dependent on the position in the read, so while the mutation itself may be spatially invariant, its position in the read is usually not invariant. Errors caused by mismapping will be likely to contain repetitive sequence or very specific sequence motifs (such as TTAGGG in the telomeres). It is therefore desirable that a model is able to accurately represent both the spatial invariance in true somatic mutations and in errors due to mapping, while simultaneously maintaining a model of base quality across the read. It follows therefore that any shallow convolutional network that depends on a fully connected layer over the read of interest to make classifications would be unable to capture the invariance in the mutations.

Recognizing these constraints and/or requirements, the inventors have designed a somatic mutational classifier Engine. The Engine, which utilizes a convolutional neural network, utilizes an eight-layer convolutional neural network with a single fully connected layer at the end inspired by the VGG architecture to correct for the spatial dependency (Simonyan & Zisserman, arXiv:1409.1556, revised Apr. 10, 2015; Alexandrov et al., Nature, 500(7463):415-421, 2013). All features (columns) at a position were convolved over using a perceptive field of size three. After two successive convolutional layers, down sampling was applied by maxpooling with a receptive field of two and a stride of two, forcing the model to retain only the most important features in small spatial areas. Two principal benefits were expected from this architecture: 1) spatial invariance was maintained when convolving over trinucleotide windows; and 2) a "quality map" was captured by collapsing the read fragment into 25 segments, each representing approximately an eight-nucleotide region. The output of the last convolutional layer was applied directly to a sigmoid fully connected layer used to make the final classification. A simple logistic regression layer instead of a multi-layer perceptron or global average pooling was used in order to retain the features associated with position in the read.

The instantly disclosed model and training scheme is named Engine. Engine is the first use of a read representation that jointly captures the genomic context of alignment, the complete read sequence, and the integration of the quality score per base. The performance of Engine shows that integrating features across a read and its alignment has set the stage for a new set of somatic mutation callers using the full mutational profile of a sample, rather than just those which are covered with high depth.

To evaluate the performance of the instant model, predictive performance of the model was investigated on an independently held out lung cancer dataset. Datasets were paired with healthy WGS data for the same patients. The model was evaluated with the metrics F1-score, precision, sensitivity, and specificity, which parameters are defined as:

$$\text{sensitivity} = \text{TP}/(\text{TP} + \text{FN}) \qquad \text{(Equation 1)}$$

$$\text{precision} = \text{TP}/(\text{TP} + \text{FP}) \qquad \text{(Equation 2)}$$

$$\text{specificity} = \text{TN}/(\text{TN} + \text{FN}) \qquad \text{(Equation 3)}$$

$$F1\text{score} = 2 \times (\text{Precision} \times \text{Recall})/(\text{Precision} + \text{Recall}) \qquad \text{(Equation 4)}$$

Table 1: Validation Test Metrics

| Sample | Purpose | F1-score | Sensitivity | Specificity | Precision | |
|---|---|---|---|---|---|---|
| CA0045 | Train | 0.946 | | 0.944 | 0.948 | 0.948 |
| CA0046 | Train | 0.962 | | 0.949 | 0.976 | 0.975 |
| CA0047 | Train | 0.944 | | 0.944 | 0.944 | 0.944 |
| CA0049 | Train | 0.976 | | 0.975 | 0.978 | 0.977 |

-continued

| | | | | | |
|---|---|---|---|---|---|
| CA0044 | Test | 0.922 | 0.903 | 0.940 | 0.938 |
| CA0040 | Cancer Control | 0.718 | 0.793 | 0.642 | 0.689 |

It was found that the model manages an average F1-score on the validation set of 0.961. The model achieves an F1-score of 0.71 on the tumor control. While the model is still sensitive on the tumor control, it exhibited some loss in specificity compared to the validation dataset. However, in the case of independent lung sample, an F1 of 0.92 was observed, which demonstrates high specificity (Table 1). The low precision and specificity in the cancer control indicates that Engine has learned specific mutation patterns associated with tobacco smoking lung cancer, while also learning general error patterns.

To further examine learning capability of Engine, an additional sample from a patient with melanoma (CA0040; Table 1) was used in the analysis. Melanoma sample typically displays a markedly distinct mutational profile due to the exposure to UV light compared to the mutational profile associated with tobacco exposure (FIG. 8A). The Engine model achieves an F1-score of 0.71 on the melanoma sample. Thus, while the model is still sensitive, the lower precision and specificity in the melanoma sample indicate that Engine has learned specific mutation patterns associated with tobacco-exposed lung cancer, while learning a more general sequencing artifact pattern which is applicable to both tumor types.

To further examine the aforementioned question, differences in tri-nucleotide context frequency between true cancer mutation variant reads and sequencing artifact containing reads from the following datasets were examined: (i) lung cancer patient samples that were included in training (CA0046, validation dataset), (ii) lung cancer patient not included in training (CA0044), and (iii) the melanoma patient (CA0040). Results are shown in FIG. 8B.

Figure 8B:
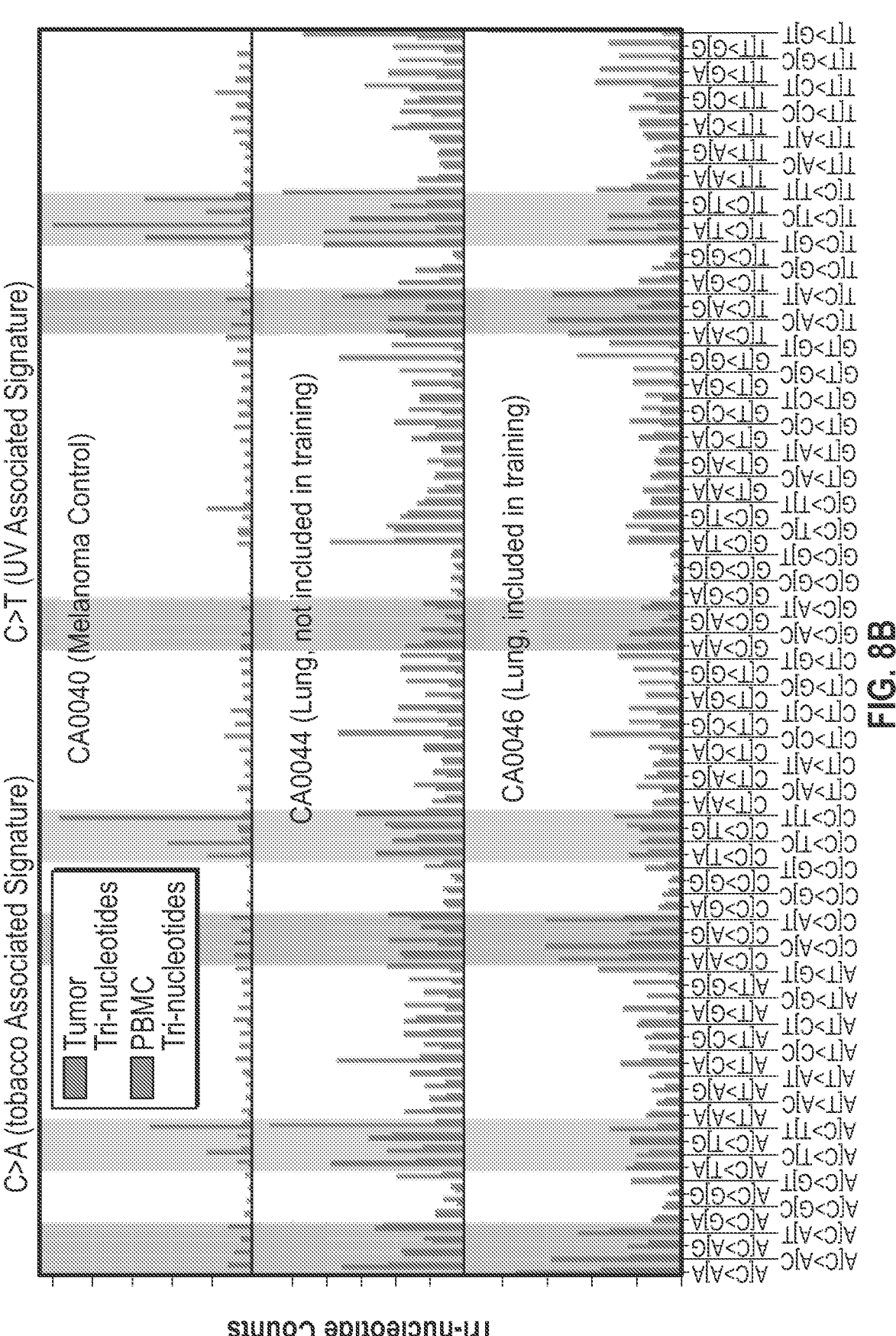
FIG. 8B shows tri-nucleotide frequencies from sample-specific Tumor and PBMC reads. Specific tri-nucleotides associated with tobacco (purple) and UV radiation (green).
Figure 8C:
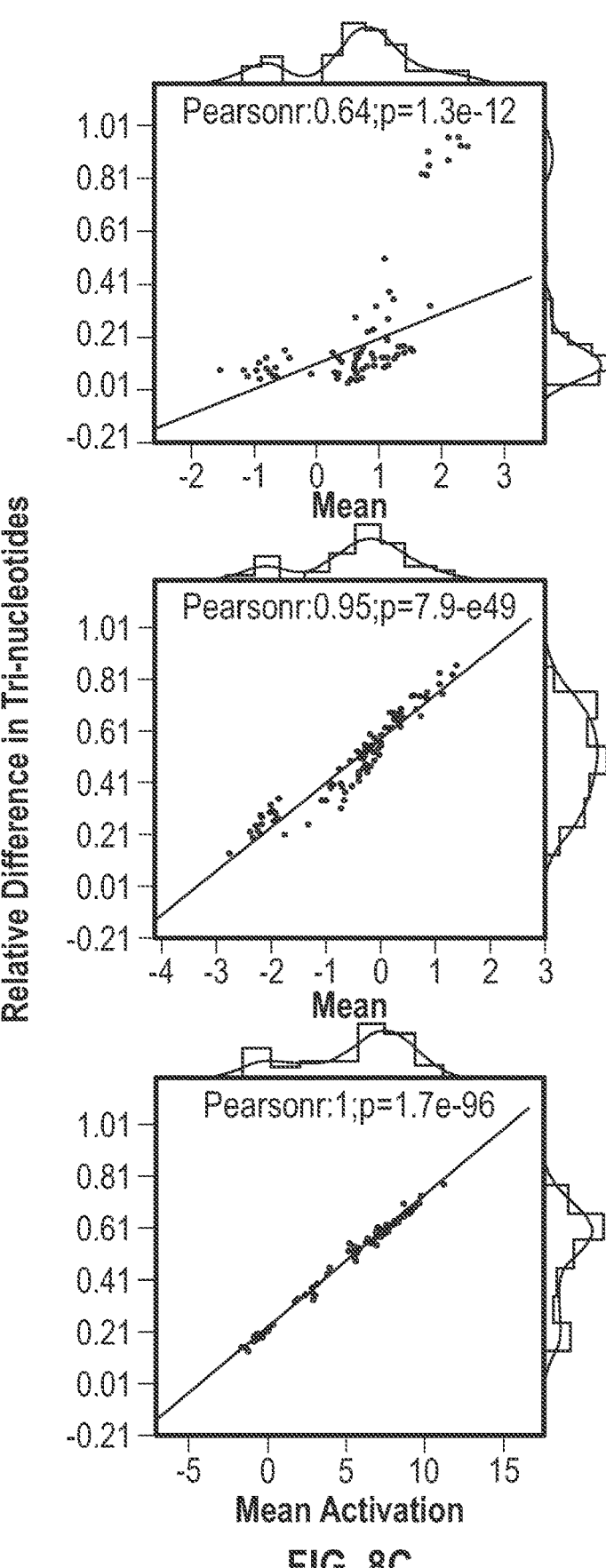
FIG. 8C shows correlation of relative difference in tri-nucleotide frequencies and mean activations of Engine.
Figure 9A:
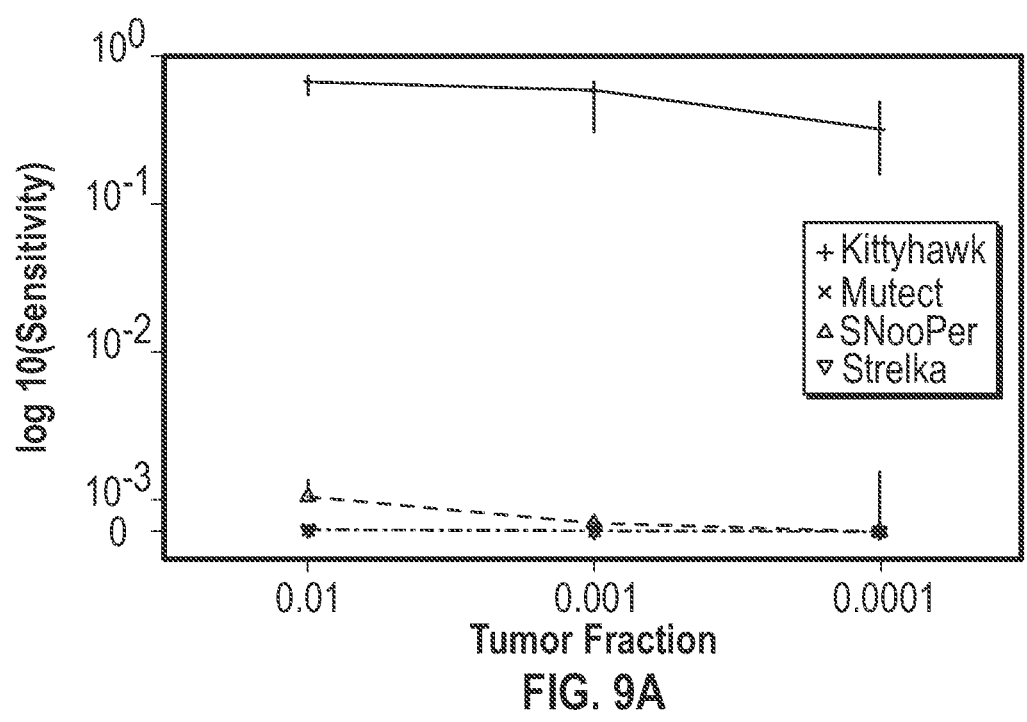
FIG. 9A shows sensitivity using patient CA0044 synthetic plasma. It can be seen that ENGINE (KITTYHAWK) of the disclosure outperforms art-known mutation callers such as MUTECT, SNOOPER, and/or STRELKA with respect to sensitivity.
Figures 9B, 9C:
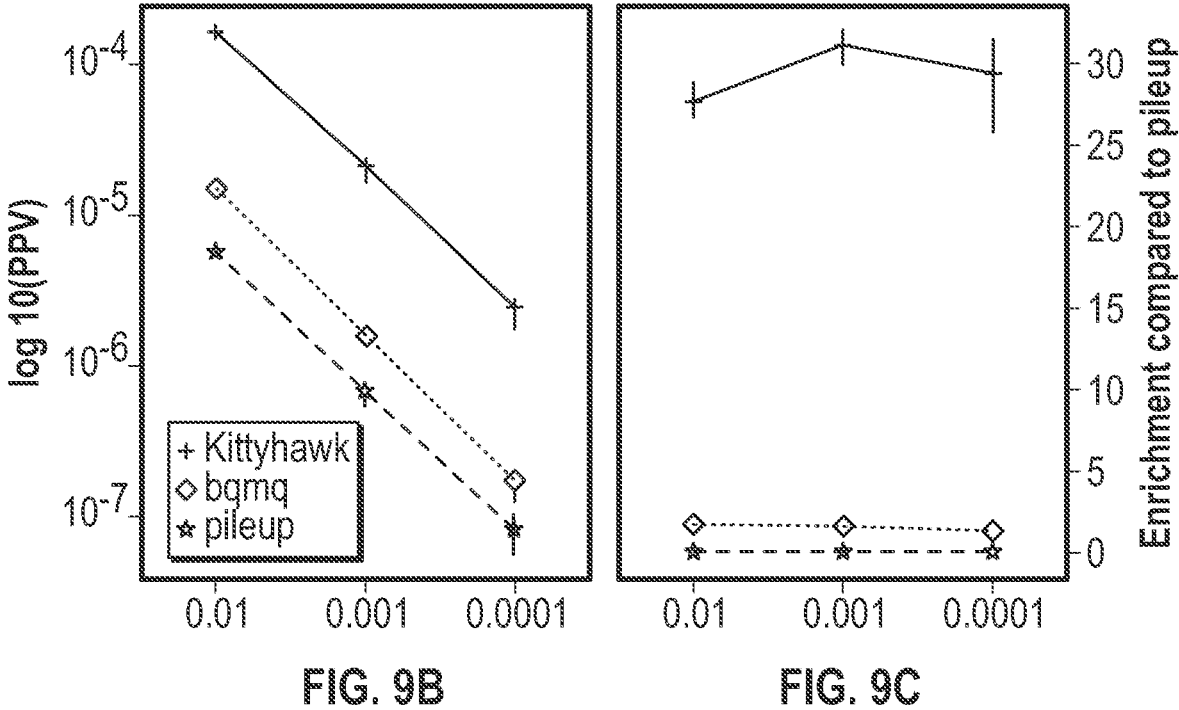
FIG. 9B shows a comparative line-graph of precision (as measured in terms of positive predictive value or PPV) attained using ENGINE on patient CA0044 synthetic plasma. MUTECT was excluded due to having only 2 detections. It can be seen that ENGINE outperforms art-known mutation callers with regard to precision.
FIG. 9C shows enrichment attained using ENGINE on patient CA0044 synthetic plasma. MUTECT was excluded due to having only 2 detections. It can be seen that ENGINE outperforms art-known mutation callers with regard to enrichment.

It was noted that as expected, the tobacco related lung adenocarcinoma samples show high enrichment in C>A transversions consistent with tobacco related mutational signature (FIG. 8B). It was therefore hypothesized that Engine may learn specific sequence contexts that are prevalent in tumor mutational data (i.e., tumor-specific mutational signature). To test this hypothesis differences in frequency between true cancer variants vs. sequencing artifacts in each tri-nucleotide context were measured, which were correlated with the average model prediction for these same reads. It was reasoned that if the model is learning the (lung) cancer specific sequence context, then a high correlation between the tri-nucleotide sequence frequency and the model output was to be expected. In line with the reasoning, a high correlation between the model prediction and tri-nucleotide enrichment was observed, both in CA0046 (included in training, Pearsons r=1) and in CA0044 (not included in training, Pearsons r=0.95). Results are shown in FIG. 8C.

To directly examine whether high correlation was a result of accurate classification that is independent of the sequence context (alternative scenario), a similar analysis was performed with the melanoma sample (CA0040). The results show a positive correlation (Pearsons r=0.64) between tri-nucleotide context and model predictions persists, indicating accurate classification derived from features other than the mutation signature alone, which was significantly lower than in the tobacco exposed lung cancer data. This finding is consistent with model learning of the specific lung cancer mutational signatures. This finding paved the way for training a separate model specifically geared towards detecting melanoma related somatic mutations. Utilizing the afore-mentioned procedure for NSCLC, an additional dataset from three melanoma patients was examined. The observations were similar with respect to performance as indicated by the high F1 score in the melanoma validation dataset, and independent melanoma sample, but a lower F1 score when the model was applied to NSCLC data (control).

Engine Sensitivity and Precision at Low Tumor Fractions in Synthetic Plasmas

To evaluate the performance of the instant systems and/or methods in low tumor fraction settings, the precision and sensitivity of Engine was compared to the state of the art callers, MUTECT, SNOOPER, and STRELKA. The results, which are shown in FIG. 9A, demonstrate the superior sensitivity achieved with Engine, especially at low tumor fractions. In contrast, MUTECT was unable to detect more than two mutations in the synthetic samples at any tumor fraction, and anytime it successfully made a mutation pre-diction, it made the same call in tumor fraction. Thus, Engine increases sensitivity over MUTECT by more than 200 fold, while improving precision over the simple filters in tumor fraction 0.01. Based on these surprisingly better results, the systems and methods of the disclosure were applied in the context of real plasma samples.

Comparisons were also made between Engine and the simple calling method, PILEUP. Results are shown in FIG. 9B and FIG. 9C. The comparative assessment was run across the filters that were implemented using Engine. Comparative assessment was further performed using another metric, called enrichment, which provides information on the increase in ratio of tumor to normal mutations when imply-ing a filter. The enrichment factor can be computed using Equation 5, below.

$$\text{enrichment} = \text{Precision}_{out}/\text{Precision}_{in} \qquad \text{(Equation 5)}$$

Although PILEUP has sufficient sensitivity to detect somatic mutations in simulated plasmas, it includes all mutations. This reflects poorly in the enrichment and pre-cision metrics. In the next stage of pipeline, filters by mutation frequency were employed. While the MF and BQ+MQ filters actually deplete the sample of tumor reads, an increase in enrichment when TF=0.01 was observed. This is a good indication that the filter is useful both for the evaluation pipeline but also for removing a large portion of the noise before presenting it to a CNN. When the CNN filter is applied, an additional (third) reduction of an order of magnitude in noise was observed. Most importantly, the concomitant reduction in sensitivity is only about 25%. With the complete pipeline an enrichment of 30 times (over PILEUP; in green line) in both tumor fraction 0.01 and in tumor fraction 0.0001 was observed. Data are shown in FIG. 9C.

Analysis of Somatic Mutations in Real cfDNA Samples Using Engine

In order to ascertain that the methods and systems of the disclosure are robust in the actual clinical setting, actual evaluations were performed on two different types of samples. The first is a cfDNA sample from healthy indi-vidual (Identifier: BB600; BB601); the second is from early stage lung cancer patient, taken before surgery (Identifier: BB1122; BB1125). While in the actual clinic, the clinicians performing the tests had no access to mutational information about patients. However, since BB1125 underwent surgery, the clinicians were able to measure the true somatic muta-tions using the standard mutation calling pipeline. These calls can be used and combined with the reads taken from cfDNA to obtain a qualified, second estimate of Engine's sensitivity, precision, and enrichment.

It was found that after applying the filtering pipeline, 27 of the 413 mutations present in the sample were successfully captured. Most strikingly, false positives were suppressed in the control from 266 errors present to 3 errors (see Table 2). The results indicate that although the pipeline as a whole actually depletes the tumor signal by about 50%, Engine, in contrast, enriches the sample it is presented with by roughly 1.7-fold.

Table 2: Performance metrics on cell-free DNA samples, Lung Cancer (BB1125)

| Sample | Method | Enrichment | Sensitivity | Precision |
|---|---|---|---|---|
| BB1125 | PILEUP(i,+321) | NA | NA | 0.0000141 |
| BB1125 | MF | 0.917 | 0.463 | 0.000013 |
| BB1125 | BQMQ | 0.399 | 0.21 | 0.00000515 |
| BB | 1125 | cfCNN | 1.692 0.675 | 0.00000872 |

The results indicate that the differences in the preprocess-ing steps may have resulted in a poor setting for the BQMQ filter. It was inferred that the base quality score of 20 may be too lenient for this sample.

Recognizing that it may be advantageous to use a training scheme that allows detection of true somatic mutations with high sensitivity while concomitantly rejecting candidate mutations caused by systemic errors, a variety of lung cancer patients were sampled and their systemic error profiles were matched. Four representative samples were selected from a variety of tobacco-smoking lung cancer patients for training to implement this scheme (Table 3).

Table 3: Training, validation, and test datasets

| Sample | Data type | #Mutations | +190 Train | #Validation/ test |
|---|---|---|---|---|
| CA0045 | Train tobacco lung | 13,759 | 716,800 | 50,269 |
| CA0046 | Train tobacco lung | 13,772 | 819,200 | 59,391 |
| CA0049 | Train tobacco lung | 19,404 | 716,800 | 80,896 |
| CA0044 | Train tobacco lung | 6,951 | 204,800 | 11,264 |

An additional tobacco-smoking lung cancer patient was held out for testing. The samples were processed and pro-vided by the Cancer Alliance at the New York Genome Center. These samples have a complete tumor sample and a healthy tissue sample from the same patient. The consensus of the three callers, STRELKA, LOFREQ, and MUTECT were taken to make final calls of somatic mutations. The reads supporting these mutations were then used as tumor reads for training.

Since it was desirable that the model learn to discriminate against sequencing artifacts, reads from the healthy sample that contained mutations occurring exactly once were taken. Because these variants are not supported by more than one read, it is highly probable that they are due to systemic errors. Such low quality variants are then filtered and reads with a base quality score at the mutation less than twenty or with a mapping quality less than forty (BQ 20, MQ 40) were filtered. These threshold BQMQ values were determined by inspection; however, a window was generated to allow for the inclusion of lower quality samples in training. Small subsets of the training set were additionally set aside to be used as a validation dataset. This dataset is used to both monitor training progress and also verify the performance of the model on independent reads (but not independent muta-tions). The performance of the model was then evaluated on the test lung dataset.

Synthetic Plasma

In order to test the ability of the model to detect somatic mutations at low frequency, four simulated plasma samples from the test lung sample (CA0044, Table 3) were generated by sampling randomly from the patient's healthy DNA and from the patient's tumor DNA. Sampling was performed with coverage of 35 and with tumor mixtures at 0%, 0.01%, 0.001%, and 0.0001%. Mixing was performed with three random seeds for robustness. A threshold rate of about 0.1 was selected as a rate of somatic mutations in cfDNA. Therefore, when preparing synthetic plasma reads for inference, only mutations supported by less than $\frac{1}{10}^{th}$ of covering read in the mixture were selected.

To evaluate the performance of the methods and/or systems of the disclosure in low tumor fraction settings, parameters such as precision, sensitivity, and enrichment, were compared between Engine and the state of the art low frequency caller, MUTECT. Comparisons were further made by including a simple calling method called PILEUP which allows for any observed mismatch. After PILEUP, the same filters used for Engine were repeatedly applied and the performance at each step was measured. The filters implemented in the methods are MF (mutation frequency), which filters PILEUP reads that occur more frequently than what is expected in plasma (mutation occurs 10% of the time), BQMQ, which filters reads that have a base quality at the mutation below 20 or a mapping quality below 40, and finally the instant filtration method using Engine.

Evaluation of cfDNA Samples

After evaluating Engine on synthetic samples, its performance on real plasma DNA samples was tested. Control sample (BB600; BB601) and tobacco smoking lung cancer patient sample (BB1125 or BB1122) were used in the analysis. Because tumor biopsy had also been performed on these patients, the true positives were measured by assuming all MUTECT called mutations from the biopsies that are also present in the cfDNA. Using these calls, the same analyses were performed as in the synthetic plasmas (supra).

Evaluating the Sensitivity, Precision, and Enrichment.

In the case of controls, all measurements were performed against the mutations for subject BB1125.

Feature Construction

To fully capture the sequencing read, alignment, and genomic context, a spatially-oriented representation of a read was created (FIG. 5). For insertions in the reference, an "N" is placed in the reference context at the location of the insertion to maintain a spatial alignment. For deletions in the reference, an "N" is placed in the read sequence at the location of the deletion. Softmasked regions are segmented such that the read is adjacent to the mapped portion of the read and the reference context is broken with consecutive "N's" until the end of the softmasked region. This is done for two reasons, to ensure the signal for softmasked regions is strong and secondly to maintain the idea of a read being independent from its alignment.

A segment (e.g., +/−25 bp) was padded from the genomic context to both sides of the read (FIG. 6). This results in a 16×200 bp matrix for 150 bp reads, in the case where a read is not 150 bp, extra context bases are added. The maximum base quality score was set at 40 (p=99:99%) and the scores were scaled to be in the interval [0, 1]. Bases not covered by a read (genomic context) received a base quality score of zero. Deletions in the read received a quality score that is the mean of the two flanking positions on the read.

Hyper-Parameters and Implementation Details

The model was trained using mini-batch stochastic gradient decent with an initial learning rate=:1 and momentum=:9. The learning rate was decreased by a factor of 10 when the validation loss reached a plateau as outlined in He et al. (In *Proceedings of the IEEE conference on computer vision and pattern recognition*, pp. 770-778, 2016). A mini-batch size of 256 was used as it seemed to provide the best trade-off between validation loss and training speed. A base of 64 filters was used, which was doubled after each down sampling layer to maintain a consistent number of parameters at each stage. This was empirically chosen after observing the inability of a 32-base filter model to perform sufficiently. After each convolutional layer, batch normalization was applied followed by a rectified linear unit. Before each pooling layer, a dropout with a drop probability=0.5 was applied.

Engine showed strong performance in the balanced tumor fraction setting. It further maintained a large portion of its performance even in the simulated plasmas. Engine also achieved an enrichment of 2 fold in tumor fraction of 0.0001, suggesting the ability to capture relevant somatic mutations even when they are 10 times rarer than sequencing noise itself. In contrast, MUTECT, a tool intentionally not designed to function in the cfDNA setting, makes less than two predictions in all tumor fractions. See, FIG. 9A-9C.

A detailed summary of results with Engine is presented in Table 4.

TABLE 4

Summary of performance metrics with Engine (F1 score, sensitivity, specificity and precision) on melanoma and lung cancer datasets.

Melanoma Table, Validation and Test Metrics

| Patient | Purpose | F1-Score | Sensitivity | Specificity | Precision |
|---|---|---|---|---|---|
| CA0035 | Train | 0.9258 | 0.9275 | 0.9256 | 0.924 |
| CA0037 | Train | 0.948 | 0.9537 | 0.9477 | 0.9424 |
| CA0038 | Train | 0.9351 | 0.9316 | 0.9353 | 0.9386 |
| CA0040 | Test | 0.9437 | 0.9427 | 0.9437 | 0.9447 |
| CA0044 | Control | 0.7626 | 0.6568 | 0.7954 | 0.9089 |

Lung Table, Validation and Test Metrics

| Patient | Purpose | F1-Score | Sensitivity | Specificity | Precision |
|---|---|---|---|---|---|
| CA0045 | Train | 0.946 | 0.944 | 0.948 | 0.946 |
| CA0046 | Train | 0.962 | 0.949 | 0.976 | 0.975 |
| CA0047 | Train | 0.944 | 0.944 | 0.944 | 0.944 |
| GA0049 | Train | 0.976 | 0.975 | 0.978 | 0.977 |
| CA0044 | Test | 0.922 | 0.903 | 0.94 | 0.938 |
| CA0040 | Control | 0.718 | 0.793 | 0.642 | 0.689 |

OTHER EMBODIMENTS

Based on the foregoing, the systems and methods can be developed into a complete early-detection engine. While Engine captures position in the read by using a fully connected sigmoid layer, there are architectures which may be more suited for capturing relative position on the read. Additionally, an extra source of information contained in the read-pair that comes from the DNA fragment, which was excluded in the preliminary testing, can be used to determine both the strand of origin (Watson or Crick) and to estimate the DNA fragment size. It has been observed that ctDNA have a distinct fragment size distribution compared to regular circulating healthy DNA (Underhill et al., *PLoS genetics*, 12(7):e1006162, 2016).

The aforementioned systems and methods can be integrated with recurrent neural networks (RNN). It has been shown that RNNs are a powerful tool for using length as a feature in bioinformatics at distances even up to 1 kb, far beyond the size of a ctDNA fragment (Hill et al., *bioRxiv*, pp. 200758, 2017). Integrating a recurrent neural network instead of a logistic regression layer could increase performance of the methods and systems of the disclosure even further.

Example 2: Methods and Systems for Detection and Validation of Tumor-Specific Low-Abundance Tumor Markers and Use of the Same in Cancer Diagnostics The systems and methods of the disclosure are useful in early diagnosis of cancer. As is known in the art, in contrast to metastatic cancer (which is characterized by a high disease burden and significantly elevated ctDNA), in the setting of early cancer or residual disease detection, ctDNA abundance limits the use of targeted sequencing technology. Given the known limited amount of cfDNA in the setting of low tumor burden, firstly, the potential of optimization of cfDNA extraction was investigated. First, to reduce variation derived from sample acquisition and inter-individual variation, commercially-available extraction kits and methods were compared using uniform cfDNA material generated through large-volume plasma collections (about 300 cc) through plasmapheresis of healthy subjects and cancer patients undergoing hematopoietic stem cell collection. The large volume of plasma allows the testing of multiple methods and protocol parameters on the same cfDNA input, enabling accurate measurement of subtle differences in yield and quality.

Kits and/or extraction methods from Capital Biosciences (Gaithersburg, MD, USA; Catalog #CFDNA-0050), Qiagen (Germantown, MD, USA), Zymo (Irvine, CA, USA; Catalog #D4076), Omega BIO-TEK (Norcross, GA, USA; Catalog #M3298), and NEOGENESTAR (Somerset, NJ, USA, Catalog #NGS-cfDNA-WPR) were used in this comparative study. These kits and reagents were uniformly utilized as per the manufacturer's instructions to perform extraction on 1 ml of the large-volume plasma sample. Multiple plasma aliquots were processed in parallel to assess both inter- and intra-method variability. The yield and purity of each recovered cfDNA sample was determined using fluorescence quantification (total mass), UV absorbance (detection of salt and protein contaminants), and on-chip electrophoresis (size distribution and gDNA contamination).

The results demonstrate that the MAG-BIND cfDNA Extraction Kit from Omega BIO-TEK outperformed all the other tested methods. A systematic optimization of each step of the manufacturer's protocol was further performed so as to reduce contaminant carryover and to improve the recovery of the cfDNA.

The optimized extraction protocol was then applied to samples from early stage lung cancer. This cohort includes 11 pre-operation early-stage lung cancer plasma samples and 4 plasma samples from benign patients (control). Exemplary patient characteristics are shown in FIG. 11. Despite optimized extraction, cfDNA yield in the low disease burden samples remained low and showed high variability between patients ranging between 0.13 ng/mL to 1.6 ng/mL). These data confirm the low and variable number of DNA molecules available for cfDNA sequencing.

Breadth of Sequencing can Supplant for Depth of Sequencing to Overcome Limitation on cfDNA Abundance in Sensitive Cancer Detection.

The above data demonstrates that detection of a single sSNV in a patient's plasma sample results from two consecutive statistical sampling processes. The first process provides the probability that the mutated fragment is sampled in the limited number of genomic equivalents present in a typical blood sample. The second process assesses the probability of detecting the mutated fragment in the sample given its abundance, sequencing depth and sequencing error (signal-to-noise). While the latter process has been at the focus of intensive investigation and technology development by the scientific community (e.g., ultra-deep error free sequencing protocols, the former stochastic process is infrequently addressed. Nevertheless, in low burden disease ctDNA detection, both processes play a critical role as shown above. If no physical fragments are present that represent the targeted sSNV, even ideal ultra-deep targeted sequencing will fail to discover the cancer signal, which is regarded to be one of the major factors responsible for the limited sensitivity of these approaches (~40%, Rosenfeld et al.). In practice this problem is further compounded by the fact that a single observation (mutated read) is rarely sufficient for confident detection.

To formulate the probability of sampling mutant fragments in a given cfDNA sample, cfDNA sampling was modeled as a Bernoulli trial, with an admixture of cfDNA fragments originating from two populations, cfDNA fragments originating from normal cells and cfDNA fragments originating from malignant origin with proportions defined by the tumor fraction (TF). Thus, the genomic equivalents present in a plasma sample constitute a random sampling of the entire pool of cfDNA fragments in the patient circulation. Therefore, the probability of sampling at least one mutant fragment in a plasma sample supporting a particular substitution can be defined as: $P=1-(1-TF)^{GE}$, where P is the probability; TF is the tumor fraction; and GE correspond to the number of genomic equivalents present in the patient cfDNA. The instant model predicts that the detection probability in TFs relevant to the early stage cancer regime (TF<1%), will exhibit a rapid decrease for low TF, and even at a frequency of 0.1% ($\frac{1}{1000}$), detection probability is predicted to be lower than 0.65 (FIG. 3A). It was noted that these limitations are observed even under idealize conditions of exhaustive sequencing that efficiently utilizes of 1000 genomic equivalents (~6 ng of cfDNA), and detection based on a single supporting DNA fragment with ideal signal-to-noise. These results show that the plasma sampling probability imposes a hard ceiling on mutation detection at low TF regimes, such as MRD and early cancer stage detection.

Conversely, the instant model also shows that this limitation on the depth of sequencing can be effectively overcome by increasing the number of detected sites (SNVs) through increased breadth, which results from repeating the Bernoulli trial for each SNV (a binomial distribution over the Bernoulli trial probability). This model can be represented by Bin(N,P), binomial distribution, where N represent the number of sites (mutations) tested and $P=1-(1-TF)^{GE}$ is the detection probability for a single site. Importantly, the mathematical model predicts the average number of detected sites, as well as the probability for at least one detection, as a function of the number of unique DNA fragments (genomic equivalent or coverage), mutation load (N, can be used also as panel size) and TF (FIG. 3B). Utilizing this model, it was found that integrating over 20,000 sSNVs (about 10 mutations/mb found in 17% of human cancer) can provide a high detection probability (up to 0.98) even at TF of 1:100,000, at a modest sequencing effort (20× coverage), such that can be readily achieved with standard whole genome sequencing (WGS) (FIG. 3C).

In Silico Validation of Integrated Genome-Wide sSNV Detection

The instant model indicates that increasing the number of sites results in significant increase of detection probability. To validate this prediction, cfDNA detection was simulated using in silico mixtures of tumor and normal WGS data from 11 cancer patients with various cancer types, including high grade tumors from lung adenocarcinoma, ductal adenocarcinoma (breast), cutaneous melanoma, urothelial carcinoma (bladder) and osteosarcoma (full clinical details at Scheme A; FIG. 1F).

All samples were deep-sequenced with ~80× tumor WGS and ~40×PBMC WGS. To generate in silico mixtures, tumor and normal WGS reads were admixed in varying proportions and obtained a dataset of patient specific virtual plasma samples of different TF (0.00001, 0.00005, 0.0001, 0.0005 0.001, 0.005, 0.01) and coverage (5, 10, 15, 20, 35), with 5 independent replicates for each condition obtained through different randomization seeds used during the down sampling process. To simulate detection in the residual disease setting, somatic mutation calling was performed on the original tumor and germline WGS data, and a patient-specific compendium of sSNVs was obtained. The number of tumor-associated mutated sites in the in silico plasma simulation mixtures was then measured through detection of at least one supporting read for the patient-specific sSNV compendium. It was found that integrating many sites also results in accumulation of noise resulting from sequencing errors that may limit the detection of the above-described signal. To estimate the extent of noise in WGS based cfDNA detection, a complementary database of down sampled normal reads without admixture of reads from tumor WGS was generated (TF=0, 20 replicates at 20× and 35× coverage). These data enable signal-to-noise measurement and demonstrate that integrated whole-genome SNV detection can confidently detect TF>1:2000 in a high mutational load tumor with 20× coverage for various tumor types.

These data also show how noise from sequencing error shapes the relationship between number of detected sites and TF, as the relative contribution of noise increases as TF decreases. A comparison with the mathematical model prediction integrated with the estimated sequencing noise showed high concordance over different TF and coverage values for all patients and cancer types. This analysis also demonstrates how increase of the mutation load (N) and coverage can increase the detection signal, with the number of detection in 1% TF varying between 40K mutation load (melanoma) to 8K mutation load (non-tobacco lung).

Characterizing the variables that underlie the estimated noise and the development of optimized filters can significantly improve signal-to-noise and detection sensitivity. Modeling the noise distribution by other independent variables such as the mutation load, coverage and cancer type. The results show a cancer-type independent error probability that reflect previously published sequencing error rates (~1/1000 bases). Also, the detected signal showed patient specific relation with negligible germ-line associated noise.

The data showed that sequencing error was found to be associated with parameters such as Base-Quality (BQ), Mapping-Quality (MQ), fragment length and variable allele frequency (VAF).

Accordingly, to reduce sequencing error rates, a joint Base-Quality (BQ) and Mapping-Quality (MQ) optimized filter was developed through optimal receiver point analysis (ROC), which reduced the measured error rate by 3 FC (to about 3×10⁻⁴). Applying this filter with alleviated 35× coverage results in detection of markers even when TF is down to 1/20,000 in a tumor at a WGS depth of 35×. These data support the use of patient-matched integrated genome-wide sSNV profiling to enable cancer detection probability even at very low TF, independent of cfDNA abundance (e.g., 1 ng of input allows 100×WGS). Moreover, the high agreement between the experimental results and the mathematical model indicates that measuring the number of detected sites (patient-specific sSNV) can be transformed to the estimation of the plasma TF, allowing for quantitative TF monitoring in the early detection settings.

Figure 12A:
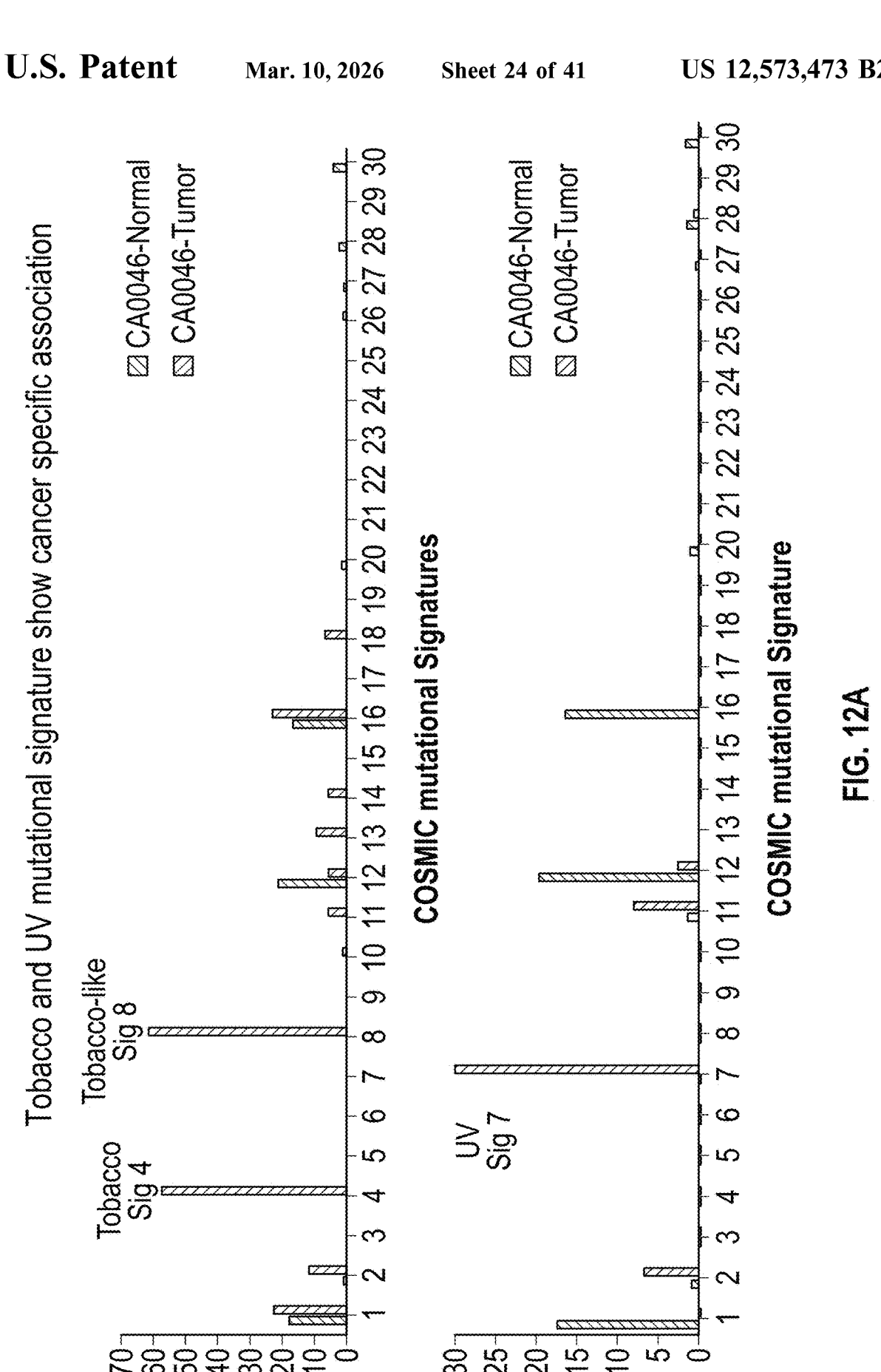
Figure 12B:
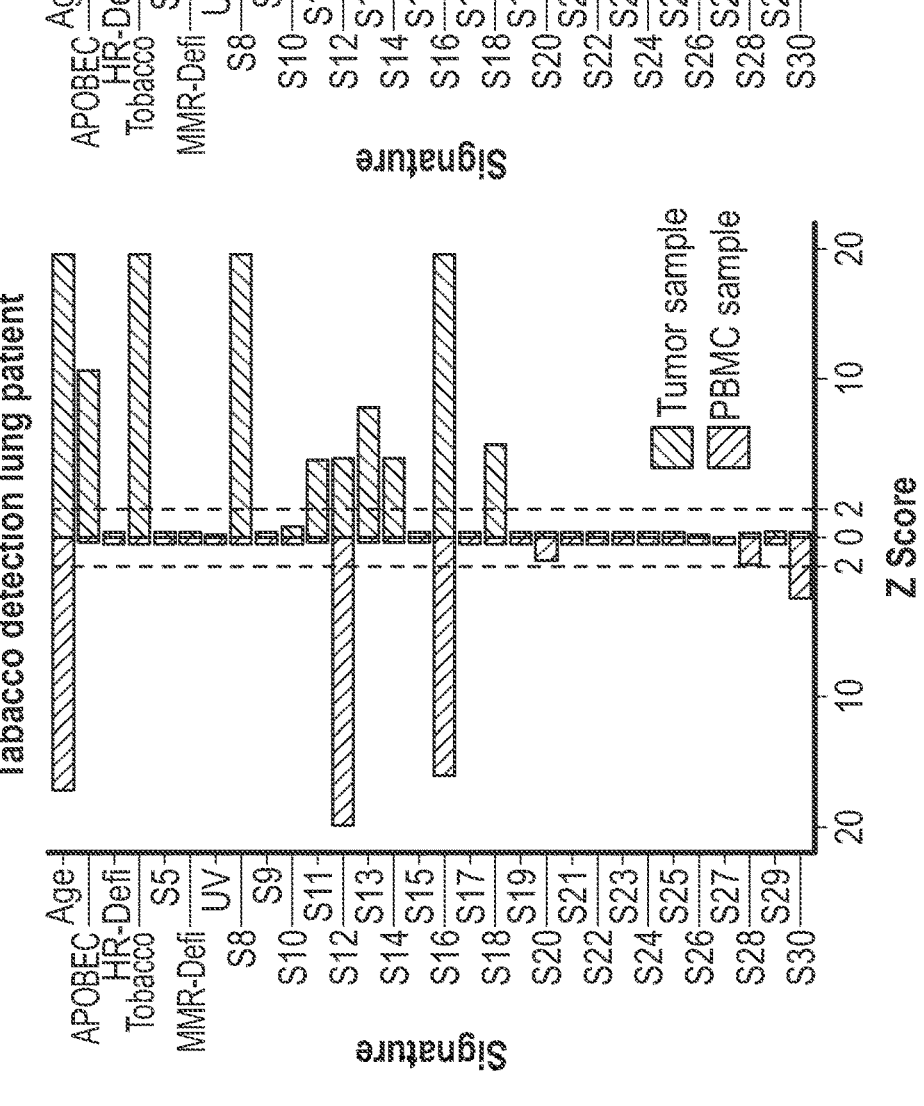
Figure 12C:
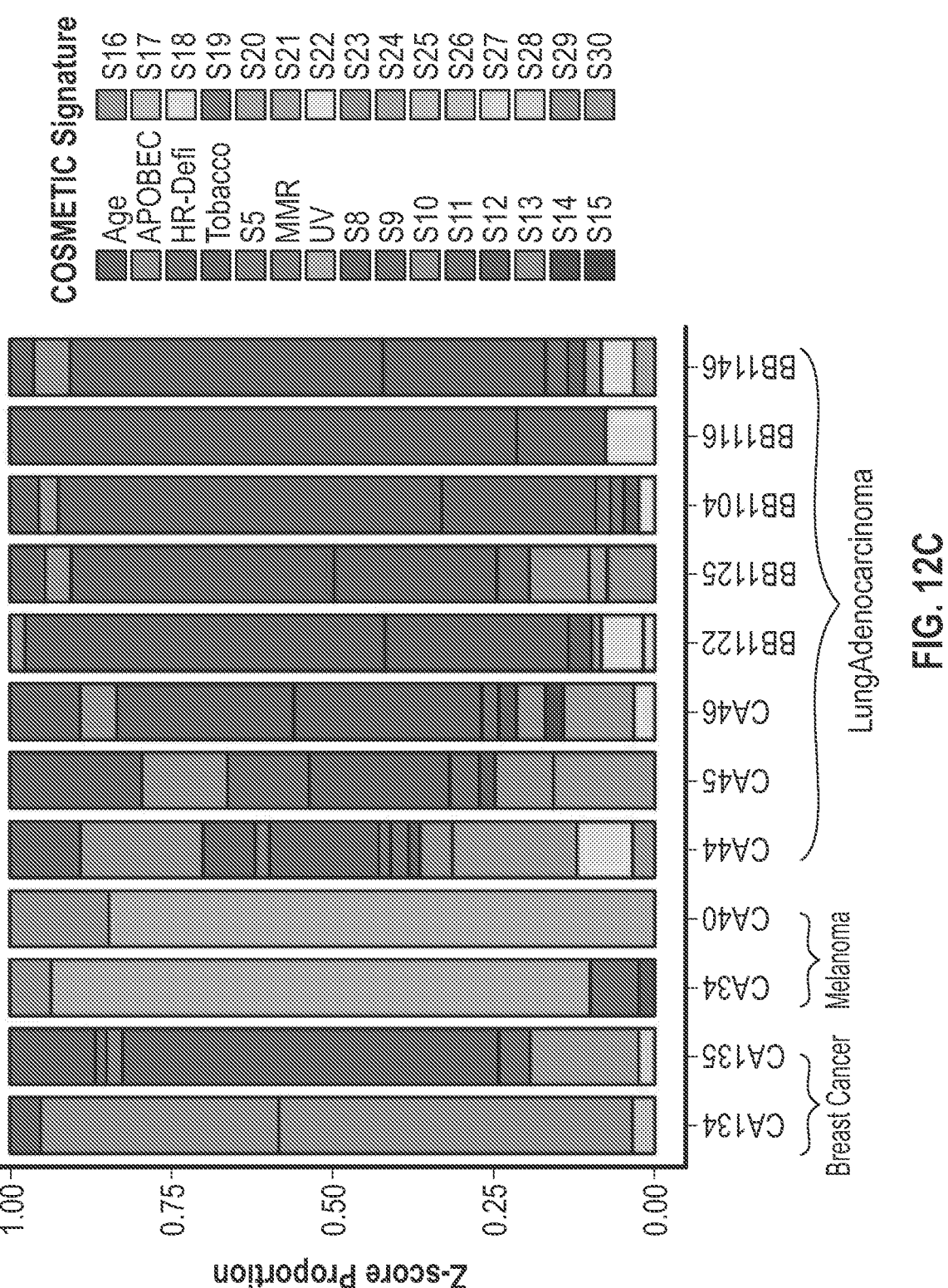

Additional parameters beyond quality metrics may be further utilized to filter remaining noise, including utilization of information on specific motifs, signature, etc. Representative methodologies include, e.g., implementation of fragment size filters (e.g., only fragments about 200 bp or shorter are considered) and variable allele frequency (VAF) filters (e.g., only alleles that have VAF greater than a threshold value, e.g., 2%, 5%, 10% are considered). Various mutational signatures for tobacco-exposure and UV-exposure are respectively shown in the top panel and the bottom panel of FIG. 12A. Differentially expressed COSMIC signatures in lung tumor, breast tumor and melanoma samples are shown in FIG. 12B and FIG. 12C.

Application

This sensitive de novo mutation detection was then applied to sequenced pre-surgery plasma of 5 early-stage patients, generating genome-wide cfDNA mutation detection. Genome-wide mutation data was aggregated to calculate the mutation compendium for each patient, followed by a novel analytical method for sensitive mutational signature detection, using novel machine learning algorithms and tools, such as, convolutional neural networks (CNN).

The CNN is based on application of a two-pronged strategy—first, the deep learning algorithms were trained over a pan-lung cancer cohort (5 patients with deep tumor and PBMC WGS) utilizing the supervised learning to identify signatures that discriminate between true tumor mutations and artefactual errors. The model obtained was then utilized to infer and to assign a confidence estimate to each individual mutation detected in early-detection plasma samples from lung adenocarcinoma early stage patients. Second, the detection signal was derived through the integration of these confidence estimates across the entire genome, followed by a novel analytical method for sensitive detection, using non-negative least square (NNLS), of specific cosmic mutational signatures in a single plasma sample. Signature detection was further validated for confidence using a comparison of cosmic mutation exposure values to the exposure values inferred for 100 random background signatures (zscore>2 STD).

The results, which are shown in FIG. 13, demonstrate that CNN of the disclosure is especially useful in early tumor detection (ED). Through this method, tobacco-specific signature was detected in lung cancer patients; a UV-specific signature was detected in melanoma patients; and a BRCA-specific signature was detected in breast cancer patients, in each case, even when TF was 1/1000 or less. To evaluate the ability of the method so as to improve upon the low positive predictive value (PPV) of current lung cancer CT screening in at-risk tobacco-exposed subjects, the method was applied to plasma samples from five early stage lung patients and four benign nodules, all of which were detected as positive in CT screenings. The data show positive detections for the early-stage lung cancer samples and less (false) positive detections for the benign nodules, thus showing an improved PPV.

Figure 14A:
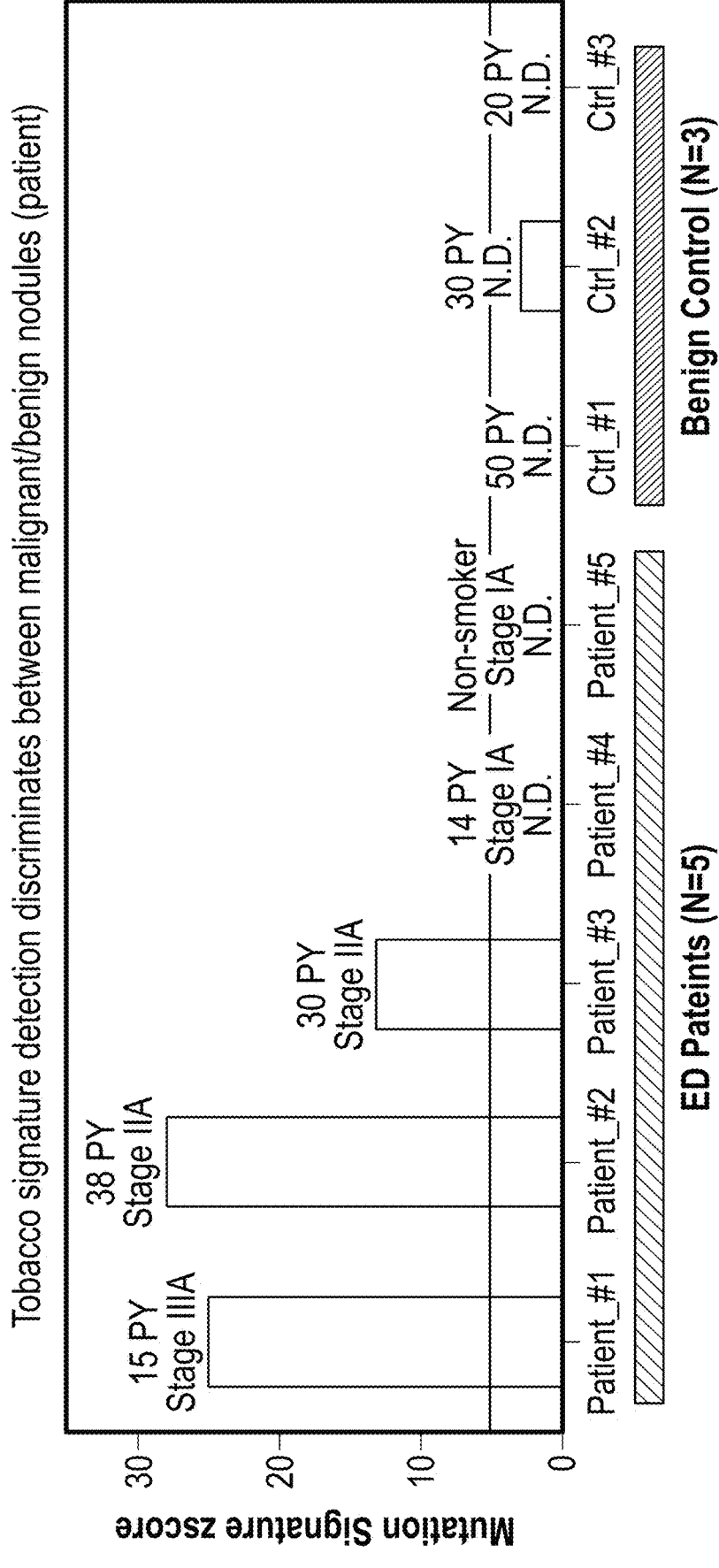
FIGS. 14A-14B show zscores of various patient samples.
Figure 14B:
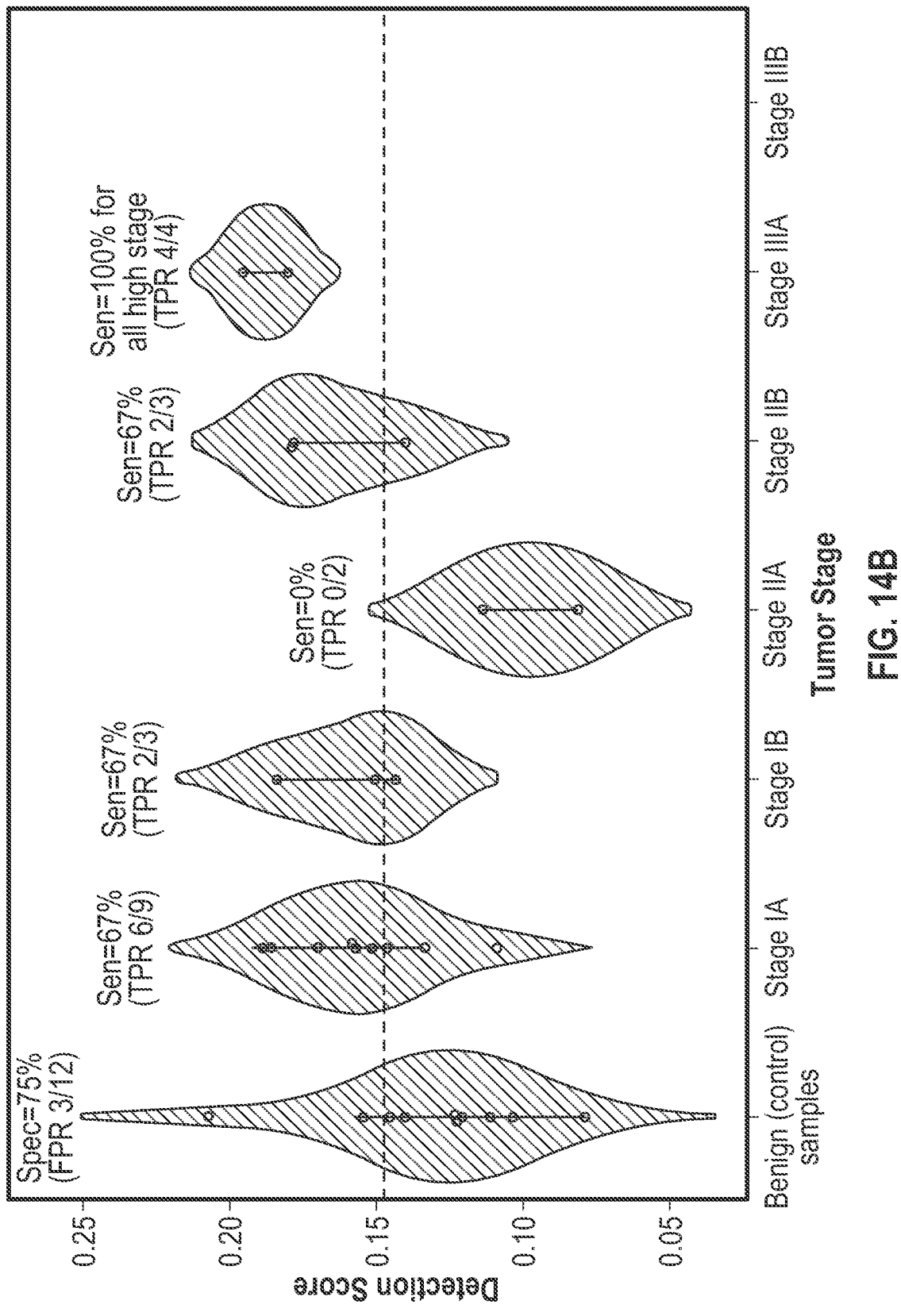

Next, patient-specific signature score (zscore) was mapped to patient characteristics such as smoker or non-smoker, smoking history, e.g., number of pack years each patient smoked (for smokers), including, histopathological features such as positive or negative (ND) for detection of nodules. The results, which are presented in FIG. 14A, reveal that tobacco signature is detected in early stage cancer plasma from patients with tobacco exposure, but not in patients with benign nodules or no smoking history. Through this method, it was possible to detect tobacco signature in 3 out of 4 early stage lung patients with previous tobacco exposure, whereas the signature was not detected (N.D.) in non-smoker lung patient and plasma samples from 3 individuals who underwent benign lung nodule resection. In all but one stage, the specificity of the tobacco signature in the detection of lung cancer patients was at least 67%, with specificity approaching 100% in high stage (e.g., stage IIIa and beyond) patients.

Application of the Diagnostic Methods Together with CT Screening to Improve PPV

To improve upon the low positive predictive value (PPV) of CT screening method, the aforementioned screening method is applied, with or without CT screening, to diagnose/prognosticate at risk tobacco-exposed subjects. First, markers and signatures (comprising SNVs, CNVs, indels and/or SVs) are detected de novo via whole genome sequencing (WGS) and analyzing the markers for noise/errors using the aforementioned methods. In this manner, a total of 30 pre-operative samples, which were collected from patient with early stage NSCLC (stage I and II), are analyzed. Further, WGS is performed on 30 age and tobacco exposure matched patients who were found to have a benign lesion through an institutional CT based screening program. The detection signal from the cfDNA data are integrated with the CT based readouts in a blinded fashion to determine whether the positive predictive value of CT screening can be improved with cfDNA information. It is estimated that the cohort is powered to detect an effect size of 20% increase in PPV from about 40% with the present methods to about 60% with integrated cfDNA and CT screening. Depending on the outcome of the study, a larger scale prospective institutional clinical trial may also be conducted.

Discussion

The data show that the methods and/or systems of the disclosure are superior to existing methods, especially in the context of detecting low abundance markers, which is used for early detection of tumor (ED). In early cancer detection matched tumor DNA is not available, which requires challenging de novo cancer variant detection. The genome-wide integration methods of the present disclosure utilize sSNV sequence context information to detect mutational signatures that have been associated with specific mutagenesis processes such as exposure to tobacco, UV light, APOBEC hyperactivity, BRCA mutation, PARP activity, or MSI. These signatures appear specifically in the tumor somatic mutation and completely absent in the PBMC somatic mutation, at all samples tested.

Sensitive and specific de novo mutation detection in cfDNA of low TF samples is fundamentally challenging to existing mutation detection algorithms. All art-known methods are devoted to comparing tumor and normal DNA at a particular genomic site. The power to detect a mutated site in the genome is derived from the observation of multiple supporting reads that cover a site that are then subjected to a statistical framework to distinguish these multiple observations from sources of sequencing noise (sequencing error, mapping error, etc.). However, in the context of early detection, the amount of mutated ctDNA is well below the sequencing depth (or the number of fragments available for sequencing at a particular site), and therefore, at best, only a single supporting read is observed at each site. For instance, application of MUTECT on the virtual-plasma data show a rapid decline in true tumor-associated somatic mutation with decreasing TF, even when considering all the detections included in the call-stats file (before variant filtration), but many more such mutation sites are called when considering detection by single-supporting read.

To allow error-free de novo single ctDNA detection at low TF requires a novel framework to enable distinction between alternate reads that originate from cancer mutations and those that result from sequencing artifacts. While mutation signatures have typically utilized the tri-nucleotide context, recent data suggest that sequence context may extend well beyond this range, and may be difficult to capture through supervised feature selection.

The instant disclosure provides novel methods and pipeline for filtering sequencing errors. For example, tumors generated from specific mutational processes give rise to distinct mutational patterns, which may be utilized to remove artefactual noise and provide enriched markers with improved subject-specificity, sensitivity, and precision. The neural networks of the present disclosure utilize machine learning, which enables them to overcome the aforementioned limitations of art-known callers. The machine learning architecture distinguishes between cancer altered sequencing reads and reads altered by sequencing errors and filters systemic sequencing noise both specifically and adaptively. In this context, the deep convolutional neural network (CNN) of the disclosure provides an artificial intelligence platform that integrates a high number of features in a supervised fashion, which is specific to solving classification problems in the context of genomic sequence reads. The approach utilized in the design of the CNN is based on rethinking of the mutation calling challenge. Unlike art-known mutation callers such as MUTECT, the CNN of the disclosure can distinguish between a read that contains a true variant versus reads that contain a sequencing artifact. The CNN of the disclosure is not static but dynamic as it can be trained on millions of true mutated reads and error using a large collection of tumor and normal WGS data.

The aforementioned features of the CNN are advantageous over art-known mutation callers, as evidenced by the greater sensitivity and specificity associated with detection of a wide variety of tumor types across many patients.

Application of the Methods and Systems of the Disclosure to Detect Lung Cancer

The aforementioned results show that integrating information across the genome can overcome a major barrier associated with detection of low abundance markers that are indicative of disease states. Applying the methods and systems of the disclosure to analytical methods helps break the ceiling of detection and enables detection of tumor fraction as low as $1/10,000$ and improves upon depth of sequencing. These advantages are especially useful in the area of lung cancer detection and detection of residual disease in patients post-surgery and/or post-therapy.

In the context of pre-malignant lung lesions, detection of minimally invasive disease is likely to be even more challenging compared with early stage NSCLC. Notably, the majority of cancer mutations are thought to occur prior to malignant transformation and therefore likely to be present even in the pre-malignant growth. Accordingly, the systems and methods described herein can be also used to detect pre-malignant lesions, especially in the context of lung tumors.

Figure 17A:
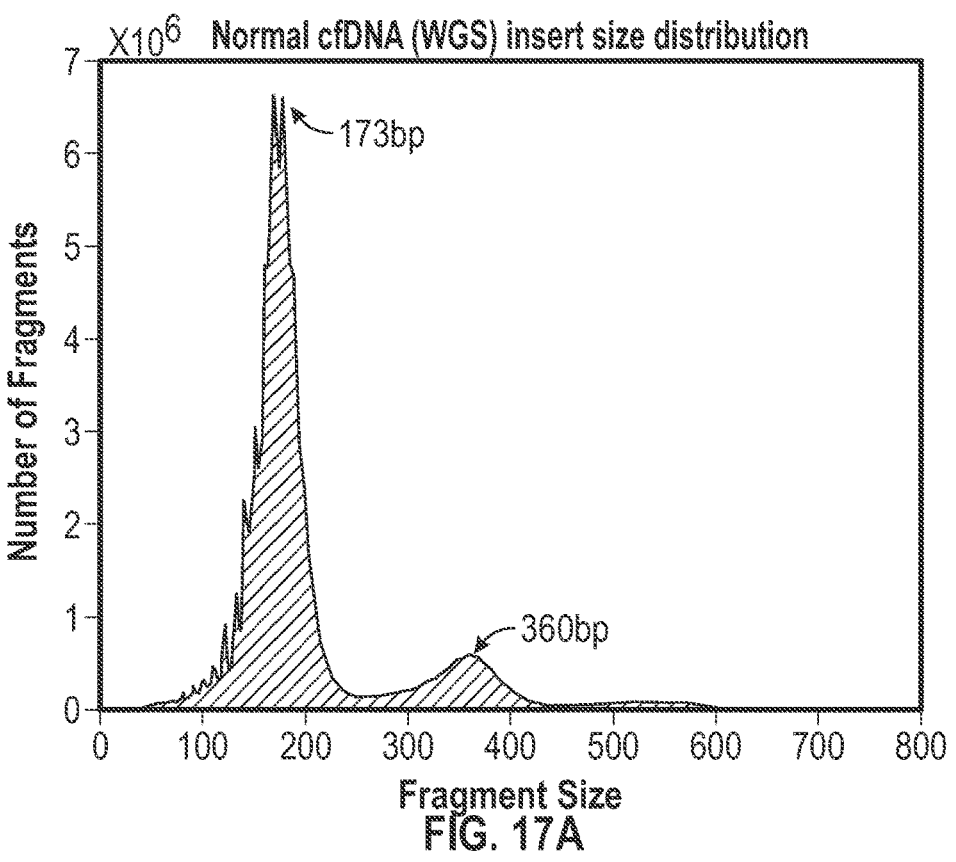
FIG. 17A-FIG. 17E show use of orthogonal features such as fragment size in the diagnostic methods of the disclosure and the concomitant effects of application of such orthogonal features in SNV-based methods.
Figure 17B:
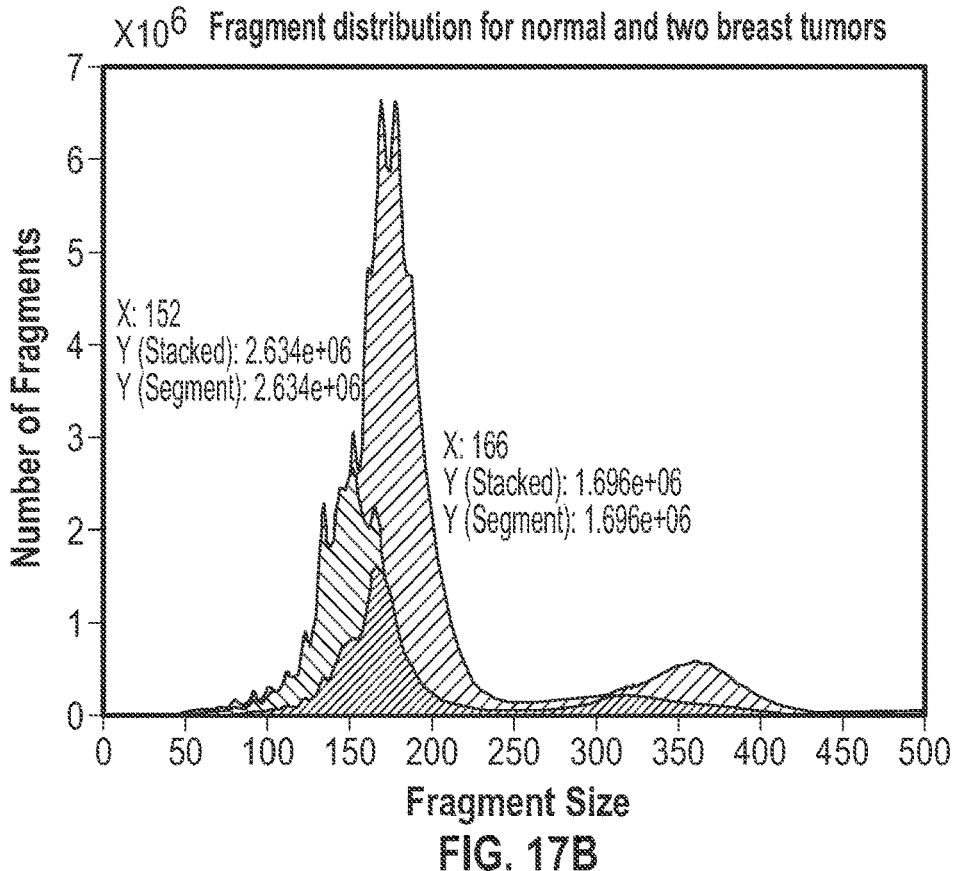
Figure 17C:
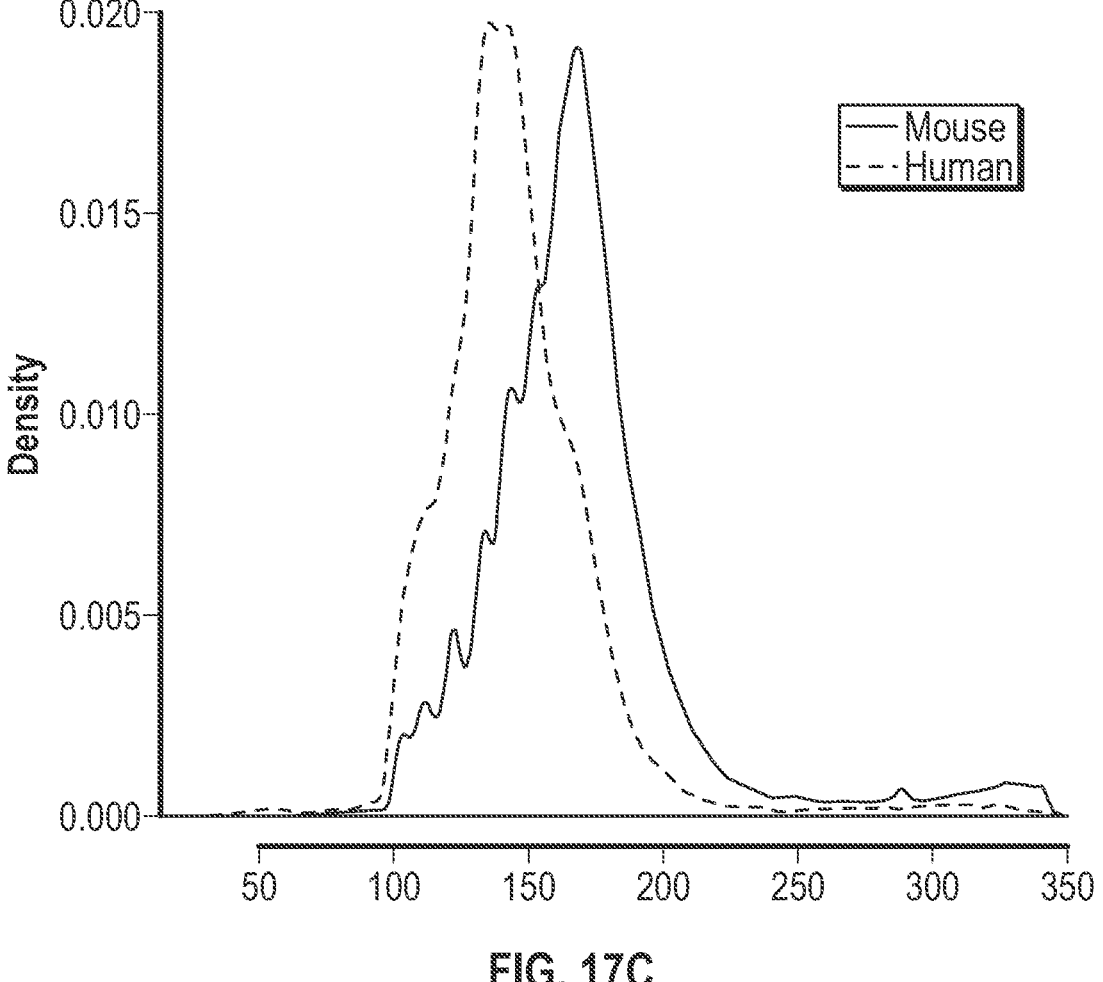

Orthogonal Integration of Fragment Size Features in SNV-Based Methods cfDNA fragment distribution have a unique profile due to the DNA degradation during blood circulation. Healthy normal cfDNA sample show the fragment size distribution shown in FIG. 17A. Circulating DNA fragments that originate from the tumor show shorter fragment size in comparison to "normal" DNA fragments that originate mainly from apoptosis of hematopoietic cells (immune cells). Breast tumor cfDNA (red and purple) show a fragment size shift compared to normal cfDNA sample (FIG. 17B). Calculating the center-of-mass (COM) of the first nucleosome (the peak around 170 bp) show a shift to lower COM that correspond linearly to the TF. Using human tumor xenograft models (PDX) in mice show that circulating DNA that is from the tumor origin (red, aligned to human) is significantly shorter than circulating DNA that is from normal origin (black, aligned to mouse). See FIG. 17C.

Figure 17D:
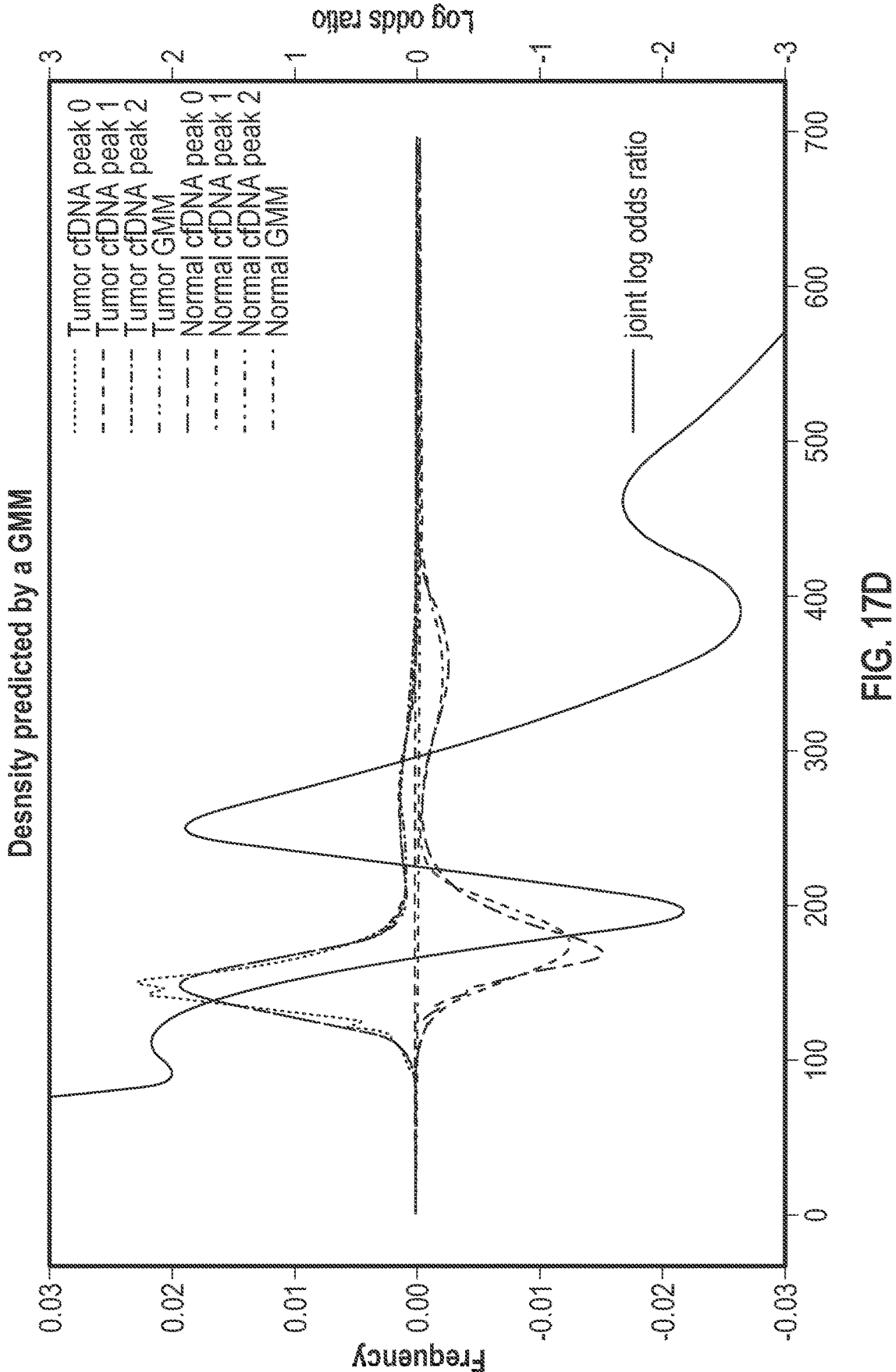

To generate a robust model that can quantify the probability of a single DNA fragment to be from tumor or normal origin we used a joint gaussian mixture model (GMM) to characterize the fragment size distribution of circulating DNA. Circulating tumor DNA model (red dashed line) was estimated by applying the GMM analysis to circulating tumor DNA extracted from our PDX samples, using only circulating DNA that is aligned to the human genome. Circulating normal DNA model (gray dashed line) was estimated by applying the GMM analysis to circulating DNA from plasma samples of healthy human volunteers. The joint log odds ratio (yellow line) was then used to estimate the probability of a fragment size of a specific circulating DNA to be from tumor or normal origin. Data are shown in FIG. 17D.

Figure 17E:
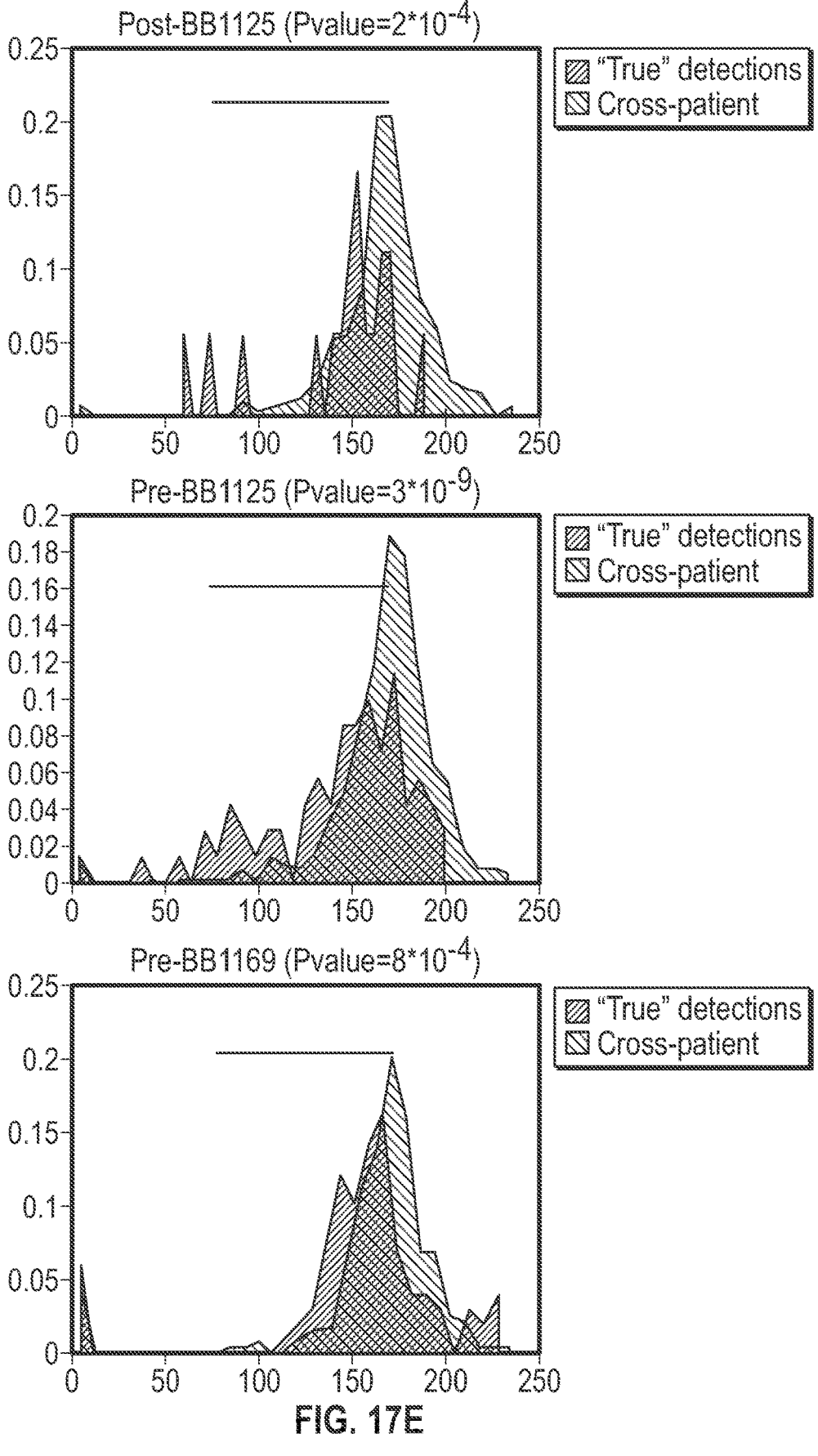

Patient specific mutation detections can be used to check if these DNA fragments correspond with tumor origin based on their fragment size distribution and the GMM joint log odds ratio. To increase confidence and decrease batch effect bias, an intra-patient control was developed using the cross-patient detection. For example, in the specific patient shown below the detected tumor mutation (gray, matched detections) are in and show tendency for a fragment size shift towards low fragment size. On the same patient sample, mutations that are associated with other patients were detected (red, cross-patient detection), these artefactual detections share the same Tobacco signature context-information patterns but are not true detection. Interestingly these cross-patient detections do not show the tendency for low fragment size shift, and their fragment size distribution is significantly different from the true tumor detections (Wilcoxon rank-sum, Pvalue $3*10^{-9}$). Using the GMM joint log odds ratio confirms that the patient specific mutation detection is from tumor origin (joint log odds ratio=0.3) while the artefactual mutations from the same patient sample are coming from normal origin (joint log odds ratio=−0.35). Representative data for three patients are shown in FIG. 17E.

Orthogonal Intergration of Fragment Size in the Context of CNV Markers cfDNA fragment distribution have a unique profile due to the DNA degradation during blood circulation. Healthy normal cfDNA sample show a variation in the distribution of the fragment sizes (see, above, FIG. 17A and FIG. 17B). Here, in the context of analyzing center-of-mass (COM) distributions, calculation of the COM of first nucleosome (the peak around 170 bp) indicates a shift to lower COM that correspond linearly to the TF.

Figure 18A:
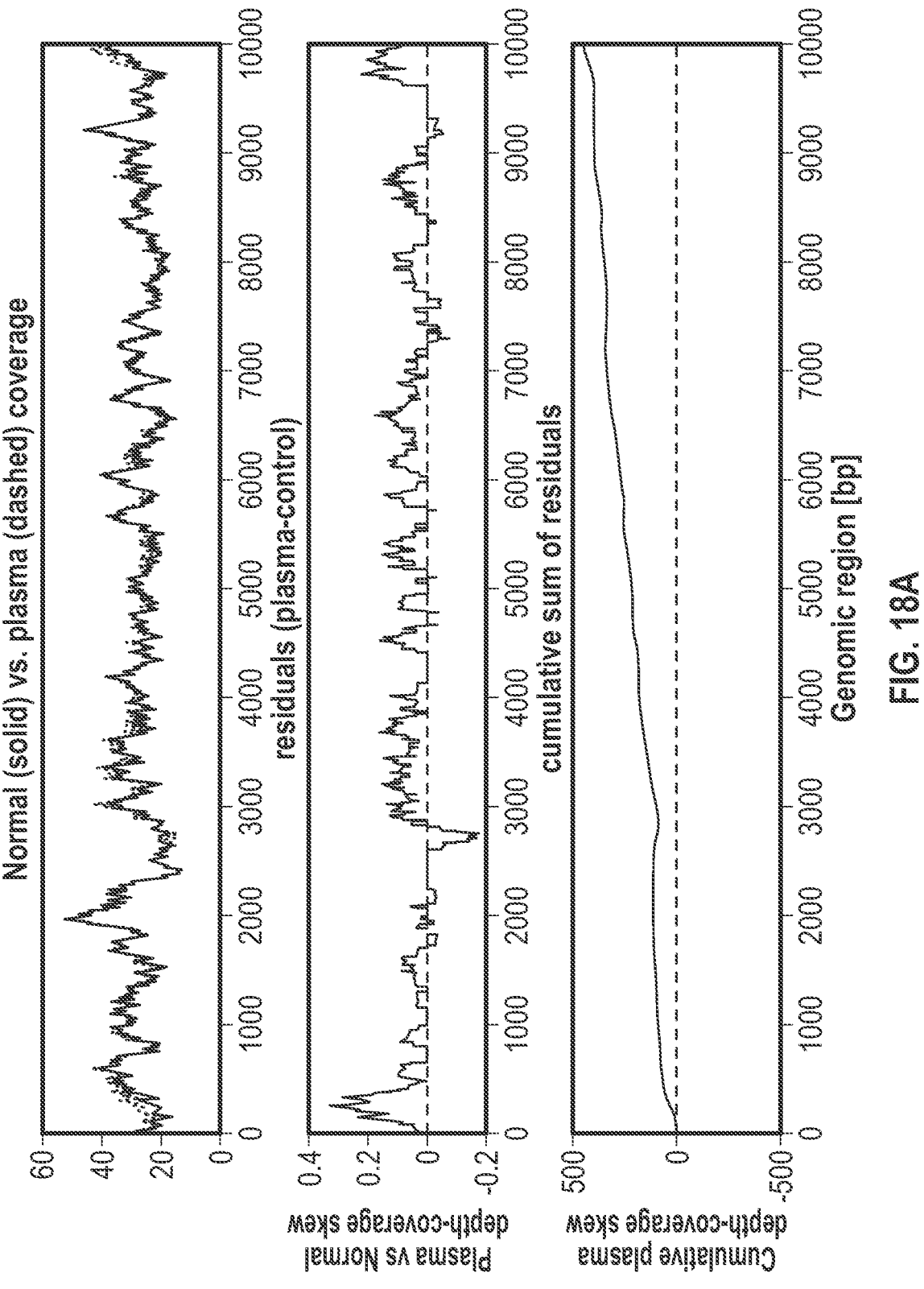
FIG. 18A-FIG. 18F show use of orthogonal features such as fragment size in the diagnostic methods of the disclosure and the concomitant effects of application of such orthogonal features in CNV-based methods.
Figure 18B:
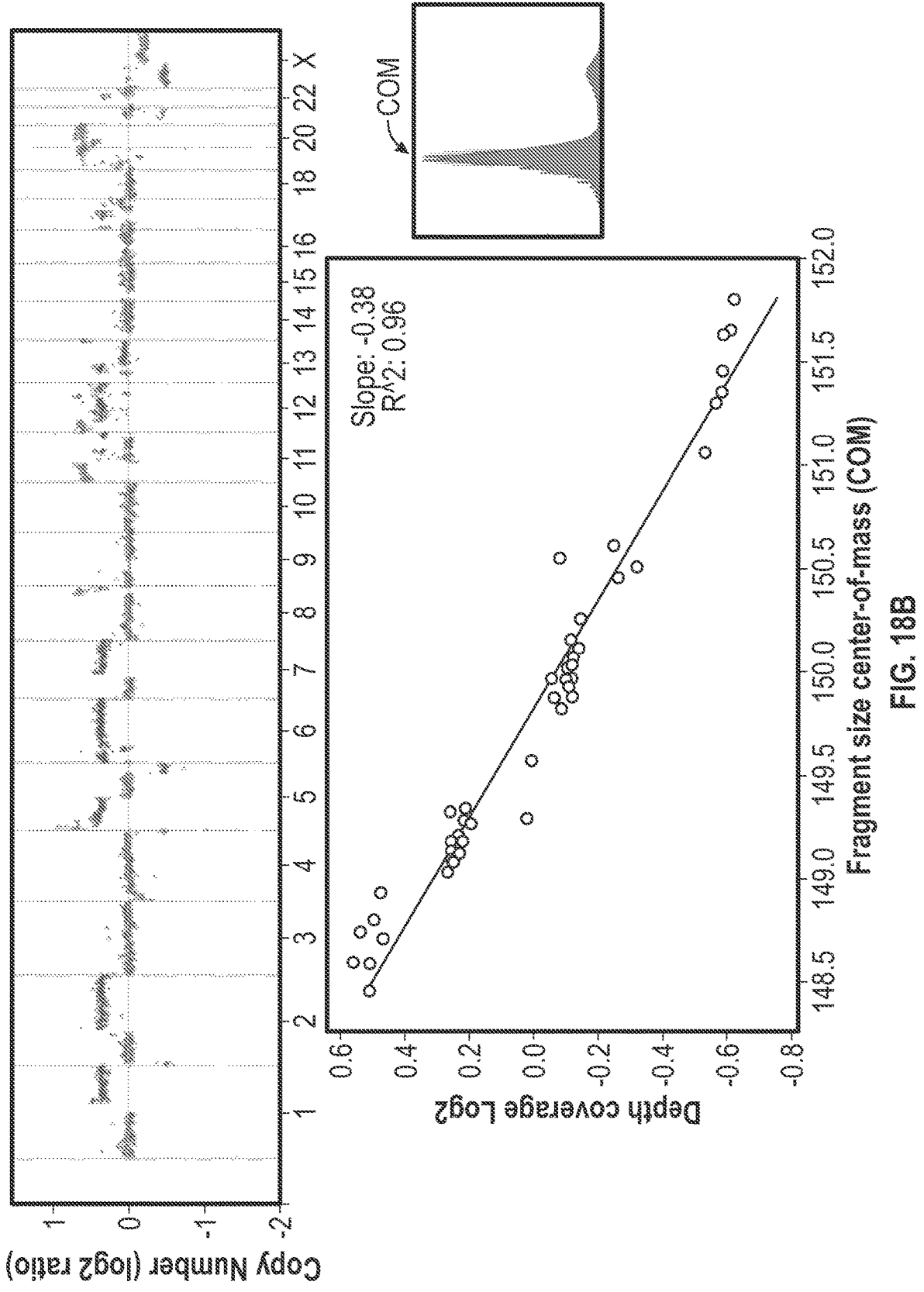

Comparative analysis of fragment size center-of-mass (COM) between patients may be limited with respect to sensitivity and may also be prone to batch effects. Intra-patient local fragment size COM can change due to epigenetic signatures or due to copy-number-events. Indeed, in amplification segments there is a local increase in tumor fraction (due to the increase in the proportion of tumor DNA) and therefore decrease in the local fragment size center-of-mass (COM). On the other end, in deletion segments there is a local decrease in tumor fraction (due to the decrease in the proportion of tumor DNA) and therefore increase in the local fragment size center-of-mass (COM). Data are shown in FIG. 18B.

Figure 18C:
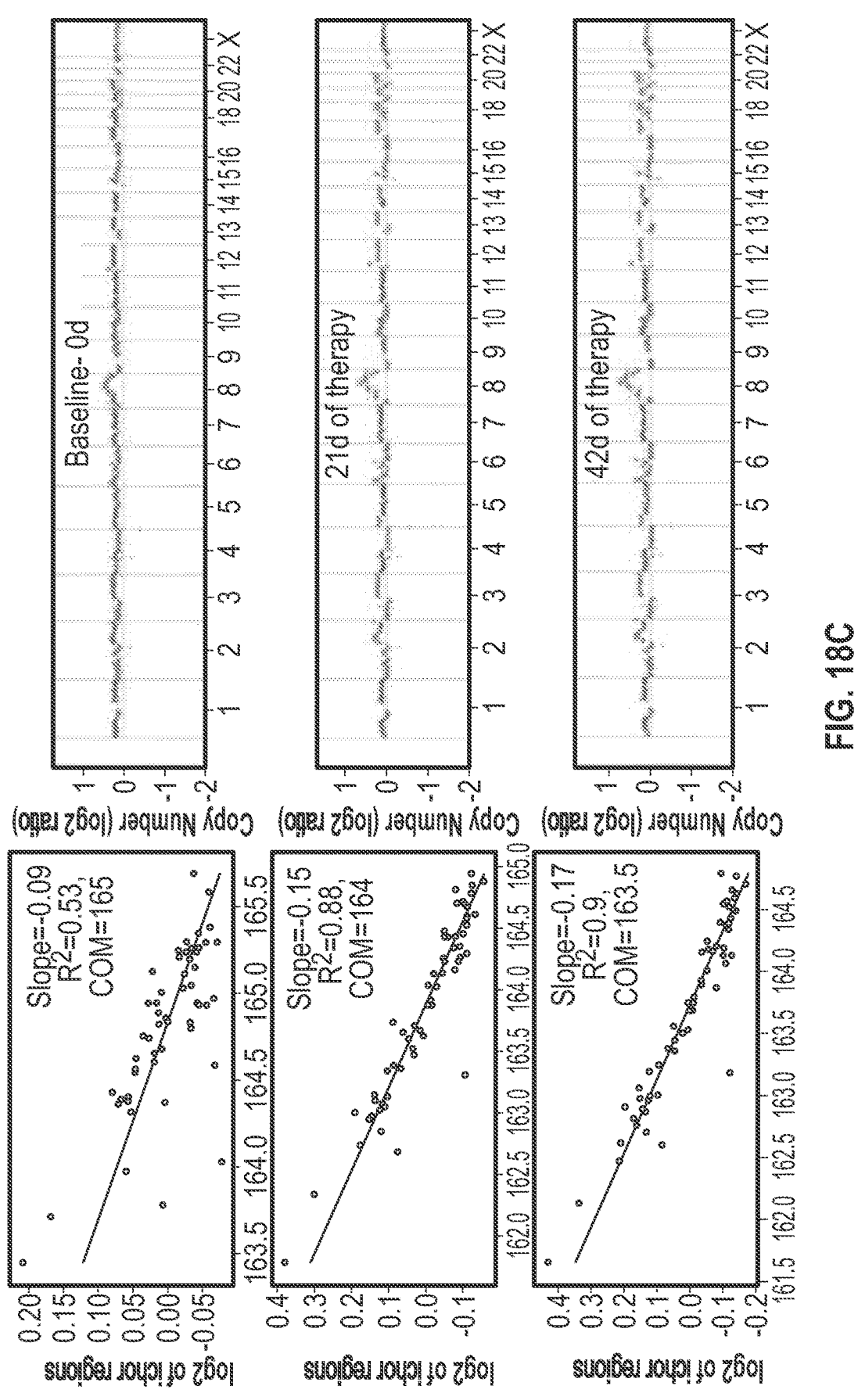

Using the estimated Log 2 and COM values of all the windows across the genome, the median sample center-of-mass (COM), the slope and $R^2$ of the Log 2/COM linear model is calculated. These features by themselves correspond with the fraction of tumor DNA (FIG. 18C). More specifically, the data show that the Log 2/FS correlation ($R^2$) has a strong relationship with the fraction of tumor DNA (FIG. 18D).

Figure 18D:
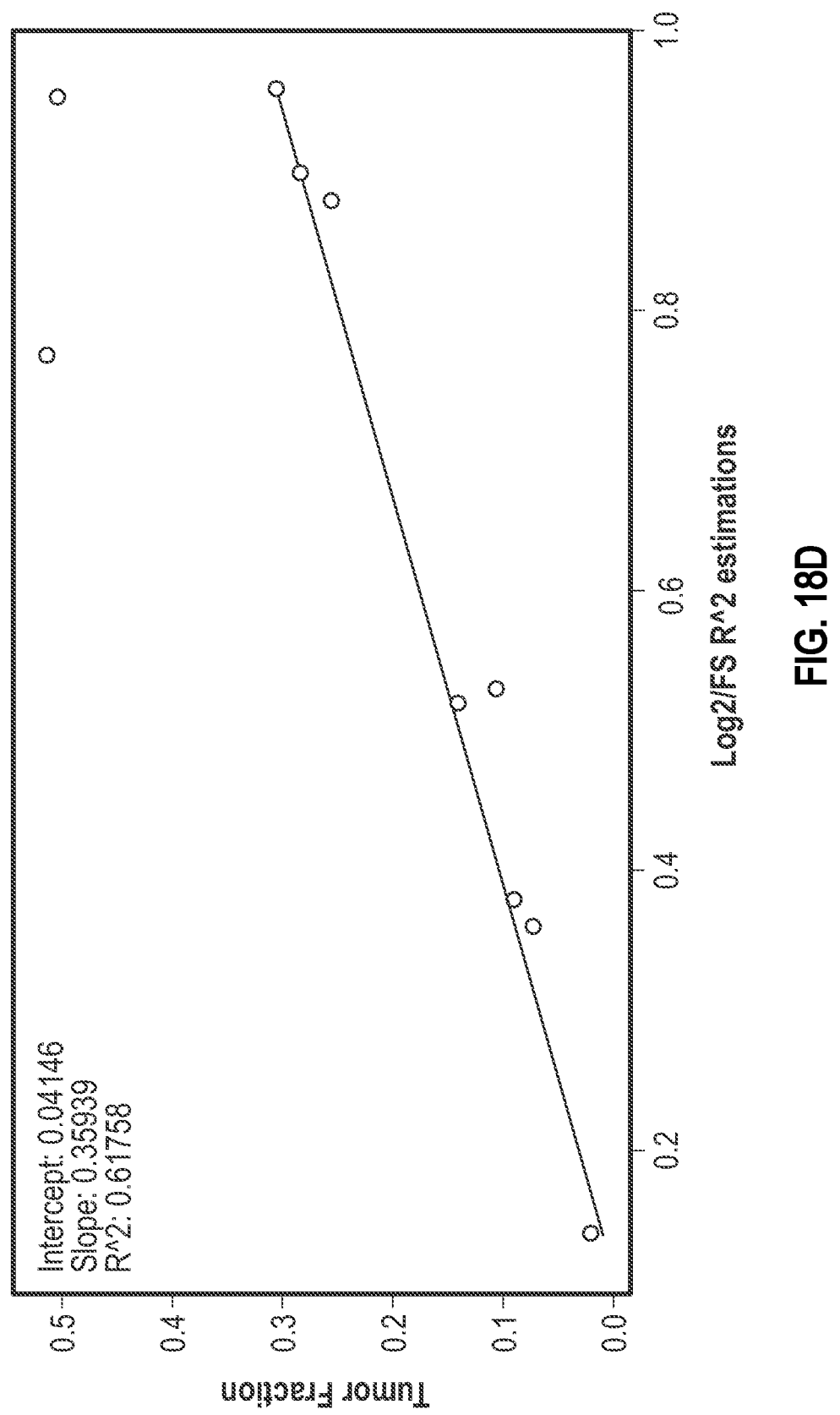
Figure 18E:
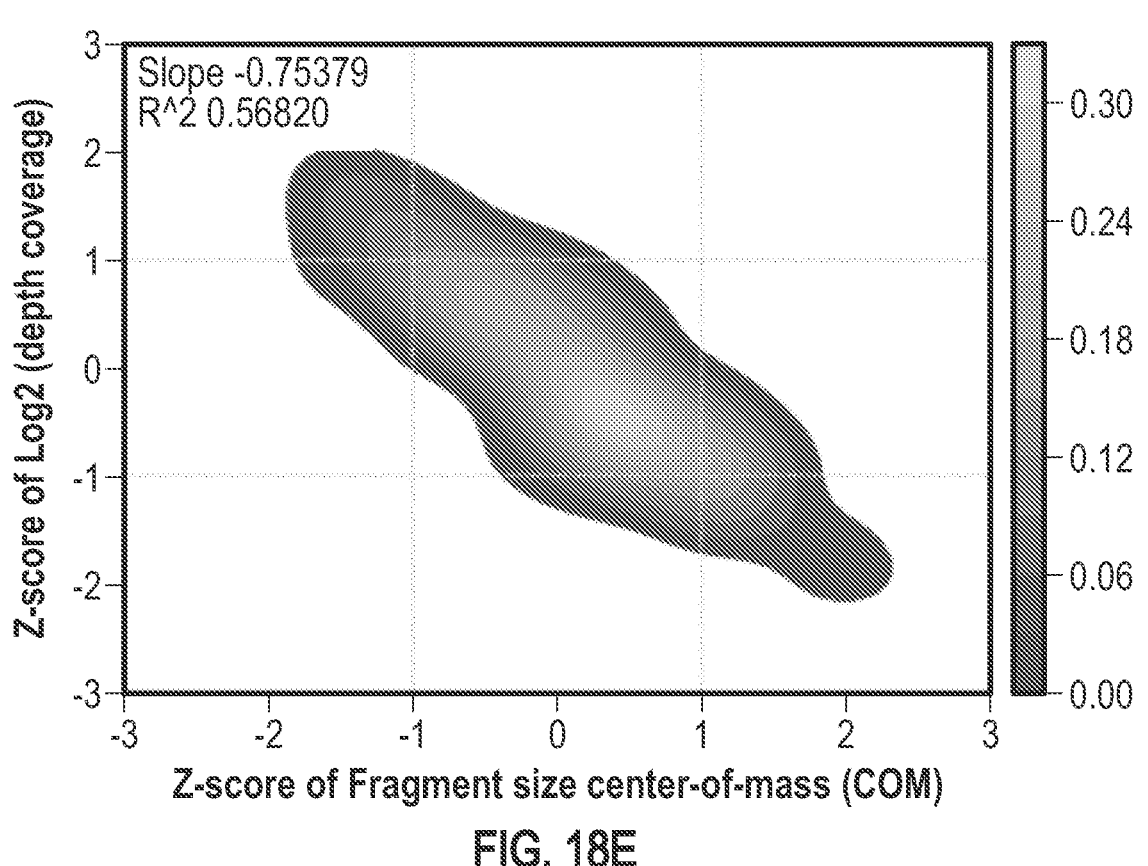
Figure 18F:
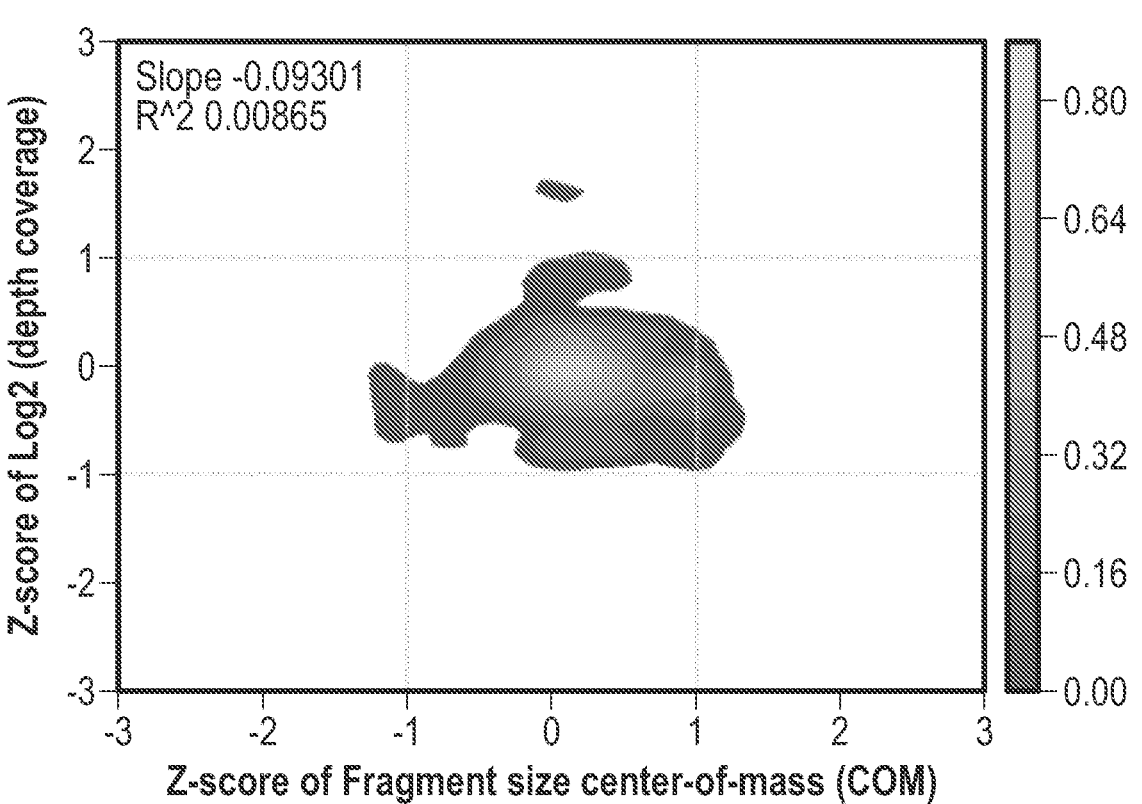

Each dot in this FIG. 18D corresponds to a patient sample. The x-axis represents the correlation ($R^2$) between all the Log 2 and COM values in all the 1 Mbp bins in this patient. This value shows strong correlation with orthogonal estimation of the sample TF (y-axis). Checking the correlation of Log 2 and COM in healthy plasma samples show extremely low correlation ($R^2$=0.008)(see FIG. 18F) in comparison to the correlation values seen in cancer patients (FIG. 18E).

The disclosure relates to the following non-limiting embodiments:

Embodiment 1. A method for genetic screening a subject for cancer, comprising (a) receiving a subject-specific genome-wide compendium of reads associated with a plurality of genetic markers from a biological sample of a subject, wherein the compendium of genetic markers is selected from the group consisting of single nucleotide variation (SNV), short insertions and deletions (Indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; (3) estimated fragment size of the read; and/or (4) estimated allele fraction of the read (VAF); (c) adaptively and/or systemically filtering sequencing noise associated with each read in the compendium by utilizing a machine learning (ML) model to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a degree of match between the subject-specific signature and a cancer signature; and (f) screening the subject for cancer if the confidence estimate that the subject's biological sample contains cancer related mutational signature exceeds a given threshold.

Embodiment 2. The method according to Embodiment 1, wherein the subject's biological sample comprises plasma, cerebral spinal fluid, pleural fluid, ocular fluid, stool, urine, or a combination thereof.

Embodiment 3. The method according to any of Embodiments 1 and 2, wherein the cancer signature comprises COSMIC tobacco signature, UV signature, Breast Cancer (BRCA) signature, microsatellite instability (MSI) signature, apolipoprotein B mRNA editing enzyme, poly (ADP-ribose) polymerase (PARP) hyperactivity signature, catalytic polypeptide-like (APOBEC) signature.

Embodiment 4. The method according to any of Embodiments 1 to 3, wherein the cancer signature comprises pattern associated with tissue specific epigenetic pattern, such as tissue specific chromatin accessibility pattern.

Embodiment 5. The method according to any of Embodiments 1 to 4, wherein the method further comprises filtering the sequencing noise associated with each read in the compendium by utilizing a machine learning (ML) model to discriminate between cancer related mutation features (true-positive) and PCR or sequencing error related features (false-positive).

Embodiment 6. The method according to any of Embodiments 1 to 5, wherein the machine learning model comprises a deep convolutional neural network (CNN), a recurrent neural network (RNN), a random forest (RF), a support vector machine (SVM), a discriminant analysis, a nearest neighbor analysis (KNN), an ensemble classifier, or a combination thereof. The method according to any of the foregoing embodiments, wherein the ML has been trained to distinguish between cancer altered sequencing reads and reads altered by sequencing or PCR errors.

Embodiment 7. The method according to any of Embodiments 1 to 6, wherein the ML has been trained on a whole-genome sequenced (WGS) cancer dataset comprising a plurality of reads across tumor mutations and normal sequencing errors.

Embodiment 8. The method according to any of Embodiments 1 to 7, wherein the ML is capable of (a) identifying, with high precision, sequencing or PCR artifacts and (b) integrating sequence context and read specific features.

Embodiment 9. The method according to any of Embodiments 1 to 8, wherein step (c) comprises implementing an optimal receiver operating characteristic (ROC) curve which comprises a probabilistic classification of the genetic markers in the compendium based on a joint base-quality (BQ), mapping-quality (MQ) score and fragment size.

Embodiment 10. The method according to any Embodiments 1 to 9, wherein the tumor is a tumor selected from the group consisting of brain cancer, lung cancer, skin cancer, nose cancer, throat cancer, liver cancer, bone cancer, lymphomas, pancreatic cancer, skin cancer, bowel cancer, rectal cancer, thyroid cancer, bladder cancer, kidney cancer, mouth cancer, stomach cancer, solid state tumor, non-small-cell lung carcinoma (NSCLC), tobacco-induced cancer (TIC), UV light-induced cancer, a cancer mediated by apolipoprotein B mRNA editing enzyme catalytic protein (APOBEC) activity, a cancer comprising breast cancer protein (BRCA) mutation, a cancer comprising poly (ADP-ribose) polymerase (PARP) activity, and a tumor comprising micro-satellite instability (MSI).

Embodiment 11. The method according to any of Embodiments 1 to 10, wherein the subject is undiagnosed for cancer and/or is asymptomatic.

Embodiment 12. The method according to any of Embodiments 1 to 11, wherein the subject is a patient with early stage cancer which is in stage I to III.

Embodiment 13. The method according to any of Embodiments 1 to 13, further comprising nomination or recommendation of a signature-based therapy based on the subject specific signature employed in the screening.

Embodiment 14. The method according to Embodiment 13, wherein the therapy nomination comprises PARP-inhibitor for BRCA signature, immunotherapy for MSI signature.

Embodiment 15. The method according to any of Embodiments 1 to 14, wherein the tumor is lung adenocarcinoma, ductal adenocarcinoma (breast tumor), non-small-cell lung carcinoma lung adenocarcinoma (NSCLC LUAD), cutaneous melanoma, urothelial carcinoma (bladder tumor), colorectal cancer (Lynch), or osteosarcoma.

Embodiment 16. The method according to any of Embodiments 1 to 15, wherein step (f) further comprises determining the confidence estimate by solving the linear optimization equation-$\min\|Ax-b\|$, $x \geq 0$, where A is the mutational signature sequence context matrix, x is the contribution of each cosmic mutational signature (the variable) and b is the patient specific sequence context compendium.

Embodiment 17. The method according to any of Embodiment 16, wherein the optimization equation is solved by Non-Negative Least square method (NNLS), Cross-Entropy global optimization method, Golden-section search method, or a combination thereof.

Embodiment 18. The method according to any of Embodiments 1 to 17, wherein step (b) further comprises removing artefactual reads from the compendium by (1) removing low mapping quality reads (e.g., <29, ROC optimized); (2) building duplication families (representing multiple PCR/sequencing copies of the same DNA fragment) and producing corrected read based on a consensus test; (3) removing low base quality reads (e.g., <21, ROC optimized); and/or (4) removing high fragment size reads (e.g., >160, ROC optimized), and step (e) further comprises calculating a sequence context similarity between the subject sequence-context compendium and a specific cosmic sequence-context compendium to determine a confidence estimate that the subject's biological sample contains cancer related mutational signature.

Embodiment 19. The method according to any of Embodiments 1 to 18, wherein step (f) further comprises estimating the similarity between the subject-specific signature and the cancer signature based on cosine-similarity, correlation, mutual-information, or a combination thereof.

Embodiment 20. The method according to any of Embodiments 1 to 19, further comprising validating the screening for confidence using a comparison of a cancer mutation signature to a plurality of random background signatures.

Embodiment 21. The method according to any of the Embodiment 20, wherein the comparison step comprises assessment of a zscore, wherein a zscore above a threshold value indicates that the subject-specific signature is specific to the cancer signature and not associated with random background signature.

Embodiment 22. The method according to any of Embodiments 1 to 22, wherein step (f) further comprises comparing the cancer specific signature confidence (zscore) to an empirical threshold calculated by a background noise model.

Embodiment 23. The method according to any of Embodiment 22, wherein the empirically-calculated background noise model comprises measuring the cancer specific signature confidence (zscore) relative to a basal noise zscore estimation for normal healthy samples, wherein a threshold noise zscore estimation of at least 1, at least 2, at least 3, at least 4, or at least 5 indicates that markers are cancer-specific.

Embodiment 24. The method according to any of Embodiments 1 to 23, wherein the subject-specific signature is matched with a cancer-specific mutation signature comprising markers that are differentially expressed in tumors but not in normal samples.

Embodiment 25. The method according to any of Embodiments 1 to 24, wherein the tumor sample comprises lung tumor, breast tumor, melanoma, bladder tumor, colorectal tumor, or bone tumor.

Embodiment 26. The method according to any of Embodiments 1 to 25, wherein a plurality of subjects are screened and the method permits early detection in at least 50% of the subjects.

Embodiment 27. The method according to any of Embodiments 1 to 27, further comprising computer tomography (CT) screening step, wherein the CT screening step is carried out prior to, concurrently with, or subsequently after any one of steps (a) to (f).

Embodiment 28. The method of Embodiment 27, wherein the cancer is a solid tumor and the CT screening comprises detection of suspicious nodules.

Embodiment 29. The method according to any of Embodiments 1 to 28, wherein the subject is a patient with a benign lesion.

Embodiment 30. The method according to any of Embodiment 29, wherein the benign lesion is identified via CT screening, histopathology, biopsy or a combination thereof.

Embodiment 31. The method according to any of Embodiments 1 to 30, further comprising discriminating between malignant and benign nodules to increase a positive predictive value (PPV) of CT screening.

Embodiment 32. The method according to any of Embodiment 31, wherein the PPV is increased by at least 30%.

Embodiment 33. A method for the early detection (ED) of a malignant tumor in a subject in need thereof, comprising, implementing a method according to any of Embodiments 1 to 32.

Embodiment 34. The method according to any of Embodiments 1 to 33, wherein step (a) further comprises aggregating genome-wide mutation data by whole genome sequencing and step (c) further comprises detecting mutational signature using a mathematical optimizing step. The method according to any of the foregoing embodiments, wherein the mathematical optimizing step comprises employing a nonnegative least square (NNLS).

Embodiment 35. A method for detecting a pre-malignant tumor signature in a subject comprising (a) generating a subject-specific genome-wide compendium of reads associated with a plurality of genetic markers from a biological sample of a subject, wherein the compendium of genetic markers is selected from the group consisting of single nucleotide variation (SNV), short insertions and deletions (Indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; and/or (3) estimated fragment size of the read (4) allele fraction of the read (VAF); (c) adaptively and/or systemically filtering sequencing noise associated with each read in the compendium by utilizing a machine learning (ML) model to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a degree of match between the subject-specific signature and a cancer signature; and (f) detecting a pre-malignant tumor signature if the confidence estimate that the subject's biological sample contains cancer related mutational signature exceeds a given threshold.

Embodiment 36. The method according to Embodiment 35, wherein the subject is a patient who is suspected of having or who has brain cancer, lung cancer, skin cancer, nose cancer, throat cancer, liver cancer, bone cancer, lymphomas, pancreatic cancer, skin cancer, bowel cancer, rectal cancer, thyroid cancer, bladder cancer, kidney cancer, mouth cancer, stomach cancer, solid state tumor, non-small-cell lung carcinoma (NSCLC), tobacco-induced cancer (TIC), UV light-induced cancer, a cancer mediated by apolipoprotein B mRNA editing enzyme catalytic protein (APOBEC) activity, a cancer comprising breast cancer protein (BRCA) mutation, a cancer comprising poly (ADP-ribose) polymerase (PARP) activity, and a tumor comprising micro-satellite instability (MSI), Lynch syndrome, or BRCA genetic deficiency.

Embodiment 37. The method according to any of Embodiments 35 and 36, wherein the machine learning (ML) model comprises a deep convolutional neural network (CNN) that adaptively and/or systemically filters sequencing noise.

Embodiment 38. The method according to Embodiment 37, wherein the CNN comprises employing a deep learning algorithm over a pan-tumor cohort to identify signatures that discriminate between true tumor mutations and artefactual errors; assigning a confidence estimate to each individual mutation detected in a sample from tumor patients; integrating the confidence estimates across the entire genome; and employing a non-negative least square (NNLS) of specific cosmic mutational signatures in the sample.

Embodiment 39. A computer readable medium comprising computer-executable instructions, which, when executed by a processor, cause the processor to carry out a method or a set of steps for early detection of tumor or detection of premalignant tumor lesion, the method or steps comprising, (a) generating a subject-specific genome-wide compendium of reads associated with a plurality of genetic markers from a biological sample of a subject, wherein the compendium of genetic markers is selected from the group consisting of single nucleotide variation (SNV), short insertions and deletions (Indels), copy number variation, structural variants (SV) and combinations thereof; (b) removing artefactual reads from the compendium by statistically classifying each read in the compendium as signal or noise on the basis of probability of detection of noise ($P_N$) as a function of (1) base-quality (BQ) of the read, (2) mapping-quality (MQ) of the read; and/or (3) estimated fragment size of the read (4) allele fraction of the read (VAF); (c) adaptively and/or systemically filtering sequencing noise associated with each read in the compendium by utilizing a machine learning (ML) model to discriminate between cancer related mutation features and PCR or sequencing error related features; (d) compiling a subject-specific signature comprising a plurality of true reads in the compendium based on the noise removal step (c) and filtering step (b); (e) statistically quantitating a confidence estimate that the subject's biological sample comprises circulating tumor DNA (ctDNA) based on a degree of match between the subject-specific signature and a cancer signature; and (f) detecting a pre-malignant tumor signature if the confidence estimate that the subject's biological sample contains cancer related mutational signature exceeds a given threshold.

Embodiment 40. The computer-readable media according to Embodiment 39, wherein the machine learning (ML) model comprises a layered convolutional neural network (CNN) with a single fully connected layer at one end, wherein the CNN maintains spatial invariance when convolving over trinucleotide windows; and maintains a quality map by collapsing the read fragment into a plurality of segments, each representing approximately an eight-nucleotide region.

Embodiment 41. The computer-readable media according to Embodiment 40, wherein the CNN comprises 8 layers comprising a single fully connected layer at one end and two successive convolutional layers, the output of which is down-sampled by maxpooling with a receptive field of two and a stride of two; wherein the 8-layered CNN maintains quality map by collapsing the read fragment into about 25 individual segments and convolves over columns at a position in the genomic read using a perceptive field of size three; and wherein the output of the last convolutional layer is applied directly to a sigmoid fully connected layer, from which a final classification of the marker is made.

Embodiment 42. The computer-readable media according to any of Embodiments 40 and 41, wherein the CNN comprises a read representation that jointly captures the genomic context of alignment, the complete read sequence, and the integration of the quality score per base.

Embodiment 43. The computer-readable media according to any of Embodiments 39 and 42, wherein steps (a) to (f) together provides enrichment of tumor specific markers comprising somatic mutations in a genomic read by about 1.12-fold to about 30-fold compared to MUTECT.

Embodiment 44. A computer readable medium comprising computer-executable instructions, which, when executed by a processor, cause the processor to carry out a method or a set of steps for diagnosing a cancer in a subject, the medium comprising a convolutional neural network (CNN) developed by the method of: (A) receiving, from a plurality of subject's sample, a compendium of genetic markers for each subject, wherein the genetic markers comprise somatic single nucleotide variations (sSNVs); somatic copy number variations (sCNVs); insertions/deletions (indel); or structural variations (SV) in a genomic read; (B) processing the compendium of genetic markers for each subject over a pan-tumor cohort to identify signatures that discriminate between true cancer markers and artefactual errors; (C) assigning a confidence estimate to each signature in the compendium based on the processing step (B); (D) integrating the confidence estimates for each signature of step (C) across the genomic read to build a tumor signature; and (E) mathematically optimizing the tumor signature by returning the results of steps (B) to (D) for each subject sample back to the CNN until the CNN achieves a preset threshold value of confidence estimate for each subject.

Embodiment 45. The computer-readable media according to Embodiment 44, wherein the assignment of confidence estimate comprises (1) calculating a confidence metric for the contribution of a cosmic mutational signature using a linear mixture optimization; or (2) calculating the similarity of the patient sequence-context compendium to a specific cosmic signature.

Embodiment 46. The computer-readable media according to Embodiment 45, wherein the linear mixture optimization comprises solving an algebraic function $\min\|Ax-b\|$, $x\geq0$, wherein A is the mutational signature sequence context matrix, x is the contribution of each cosmic mutational signature and b is the patient specific sequence context compendium.

Embodiment 47. The computer-readable media according to Embodiment 46, wherein A comprises the at least 5, at least 10, at least 15, at least 20, at least 25 or at least 30 COSMIC signatures along with 100 random mutational signatures.

Embodiment 48. The computer-readable media according to any of Embodiments 45 and 47, wherein the linear mixture optimization comprises calculating a distribution of the contribution of random signatures comprising extraction E_random (average contribution score) and std_random (std contribution score); and checking the confidence of contribution detection for each COSMIC signature by zscore, comprising computing a metric (cosmic_sig_contribution-E_random)/std_random, wherein the metric represents the significance of a particular signature in comparison to a random set.

Embodiment 49. The computer-readable media according to any of Embodiments 44 and 48, wherein the mathematical optimizing step comprises employing a non-negative least square (NNLS).

Embodiment 50. A system for diagnosing a tumor in a subject in need thereof, comprising: a data acquisition unit configured to receive a plurality of reads comprising genetic markers amplified and sequenced from a biological sample comprising a plasma sample and a normal cell sample of the subject; a marker identification unit configured to identify a plurality of subject-specific markers in the subject-specific compendium of genetic markers, the marker identification unit communicatively connected to the data acquisition unit, comprising: a noise removing unit that removes artefactual noise on the basis of base quality of the read, mapping quality of the read, fragment size of the read, and/or variable allele frequency of the read (VAF); a classification engine configured to statistically classify each noise-removed read in the compendium on the basis of a confidence interval score which indicates a statistical level of a statistical association between the read and the tumor, wherein the classification engine utilizes a machine learning (ML) model to adaptively and systematically filter noise introduced during the amplification step or the sequencing step and further match the noise-removed ML-filtered reads in the compendium with one or more known cancer signatures; and a diagnosing unit configured to diagnose a tumor based on the match.

Embodiment 51. The system according to Embodiment 50, wherein the classification engine is further configured to match the noise-removed ML-filtered reads in the compendium with one or more known cancer signatures by computing a confidence metric using a linear mixture optimization problem.

Embodiment 52. The system according to Embodiment 51, wherein the linear mixture optimization comprises computing a zscore confidence estimation for the association between tumor incidence and a tumor mediator selected from tobacco exposure, UV light exposure, deregulated DNA repair, faulty DNA editing, microsatellite instability, or a combination thereof.

Embodiment 53. The system according to Embodiment 52, wherein the zscore confidence estimation comprises solving an algebraic function comprising $\min\|Ax-b\|$, $x \geq 0$, wherein A is the mutational signature sequence context matrix, x is the contribution of each cosmic mutational signature; and b is the patient specific sequence context compendium.

Embodiment 54. The system according to any of Embodiments 52 and 53, wherein the zscore confidence estimation comprises solving an algebraic function comprising $\min\|Ax-b\|$, $x \geq 0$, wherein A comprises 30 cosmic signatures and 100 random mutational signatures; and calculating a distribution of the contribution of cosmic signatures (CSC) random signatures (E_random) comprising an average contribution score (ACS) and a standard contribution score (std_random); and checking the confidence of contribution for each cosmic signature by computing a zscore metric with the function (CSC-E_random)/std_random, wherein the zscore represents the significance of a particular signature contribution in comparison to the random set.

Embodiment 55. The system according to any of Embodiments 52 and 54, wherein the zscore confidence estimation comprises calculating the similarity of the patient sequence-context compendium to a specific cosmic signature.

Embodiment 56. The system according to any of Embodiments 52 and 55, wherein the zscore confidence estimation comprises normalizing a patient sequence-context compendium to obtain a density function; calculating a cosine-similarity between the patient sequence-context density function and the cosmic signature density function; and normalize the cosine similarity by dividing by the cosine similarity between the patient sequence-context density function and non-informative uniform density function.

Embodiment 57. The system according to any of Embodiments 52 and 56, wherein the zscore confidence estimation comprises checking whether the zscore exceeds a detection threshold, wherein the threshold comprises empirically estimated basal noise in healthy samples.

Embodiment 58. The system according to any of Embodiments 52 and 57, wherein the cancer signature comprises tobacco signature, and a positive confidence interval comprises a zscore that is greater than 2, 3, 4, preferably greater than 5 standard deviations.

Embodiment 59. The system according to any of Embodiments 50 and 58, wherein the genetic markers comprise SNVs, CNVs, indels and/or SVs in the DNA and the receiving unit receives whole genome sequenced (WGS) genetic data.

Embodiment 60. The system according to any of Embodiments 50 and 59, wherein the biological sample comprising a plasma sample comprises cell-free DNA (cfDNA); the normal cell sample comprises peripheral mononuclear blood cells (PMBC) and the marker comprises somatic single nucleotide variation (sSNV) or somatic copy number variation (sCNV) or a combination thereof.

Embodiment 61. The system according to Embodiment 60, wherein the amount of cfDNA in the sample is between about 0.1 ng/ml to about 20.0 ng/ml.

Embodiment 62. The system according to any of Embodiments 50 and 61, wherein the sample has a low tumor fraction (TF), as measured by ratio of an amount of tumor DNA molecules in relation to normal DNA molecules.

Embodiment 63. The system according to Embodiment 62, wherein the tumor fraction (TF) is between about 0.0001% (1 to a million molecules) to about 20%.

Embodiment 64. The system according to any of Embodiments 50 and 6, wherein the artefactual noise-removing engine is configured to implement an optimal receiver operating characteristic (ROC) curve which comprises a probabilistic classification of the reads in the compendium based on base-quality (BQ) score of the read; mapping-quality (MQ) score of the read; fragment size of the read; or variable allele frequency (VAF) of the read.

Embodiment 65. The system according to any of Embodiments 50 and 64, wherein the artefactual noise-removing engine is further configured to filter noise on the basis of (iii) position in the read (RP); (iv) sequence context (SC) of the read; (v) abundance of the read; (vi) sequencing depth and/or (vii) sequencing error.

Embodiment 66. A method for genetic screening a subject for cancer, comprising (A) receiving a subject-specific genome-wide compendium of reads associated with a plurality of genetic markers from a biological sample of a subject, the biological sample comprising a plasma sample, wherein the compendium of reads each comprise reads of a single base pair length; (B) filtering artefactual sites from the compendium of reads, wherein the filtering comprises (a) removing, from the compendium of reads, recurring sites generated over a cohort of reference healthy samples; and/or (b) identifying germ line mutations in the biological sample and/or identifying shared mutations between the tumor sample and peripheral blood mononuclear cells of a normal cell sample as germ line mutations, and removing said germ line mutations from the compendium of reads; (C) filtering noise from the compendium of reads using at least one error suppression protocol to produce a filtered read set for the genome-wide compendium of reads, wherein the at least one error suppression protocol comprises (a) calculating the probability that any single nucleotide variation in the compendium is an artefactual mutation, and removing said mutation, wherein the probability is calculated as a function of features selected from the group comprising mapping-quality (MQ), variant base-quality (MBQ), position-in-read (PIR), mean read base quality (MRBQ), and combinations thereof; and/or (b) removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family; (D) compiling a subject-specific signature using the filtered read set, based on comparison to specific mutational signatures associated with a pre-determined mutagenesis process; (E) statistically quantitating a confidence estimate that the subject's biological sample, via the subject-specific signature, comprises a cancer related mutational signature based on comparison of the cancer related mutational signature exposure value to a cohort of background mutation signatures; and (F) screening the subject for cancer if the confidence estimate that the subject's biological sample contains the cancer related mutational signature exceeds a given threshold.

Embodiment 67. A method for genetic screening a subject for cancer, comprising, (A) receiving a subject-specific genome-wide compendium of reads associated with a plurality of genetic markers from a biological sample of a subject, the biological sample comprising a plasma sample, wherein the compendium of reads each comprise a copy number variation (CNV) or structural variation (SV); (B) dividing the compendium of reads into a plurality of windows; (C) calculating a set of features per window, the features comprising a median depth coverage per window and a representative fragment size per window, and optionally split reads; (D) filtering artefactual sites from the compendium of reads, wherein the filtering comprises removing, from the compendium of reads, recurring sites generated over a cohort of reference healthy samples; (E) normalizing the compendium of reads to produce a filtered read set for the genome-wide compendium of reads; (F) computing an estimated tumor fraction using the filtered read set (i) by calculating a linear relationship between the set of features per window and converting the calculated relationship to estimated tumor fraction using a regression model, and/or (ii) on the basis of one or more integrative mathematical models as a function of the calculated set of features per window across the subject-specific genome-wide compendium of reads; and (G) screening the subject for cancer if the estimated tumor fraction exceeds an empirical threshold.

Embodiment 68. A system for genetic screening a subject for cancer, comprising, an analyzing unit, the analyzing unit comprising a pre-filter engine configured and arranged to receive a subject-specific genome-wide compendium of reads associated with a plurality of genetic markers from a biological sample of a subject, the biological sample comprising a plasma sample, wherein the compendium of reads each comprise reads of a single base pair length; and filter artefactual sites from the compendium of reads, wherein the filtering comprises removing, from the compendium of reads, recurring sites generated over a cohort of reference healthy samples; and/or identifying germ line mutations in the biological sample and/or identifying shared mutations between the tumor sample and peripheral blood mononuclear cells of the normal cell sample as germ line mutations, and removing said germ line mutations from the compendium of reads; a correction engine configured and arranged to filter noise from the compendium of reads using at least one error suppression protocol to produce a filtered read set for the genome-wide compendium of reads, wherein the at least one error suppression protocol comprises (a) calculating the probability that any single nucleotide variation in the compendium is an artefactual mutation, and removing said mutation, wherein the probability is calculated as a function of features selected from the group comprising mapping-quality (MQ), variant base-quality (MBQ), position-in-read (PIR), mean read base quality (MRBQ), and combinations thereof; and/or (b) removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family; and a computing unit configured and arranged to compile a subject-specific signature using the filtered read set, based on comparison to specific mutational signatures associated with a pre-determined mutagenesis process; statistically quantitating a confidence estimate that the subject's biological sample, via the subject-specific signature, comprises a cancer related mutational signature based on comparison of the cancer related mutational signature exposure value to a cohort of background mutation signatures; and screen the subject for cancer if the confidence estimate that the subject's biological sample contains the cancer related mutational signature exceeds a given threshold.

Embodiment 69. A system for detecting residual disease in a subject in need thereof, comprising, an analyzing unit, the analyzing unit comprising a binning engine configured and arranged to receive a subject-specific genome-wide compendium of reads associated with a plurality of genetic markers from a biological sample of a subject, the biological sample comprising a plasma sample, wherein the compendium of reads each comprise a copy number variation (CNV); divide the compendium of reads into a plurality of windows; and calculate a set of features per window, the features comprising a median depth coverage per window and a representative fragment size per window; a pre-filter engine configured and arranged to filter artefactual sites from the compendium of reads, wherein the filtering comprises removing, from the compendium of reads, recurring sites generated over a cohort of reference healthy samples; and a normalization engine configured and arranged to normalize the compendium of reads to produce a filtered read set for the genome-wide compendium of reads; and a computing unit configured and arranged to compute an estimated tumor fraction using the filtered read set (i) by calculating a linear relationship between the set of features per window and converting the calculated relationship to estimated tumor fraction using a regression model, and/or (ii) on the basis of one or more integrative mathematical models as a function of the calculated set of features per window across the subject-specific genome-wide compendium of reads; and screen the subject for cancer if the estimated tumor fraction exceeds an empirical threshold.

Embodiment 70. The method of Embodiment 66, wherein the markers comprise single nucleotide variations (SNVs) or insertion/deletions (indels); preferably SNV.

Embodiment 71. The method of any one of Embodiments 66 and 70, wherein filtering recurring sites generated over a cohort of reference healthy samples comprises generating a panel of normal (PON) blacklist or mask.

Embodiment 72. The method of any one of Embodiments 66 and 70 to 71, wherein the reference healthy sample comprises peripheral blood mononuclear cells (PBMC).

Embodiment 73. The method of any one of Embodiments 66 and 70 to 73, wherein step (C) comprises employing a machine learning (ML) algorithm, e.g., deep convolutional neural network (CNN), recurrent neural network (RNN), random forest (RF), support vector machine (SVM), discriminant analysis, nearest neighbor analysis (KNN), ensemble classifier, or a combination thereof; preferably, support vector machine (SVM), to filter artefactual noise.

Embodiment 74. The method of any one of Embodiments 66 and 70 to 73 wherein in step (C)(b), the correction of artefactual variation includes correction of artefactual mutations generated by PCR or sequencing using the comparison of independent replicates of the original nucleic acid fragment.

Embodiment 75. The method of Embodiment 74, wherein in step (C)(b), artefactual variations generated by paired-end 150 bp sequencing, which results in overlapping paired reads (R1 and R2), are removed by correcting back, to the corresponding reference genome, discordance between R1 and R2 pairs.

Embodiment 76. The method of any one of Embodiments 66 and 70 to 75, wherein in step (C)(b), the artefactual variations generated by duplication during sequencing and/or PCR amplification are corrected, wherein the duplication families are recognized by 5' and 3' similarity as well as alignment position and wherein each duplication family is used to check the consensus of a specific mutation across independent replicates, thereby correcting artefactual mutations that do not show concordance in a majority of the duplication family.

Embodiment 77. The method of any one of Embodiments 66 and 70 to 76, wherein in step (D), specific mutational signatures in a single plasma sample are identified using non-negative least square (NNLS) method.

Embodiment 78. The method of any one of Embodiments 66 and 70 to 77, wherein in step (E), the specific mutational signatures are further validated for confidence using a comparison of the cancer-specific mutation signature exposure values to the exposure values inferred for a plurality of random background signatures.

Embodiment 79. The method of Embodiment 78, wherein in step (F), the subject is identified as having cancer if the confidence estimate that the subject's biological sample contains the cancer related mutational signature exceeds a given threshold for z-score>2std.

Embodiment 80. The method of any one of Embodiments 66 and 70 to 79, wherein in step (D), additionally or alternatively comprises employing a machine learning (ML) algorithm, e.g., deep learning method, to distinguish between cancer altered sequencing reads and reads altered by sequencing errors.

Embodiment 81. The method of Embodiment 80, wherein the ML is trained on a plurality of true mutated reads and error using a large collection of tumor and normal WGS data and the trained ML is capable of distinguishing between a read that contains a true variant versus a read that contain a sequencing artifact.

Embodiment 82. The method of any one of Embodiments 66 to 81, further comprising orthogonal integration of a secondary feature comprising fragment size shift.

Embodiment 83. The method of Embodiment 82, wherein intra-patient fragment size shifts in the list of tumor-specific markers and random markers are analyzed using statistical methods, e.g., tests for significance or Gaussian mixture model (GMM).

Embodiment 84. The method of any one of Embodiment 67, wherein the markers comprise copy number variations (CNVs).

Embodiment 85. The method of any one of Embodiments 67 and 84, wherein in step (B), each window is at least ≥150 bp.

Embodiment 86. The method of any one of Embodiments 67 and 84 to 85, wherein step (C) comprises extraction of depth coverage (Log 2) and fragment size (COM) relationship (slope, R^2) from the genome-wide feature vectors.

Embodiment 87. The method of any one of Embodiments 67 and 84 to 86, wherein step (D) comprises filtering recurring sites generated over a cohort of reference healthy plasma samples by generating a panel of normal (PON) blacklist or mask; and/or filtering windows of low mappability or coverage.

Embodiment 88. The method of any one of Embodiments 67 and 84 to 87, wherein the normalization step includes normalizing depth coverage values to correct for GC-content and mappability biases by performing two LOESS regression curve-fitting on the bin-wise GC-fraction and mappability score.

Embodiment 89. The method of any one of Embodiments 67 and 84 to 88, wherein the normalization step includes batch-effect correction using a robust-zscore normalization, which is applied to each sample separately.

Embodiment 90. The method of Embodiment 89, wherein the zscore normalization includes calculation of median and median-absolute-deviation (MAD) based on the neutral regions of each sample and normalizing all CNV bins are normalized by subtracting the median value and dividing the differential by MAD.

Embodiment 91. The method of any one of Embodiments 67 and 84 to 90, wherein step (E) includes calculating depth coverage skew and/or fragment size center-of-mass (COM) skew in the plasma sample in comparison to a panel of normal (PON) healthy plasma samples.

Embodiment 92. The method of any one of Embodiments 67 and 84 to 91, wherein step (F) includes copy-number-variation (CNV) calling and calculation of tumor fraction of the filtered read set using a hidden Markov model or a self-organizing neural networks, e.g., a neural network based on Adaptive Resonance Theory (ART) or self organizing map (SOM).

Embodiment 93. The method of any one of Embodiments 67 and 84 to 92, further comprising orthogonal integration of a secondary feature comprising fragment size shift.

Embodiment 94. The method of any one of Embodiment 93, wherein intra-patient fragment size shifts in the list of tumor-specific markers and random markers are analyzed using statistical methods, e.g., tests for significance or Gaussian mixture model (GMM).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope. For convenience, certain terms employed in the specification, examples and claims are collected here. Unless defined otherwise, all technical and scientific terms used in this disclosure have the same meanings as commonly understood by one of ordinary skill in the art to which this disclosure belongs.

Throughout this disclosure, various patents, patent applications and publications are referenced. The disclosures of these patents, patent applications, accessioned information (e.g., as identified by PUBMED, PUBCHEM, NCBI, UNI-PROT, or EBI accession numbers) and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

We claim:

1. A method for genetic screening a subject for cancer, comprising:

(A) receiving, via whole genome sequencing, a subject-specific genome-wide compendium of reads associated with a plurality of genetic markers from a biological sample of a subject, the biological sample comprising a plasma sample;

(B) filtering recurring sites and/or germ line mutations from the subject-specific genome-wide compendium of reads, the recurring sites based on a cohort of reference healthy samples;

(C) filtering artefactual mutations from the subject-specific genome-wide compendium of reads using at least one error suppression protocol to produce a filtered read set for the subject-specific genome-wide compendium of reads;

(D) compiling a subject-specific signature using the filtered read set, based on comparison to specific mutational signatures associated with a pre-determined mutagenesis process;

(E) statistically quantitating a confidence estimate that the subject's biological sample, via the subject-specific signature, comprises a cancer related mutational signature based on comparison of the cancer related mutational signature exposure value to a cohort of background mutation signatures; and (F) diagnosing the subject for cancer based on the confidence estimate that the subject's biological sample contains the cancer related mutational signature exceeding a given threshold, wherein the sample comprises a low tumor fraction (TF) having a ratio of tumor DNA molecules to normal DNA molecules of less than about 0.1%.

2. The method of claim 1, wherein the markers comprise single nucleotide variations (SNVs) or insertion/deletions (indels).

3. The method of claim 2, wherein the markers comprise single nucleotide variations (SNVs).

4. The method of claim 1, wherein filtering recurring sites based on the cohort of reference healthy samples comprises generating a panel of normal (PON) blacklist or mask.

5. The method of claim 1, wherein the reference healthy sample comprises peripheral blood mononuclear cells (PBMC).

6. The method of claim 1, wherein step (C) comprises employing a machine learning (ML) algorithm.

7. The method of claim 6, wherein step (C) comprises employing support vector machine (SVM) to filter artefactual noise.

8. The method of claim 6, wherein the ML algorithm comprises a deep convolutional neural network (CNN), a recurrent neural network (RNN), a random forest (RF), a support vector machine (SVM), a discriminant analysis, a nearest neighbor analysis (KNN), an ensemble classifier, or a combination thereof.

9. The method of claim 1, wherein in step (C), the at least one error suppression protocol comprises removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family, wherein the filtering of artefactual mutations includes correction of artefactual mutations generated by PCR or sequencing using the comparison of independent replicates of the original nucleic acid fragment.

10. The method of claim 9, wherein in step (C), the at least one error suppression protocol comprises removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family, wherein artefactual variations generated by paired-end 150 bp sequencing, which results in overlapping paired reads (R1 and R2), are removed by correcting back, to the corresponding reference genome, discordance between R1 and R2 pairs.

11. The method of claim 1, wherein in step (C), the at least one error suppression protocol comprises removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family, wherein artefactual mutations generated by duplication during sequencing and/or PCR amplification are corrected, wherein the duplication families are recognized by 5' and 3' similarity as well as alignment position and wherein each duplication family is used to check the consensus of a specific mutation across independent replicates, thereby correcting artefactual mutations that do not show concordance in a majority of the duplication family.

12. The method of claim 1, wherein in step (D), specific mutational signatures in a single plasma sample are identified using non-negative least square (NNLS) method.

13. The method of claim 1, wherein in step (E), the specific mutational signatures are further validated for confidence using a comparison of the cancer-specific mutation signature exposure values to the exposure values inferred for a plurality of random background signatures.

14. The method of claim 13, wherein in step (F), the subject is identified as having cancer if the confidence estimate that the subject's biological sample contains the cancer related mutational signature exceeds a given threshold for z-score>2std.

15. The method of claim 1, wherein step (D), additionally comprises employing a machine learning (ML) algorithm to distinguish between cancer altered sequencing reads and reads altered by sequencing errors.

16. The method of claim 15, wherein the ML is trained on a plurality of true mutated reads and error using a large collection of tumor and normal WGS data and the trained ML is capable of distinguishing between a read that contains a true variant versus a read that contain a sequencing artifact.

17. The method of claim 15, wherein the ML algorithm comprises a deep learning method.

18. The method of claim 1, further comprising orthogonal integration of a secondary feature comprising fragment size shift.

19. The method of claim 18, wherein intra-patient fragment size shifts in the list of tumor-specific markers and random markers are analyzed using a statistical method.

20. The method of claim 19, wherein the statistical method comprises a test for significance or a Gaussian mixture model (GMM).

21. The method of claim 1, wherein the ratio of tumor DNA molecules to normal DNA molecules is between about 0.0001% to about 0.1%.

22. The method of claim 1, wherein the subject is undiagnosed and/or asymptomatic.

23. The method of claim 1, wherein the subject has early stage cancer which is in stage I to III.

24. The method of claim 1, wherein in step (C), the at least one error suppression protocol comprises:
(a) calculating the probability that any single nucleotide variation in the compendium is an artefactual mutation, and removing said mutation, wherein the probability is calculated as a function of features selected from the group comprising mapping-quality (MQ), variant base-quality (MBQ), position-in-read (PIR), mean read base quality (MRBQ), and combinations thereof; and/or
(b) removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family.

25. The method of claim 1, further comprising:
(G) generating a therapy recommendation for the subject based on the cancer related mutational signature and responsive to the statistically quantitated confidence estimate exceeding a given threshold, wherein the sample comprises a low tumor fraction (TF) having a ratio of tumor DNA molecules to normal DNA molecules of less than about 0.1%.

26. The method of claim 1, further comprising:
(G) administering a therapy to the subject based on the cancer related mutational signature and responsive to the statistically quantitated confidence estimate exceeding a given threshold, wherein the sample comprises a low tumor fraction (TF) having a ratio of tumor DNA molecules to normal DNA molecules of less than about 0.1%.

27. A system, comprising:
a memory storing computer readable instructions; and
a processor coupled to the memory and configured to:
receive, via whole genome sequencing, a subject-specific genome-wide compendium of reads associated with a plurality of genetic markers from a biological sample of a subject, the biological sample comprising a plasma sample;
filter recurring sites and/or germ line mutations from the subject-specific genome-wide compendium of reads, the recurring sites generated over a cohort of reference healthy samples;
filter artefactual noise from the subject-specific genome-wide compendium of reads using at least one error suppression protocol to produce a filtered read set for the subject-specific genome-wide compendium of reads;
compile a subject-specific signature using the filtered read set, based on comparison to specific mutational signatures associated with a pre-determined mutagenesis process;
statistically quantitate a confidence estimate that the subject's biological sample, via the subject-specific signature, comprises a cancer related mutational signature based on comparison of the cancer related mutational signature exposure value to a cohort of background mutation signatures; and
diagnosing the subject for cancer based on the confidence estimate that the subject's biological sample contains the cancer related mutational signature exceeding a given threshold, wherein the sample comprises a low tumor fraction (TF) having a ratio of tumor DNA molecules to normal DNA molecules of less than about 0.1%.

28. The system of claim 27, wherein the at least one error suppression protocol comprises:
(a) calculating the probability that any single nucleotide variation in the compendium is an artefactual mutation, and removing said mutation, wherein the probability is calculated as a function of features selected from the group comprising mapping-quality (MQ), variant base-quality (MBQ), position-in-read (PIR), mean read base quality (MRBQ), and combinations thereof; and/or
(b) removing artefactual mutations using discordance testing between independent replicates of the same DNA fragment generated from polymerase chain reaction or sequencing processing, and/or duplication consensus wherein artefactual mutations are identified and removed when lacking concordance across a majority of a given duplication family.

29. The system of claim 27, wherein the processor is further configured to:
generate a therapy recommendation for the subject based on the cancer related mutational signature and responsive to the statistically quantitated confidence estimate exceeding a given threshold, wherein the sample comprises a low tumor fraction (TF) having a ratio of tumor DNA molecules to normal DNA molecules of less than about 0.1%.

30. The system of claim 27, wherein the processor is further configured to:
administer a therapy to the subject based on the cancer related mutational signature and responsive to the statistically quantitated confidence estimate exceeding a given threshold, wherein the sample comprises a low tumor fraction (TF) having a ratio of tumor DNA molecules to normal DNA molecules of less than about 0.1%.

* * * * *